United States Patent
Xu et al.

(10) Patent No.: US 12,398,141 B2
(45) Date of Patent: Aug. 26, 2025

(54) JAK KINASE INHIBITOR, PREPARATION METHOD FOR SAME, AND APPLICATIONS THEREOF IN FIELD OF MEDICINE

(71) Applicants: SHANGHAI SYNERGY PHARMACEUTICAL SCIENCES CO., LTD, Shanghai (CN); ZHEJIANG HUAHAI PHARMACEUTICAL CO., LTD., Zhejiang (CN)

(72) Inventors: Xin Xu, Shanghai (CN); Jia Chen, Shanghai (CN); Zhen Zhang, Shanghai (CN); Guan Wang, Shanghai (CN); Linli Zhang, Shanghai (CN); Qiang Li, Shanghai (CN); Chenghao Xi, Shanghai (CN); Minkai Qu, Shanghai (CN); Xiaojuan Zhang, Shanghai (CN); Chunqiao Chen, Shanghai (CN); Fan Yang, Shanghai (CN); Xiaoer Xia, Shanghai (CN); Yijin Wang, Shanghai (CN); Yunfei Li, Shanghai (CN); Jian Ge, Shanghai (CN)

(73) Assignees: SHANGHAI SYNERGY PHARMACEUTICAL SCIENCES CO., LTD, Shanghai (CN); ZHEJIANG HUAHAI PHARMACEUTICAL CO., LTD., Zhejiang (CN)

( * ) Notice: Subject to any disclaimer, the term of this patent is extended or adjusted under 35 U.S.C. 154(b) by 946 days.

(21) Appl. No.: 17/437,944

(22) PCT Filed: Mar. 11, 2020

(86) PCT No.: PCT/CN2020/078826
§ 371 (c)(1),
(2) Date: Sep. 10, 2021

(87) PCT Pub. No.: WO2020/182159
PCT Pub. Date: Sep. 17, 2020

(65) Prior Publication Data
US 2022/0185816 A1    Jun. 16, 2022

(30) Foreign Application Priority Data

Mar. 14, 2019 (CN) .......................... 201910193017.6

(51) Int. Cl.
  *C07D 487/04* (2006.01)
  *C07D 471/04* (2006.01)
  *C07D 519/00* (2006.01)
(52) U.S. Cl.
  CPC ......... *C07D 487/04* (2013.01); *C07D 471/04* (2013.01); *C07D 519/00* (2013.01)

(58) Field of Classification Search
  CPC .............. A61K 31/437; A61K 31/4545; A61K 31/496; A61K 45/06; A61K 2300/00; C07D 471/04; C07D 487/04; C07D 519/00; A61P 17/00; A61P 25/28; A61P 3/10; A61P 35/00; A61P 37/00; A61P 31/12

See application file for complete search history.

(56) References Cited

U.S. PATENT DOCUMENTS

2017/0247372 A1* 8/2017 Thorarensen ............ A61P 9/10
2020/0347053 A1* 11/2020 Jacobsen ............. A61K 31/437

FOREIGN PATENT DOCUMENTS

| CN | 101578285 A | 11/2009 |
|---|---|---|
| CN | 102127078 A | 7/2011 |
| CN | 103748095 A | 4/2014 |
| CN | 106061973 A | 10/2016 |
| CN | 108570048 A | 9/2018 |
| EP | 2 924 026 A1 | 9/2015 |
| JP | 2006-525998 A | 11/2006 |
| JP | 2009-501130 A | 1/2009 |
| JP | 2009-522206 A | 6/2009 |
| JP | 2016-539137 A | 12/2016 |
| JP | 2017-506656 A | 3/2017 |
| KR | 2008-0026654 A | 3/2008 |

(Continued)

OTHER PUBLICATIONS

Japan Patent Office, Notice of Reasons for Refusal issued in Japanese Patent Application No. 2021-555325 (Sep. 28, 2022).

(Continued)

*Primary Examiner* — Sarah Pihonak
*Assistant Examiner* — Padmaja S Rao
(74) *Attorney, Agent, or Firm* — Leydig, Voit & Mayer, Ltd.

(57) ABSTRACT

Related are a JAK kinase inhibitor, a preparation method for same, and applications thereof in the field of medicine, related to the field of medicinal chemistry. Provided is a novel small molecule JAK inhibitor, which has the structure as represented by formula (II). The compound provides improved efficacy and safeness in preventing or treating a JAK-related indication.

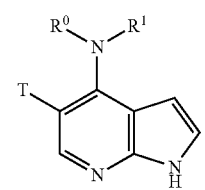

20 Claims, No Drawings

(56) References Cited

FOREIGN PATENT DOCUMENTS

| | | | |
|---|---|---|---|
| KR | 101930603 B1 | 12/2018 | |
| WO | WO-2007007919 A2 * | 1/2007 | ......... A61K 31/4745 |
| WO | WO 2008/084861 A1 | 7/2008 | |
| WO | WO 2015/083028 A1 | 6/2015 | |

OTHER PUBLICATIONS

Chinese Patent Office, International Search Report in International Patent Application No. PCT/JP2020/078826 (Jun. 2, 2020).
European Patent Office, Extended European Search Report in European Patent Application No. 20769246.8 (Mar. 10, 2022).
Korean Intellectual Property Office, Request for Submission of an Opinion (first office action) in Korean Patent Application No. 10-2021-7031742 (Nov. 10, 2023).
State Intellectual Property Office, Office Action issued in Chinese Patent Application No. 202080015759.0 (Mar. 3, 2023).

* cited by examiner

JAK KINASE INHIBITOR, PREPARATION METHOD FOR SAME, AND APPLICATIONS THEREOF IN FIELD OF MEDICINE

The present application claims the priority of the Chinese Patent Application No. 201910193017.6, with the title of "JAK KINASE INHIBITOR, PREPARATION METHOD FOR SAME, AND APPLICATIONS THEREOF IN FIELD OF MEDICINE", filed on Mar. 14, 2019 before the China National Intellectual Property Administration, which is hereby incorporated by reference in its entirety.

FIELD OF THE INVENTION

The present application belongs to the field of medicinal chemistry, and relates to a JAK kinase inhibitor, a preparation method for same, and applications thereof in preventing and treating Janus kinase (JAK)-related diseases comprising inflammatory disease, autoimmune disease and the like.

BACKGROUND OF THE INVENTION

Protein kinases is a kind of enzyme catalyzing a protein phosphorylation reaction, which can transfer a γ-phosphoric acid on adenosine triphosphate (ATP) to an amino acid residue of protein, such as serine, threonine, tyrosine, histidine and other residues, thereby modifying a conformation and activity of a protein. The protein phosphorylation is an important step in a variety of signal transduction pathways, and protein phosphorylation is indispensable for most of important life processes in cells. Protein kinase is mainly responsible for controlling the processes of signal transduction in cells, including regulating a variety of important biological processes, such as cell growth, survival and differentiation, organofaction and morphogenesis, neovascularization, repair and remodeling of tissues. Many diseases are related to abnormal responses in cells caused by abnormal regulations of protein kinase.

Janus kinase (JAK) is a non-receptor tyrosine kinase in cells. Four members of human JAK family are JAK1, JAK2, JAK3 and non-receptor tyrosine kinase 2 (TYK2). JAK1, JAK2 and TYK2 are widely distributed, while JAK3 is only distributed in bone marrow and lymphatic system. The molecular weight of JAK family member is about 120-140 kDa, consisting of more than 1,000 amino acid residues (Leonard, W., O'Shea, J. J., *JAKS and STATS: Biological implications. Annu. Rev. Immunol.* 1998, 16, 293-322). These members have 7 JAK homology (JH) domains, wherein JH1 domain close to C-terminal is kinase domain, containing certain tyrosine required for JAK activation. After the phosphorylation of these tyrosine, the protein conformation of JAK is modified, thus helpful to combine with downstream substrate; JH2 domain is a "false" kinase domain, regulating the activity of JH1; JH4-JH7 consist of a four-in-one domain, regulating a combination of JAK with cytokine receptors (Kisseleva, T., Bhattacharya, S., Braunstein, J., Schindler, C. W. *Signaling through the JAK/STAT pathway, recent advances and future challenges. Gene.* 2002, 285 (1-2), 1-24).

Signal transducer and activator of transcription (STAT) is a set of cytoplasmic protein capable of binding to the DNA of regulatory region of target gene and is a downstream substrate of JAK. STAT family includes 7 members, STAT1, STAT2, STAT3, STAT4, STAT5a, STAT5b and STAT6. Interaction between JAK and STAT plays an important role in signal pathway of cytokine receptor (O'Sullivan, L. A., Liongue, C., Lewis, R. S., Stephenson, S. E. M., Ward, A. C. *Cytokine receptor signaling through the Jak Stat pathway in disease. Mol. Immunol,* 2007, 44 {10}: 2497-2506). After the cytokine binds to a specific receptor on its target cell, a subunit of the receptor dimerizes or polymerizes, and JAK binding to each subunit is phosphorylated due to being close to each other. A tyrosine residue of the receptor is phosphorylated under catalysis of activated JAK, forming a "docking site" between corresponding STAT and receptor complex. STAT binds to a phosphotyrosine residue of the receptor molecule by SH2 domain, and then achieves phosphorylation of C-terminal tyrosine residue by JAK. Phosphorylated STAT interacts to form a homo-/heterodimer in nucleus, binding to promoter region of corresponding gene, thereby regulating gene transcription and expression. JAK-STAT pathways may interact with other signal transduction pathways and participate in the development, differentiation, maturation, apoptosis and functional expression of various immune and hematopoietic cells, thus significantly influence the regulation of immune response, immune cell differentiation and development, and inflammatory response. The regulation of many abnormal immune responses, for example, autoimmune diseases such as allergy, asthma, allograft rejection, rheumatoid arthritis, amyotrophic lateral sclerosis and multiple sclerosis, hematological malignant tumor such as myelodysplastic syndrome, leukemia and lymphoma is related to JAK/STAT pathways.

JAK is an important drug target. Some researches have been made regarding JAK inhibitor (e.g., Norman, P. *Selective JAK inhibitors in development for rheumatoid arthritis. Expert Opin. Investig. Drugs,* 2014, 23, 1067-1077), in which JAK inhibitor can be used in treatment of diseases such as rheumatoid arthritis, polycythemia vera, psoriasis, primary thrombocythemia and myelofibrosis. For example, Ruxolitinib is a selective inhibitor of JAK1 and JAK2, which was approved by FDA in 2011 and can be used in treating myelofibrosis; Baricitinib is also a selective inhibitor of JAK1 and JAK2 (see CN102026999), which has been approved by EMA in European and Ministry of Health, Labour and Welfare in Japan in treating moderate to severe rheumatoid arthritis, but it is rejected by FDA temporarily; JAK1 selective inhibitor Filgotinib (see CN102482273) and Upadactinib (ABT-494, see CN104370909) specific to multiple indications like rheumatoid arthritis are undergoing clinical Phase III trials; Tofacitinib is the only one selective inhibitor of JAK1 and JAK3 approved by FDA for treating rheumatoid arthritis (Kremer, J. M. etc, "*The safety and efficacy of a JAK inhibitor inpatients with active rheumatoid arthritis: Results of a double-blind, placebo-controlled phase IIa trial of three dosage levels of CP-*690, 550 versus placebo. Arthritis & Rheumatology, 2009, 60(7), 1895-1905). However, patients may suffer from some adverse reactions after taking Tofacitinib, for example, possible severe infection and increased risks of cancers and cardiac failure (FDA sets serious infection and malignant tumor as boxed warning).

In addition to the above several JAK inhibitors, currently related patent documents including WO2008109943, WO2011112662, WO2013091539, WO2014128591 and WO2016027195 also disclose JAK inhibitors.

Though a series of JAK inhibitors have been disclosed currently, these JAK inhibitors already on the market or in the research stage can be still improved in efficacy and safety, and it is necessary to develop novel JAK inhibitors with better effect and safety to provide a better curative effect and to reduce adverse reaction of the patients.

SUMMARY OF THE INVENTION

The present application relates to a novel small molecule JAK inhibitor and provides a compound as represented by formula (II), or tautomers, mesomers, racemes, enantiomers, diastereoisomers and mixtures thereof, and pharmaceutically acceptable salts, polymorphs, solvates, prodrugs, metabolites, isotope derivatives and pharmaceutical compositions comprising the compound, which can be used for preventing or treating JAK-related indication,

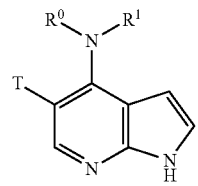

(II)

wherein, T is —CN or —CF$_3$;

R$^0$ is hydrogen, halogen, hydroxyl, C$_{1-6}$ alkyl, C$_{2-6}$ alkenyl or C$_{2-6}$ alkynyl; R$^0$ is further preferably —H or —C$_{1-3}$ alkyl;

R$^1$ is C$_{3-6}$ cycloalkyl, C$_{3-7}$ heterocycloalkyl, C$_{6-10}$ aryl, C$_{1-9}$ heteroaryl, C$_{6-12}$ fused bicyclic group or C$_{5-12}$ fused heterobicyclic group; wherein heteroatoms of the C$_{3-7}$ heterocycloalkyl, C$_{1-9}$ heteroaryl or C$_{5-12}$ fused heterobicyclic group can be substituted by R$^2$, and hydrogen atoms of C$_{3-6}$ cycloalkyl, C$_{3-7}$ heterocycloalkyl, C$_{6-10}$ aryl, C$_{1-9}$ heteroaryl, C$_{6-12}$ fused bicyclic group or C$_{5-12}$ fused heterobicyclic group can be substituted by R$^3$ or —NHR$^2$, and hydrogen atoms of rings having aromaticity can be substituted by R$^7$; R$^1$ is further preferably

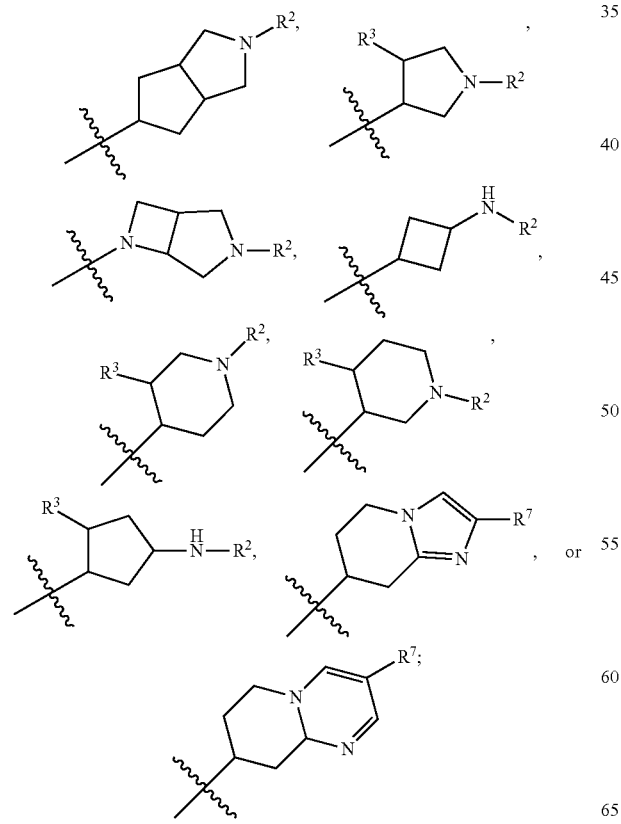

R$^2$ is —C(O)R$^4$, —C(O)OR$^4$, —C(O)NR$^5$R$^6$, —S(O)R$^4$, —S(O)$_2$R$^4$, —S(O)NR$^5$R$^6$ or —S(O)$_2$NR$^5$R$^6$; R$^2$ is further preferably —C(O)R$^4$, —S(O)$_2$R$^4$ or —C(O)NR$^5$R$^6$;

R$^3$ is —H, —C$_{1-4}$ alkyl, C$_{2-6}$ alkenyl, C$_{2-6}$ alkynyl, —C$_{3-6}$ cycloalkyl or C$_{3-7}$ heterocycloalkyl, wherein the —C$_{1-4}$ alkyl, C$_{2-6}$ alkenyl, C$_{2-6}$ alkynyl, —C$_{3-6}$ cycloalkyl and C$_{3-7}$ heterocycloalkyl can be substituted by the following groups: —OH, —C$_{1-3}$ alkyl, —O—C$_{1-4}$ alkyl, —NH$_2$, halogen, phenyl or cyano; R$^3$ is further preferably H or —C$_{1-4}$ alkyl or —C$_{3-6}$ cycloalkyl, wherein the —C$_{1-4}$ alkyl can be substituted by the following groups: —OH, —C$_{1-3}$ alkyl, —O—C$_{1-4}$ alkyl, —NH$_2$, halogen, phenyl or cyano; R$^3$ is further preferably H, —C$_{1-4}$ alkyl or —C$_{3-6}$ cycloalkyl; R$^3$ is specifically H, —CH$_2$, —CH$_2$CH$_3$, or

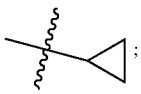

R$^4$ is —C$_{1-5}$ alkyl, —C$_{2-4}$ alkenyl, —C$_{2-5}$ alkynyl, —C$_{3-6}$ cycloalkyl, 4- to 6-membered heterocyclyl, 5- to 10-membered heteroaryl, phenyl, -heterocyclyl-O—R$^e$, -heterocyclyl-NH—R$^e$-heterocyclyl-R$^{4a}$—O—R$^e$ or -heterocyclyl-R$^{4a}$—NH—R$^e$, wherein the —C$_{1-5}$ alkyl can be substituted by the following groups: —OH, —C$_{1-3}$ alkyl, —C$_{5-6}$ cycloalkyl, 4- to 6-membered heterocyclyl, 5- to 10-membered heteroaryl, —O—C$_{1-4}$ alkyl, —NH$_2$, halogen, CF$_3$, phenyl or cyano; R$^4$ is further preferably —C$_{1-5}$ alkyl, —C$_{2-4}$ alkenyl, —C$_{2-5}$ alkynyl, —C$_{3-6}$ cycloalkyl, 4- to 6-membered heterocyclyl, 5- to 10-membered heteroaryl, phenyl, -heterocyclyl-O—R$^e$, -heterocyclyl-NH—R$^e$-heterocyclyl-R$^{4a}$—O—R$^e$, -heterocyclyl-R$^{4a}$—NH—R$^e$, wherein the —C$_{1-5}$ alkyl can be substituted by the following groups: —OH, —C$_{1-3}$ alkyl, —O—C$_{1-4}$ alkyl, —NH$_2$, halogen, CF$_3$, phenyl or cyano; R$^4$ is specifically methyl, ethyl, propyl, —(CH$_2$)$_n$—CH$_2$CN, —(CH$_2$)$_n$—CH$_2$CF$_3$, —CH(OH)—(CH$_2$)$_n$CH$_3$,

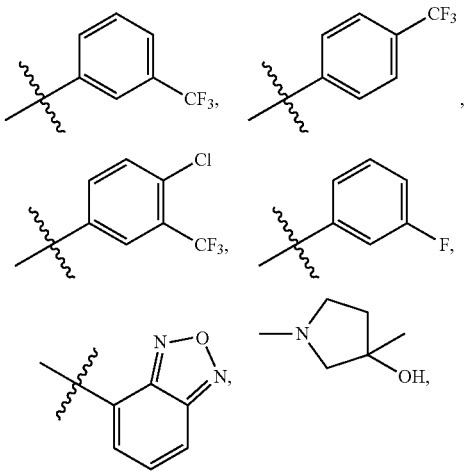

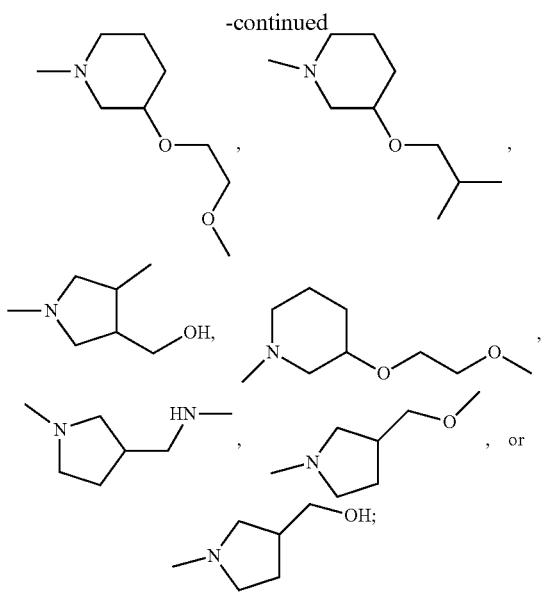

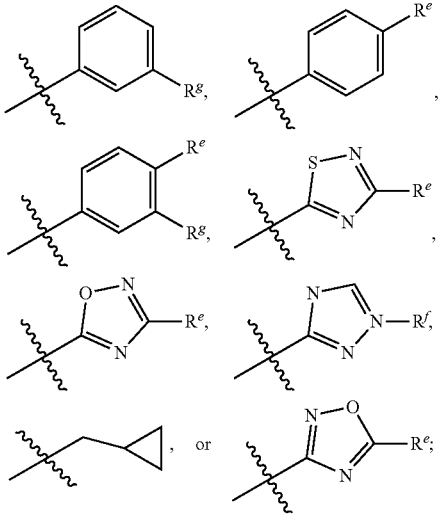

R$^{4a}$ is —C$_{1-3}$ alkylene; wherein the cycloalkyl, heterocyclyl, heteroaryl or phenyl of R$^4$ can be substituted by R$^e$;

R$^5$ is hydrogen, halogen, hydroxy or C$_{1-6}$ alkyl; R$^5$ is further preferably H or —C$_{1-3}$ alkyl; R$^5$ is specifically H;

R$^6$ is —C$_{1-4}$ alkyl, —C$_{2-4}$ alkenyl, —C$_{2-4}$ alkynyl, —C$_{3-6}$ cycloalkyl, 4- to 6-membered heterocyclyl, phenyl, —CHF$_2$ or —CH$_2$CF$_2$CF$_3$, wherein the —C$_{1-4}$ alkyl can be substituted by the following groups: —OH, —C$_{1-3}$ alkyl, —C$_{3-6}$ cycloalkyl, 4- to 6-membered heterocyclyl, 5- to 10-membered heteroaryl, —O—C$_{1-4}$ alkyl, —NH$_2$, halogen, CF$_3$, phenyl or cyano group, wherein phenyl can be substituted by R$^e$ or R$^g$ or R$^e$ and R$^g$, hydrogen atoms and heteroatoms of 4- to 6-membered heterocyclyl can be substituted by R$^e$ and R$^f$, respectively; R$^6$ is further preferably —C$_{1-4}$ alkyl, —C$_{3-6}$ cycloalkyl, 4- to 6-membered heterocyclyl, phenyl and 4- to 6-membered heterocyclyl, or

wherein the phenyl can be substituted by R$^e$ or R$^g$ or R$^e$ and R$^g$, hydrogen atoms and heteroatoms of 4- to 6-membered heterocyclyl can be substituted by R$^e$ and R$^f$, respectively; —C$_{1-4}$ alkyl can be substituted by the following groups: —OH, —C$_{1-3}$ alkyl, —C$_{3-6}$ cycloalkyl, 4- to 6-membered heterocyclyl, 5- to 10-membered heteroaryl, —O—C$_{1-4}$ alkyl, —NH$_2$, halogen, CF$_3$, phenyl or cyano; R$^6$ is further preferably —(CH$_2$)$_n$—CH$_2$CF$_3$, —(CH$_2$)$_n$—CF$_2$CF$_3$, —(CH$_2$)$_n$—CH$_2$CN, 4- to 6-membered heterocyclyl, phenyl, or

wherein the phenyl can be substituted by R$^e$ or R$^g$ or R$^e$ and R$^g$, hydrogen atoms and heteroatoms of 4- to 6-membered heterocyclyl can be substituted by R$^e$ and R$^f$, respectively; R$^6$ is further preferably —(CH$_2$)$_n$—CH$_2$CF$_3$, —(CH$_2$)$_n$—CF$_2$CF$_3$, —(CH$_2$)$_n$—CH$_2$CN, R$^e$ and R$^g$ are each independently halogen, C$_{1-4}$ alkyl, alkoxy, 3- to 6-membered cycloalkyl, —NR$^c$R$^d$, —(CH$_2$)$_n$—NR$^c$R$^d$, —(CH$_2$)$_n$—OH, —(CH$_2$)$_n$—CF$_3$, —(CH$_2$)$_n$—CN or C(O)OCH$_3$, wherein the —C$_{1-4}$ alkyl, alkoxy and cycloalkyl can be monosubstituted or disubstituted by the following substituents: halogen, —OH, —NH$_2$, —C$_{1-3}$ alkyl, —O—C$_{1-4}$ alkyl, CF$_3$, phenyl or cyano; R$^e$ and R$^g$ can specifically be —F, —Cl, methyl, ethyl, propyl, —CH(CH$_3$)—(CH$_2$)$_n$CH$_3$, —CH$_2$CH(CH$_3$)$_2$, —CH(CH$_3$)CH(CH$_3$)$_2$, —CH$_2$C(CH$_3$)$_3$, —C(CH$_3$)$_2$—(CH$_2$)$_n$CH$_3$, —O—(CH$_2$)$_n$CH$_3$, —O—(CH$_2$)$_n$CH$_2$—O—CH$_3$, —(CH$_2$)$_n$OCH$_3$, —O—(CH$_2$)$_n$—CH$_2$—C(CH$_3$)$_2$—OH, —O—(CH$_2$)$_n$—CH$_2$—C(CH$_3$)$_2$—NH$_2$, 3- to 6-membered cycloalkyl, —(CH$_2$)$_n$NR$^c$R$^d$, —(CH$_2$)$_n$—OH, —(CH$_2$)$_n$—CF$_3$, —(CH$_2$)$_n$—CHF$_2$, —(CH$_2$)$_n$—CN or —C(O)—O—CH$_3$;

R$^f$ is —C$_{1-4}$ alkyl or 3- to 6-membered cycloalkyl, wherein the —C$_{1-4}$ alkyl and cycloalkyl can be substituted by the following substituents: halogen, —OH, —NH$_2$, —C$_{1-3}$ alkyl, —O—C$_{1-4}$ alkyl, CF$_3$, phenyl or cyano; R is further preferably —C$_{1-4}$ alkyl, wherein the —C$_{1-4}$ alkyl can be substituted by the following substituents: halogen, —OH; R can specifically be methyl, ethyl or propyl;

R$^c$ and R$^d$ are each independently hydrogen, —C$_{1-3}$ alkyl, —C$_{1-4}$ alkylene-OH, —C$_{1-4}$ alkylene-CF$_3$, —C$_{2-4}$ alkylene-OCH$_3$, 3- to 6-membered cycloalkyl, or 4- to 6-membered heterocyclyl; R$^c$ and R$^d$ are further preferably hydrogen, —C$_{1-3}$ alkyl, —C$_{1-4}$ alkylene-OH, —C$_{2-4}$ alkylene-OCF$_3$; R$^c$ and R$^d$ can specifically be —H, methyl, ethyl or propyl;

R$^7$ is halogen, —C$_{1-4}$ alkyl, alkoxy, 3- to 6-membered cycloalkyl, —NR$^c$R$^d$, —(CH$_2$)$_n$—NR$^c$R$^d$, —(CH$_2$)$_n$—OH, —(CH$_2$)$_n$—CF$_3$, —(CH$_2$)$_n$—CN or C(O)OCH$_3$, wherein the —C$_{1-4}$ alkyl, alkoxy and cycloalkyl can be monosubstituted or disubstituted by the following substituents: halogen, —OH, —NH$_2$, —C$_{1-3}$ alkyl, —O—C$_{1-4}$ alkyl, CF$_3$, phenyl or cyano; R$^7$ is further preferably halogen, C$_{1-4}$ alkyl, alkoxy, —(CH$_2$)$_n$—OH, —(CH$_2$)$_n$—CF$_3$, or —(CH$_2$)$_n$—CN; R$^7$ is further preferably —(CH$_2$)$_n$—OH, —(CH$_2$)$_n$—CF$_3$, or —(CH$_2$)$_n$—CN; and n is 0, 1, 2, 3 or 4.

The present application provides a method for preparing a compound represented by formula (II). The compound represented by formula (II) is prepared by the following schemes:

Scheme 1

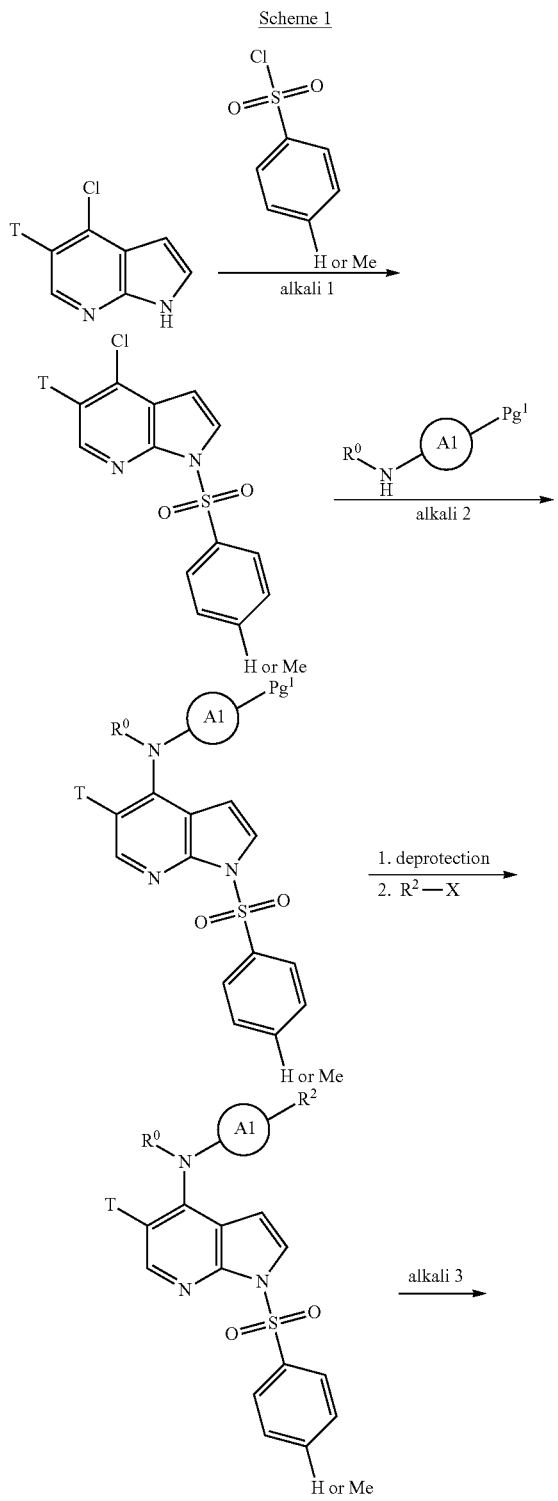

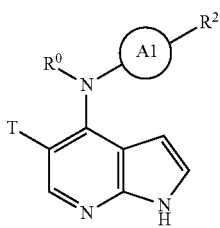

Scheme 2

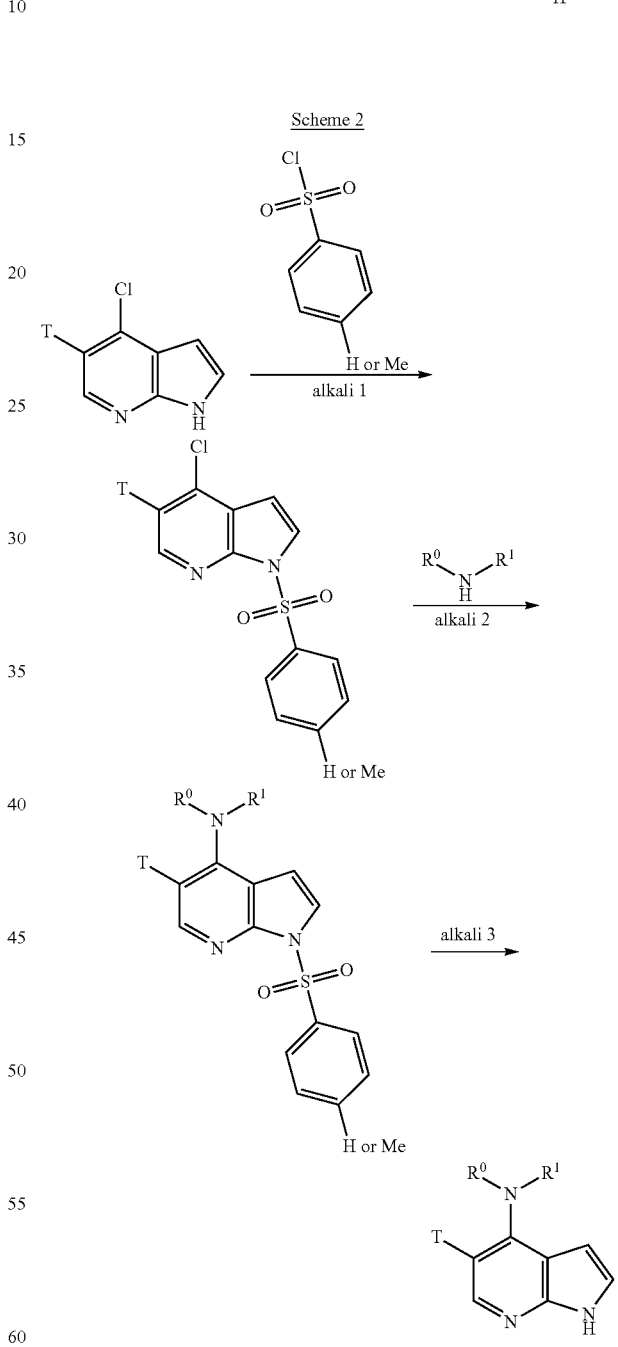

wherein, Pg$^1$ is an aliphatic amine protecting group, specifically tert-butoxycarbonyl or benzyloxycarbonyl, and A1 is

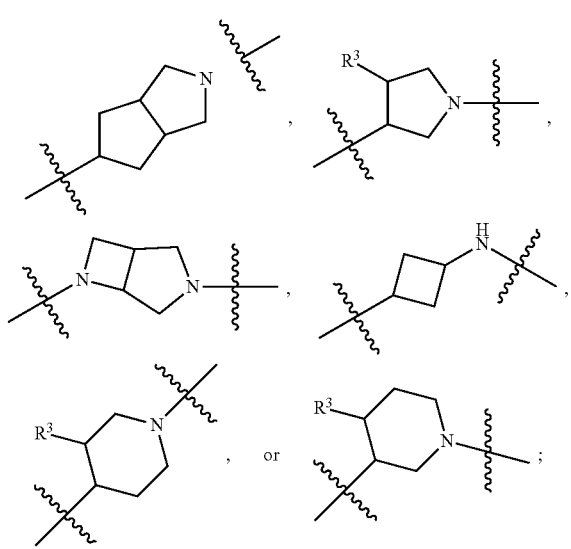

R²—X is an active form of R², and X is preferably selected from the group consisting of chloride, bromine, phenoxyl and p-nitro phenoxy, or R²—X is isocyanate form of R²; alkali 1, alkali 2 and alkali 3 are each independently selected from the group consisting of triethylamine, diisopropyl ethylamine, potassium carbonate, cesium carbonate, sodium carbonate, sodium hydroxide and potassium hydroxide.

According to the compound represented by formula (II) of the present invention and medicinal salt thereof, the compound is specifically:

(cis)-4-({4-ethyl-1-[(2,2,2-trifluoroethyl)carbamoyl)]pyrrolidin-3-yl}amino)-1H-pyrrolo[2,3-b]pyridin-5-carbonitrile;

(cis)-4-({4-ethyl-1-[(2,2,2-trifluoroethyl)carbamoyl)]pyrrolidin-3-yl}-methyl-amino)-1H-pyrrolo[2,3-b]pyridin-5-carbonitrile;

(cis)-4-{[4-ethyl-1-(3,3,3-trifluoropropionyl)pyrrolidin-3-yl]-methyl-amino}-1H-pyrrolo[2,3-b]pyridin-5-carbonitrile;

(cis)-4-({4-methyl-1-[(2,2,2-trifluoroethyl)carbamoyl)]pyrrolidin-3-yl}-methyl-amino)-1H-pyrrolo[2,3-b]pyridin-5-carbonitrile;

(cis)-4-{[4-methyl-1-(2-cyanoacetyl)pyrrolidin-3-yl]-methyl-amino}-1H-pyrrolo[2,3-b]pyridin-5-carbonitrile;

(3aR,5R,6aS)-4-{[2-((2S)-2-hydroxypropionyl)-hexahydrocyclopenta[c]pyrrole-5-yl]-methyl-amino}-1H-pyrrolo[2,3-b]pyridin-5-carbonitrile;

(3aR,5s,6aS)-4-({2-[(3-methoxy-1,2,4-thiadiazole-5-yl)-carbamoyl]-hexahydrocyclopenta[c]pyrrole-5-yl}-methyl-amino)-1H-pyrrolo[2,3-b]pyridin-5-carbonitrile;

(3aR,5s,6aS)-4-({2-[(3-ethyl-1,2,4-thiadiazole-5-yl)-carbamoyl]-hexahydrocyclopenta[c]pyrrole-5-yl}-methyl-amino)-1H-pyrrolo[2,3-b]pyridin-5-carbonitrile;

4-{[3-(3-trifluoromethyl-benzenesulfonamido)-cyclobutyl-1-yl]-methyl-amino}-1H-pyrrolo[2,3-b]pyridin-5-carbonitrile;

4-{[3-(3,3,3-trifluoro-propanesulfonamido)-cyclobutyl-1-yl]-methyl-amino}-1H-pyrrolo[2,3-b]pyridin-5-carbonitrile;

4-{[(3R,4R)-1-(2-cyanoacetyl)-4-methylpiperidin-3-yl]-methyl-amino}-1H-pyrrolo[2,3-b]pyridin-5-carbonitrile;

(cis)-4-{[3-(3,3,3-trifluoro-propanesulfonamido)-cyclobutyl-1-yl]-amino}-1H-pyrrolo[2,3-b]pyridin-5-carbonitrile;

(cis)-4-{[3-(3-trifluoromethyl-benzenesulfonamido)-cyclobutyl-1-yl]-amino}-1H-pyrrolo[2,3-b]pyridin-5-carbonitrile;

(cis)-4-{[3-(propanesulfonamido)-cyclobutyl-1-yl]-methyl-amino}-1H-pyrrolo[2,3-b]pyridin-5-carbonitrile;

(cis)-4-{[3-(3,3,3-trifluoro-propanesulfonamido)-cyclobutyl-1-yl]-methyl-amino}-1H-pyrrolo[2,3-b]pyridin-5-carbonitrile;

(cis)-4-{[3-(4-trifluoromethyl-benzenesulfonamido)-cyclobutyl-1-yl]-methyl-amino}-1H-pyrrolo[2,3-b]pyridin-5-carbonitrile;

(cis)-4-{[3-(4-trifluoromethyl-benzenesulfonamido)-cyclobutyl-1-yl]-amino}-1H-pyrrolo[2,3-b]pyridin-5-carbonitrile;

(cis)-4-{[3-(benzo[c][1,2,5]oxadiazole-4-sulfonamido)-cyclobutyl-1-yl]-methyl-amino}-1H-pyrrolo[2,3-b]pyridin-5-carbonitrile;

(cis)-4-{[3-(benzo[c][1,2,5]oxadiazole-4-sulfonamido)-cyclobutyl-1-yl]-amino}-1H-pyrrolo[2,3-b]pyridin-5-carbonitrile;

(3aR,5s,6aS)-5-((5-cyano-1H-pyrrolo[2,3-b]pyridin-4-yl)amino)-N-(3-methoxy-1,2,4-thiadiazole-5-yl)hexahydrocyclopentadiene[c]pyrrole-2(1H)-carboxamide;

(3aR,5s,6aS)-4-({2-[(3-tert-butyl-1,2,4-thiadiazole-5-yl)-carbamoyl]-hexahydrocyclopenta[c]pyrrole-5-yl}-methyl-amino)-1H-pyrrolo[2,3-b]pyridin-5-carbonitrile;

(3aR,5s,6aS)-4-({2-[(2,2,2-trifluoroethyl)-carbamoyl]-hexahydrocyclopenta[c]pyrrole-5-yl}-methyl-amino)-1H-pyrrolo[2,3-b]pyridin-5-carbonitrile;

(3aR,5S,6aS)-4-{[2-((2S)-2-hydroxypropionyl)-hexahydrocyclopenta[c]pyrrole-5-yl]-methyl-amino}-1H-pyrrolo[2,3-b]pyridin-5-carbonitrile;

4-(methyl((3aR,5s,6aS)-2-((3-(trifluoromethyl)phenyl)sulfonyl)octahydrocyclopentadiene[c]pyrrole-5-yl)amino-1H-pyrrolo[2,3-b]pyridin-5-carbonitrile;

(3aR,5s,6aS)-N-(4-chloro-3-(trifluoromethyl)phenyl)-5-((5-cyano-1H-pyrrolo[2,3-b]pyridin-4-yl)(methyl)amino)hexahydrocyclopentadiene[c]pyrrole-2(1H)-carboxamide;

(3aR,5s,6aS)-5-((5-cyano-1H-pyrrolo[2,3-b]pyridin-4-yl)(methyl)amino)-N-(3-cyclopropyl-1,2,4-thiadiazole-5-yl)hexahydrocyclopentadiene[c]pyrrole-2(1H)-carboxamide;

4-(methyl((3aR,5s,6aS)-2-((3,3,3-(trifluoropropyl)sulfonyl)octahydrocyclopentadiene[c]pyrrole-5-yl)amino-1H-pyrrolo[2,3-b]pyridin-5-carbonitrile;

4-(((3aR,5s,6aS)-2-((3-fluorophenyl)sulfonyl)octahydrocyclopentadiene[c]pyrrole-5-yl)methyl-amino)-1H-pyrrolo[2,3-b]pyridin-5-carbonitrile;

(cis)-1-(3-((5-cyano-1H-pyrrolo[2,3-b]pyridin-4-yl)(methyl)amino)cyclobutyl)-3-(3-methoxy-1,2,4-thiadiazole-5-yl)urea;

(3aR,5s,6aS)-4-({2-[(3-isopropyl-1,2,4-thiadiazole-5-yl)carbamoyl]-hexahydrocyclopenta[c]pyrrole-5-yl}-methyl-amino)-1H-pyrrolo[2,3-b]pyridin-5-carbonitrile;

(3aR,5s,6aS)-4-({2-[(1-ethyl-1H-1,2,4-triazole-3-yl)carbamoyl]-hexahydrocyclopenta[c]pyrrole-5-yl}-methyl-amino)-1H-pyrrolo[2,3-b]pyridin-5-carbonitrile;

(3aR,5s,6aS)-4-({2-[(3-cyclopropyl-1,2,4-oxadiazole-5-yl)-carbamoyl]-hexahydrocyclopenta[c]pyrrole-5-yl}-methyl-amino)-1H-pyrrolo[2,3-b]pyridin-5-carbonitrile;

(3aR,5s,6aS)-4-({2-[(3-dimethylamino-1,2,4-thiadiazole-5-yl)-carbamoyl]-hexahydrocyclopenta[c]pyrrole-5-yl}-methyl-amino)-1H-pyrrolo[2,3-b]pyridin-5-carbonitrile;

4-((1-((3-(trifluoromethyl)phenyl)sulfonyl)piperidin-4-yl)amino)-2,3-dihydro-1H-pyrrolo[2,3-b]pyridin-5-carbonitrile;

4-((1-((3-(trifluoromethyl)phenyl)sulfonyl)piperidin-4-yl)-
methyl-amino)-2,3-dihydro-1H-pyrrolo[2,3-b]pyridin-5-
carbonitrile;
3-((5-cyano-1H-pyrrolo[2,3-b]pyridin-4-yl)amino)-N-(2,2,
2-trifluoroethyl)pyrrolidin-1-carboxamide;
3-((5-cyano-1H-pyrrolo[2,3-b]pyridin-4-yl)-methyl-
amino)-N-(2,2,2-trifluoroethyl)pyrrolidin-1-carboxam-
ide;
(3aR,5s,6aS)-5-((5-cyano-1H-pyrrolo[2,3-b]pyridin-4-yl)
(methyl)amino)-N-(3-hydroxy-1,2,4-thiadiazol-5-yl)
hexahydrocyclopentadiene[c]pyrrole-2(1H)-carboxam-
ide;
6-(5-cyano-1H-pyrrolo[2,3-b]pyridin-4-yl)-N-(2,2,2-trif-
luoroethyl)-3,6-diazabicyclo[3.2.0]heptane-3-carboxam-
ide;
(3S,4S)-4-({4-methyl-1-[(2,2,2-trifluoroethyl)carbamoyl)]
pyrrolidin-3-yl}amino)-1H-pyrrolo[2,3-b]pyridin-5-car-
bonitrile;
(3aR,5s,6aS)-5-((5-cyano-1H-pyrrolo[2,3-b]pyridin-4-yl)
(methyl)amino)-N-(3-(methyl-amino)-1,2,4-thiadiazole-
5-yl)hexahydrocyclopentadiene[c]pyrrole-2(1H)-carbox-
amide;
(3aR,5s,6aS)-5-((5-cyano-1H-pyrrolo[2,3-b]pyridin-4-yl)
(methyl)amino)-N-(3-hydroxymethyl-1,2,4-thiadiazole-
5-yl)hexahydrocyclopentadiene[c]pyrrole-2(1H)-carbox-
amide;
(3aR,5s,6aS)-5-((5-cyano-1H-pyrrolo[2,3-b]pyridin-4-yl)
(methyl)amino)-N-(3-methoxy-1,2,4-oxadiazol-5-yl)
hexahydrocyclopentadiene[c]pyrrole-2(1H)-carboxam-
ide;
(3aR,5s,6aS)-5-((5-cyano-1H-pyrrolo[2,3-b]pyridin-4-yl)
(methyl)amino)-N-(3-(2-hydroxy-2-methyl-propoxy)-1,
2,4-thiadiazol-5-yl)hexahydrocyclopentadiene[c]pyr-
role-2(1H)-carboxamide;
(3aR,5s,6aS)-5-((5-cyano-1H-pyrrolo[2,3-b]pyridin-4-yl)
(methyl)amino)-N-(3-(2-amino-2-methyl-propoxy)-1,2,
4-thiadiazol-5-yl)hexahydrocyclopentadiene[c]pyrrole-
2(1H)-carboxamide;
(cis)-4-{[3-(propanesulfonamido)-cyclobutyl-1-yl]-amino}-
1H-pyrrolo[2,3-b]pyridin-5-carbonitrile;
(3aR,5s,6aS)-5-((5-cyano-1H-pyrrolo[2,3-b]pyridin-4-yl)
(methyl)amino)-N-(3-ethoxy-1,2,4-oxadiazol-5-yl)
hexahydrocyclopentadiene[c]pyrrole-2(1H)-carboxam-
ide;
(3aR,5s,6aS)-5-((5-cyano-1H-pyrrolo[2,3-b]pyridin-4-yl)
(methyl)amino)-N-(5-ethoxy-1,2,4-oxadiazol-3-yl)
hexahydrocyclopentadiene[c]pyrrole-2(1H)-carboxam-
ide;
(3aR,5s,6aS)-5-((5-cyano-1H-pyrrolo[2,3-b]pyridin-4-yl)
amino)-N-(3-cyclopropyl-1,2,4-thiadiazol-5-yl)hexahy-
drocyclopentadiene[c]pyrrole-2(1H)-carboxamide;
(3aR,5s,6aS)-5-((5-trifluoromethyl-1H-pyrrolo[2,3-b]pyri-
din-4-yl)amino)-N-(3-methoxy-1,2,4-thiadiazol-5-yl)
hexahydrocyclopentadiene[c]pyrrole-2(1H)-carboxam-
ide;
(3aR,5s,6aS)-5-((5-cyano-1H-pyrrolo[2,3-b]pyridin-4-yl)
(methyl)amino)-N-(3-(2-methoxyethoxy)-1,2,4-thiadiaz-
ole-5-yl)hexahydrocyclopenta[c]pyrrole-2(1H)-carbox-
amide;
(3aR,5s,6aS)-5-((5-cyano-1H-pyrrolo[2,3-b]pyridin-4-yl)
amino)-N-(3-(2-methoxyethoxy)-1,2,4-thiadiazol-5-yl)
hexahydrocyclopenta[c]pyrrole-2(1H)-carboxamide;
methyl 5-((3aR,5s,6aS)-5-((5-cyano-1H-pyrrole[2,3-b]pyri-
din-4-yl)(methyl)amino)octahydrocyclopenta[c]pyrrole-
2-formamido)-1,2,4-thiadiazole-3-carboxylate;
(3aR,5s,6aS)-5-((5-cyano-1H-pyrrole[2,3-b]pyridin-4-yl)
(methyl)amino)-N-(3-((dimethylamino)methyl)-1,2,4-
thiadiazole-5-yl)hexahydrocyclopenta[c]pyrrole-2(1H)-
carboxamide;
(3aR,5s,6aS)-5-((5-cyano-1H-pyrrole[2,3-b]pyridin-4-yl)
amino)-N-(3-((dimethylamino)methyl)-1,2,4-thiadiazole-
5-yl)hexahydrocyclopenta[c]pyrrole-2(1H)-carboxamide;
(3aR,5s,6aS)-5-((5-cyano-1H-pyrrole[2,3-b]pyridin-4-yl)
(methyl)amino)-N-(3-methoxymethyl)-1,2,4-thiadiazole-
5-yl)hexahydrocyclopenta[c]pyrrole-2(1H)-carboxamide;
(3aR,5s,6aS)-5-((5-cyano-1H-pyrrole[2,3-b]pyridin-4-yl)
amino)-N-(3-methoxymethyl)-1,2,4-thiadiazole-5-yl)
hexahydrocyclopenta[c]pyridin-2(1H)-carboxamide;
N-(3-((5-cyano-1H-pyrrolo[2,3-b]pyridin-4-yl)amino)-4-
ethylcyclopentyl)benzo[c][1,2,5]oxadiazole-4-sulfamide;
N-(3-((5-cyano-1H-pyrrolo[2,3-b]pyridin-4-yl)amino)-4-
ethylcyclopentyl)-4,4,4-trifluorobutanamide;
N-(3-((5-cyano-1H-pyrrolo[2,3-b]pyridin-4-yl)amino)-4-
ethylcyclopentyl)-3-(trifluoromethyl)benzsulfamide;
1-((3S,4R)-3-((5-cyano-1H-pyrrolo[2,3-b]pyridin-4-yl)
amino)-4-ethylcyclopentyl)-3-(3-methoxy-1,2,4-thiadiaz-
ole-5-yl)urea;
4-((4-((((3-hydroxy-3-methylpyrrolidin-1-yl)sulfonyl)
methyl)cyclohexyl)(methyl)amino)-1H-pyrrolo[2,3-b]
pyridin-5-carbonitrile;
trans-4-(methyl((1r,4r)-4-(((4-methylpiperazin-1-yl)sulfo-
nyl)methyl)cyclohexyl)amino)-1H-pyrrolo[2,3-b]pyri-
din-5-carbonitrile;
4-((trans-4-(((3-isobutoxypiperidin-1-yl)sulfonyl)methyl)
cyclohexyl)(methyl)amino)-1H-pyrrolo[2,3-b]pyridin-5-
acetonitrile;
4-((trans-4-(((trans-3-(hydroxymethyl)-4-methylpyrrolidin-
1-yl)sulfonyl)methyl)cyclohexyl)(methyl)amino)-1H-
pyrrolo[2,3-b]pyridin-5-carbonitrile;
4-(methyl-(trans-4-(((3-((methylamino)methyl)pyrrolidin-
1-yl)sulfonyl)methyl)cyclohexyl)amino)-1H-pyrrolo[2,3-
b]pyridin-5-carbonitrile;
4-((trans-4-(((3-(methoxymethyl)pyrrolidin-1-yl)sulfonyl)
methyl)cyclohexyl)(methyl)amino)-1H-pyrrolo[2,3-b]
pyridin-5-carbonitrile;
4-((cis-3-(((3-(2-methoxyethoxy)piperidin-1-yl)sulfonyl)
methyl)cyclopentyl)(methyl)amino)-1H-pyrrolo[2,3-b]
pyridin-5-carbonitrile;
4-((trans-3-(((3-((hydroxymethyl)pyrrolidin-1-yl)sulfonyl)
methyl)cyclopentyl)(methyl)amino)-1H-pyrrolo[2,3-b]
pyridin-5-carbonitrile;
(R)-7-((5-cyano-1H-pyrrolo[2,3-b]pyridin-4-yl)amino)-N-
(2,2,2-trifluoroethyl)-5-azaspiro[2.4]heptane-5-carbox-
amide;
(cis)-3-isopropyl-4-(imidazo[4,5-d]pyrrolo[2,3-b]pyridin-1
(6H)-yl)-N-(2,2,2-trifluoroethyl) pyrrolidin-1-carboxam-
ide;
(cis)-3-((5-cyano-1H-pyrrolo[2,3-b]pyridin-4-yl)amino)-4-
cyclopropyl-N-isobutylpyrrolidin-1-carboxamide;
(cis)-3-((5-cyano-1H-pyrrolo[2,3-b]pyridin-4-yl)amino)-4-
ethyl-N-isobutylpyrrolidin-1-carboxamide;
4-(((cis)-4-ethyl-1-((3,3,3-trifluoropropyl)sulfonyl)pyrroli-
din-3-yl)amino)-1H-pyrrolo[2,3-b]pyridin-5-carbonitrile;
4-(((cis)-4-ethyl-1-(4,4,4-trifluorobutyryl)pyrrolidin-3-yl)
amino)-1H-pyrrolo[2,3-b]pyridin-5-carbonitrile;
4-((4-ethyl-1-(2-cyanoacetyl)pyrrolidin-3-yl)amino)-1H-
pyrrolo[2,3-b]pyridin-5-carbonitrile;
(cis)-3-((5-cyano-1H-pyrrolo[2,3-b]pyridin-4-yl)amino)-4-
ethyl-N-isobutylpyrrolidin-1-carboxamide;
4-(((cis)-4-ethyl-1-(3-methoxy-1,2,4-thiadiazole-5-ami-
nocarbonyl)pyrrolidin-3-yl)amino)-1H-pyrrolo[2,3-b]
pyridin-5-carbonitrile;

4-(((cis)-1-(3-cyanopropionyl)-4-ethylpyrrolidin-3-yl) amino)-1H-pyrrolo[2,3-b]pyridin-5-carbonitrile;

3-((5-cyano-1H-pyrrolo[2,3-b]pyridin-4-yl)amino)-4-ethyl-N-(cyclopropylmethyl)pyrrolidin-1-carboxamide;

3-((5-cyano-1H-pyrrolo[2,3-b]pyridin-4-yl)amino)-4-ethyl-N-(2,2,3,3,3-pentafluoropropyl)-pyrrolidin-1-carboxamide;

(cis)-3-((5-cyano-1H-pyrrolo[2,3-b]pyridin-4-yl)amino)-N-cyclopropyl-4-ethylpyrrolidin-1-carboxamide;

(cis)-3-((5-cyano-1H-pyrrolo[2,3-b]pyridin-4-yl)amino)-4-ethyl-N-(3-methylbutane-2-yl)pyrrolidin-1-carboxamide;

(cis)-3-((5-cyano-1H-pyrrolo[2,3-b]pyridin-4-yl)amino)-4-ethyl-N-neopentyl-pyrrolidin-1-carboxamide;

3-((5-cyano-1H-pyrrolo[2,3-b]pyridin-4-yl)amino)-N-(2,2-difluoroethyl)-4-ethylpyrrolidin-1-carboxamide;

4-(((cis)-1-(2-cyanoethyl)-4-ethylpyrrolidin-3-yl)amino)-1H-pyrrolo[2,3-b]pyridin-5-carbonitrile;

(cis)-3-((5-cyano-1H-pyrrolo[2,3-b]pyridin-4-yl)amino)-N-(2,2-difluoropropyl)-4-ethylpyrrolidin-1-carboxamide;

7-((5-cyano-1H-pyrrolo[2,3-b]pyridin-4-yl)amino)-5,6,7,8-tetrahydroimidazo[1,2-a]pyridin-2-carbonitrile;

(cis)-3-cyclopropyl-N-(2,2,2-trifluoroethyl)-4-((5-(trifluoromethyl)-1H-pyrrolo[2,3-b]pyridin-4-yl)amino)pyrrolidin-1-carboxamide;

(cis)-3-ethyl-N-(2,2,2-trifluoroethyl)-4-((5-(trifluoromethyl)-1H-pyrrolo[2,3-b]pyridin-4-yl)amino)pyrrolidin-1-carboxamide;

(cis)-3-ethyl-N-(cyanomethyl)-4-((5-(trifluoromethyl)-1H-pyrrolo[2,3-b]pyridin-4-yl)amino) pyrrolidin-1-carboxamide.

The pharmaceutically acceptable salts of the compounds of the invention include acid addition salts and alkali addition salts thereof.

Suitable acid addition salts are formed by acids that form nontoxic salts. Examples include but not limit to hydrochloride, sulfate/bisulfate, nitrate, phosphate/hydrophosphate/dihydric phosphate, hydrobromide, hydriodate, acetate, lactate, mesylate, citrate, malate, maleate, fumarate, tartrate, salicylate, stearate and analogues thereof.

Suitable alkali addition salts are formed by alkalis that form nontoxic salts, for example alkali metal salts and alkaline earth metal salts, or ammonium salts. Examples include but not limit to sodium salts, potassium salts, calcium salts and magnesium salts, or salts with ammonia or organic amine such as ethylamine, ethanolamine, triethanolamine or amino acid.

A review of the suitable salts is provided in Stahl, P. H. and Wermuth, C. G., "Handbook of Pharmaceutical Salts: Properties, Selection, and Use, $2^{nd}$ Revised Edition" (Wiley-VCH, 2011).

If the compound of formula (II) contains both acidic group and basic group within its molecule, the invention also includes inner salt or betaine (zwitterion) in addition to the mentioned salt form.

Methods for preparing pharmaceutically acceptable salts of the compounds of the present invention are known to those skilled in the art, for example contacting these compounds with organic or inorganic acids or alkalis in an solvent or dispersant, or anion exchange or cation exchange with other salts.

The compound of formula (II) can be present in a crystal form or an amorphous form. Furthermore, some crystals forms of the compound of formula (II) can be a polymorphism form, which are included within the scope of the present invention. Many conventional analysis techniques including but not limited to single crystal X-Ray Powder diffraction (XRPD) pattern, infrared spectroscopy (IR), Raman spectrum, differential scanning calorimetry (DSC), thermogravimetric analysis (TGA) and solid nuclear magnetic resonance (ssNMR) characterization can be used to distinguish the polymorphism of the compound.

The compounds of the present invention also include a tautomeric form. The tautomeric form is resulted from a conversion of single bond and adjacent double bond with an accompanying migration of proton. The tautomeric form includes prototropic tautomerism, which is an isomeric protonation state having a same empirical formula and total charge. Examples of prototropic tautomerism include keto-enol paris, amide-imidic acid pairs, lactam-lactim pairs, enamine-imine pairs, and cyclic forms in which protons can occupy two or more positions in the heterocyclic system, such as 1H- and 3H-imidazole, 1H-, 2H- and 4H-1,2,4-triazole, 1H- and 2H-isoindole, and 1H- and 2H-pyrazol. Tautomeric forms may be in equilibrium or spatially fixed to one form by appropriate substitution.

The present invention also relates to the compound of formula (II) or its tautomer, mesomer, raceme, enantiomer, diastereoisomer and mixtures thereof, pharmaceutically acceptable salt thereof, or a pharmaceutical composition comprising the same, for use in preparing a medicament for inhibiting JAK kinase; the JAK kinase is preferably JAK1, JAK2 or JAK3.

The present invention also relates to the compound of formula (II) or its tautomers, mesomers, racemes, enantiomers, diastereoisomers and mixtures thereof, pharmaceutically acceptable salts thereof, or a pharmaceutical compositions comprising the same, for use in preparing a medicament for inhibiting JAK kinase, wherein the medicament optionally contains additional one or more agents, anticarcinogen or anti-inflammatory agents that regulate the immune systems of mammals.

The present invention also relates to the compound of formula (II) or its tautomers, mesomers, racemes, enantiomers, diastereoisomers and mixtures thereof, pharmaceutically acceptable salts thereof, or a pharmaceutical compositions comprising same, for use in preparing a medicament for inhibiting JAK kinase, wherein the medicament is used in treating or preventing the following disorders or diseases: immune system diseases, for example, organ-graft rejection (e.g., allograft rejection and graft-versus-host disease); autoimmune diseases, for example, lupus, multiple sclerosis, rheumatoid arthritis, juvenile arthritis, psoriasis, ulcerative colitis, Crohn's disease, autoimmune thyroid diseases; dermatosis, for example, psora, skin rash, atopic dermatitis; allergic diseases, for example, asthma, rhinitis; viral diseases, for example, hepatitis B, hepatitis C, varicella-zoster virus; type 1 diabetes and diabetic complication; alzheimer disease, xerophthalmia, myelofibrosis, thrombocytosis, polycythemia or leukemia; cancers, for example, solid tumor (e.g., prostate cancer, renal carcinoma, liver cancer, pancreatic cancer, gastric cancer, breast cancer, lung cancer, head-neck carcinoma, thyroid cancer, glioblastoma, melanoma), hematologic malignancy (e.g., lymphoma, leukemia), skin cancer (e.g., cutaneous T-cell lymphoma, cutaneous B-cell lymphoma).

The present invention also relates to the compound of formula (II) or its tautomers, mesomers, racemes, enantiomers, diastereoisomers and mixtures thereof, pharmaceutically acceptable salts thereof, or a pharmaceutical compositions comprising same, for use in preparing a medicament for inhibiting JAK kinase, wherein the medicament optionally includes additional one or more agents, anticarcinogen or anti-inflammatory agents that regulate immune systems of mammals, for treating or preventing the following disorders or diseases: immune system diseases, for example, organ-graft rejection (e.g., allograft rejection and graft-versus-host disease); autoimmune diseases, for example, lupus, multiple sclerosis, rheumatoid arthritis, juvenile arthritis, psoriasis, ulcerative colitis, Crohn's disease, autoimmune thyroid diseases; dermatosis, for example, psora, skin rash, atopic dermatitis; allergic diseases, for example, asthma, rhinitis; viral diseases, for example, hepatitis B, hepatitis C, varicella-zoster virus; type 1 diabetes and diabetic complication; alzheimer disease, xerophthalmia, myelofibrosis, thrombocytosis, polycythemia or leukemia; cancers, for example, solid tumor (e.g., prostate cancer, renal carcinoma, liver cancer, pancreatic cancer, gastric cancer, breast cancer, lung cancer, head-neck carcinoma, thyroid cancer, glioblastoma, melanoma), hematologic malignancy (e.g., lymphoma, leukemia), and skin cancer (e.g., cutaneous T-cell lymphoma, cutaneous B-cell lymphoma). The mammals are humans.

The present invention further relates to the compound of formula (II) or its tautomers, mesomers, racemes, enantiomers, diastereoisomers and mixtures thereof, pharmaceutically acceptable salts thereof, or a pharmaceutical compositions comprising the same, as a medicament for inhibiting JAK kinase. The JAK kinase is preferably JAK1, JAK2 or JAK3.

The present invention further relates to the compound of formula (II) or its tautomer, mesomer, raceme, enantiomer, diastereoisomer and mixtures thereof, pharmaceutically acceptable salt thereof, or a pharmaceutical composition comprising same, which is further used in combination with additional one or more agents, anticarcinogen or anti-inflammatory agents that regulate immune systems of mammals.

The present invention further relates to the compound of formula (II) or its tautomers, mesomers, racemes, enantiomers, diastereoisomers and mixtures thereof, pharmaceutically acceptable salts thereof, or a pharmaceutical compositions comprising the same, which is used in treating or preventing the following disorders or diseases: immune system diseases, for example, organ-graft rejection (e.g., allograft rejection and graft-versus-host disease); autoimmune diseases, for example, lupus, multiple sclerosis, rheumatoid arthritis, juvenile arthritis, psoriasis, ulcerative colitis, Crohn's disease, autoimmune thyroid diseases; dermatosis, for example, psora, skin rash, atopic dermatitis; allergic diseases, for example, asthma, rhinitis; viral diseases, for example, hepatitis B, hepatitis C, varicella-zoster virus; type 1 diabetes and diabetic complication; alzheimer disease, xerophthalmia, myelofibrosis, thrombocytosis, polycythemia or leukemia; cancers, for example, solid tumor (e.g., prostate cancer, renal carcinoma, liver cancer, pancreatic cancer, gastric cancer, breast cancer, lung cancer, head-neck carcinoma, thyroid cancer, glioblastoma, melanoma), hematologic malignancy (e.g., lymphoma, leukemia), skin cancer (e.g., cutaneous T-cell lymphoma, cutaneous B-cell lymphoma).

The present invention further relates to the compound of formula (II) or its tautomers, mesomers, racemes, enantiomers, diastereoisomers and mixtures thereof, pharmaceutically acceptable salts thereof, or a pharmaceutical compositions comprising the same, which is further used in combination with additional one or more agents, anticarcinogen or anti-inflammatory agents that regulate immune systems of mammals in treating or preventing following disorders or diseases: immune system diseases, for example, organ-graft rejection (e.g., allograft rejection and graft-versus-host disease); autoimmune diseases, for example, lupus, multiple sclerosis, rheumatoid arthritis, juvenile arthritis, psoriasis, ulcerative colitis, Crohn's disease, autoimmune thyroid diseases; dermatosis, for example, psora, skin rash, atopic dermatitis; allergic diseases, for example, asthma, rhinitis; viral diseases, for example, hepatitis B, hepatitis C, varicella-zoster virus; type 1 diabetes and diabetic complication; alzheimer disease, xerophthalmia, myelofibrosis, thrombocytosis, polycythemia or leukemia; cancers, for example, solid tumor (e.g., prostate cancer, renal carcinoma, liver cancer, pancreatic cancer, gastric cancer, breast cancer, lung cancer, head-neck carcinoma, thyroid cancer, glioblastoma, melanoma), hematologic malignancy (e.g., lymphoma, leukemia), and skin cancer (e.g., cutaneous T-cell lymphoma, cutaneous B-cell lymphoma).

In other words, the present invention relates to a method for inhibiting JAK kinase, comprising administering an effective amount of the compound of formula (II) or its tautomers, mesomers, racemes, enantiomers, diastereoisomers and mixtures thereof, pharmaceutically acceptable salts thereof, or a pharmaceutical compositions comprising the same to patients in need. Further, the compound of formula (II) or its tautomer, mesomer, raceme, enantiomer, diastereoisomer and mixtures thereof, pharmaceutically acceptable salt thereof, or a pharmaceutical composition comprising the same is used in combination with additional one or more agents, anticarcinogen or anti-inflammatory agents that regulate immune systems of mammals.

The present invention further relates to a method for treating or preventing immune system disorders or diseases, comprising administering an effective amount of the compound of formula (II) or its tautomers, mesomers, racemes, enantiomers, diastereoisomers and mixtures thereof, pharmaceutically acceptable salts thereof, or a pharmaceutical compositions comprising the same, to patients in need, wherein the immune system disorders or diseases are selected from the group consisting of: immune system diseases, for example, organ-graft rejection (e.g., allograft rejection and graft-versus-host disease); autoimmune diseases, for example, lupus, multiple sclerosis, rheumatoid arthritis, juvenile arthritis, psoriasis, ulcerative colitis, Crohn's disease, autoimmune thyroid diseases; dermatosis, for example, psora, skin rash, atopic dermatitis; allergic diseases, for example, asthma, rhinitis; viral diseases, for example, hepatitis B, hepatitis C, varicella-zoster virus; type 1 diabetes and diabetic complication; alzheimer disease, xerophthalmia, myelofibrosis, thrombocytosis, polycythemia or leukemia; cancers, for example, solid tumor (e.g., prostate cancer, renal carcinoma, liver cancer, pancreatic cancer, gastric cancer, breast cancer, lung cancer, head-neck carcinoma, thyroid cancer, glioblastoma, melanoma), hematologic malignancy (e.g., lymphoma, leukemia), skin cancer (e.g., cutaneous T-cell lymphoma, cutaneous B-cell lymphoma).

The present invention further relates to a method for treating or preventing immune system disorders or diseases, comprising administering an effective amount of the compound of formula (II) or its tautomers, mesomers, racemes, enantiomers, diastereoisomers and mixtures thereof, pharmaceutically acceptable salts thereof, or a pharmaceutical compositions comprising the same, and additional one or more agents, anticarcinogen or anti-inflammatory agents that regulate immune systems of mammals, to patients in need, wherein the immune system disorders or diseases are selected from the group consisting of: immune system diseases, for example, organ-graft rejection (e.g., allograft rejection and graft-versus-host disease); autoimmune diseases, for example, lupus, multiple sclerosis, rheumatoid arthritis, juvenile arthritis, psoriasis, ulcerative colitis, Crohn's disease, autoimmune thyroid diseases; dermatosis, for example, psora, skin rash, atopic dermatitis; allergic diseases, for example, asthma, rhinitis; viral diseases, for example, hepatitis B, hepatitis C, varicella-zoster virus; type 1 diabetes and diabetic complication; alzheimer disease, xerophthalmia, myelofibrosis, thrombocytosis, polycythemia or leukemia; cancers, for example, solid tumor (e.g., prostate cancer, renal carcinoma, liver cancer, pancreatic cancer, gastric cancer, breast cancer, lung cancer, head-neck carcinoma, thyroid cancer, glioblastoma, melanoma), hematologic malignancy (e.g., lymphoma, leukemia), skin cancer (e.g., cutaneous T-cell lymphoma, cutaneous B-cell lymphoma).

The compounds of the present invention can be formulated in a conventional manner using one or more pharmaceutically acceptable carriers. Therefore, the active compounds of the invention can be formulated into dosage forms for oral, buccal, intranasal, parenteral (e.g., intravenous, intramuscular or subcutaneous) or rectal administration, or into dosage forms which are suitable for inhalation or insufflation administration. The compounds of the invention can be also formulated into a sustained release dosage forms.

Depending on the purpose of treatment, the pharmaceutical composition can be formulated into various types of unit dosage forms, such as a tablet, pill, powder, liquid, suspension, emulsion, granule, capsule, suppository and injection (solution and suspension), or dosage forms which are suitable for inhalation or insufflation administration.

Any excipient known and widely used in the art can be used to formulate a pharmaceutical composition to the tablet form. For example, carriers, such as lactoses, white sugar, sodium chlorides, glucoses, urea, starches, calcium carbonates, kaolins, crystalline celluloses, silicic acids and the like; adhesives, such as water, ethanol, propanol, regular syrup, dextrose solutions, starch solutions, gelatin solutions, carboxymethylcelluloses, shellacs, methyl celluloses, potassium phosphates, polyvinylpyrrolidone and the like; disintegrants, such as dry starches, sodium alginates, agar powder, kelp powder, sodium bicarbonates, calcium carbonates, polyoxyethylene sorbitan fatty acid esters, sodium dodecyl sulfates, monoglyceride stearates, starches, lactoses and the like; disintegration inhibiting agents, such as white sugar, glycerol tristearates, coconut oil and hydrogenated oil; absorptive accelerators, such as quaternary ammonium hydroxide, sodium dodecyl sulfates and the like; humectants, such as glycerol, starches and the like; adsorbents, such as starches, lactoses, kaolins, bentonites, colloid silicic acids and the like; and lubricants, such as pure talcs, stearates, boric acid powder, polyethylene glycol and the like. It can also be made into sugar-coated tablets, gelatin-coated tablets, casing tablets, coated tablets, double-layer film tablets and multi-layer tablets according to needs.

Any excipient known and widely used in the art can be used, such as carriers, e.g. lactose, starch, coconut oil, hydrogenated oil, kaolin, talcum powder and the like; adhesives, e.g. gum acacia powder, gum tragacanth powder, gelatin, ethanol and the like; disintegrants, agar, kelp powder and the like to formulate a pharmaceutical composition to the pill form.

Any excipient known and widely used in the art can be used, such as polyethylene glycol, coconut oil, higher alcohol, ester of higher alcohol, gelatin, semisynthetic glyceride and the like to formulate a pharmaceutical composition to the suppository form.

Solution and suspension can be formulated into an injection after disinfection (preferably adding appropriate amount of sodium chloride, glucose or glycerinum) to prepare a pharmaceutical composition at an isotonic pressure with blood. When preparing an injection, any common carriers in the art can also be used. For example, water, ethanol, propanediol, sulphate-ethoxylated isostearyl alcohol, polyethoxylated isostearyl alcohol, fatty acid ester of polyethylene sorbitan monooleate and the like. Furthermore, a common dissolving agent, buffer agent, analgesic and the like can also be added.

For intranasal administration or inhalation administration, the active compounds of the invention are suitably released in a form of solution or suspension from an absorption or extrusion or sorption pump spray, or in a form of spray form a pressurizing vessel or sprayer, wherein the release utilizes a suitable propellant, such as dichlorodifluoromethane, trichlorofluoromethane, dichlorotetrafluoroethane, carbon dioxide or other suitable gases. In the case of a pressurized aerosol, a dosage unit can be determined by a valve providing metered release. The pressurizing vessel and sprayer can contain a solution or suspension of the active compound. A capsule or cartridge (e.g., made of gelatin) used in an inhaler or insufflator can be formulated into a powder mixture containing the compounds of the invention and suitable powdered substrates such as lactose or starch.

Unless stated to the contrary, terms used in the specification and claims have the following meanings.

The term "stereoisomer" represents an isomer formed by at least an asymmetric center. In the compound having one or more (such as 1, 2, 3 or 4) asymmetric centers, raceme, racemic mixture, mesomer, single enantiomer, mixtures of diastereomers and single diastereoisomer can be formed. Specific individual molecules can also be present as geometrical isomer (cis/trans).

The term "solvate" represents a form of the compound generally physically combined with a solvent by a solvolytic reaction. This physical combination includes hydrogen bonding. Conventional solvents include water, ethanol, methanol, acetic acid and the like. The compound of formula (II) can be prepared in the form of crystal and present in the form of solvate (e.g., the form of hydrate). Suitable solvates include pharmaceutically acceptable solvates (e.g., hydrates) and further include stoichiometric solvates and non-stoichiometric solvates. In some instances, for example, when one or more solvent molecules are incorporated in lattices of crystalline solid, a solvate may dissociate. "Solvate" encompasses solutions and dissociable solvates. Representative solvates include hydrates, ethanolate, methanolate and the like.

The term "prodrug" represents derivatives that are convert to the compound of the present invention by reacting with enzymes, gastric acids, and the like under physiological conditions in vivo, such as by oxidation, reduction, hydrolysis, and the like, each of which is catalyzed by an enzyme.

The term "metabolite" represents all molecules derived from the compounds of the invention in cells or organisms, preferably humans.

The term "isotope derivative" represents the compounds containing isotopes in non-natural proportion at one or more atoms that form the compounds. For example, deuterium ($^2$H or D), tritium ($^3$H or T), carbon-13 ($^{13}$C), nitrogen-15 ($^{15}$N), oxygen-18 ($^{18}$O), etc.

The term "pharmaceutical composition" represents one or more compounds of the invention or physiologically/pharmacologically acceptable salts or mixtures of prodrugs and other chemicals such as physiologically/pharmacologically acceptable carriers and excipients. The aim of the pharmaceutical composition is to facilitate the administration to organisms, which is beneficial to the absorption of the active ingredients to further develop biological activity.

The carriers include all pharmaceutical preparations in the pharmaceutical field that are capable to be formulated for injection and non-injection administration routes, e.g., a diluent, humectant, filler, adhesive, moistening agent, disintegrant, sorbefacient, surfactant, retardant, adsorbent, suspending agent, flocculant, deflocculant, emulgator, common substrate, solubilizer, cosolvent, preservative, corrigent, colorant, antioxygen, buffer, bacteriostat, isoosmotic adjusting agent, pH adjuster, metal ion chelating agent, hardener, thickener and the like.

DETAILED DESCRIPTION OF THE INVENTION

The following examples are used to further describe the invention, but are not intended to limit the scope of the invention. Experimental methods for which specific conditions are not indicated in the examples of the present invention are usually performed under conventional conditions or as suggested by the manufacturer of the raw material or commodity. Reagents without indicating specific sources are the conventional reagents purchased in the market.

Abbreviations in the present invention have the following meanings:

| Abbreviations | Meanings of abbreviations |
| --- | --- |
| ACN | acetonitrile |
| Boc- | tert-butoxycarbonyl- |
| Cbz- | carbobenzoxy- |
| CDI | carbonyldiimidazole |
| m-CPBA | meta-chloroperoxybenzoic acid |
| DAST | (diethylamino)sulfur fluoride |
| DBU | 1,8-diazabicyclo[5.4.0]undec-7-ene |
| DCM | dichloromethane |
| DIEA/DIPEA | N,N-diisopropylethylamine |
| DMAP | 4-dimethylaminopyridine |
| DMF | N,N-dimethylformamide |
| DMSO | dimethyl sulfoxide |
| DPPA | diphenylphosphoryl azide |
| EA | ethyl acetate |
| EDC | 1-(3-dimethylaminopropyl)-3-ethylcarbodiimide hydrochloride |
| EtOH | ethanol |
| h | hour |
| HATU | O-(7-azabenzotriazol-1-yl)-N,N,N',N'-tetramethyluronium hexafluorophosphate |
| HCl | hydrochloric acid |
| HOBt | 1-hydroxybenzotriazole |
| HPLC | high performance liquid chromatography |
| LDA | lithium diisopropylamide |
| MeOH | methanol |
| LiHMDS | lithium bis (trimethylsilyl)amide |
| min | minute |
| MS | mass spectrum |
| NCS | N-chlorosuccinimide |
| NMP | N-methylpyrrolidone |
| NMR | nuclear magnetic resonance |
| PE | petroleum ether |
| Pd$_2$(dba)$_3$ | tris(dibenzylideneacetone)dipalladium |
| Pd(dppf)Cl$_2$ | [1,1'-bis(diphenylphosphino)ferrocene]dichloropalladium |
| Pd(PPh$_3$)$_4$ | tetrakis(triphenylphosphine)palladium |
| Pd(OAc)$_2$ | palladium acetate |
| rt | room temperature |
| R$_t$ | retention time |
| SEM- | [2-(trimethylsilyl)ethoxy]methyl- |
| TBAF | tetrabutylammonium fluoride |
| TEA | triethylamine |
| TFA | trifluoroacetic acid |
| TFAA | trifluoroacetic anhydride |
| THF | tetrahydrofuran |
| TLC | thin layer chromatography |
| TsCl | para-toluensulfonyl chloride |
| XantPhos | 9,9-dimethyl-4,5-bis(diphenylphosphino)xanthene |

Structures of the compound are determined by nuclear magnetic resonance (NMR) and/or mass spectrum (MS). NMR chemical shift ($\delta$) is expressed in units of $10^{-6}$ (ppm). Test solvents are deuterated dimethyl sulfoxide (DMSO-d$_6$), deuterated chloroform (CDCl$_3$) and deuterated methanol (CD$_3$OD), and the internal standard is tetramethylsilane (TMS).

EXAMPLE

Method for Preparing Intermediates

1. Preparation of 4-chloro-1-benzenesulfonyl-1H-pyrrolo[2,3-b]pyridin-5-carbonitrile I-1

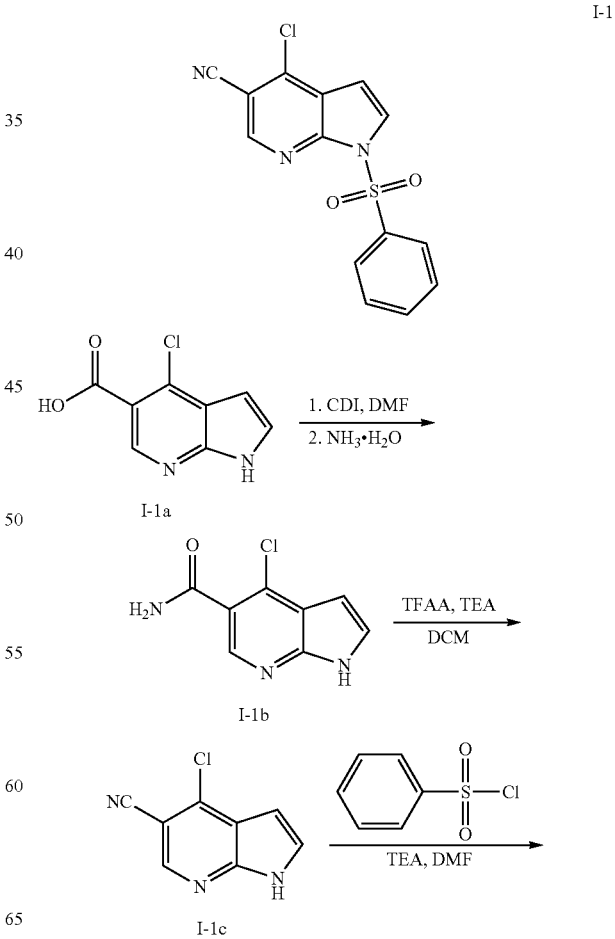

-continued

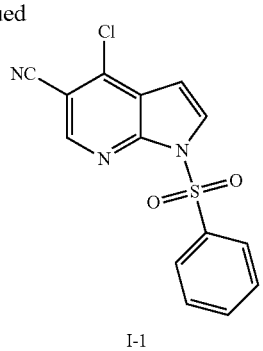

I-1

First Step: Preparation of 4-chloro-1-benzenesulfonyl-1H-pyrrolo[2,3-b]pyridin-5-carbonitrile I-1b Compound 4-chloro-1H-pyrrolo[2,3-b]pyridin-5-carboxylic acid I-1a (1.00 g, 5.10 mmol) and DMF (10 mL) were added into a reaction flask, and then CDI (0.91 g, 5.61 mmol) was added, stirred at room temperature for 1 h, and cooled in an ice-water bath. Then, $NH_3 \cdot H_2O$ (1.12 mL) was added at 0° C. The system was stirred at room temperature for 1 h. After the reaction was completed under TLC monitoring, the system was poured into water, extracted with ethyl acetate for three times, and organic phases were combined, washed with water and saturated sodium chloride, dried with anhydrous sodium sulfate, and then concentrated, slurried by dichloromethane/petroleum ether=5 ml/1 ml, filtered by suction, and dried by a spin drier to obtain the titled compound I-1b (0.6 g, 3.08 mmol) with a yield of 60.3%.

LCMS (ESI) m/z: 196 $[M+H]^+$. $^1$H NMR (400 MHz, DMSO-$d_6$, δ ppm): 8.29 (s, 1H), 7.91 (s, 1H), 7.65-7.59 (m, 2H), 7.21 (br s, 1H), 6.57-6.56 (d, J=3.2 Hz, 1H).

Second Step: Preparation of 4-chloro-1H-pyrrolo[2,3-b]pyridin-5-carbonitrile I-1c Compound 4-chloro-1H-pyrrolo[2,3-b]pyridin-5-carboxamide I-1b (300 mg, 1.54 mmol), triethylamine (6 mL) and dichloromethane (6 mL) were added into a reaction flask, and then trifluoroacetic anhydride (3 mL) was added dropwise at room temperature. The system was stirred at room temperature for 6 hours. After the reaction was completed under TLC monitoring, the system was poured into ice water, extracted with dichloromethane for three times, and organic phases were combined, washed with water and saturated sodium chloride, dried with anhydrous sodium sulfate, and concentrated at a low temperature, followed by purification by column chromatography (v/v, dichloromethane/methanol=100:1-50:1) to obtain the titled compound I-1c (200 mg, 1.13 mmol) with a yield of 73.4%.

LCMS (ESI) m/z: 178 $[M+H]^+$. $^1$H NMR (400 MHz, DMSO-$d_6$, δppm): 12.69 (br s, 1H), 8.67 (s, 1H) 7.834-7.825 (d, J=3.6 Hz, 1H), 6.72-6.71 (d, J=3.6 Hz, 1H).

Third Step: Preparation of 4-chloro-1-benzenesulfonyl-1H-pyrrolo[2,3-b]pyridin-5-carbonitrile I-1

DMF (5 mL) was added into a reaction flask, and then compound 4-chloro-1H-pyrrolo[2,3-b]pyridin-5-carbonitrile I-1c (100 mg, 0.57 mmol), triethylamine (114 mg, 1.13 mmol) and benzene sulfonyl chloride (150 mg, 0.85 mmol) were added separately. The system was stirred at room temperature overnight. After the reaction was completed under TLC monitoring, the reaction system was poured into water, extracted with ethyl acetate for three times. Organic phases were combined, washed with water and saturated sodium chloride, dried with anhydrous sodium sulfate, and then concentrated, followed by purification by column chromatography (v/v, petroleum ether/ethyl acetate=20:1-5:1) to obtain the titled compound I-1 (120 mg, 0.38 mmol) with a yield of 67%.

LCMS (ESI) m/z: 318 $[M+H]^+$. $^1$H NMR (400 MHz, DMSO-$d_6$, δppm): 8.88 (s, 1H), 8.26-8.25 (d, J=3.6 Hz, 1H), 8.17-8.15 (d, J=7.6 Hz, 2H), 7.81-7.77 (t, J=7.6 Hz, 1H), 7.69-7.65 (t, J=8.0 Hz, 2H), 7.07-7.06 (d, J=4.0 Hz, 1H).

Examples of the Method for Preparing Final Product

Example 1

Preparation of (cis)-4-({4-ethyl-1-[(2,2,2-trifluoroethyl)carbamoyl]pyrrolidin-3-yl}amino)-1H-pyrrolo[2,3-b]pyridin-5-carbonitrile H01

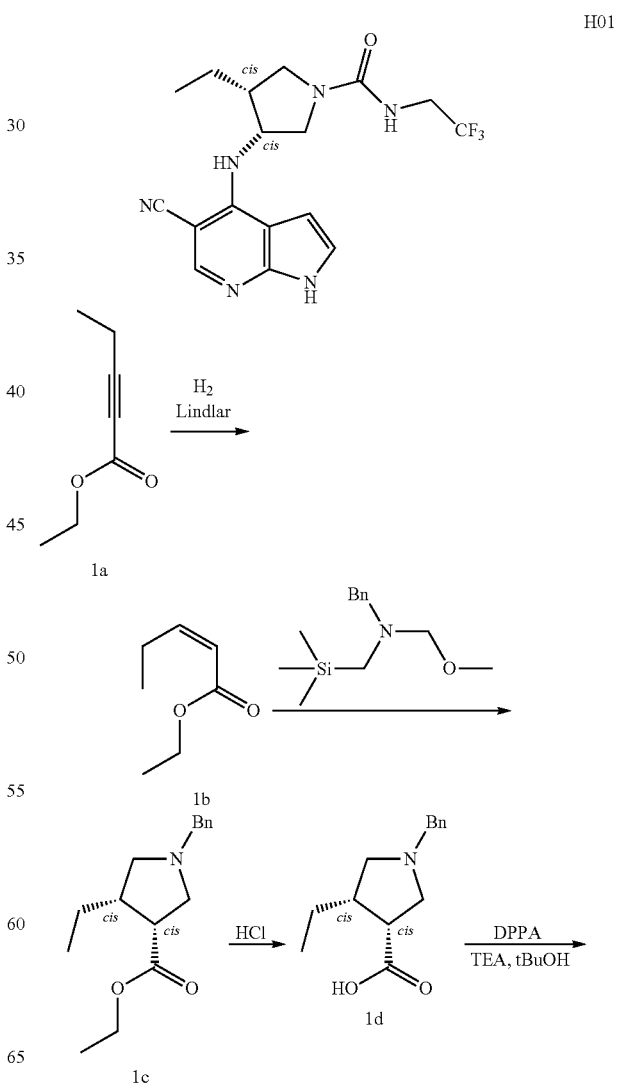

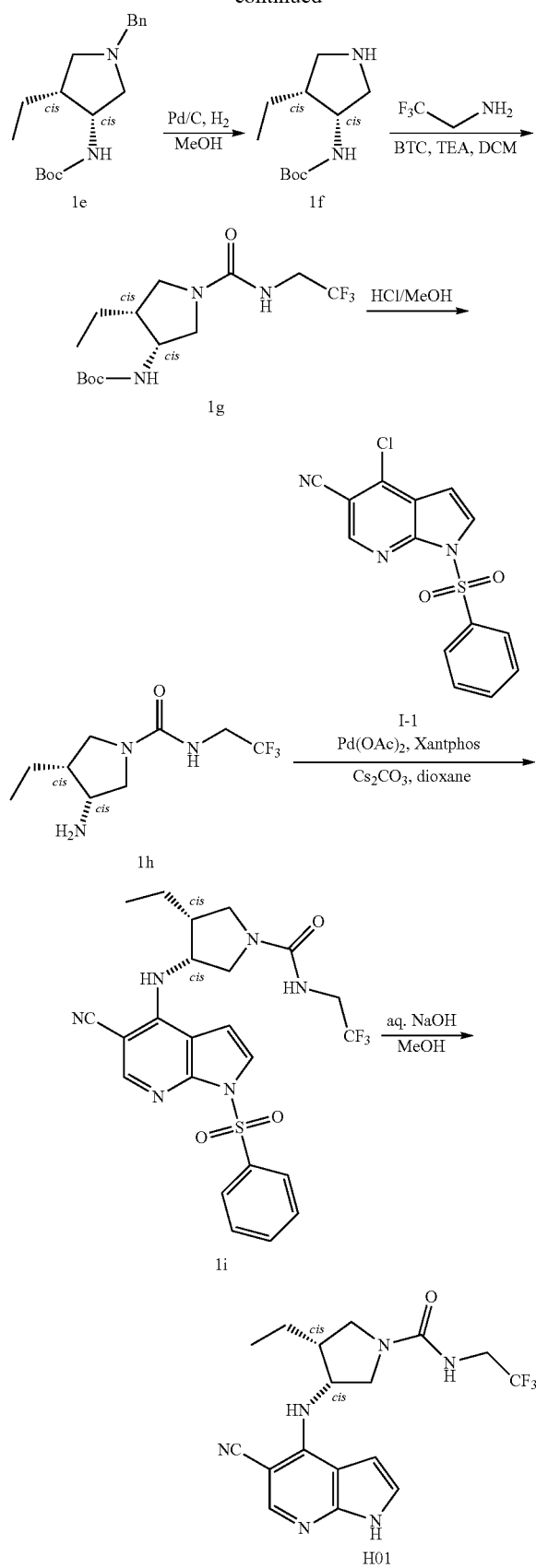

First Step: Preparation of (cis)-ethyl 2-pentenoate 1b

Compound ethyl 2-pentynoate 1a (130 g, 1.03 mol) and anhydrous tetrahydrofuran (1.3 L) were added into a reaction flask, and then quinoline (13 mL) and lindlar catalyst (13.0 g) were added. The system was stirred for 5 h under the protection of hydrogen balloon. After the reaction was completed under TLC monitoring, the system was filtered with kieselguhr, dried by a spin drier (10-15° C.) to obtain crude products, followed by purification by column chromatography (petroleum ether) to obtain the titled compound 1b (70 g, 0.55 mol) with a yield of 53%.

$^1$H NMR (400 MHz, CDCl$_3$, δppm): 6.21-6.16 (m, 1H), 5.75-5.71 (m, 1H), 4.19-4.14 (m, 2H), 2.67-2.63 (m, 2H), 1.30-1.26 (t, J=7.2 Hz, 3H), 1.07-1.03 (t, J=7.6 Hz, 3H).

Second Step: Preparation of (cis)-1-benzyl-4-ethyl-pyrrolidin-3-ethyl formate 1c Dichloromethane (1.4 L) was added into a reaction flask, then compound (cis)-ethyl 2-pentenoate 1b (70.0 g, 0.54 mol) and N-(methoxymethyl)-N-(trimethylsilyl)benzylamine (130 g, 0.54 mol) were added separately. The system was cooled to 0° C., and trifluoroacetic acid (6.20 g, 0.054 mol) was added dropwise, followed by stirred for 2 h at an ice-water bath. After the reaction was completed under TLC monitoring, the system was concentrated and dried by a spin drier, and purified by column chromatography (v/v, petroleum ether/ethyl acetate=50:1-5:1) to obtain the titled compound 1c (70.0 g, 0.27 mol) with a yield of 49%.

LCMS (ESI) m/z: 262 [M+H]$^+$. $^1$H NMR (400 MHz, CDCl$_3$, δppm): 7.35-7.28 (m, 5H), 4.16-4.10 (m, 2H), 3.65 (s, 2H), 3.12-3.02 (m, 3H), 2.70-2.64 (m, 1H), 2.40-2.35 (m, 1H), 2.11-2.06 (t, J=9.2 Hz, 1H), 1.49-1.43 (m, 1H), 1.29-1.23 (m, 1H), 1.28-1.24 (t, J=6.8 Hz, 3H), 0.87-0.84 (t, J=7.6 Hz, 3H).

Third Step: Preparation of (cis)-1-benzyl-4-ethyl-pyrrolidin-3-carboxylic acid 1d Compound (cis)-1-benzyl-4-ethyl-pyrrolidin-3-ethyl formate 1c (70.0 g, 0.27 mol) was dissolved in 1,4-dioxane (700 mL), and then concentrated hydrochloric acid (700 mL) was added. The system was stirred for 16 h at 90° C. After the reaction was completed under TLC monitoring, the system was adjusted to pH=9 with 6 mol/L sodium hydroxide solution in an ice-water bath, and then extracted with ethyl acetate (700 mL×2). The water phase was adjusted to pH=7 with 2 mol/L hydrochloric acid, then dried by a spin drier to obtain crude products. The crude products were slurried by ethanol (200 mL), filtered and dried by a spin drier to obtain the titled compound 1d (35.0 g, 0.15 mol) with a yield of 56%.

LCMS (ESI) m/z: 234 [M+H]$^+$. $^1$H NMR (400 MHz, CDCl$_3$, δppm): 7.60-7.58 (m, 2H), 7.39-7.37 (m, 3H), 4.43-4.34 (m, 2H), 3.66-3.62 (m, 1H), 3.49-3.42 (m, 2H), 3.26-3.22 (m, 1H), 3.02-2.97 (m, 1H), 2.62-2.55 (m, 1H), 1.63-1.56 (m, 1H), 1.41-1.34 (m, 1H), 0.94-0.90 (t, J=7.2, 3H).

Fourth Step: Preparation of (cis)-(1-benzyl-4-ethyl-pyrrolidin-3-yl) tert-butyl carbamate 1e Compound (cis)-1-benzyl-4-ethyl-pyrrolidin-3-carboxylic acid 1d (2.00 g, 8.58 mmol), triethylamine (1.73 g, 17.2 mmol) and diphenylphosphoryl azide (3.54 g, 12.9 mmol) were added into tertiary butanol (20 mL), stirred for 2 h at room temperature and for 16 h at 90° C. under the protection of nitrogen. After the reaction was completed under TLC monitoring, the system was concentrated, dried by a spin drier, extracted with ethyl acetate, and the organic phases were washed with water and saturated sodium chloride, dried with anhydrous sodium sulfate, followed by purification by column chromatography (v/v, petroleum ether/ethyl acetate=50:1-10:1) to obtain the titled compound 1e (0.55 g, 1.81 mmol) with a yield of 20%.

$^1$H NMR (400 MHz, CDCl$_3$, δppm): 7.33-7.23 (m, 5H), 4.81-4.78 (m, 1H), 4.23-4.21 (m, 1H), 3.66-3.55 (m, 2H), 2.82-2.78 (m, 1H), 2.67-2.63 (1, J=9.2 Hz, 1H), 2.46-2.43 (m, 1H), 2.32-2.29 (m, 1H), 2.19-2.14 (m, 1H), 1.48-1.43 (m, 1H), 1.44 (s, 9H), 1.28-1.18 (m, 1H), 0.89-0.85 (t, J=7.2 Hz, 3H).

Fifth Step: Preparation of (cis)-(4-ethyl-pyrrolidin-3-yl) tert-butyl carbamate 1f Compound (cis)-(1-benzyl-4-ethyl-pyrrolidin-3-yl) tert-butyl carbamate 1e (10.0 g, 32.9 mmol), methanol (100 mL) and Pd/C (10.0 g) were added into a hydrogenation flask, stirred for 6 h under 50 psi hydrogen pressure at room temperature. After the reaction was completed under TLC monitoring, the system was filtered with kieselguhr to obtain a filtrate, which was concentrated and dried by a spin drier to obtain the titled compound 1f (6.00 g, 28.0 mmol) with a yield of 85%.

$^1$H NMR (400 MHz, CDCl$_3$, δppm): 4.82 (br s, 1H), 4.16 (br s, 1H), 3.21-3.14 (m, 2H), 2.80-2.77 (m, 1H), 2.55-2.49 (t, J=10.0 Hz, 1H), 2.32-2.26 (m, 1H), 2.05-2.01 (m, 1H), 1.51-1.45 (m, 1H), 1.44 (s, 9H), 1.31-1.24 (m, 1H), 0.95-0.92 (t, J=7.2 Hz 3H).

Sixth Step: Preparation of (cis)-{4-ethyl-1-[(2,2,2-trifluoroethyl)carbamoyl]pyrrolidin-3-yl} tert-butyl carbamate 1g Dichloromethane (60 mL), triethylamine (5.67 g, 56.1 mmol) and trifluoroethylamine (2.78 g, 28.0 mmol) were added into a reaction flask, and then triphosgene (3.32 g, 11.2 mmol) was added at 0° C., stirred for 2 h at 0° C., and then compound (cis)-(4-ethyl-pyrrolidin-3-yl) tert-butyl carbamate 1f (6.00 g, 28.0 mmol) was added at 0° C. Then the system was returned to room temperature and stirred for 6 h. After reaction was completed under TLC monitoring, the system was poured into water, extracted with dichloromethane, washed with water and saturated sodium chloride, dried with anhydrous sodium sulfate and concentrated, followed by purification by column chromatography (v/v, petroleum ether/ethyl acetate=30:1-2:1) to obtain the titled compound 1g (2.50 g, 7.37 mmol) with a yield of 26%.

LCMS (ESI) m/z: 362 [M+Na]$^+$. $^1$H NMR (400 MHz, DMSO-d$_6$, δppm): 7.14-7.09 (d, J=8.8 Hz, 1H), 6.73-6.70 (t, J=6.4 Hz, 1H), 4.04 (br s, 1H), 3.82-3.73 (m, 2H), 3.41-336 (m, 2H), 3.20-3.17 (d, J=10.8 Hz, 1H), 3.10-3.05 (t, J=10.0 Hz, 1H), 2.10 (br s, 1H), 1.38 (s, 9H), 1.36-1.34 (m, 1H), 1.30-1.23 (m, 1H), 0.87-0.83 (t, J=7.2 Hz, 3H).

Seventh Step: Preparation of (cis)-3-amino-4-ethyl-N-(2,2,2-trifluoroethyl) pyrrolidin-1-carboxamide 1h Compound (cis)-{4-ethyl-1-[(2,2,2-trifluoroethyl)carbamoyl]pyrrolidin-3-yl}tert-butyl carbamate 1g (2.50 g, 7.37 mmol) was dissolved in hydrochloric acid-methanol (25 mL, 4.8 mol/L) at 0° C. and stirred for 2 h at room temperature. After the reaction was completed under TLC monitoring, the system was concentrated, followed by addition of water, adjusted to pH=9 with sodium hydroxide solution (2 mol/L), and extracted with ethyl acetate. The organic phase was dried with anhydrous sodium sulfate, concentrated and dried by a spin drier to obtain the titled compound 1h (1.5 g, 6.20 mmol) with a yield of 85%.

LCMS (ESI) m/z: 240 [M+H]$^+$. $^1$H NMR (400 MHz, DMSO-d$_6$, δ ppm): 4.52 (br s, 1H), 3.98-3.85 (m, 2H), 3.55-3.50 (m, 3H), 3.32-3.30 (m, 1H), 3.15-3.10 (t, J=9.6 Hz, 1H), 2.12-2.07 (m, 1H), 1.57-1.41 (m, 2H), 1.25 (br s, 2H), 1.00-0.96 (t, J=7.2 Hz, 3H).

Eighth Step: Preparation of (cis)-3-[(5-cyano-1-benzenesulfonyl-1H-pyrrolo[2,3-b]pyridin-4-yl) amino]-4-ethyl-N-(2,2,2-trifluoroethyl)pyrrolidin-1-carboxamide 1i Dioxane (12 mL) was added into a reaction flask, followed by addition of compound 4-chloro-1-benzenesulfonyl-1H-pyrrolo[2,3-b]pyridin-5-carbonitrile I-1 (240 mg, 0.76 mmol), (cis)-3-amino-4-ethyl-N-(2,2,2-trifluoroethyl) pyrrolidin-1-carboxamide 1h (199 mg, 0.83 mmol), cesium carbonate (740 mg, 2.27 mmol), Xantphos (175 mg, 0.30 mmol) and Pd(OAc)$_2$ (33.9 mg, 0.15 mmol). The system was heated to 100° C. and stirred for 6 h. After the reaction was completed under TLC monitoring, the system was cooled to room temperature and filtered, poured into water, and extracted with dichloromethane and water for three times. The organic phases were combined, washed with water and saturated sodium chloride, dried with anhydrous sodium sulfate and concentrated to obtain crude products. The crude products were purified with preparative TLC to obtain the titled compound 1i (100 mg, 0.19 mmol) with a yield of 25.4%. LCMS (ESI) m/z: 521 [M+H]$^+$.

Ninth Step: Preparation of (cis)-4-({4-ethyl-1-[(2,2,2-trifluoroethyl)carbamoyl)]pyrrolidin-3-yl}amino)-1H-pyrrolo[2,3-b]pyridin-5-carbonitrile H01

Methanol (1 mL) was added into a reaction flask, followed by addition of (cis)-3-[(5-cyano-1-benzenesulfonyl-1H-pyrrolo[2,3-b]pyridin-4-yl)amino]-4-ethyl-N-(2,2,2-trifluoroethyl)pyrrolidin-1-carboxamide 1i (40.0 mg, 0.074 mmol) and sodium hydroxide solution (0.15 mL, 0.15 mmol, 1 mol/L). The reaction system was stirred for 12 h at room temperature. After the reaction was completed under TLC monitoring, the reaction system was extracted with ethyl acetate and water for three times. The organic phases were combined, washed with water and saturated sodium chloride, dried with anhydrous sodium sulfate and concentrated to obtain crude products. The crude products were purified with preparative TLC to obtain the titled compound H01 (26 mg, 0.063 mmol) with a yield of 83.3%. LCMS (ESI) m/z: 381 [M+H]$^+$.

$^1$H NMR (400 MHz, DMSO-d6) δ 11.87 (s, 1H), 8.11 (s, 1H), 7.27 (dd, J=3.6, 2.5 Hz, 1H), 6.95-6.80 (m, 2H), 6.63 (dd, J=9.1 Hz, 1H), 4.89-4.78 (m, 1H), 3.86-3.73 (m, 2H), 3.71-3.63 (m, 1H), 3.61-3.46 (m, 2H), 3.40-3.33 (m, 1H), 2.46-2.36 (m, 1H), 1.56-1.46 (m, 1H), 1.44-1.34 (m, 1H), 0.84 (t, J=7.4 Hz, 3H).

Example 2
Preparation of (cis)-4-({4-ethyl-1-[(2,2,2-trifluoroethyl)carbamoyl)]pyrrolidin-3-yl}-methyl-amino)-1H-pyrrolo[2,3-b]pyridin-5-carbonitrile H02
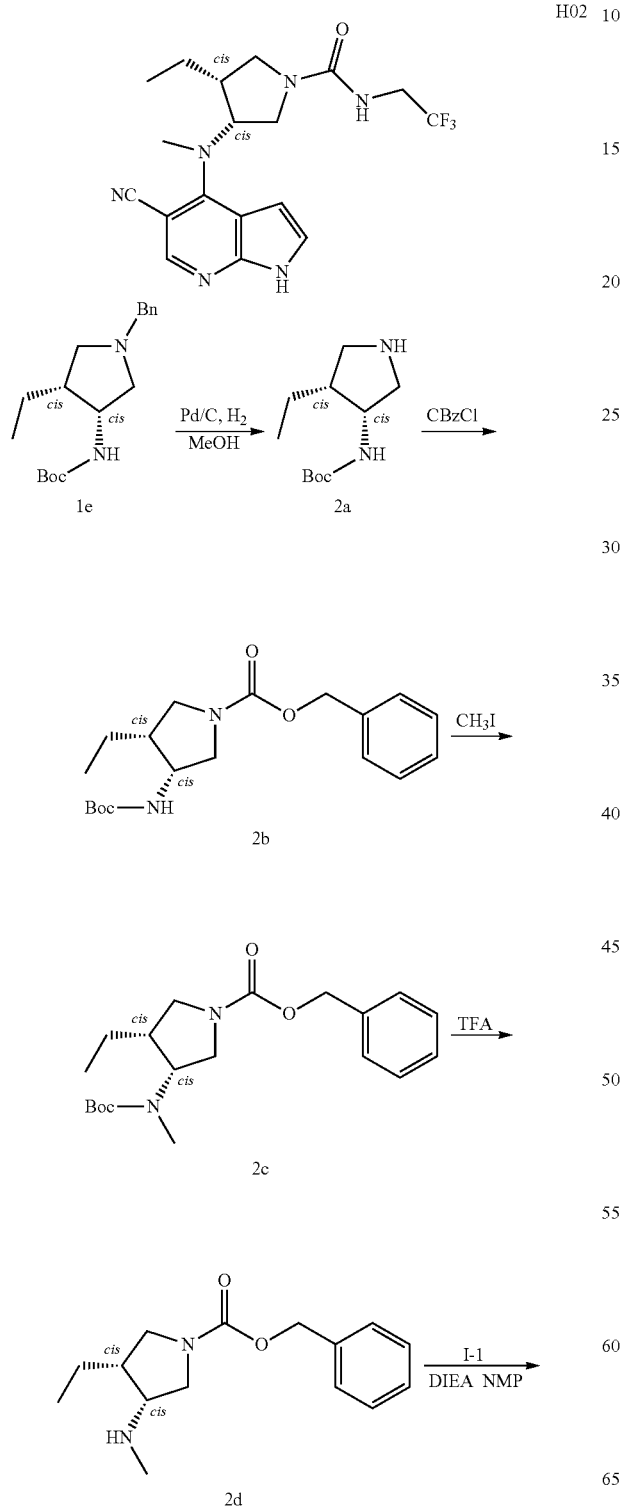
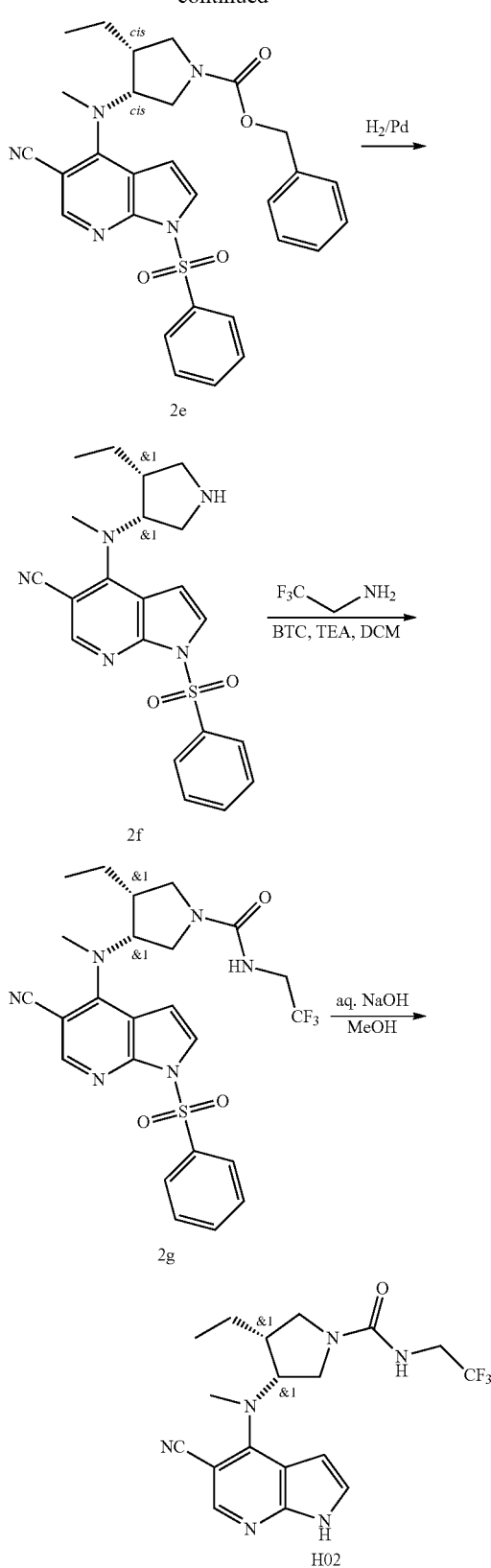

First Step: Preparation of (cis)-(4-ethyl-pyrrolidin-3-yl) tert-butyl carbamate 2a Compound 1e (3.5 g, 11.5 mmol) and methanol (50 mL) were added into a reaction flask, and then palladium on carbon (300 mg) was added. The system was stirred for 5 h under the protection of hydrogen balloon. After the reaction was completed under TLC monitoring, the system was filtered with kieselguhr, dried by a spin drier (10-15° C.) to obtain crude products, followed by purification by column chromatography (petroleum ether) to obtain the titled compound 2a (2.1 g, 9.8 mmol) with a yield of 85.2%. LCMS (ESI) m/z: 215 [M+H]$^+$.

Second Step: Preparation of (cis)-(1-benzyloxycarbonyl-4-ethyl-pyrrolidin-3-yl) tert-butyl carbamate 2b Compound 2a (2.1 g, 9.8 mmol) and dichloromethane (30 mL) were added into a reaction flask, and then triethylamine (2.0 g, 19.6 mmol) and benzyl chloroformate (2.5 g, 14.7 mmol) were added, and the system was stirred for 2 h at room temperature. After the reaction was completed under TLC monitoring, the system was extracted with dichloromethane and water. The organic phase was washed with water and saturated sodium chloride, dried with anhydrous sodium sulfate and concentrated, followed by purification by column chromatography (v/v, petroleum ether/ethyl acetate=4:1-2:1) to obtain the titled compound 2b (820 mg, 2.48 mmol) with a yield of 25.3%. LCMS (ESI) m/z: 371 [M+Na]$^+$.

Third Step: Preparation of (cis)-(1-benzyloxycarbonyl-4-ethyl-pyrrolidin-3-yl)-methyl-tert-butyl carbamate 2c Compound 2b (0.2 g, 0.57 mmol) and N,N-dimethylformamide (5 mL) were added into a reaction flask, and then sodium hydride (46 mg, 1.15 mmol, 60%) was added. After the system was stirred for 10 min at room temperature, iodomethane (121 mg, 0.86 mmol) was added. The system was stirred for 2 h at room temperature. After the reaction was completed under TLC monitoring, the system was extracted with ethyl acetate and water. The organic phases were washed with water and saturated sodium chloride, dried with anhydrous sodium sulfate and concentrated to obtain the titled compound 2c (200 mg, 0.55 mmol) with a crude yield of 96.5%. LCMS (ESI) m/z: 363 [M+H]$^+$.

Fourth Step: Preparation of (cis)-(1-benzyloxycarbonyl-4-ethyl-pyrrolidin-3-yl)-methyl-amine 2d Compound 2c (0.2 g, 0.55 mmol) and dichloromethane (5 mL) were added into a reaction flask, and then trifluoroacetic acid (0.5 mL) was added, and the system was stirred for 30 min at room temperature. After the reaction was completed under TLC monitoring, the system was concentrated, followed by another addition of dichloromethane, and concentrated again. This step was repeated for three times to obtain trifluoroacetate of the titled compound 2d (160 mg, 0.45 mmol) with a yield of 81.8%. LCMS (ESI) m/z: 263 [M+H]$^+$.

Fifth Step: Preparation of (cis)-3-[(5-cyano-1-benzenesulfonyl-1H-pyrrolo[2,3-b]pyridin-4-yl)-methyl-amino]-4-ethyl-pyrrolidin-1-benzyl formate 2e Compound 2d (160 mg, 0.45 mmol) and N-methyl pyrrolidone (2 mL) were added into a reaction flask, then intermediate I-1 (143 mg, 0.45 mmol) and N-isopropyldiethylamine (116 mg, 0.90 mmol) were added. The system was subjected to a microwave reaction for 1 h at 170° C. After the reaction was completed under TLC monitoring, the system was extracted with ethyl acetate and water. The organic phase was washed with water and saturated sodium chloride, dried with anhydrous sodium sulfate and concentrated, followed by purification by column chromatography (v/v, petroleum ether/ethyl acetate=4:1-2:1) to obtain the titled compound 2e (50 mg, 0.092 mmol) with a yield of 20.4%. LCMS (ESI) m/z: 544 [M+H]$^+$.

Sixth Step: Preparation of (cis)-3-[(5-cyano-1-benzenesulfonyl-1H-pyrrolo[2,3-b]pyridin-4-yl)-methyl-amino]-4-ethyl-pyrrolidine 2f Compound 2e (50 mg, 0.092 mmol) and methanol (10 mL) were added into a reaction flask, and then palladium on carbon (30 mg) was added. The system was stirred for 5 h under the protection of hydrogen balloon. After the reaction was completed under TLC monitoring, the system was filtered with kieselguhr, dried by a spin drier (10-15° C.) to obtain the titled compound 2f (36 mg, 0.088 mmol) with a yield of 95.7%. LCMS (ESI) m/z: 410 [M+H]$^+$.

Seventh Step: Preparation of (cis)-3-[(5-cyano-1-benzenesulfonyl-1H-pyrrolo[2,3-b]pyridin-4-yl)-methyl-amino]-4-ethyl-N-(2,2,2-trifluoroethyl)pyrrolidin-1-carboxamide 2g Dichloromethane (60 mL), triethylamine (18 mg, 0.176 mmol) and trifluoroethylamine (9 mg, 0.088 mmol) were added into a reaction flask, and then triphosgene (10 mg, 0.035 mmol) was added at 0° C. The system was stirred for 2 h at 0° C., and then compound 2f (36 mg, 0.088 mmol) was added at 0° C. Then the system was returned to room temperature and stirred for 6 h. After the reaction was completed under TLC monitoring, the system was poured into water, extracted with dichloromethane, washed with water and saturated sodium chloride, dried with anhydrous sodium sulfate and concentrated, followed by layer chromatography to obtain the titled compound 2g (10 mg, 0.019 mmol) with a yield of 21.6%. LCMS (ESI) m/z: 535 [M+H]$^+$.

Eighth Step: Preparation of (cis)-4-({4-ethyl-1-[(2,2,2-trifluoroethyl)carbamoyl)]pyrrolidin-3-yl}-methyl-amino)-1H-pyrrolo[2,3-b]pyridin-5-carbonitrile H02

Methanol (1 mL) was added into a reaction flask, and then compound 2g (10.0 mg, 0.019 mmol) and sodium hydroxide solution (0.15 mL, 0.15 mmol, 1 mol/L) were added separately. The reaction system was stirred for 12 h at room temperature. After the reaction was completed under TLC monitoring, the reaction system was extracted with ethyl acetate and water for three times. The organic phases were combined, washed with water and saturated sodium chloride, dried with anhydrous sodium sulfate and concentrated to obtain crude products. The crude products were purified by preparative TLC to obtain the titled compound H02 (6 mg, 0.015 mmol) with a yield of 78.9%. LCMS (ESI) m/z: 395 [M+H]$^+$.

$^1$H NMR (400 MHz, DMSO-d$_6$) δ 12.01 (s, 1H), 8.20 (s, 1H), 7.41-7.36 (m, 1H), 6.98-6.91 (m, 1H), 6.61-6.56 (m,

1H), 4.81-4.74 (m, 1H), 3.84-3.57 (m, 5H), 3.33-3.30 (m, 1H), 3.13 (s, 3H), 2.42-2.32 (m, 1H), 1.55-1.34 (m, 2H), 0.71 (t, J=8.0 Hz, 3H).

Example 3

Preparation of (cis)-4-{[4-ethyl-1-(3,3,3-trifluoropropionyl)pyrrolidin-3-yl]-methyl-amino}-1H-pyrrolo[2,3-b]pyridin-5-carbonitrile H03

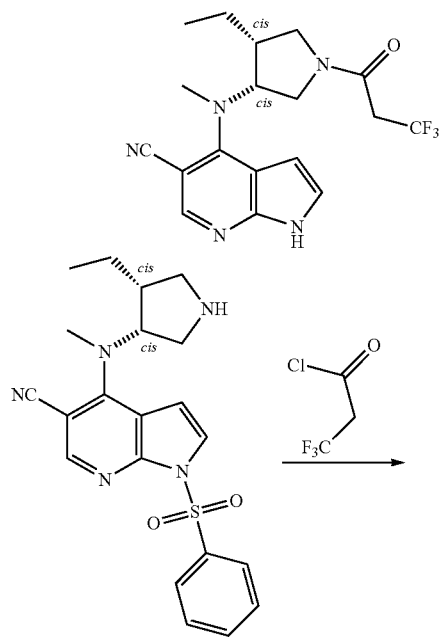

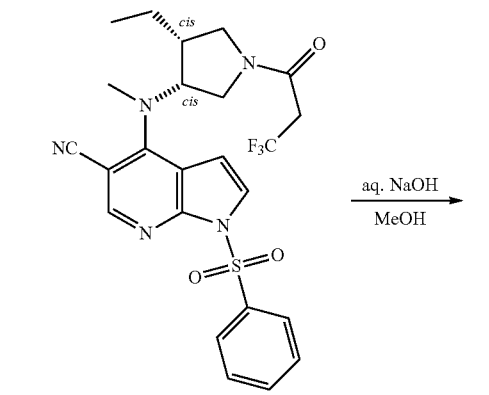

First Step: Preparation of (cis)-1-benzenesulfonyl-4-{[4-ethyl-1-(3,3,3-trifluoropropionyl)pyrrolidin-3-yl]-methyl-amino}-1H-pyrrolo[2,3-b]pyridin-5-carbonitrile 3a Compound 2f (100 mg, 0.24 mol) and dichloromethane (30 mL) were added into a reaction flask, and then triethylamine (24 mg, 0.24 mmol) and 3,3,3-trifluoropropanoyl chloride (35 mg, 0.24 mmol) were added. The system was stirred for 2 h at room temperature. After the reaction was completed under TLC monitoring, the system was extracted with dichloromethane and water. The organic phase was washed with water and saturated sodium chloride, dried with anhydrous sodium sulfate and concentrated, followed by purification by column chromatography (v/v, petroleum ether/ethyl acetate=4:1-2:1) to obtain the titled compound 3a (40 mg, 0.077 mmol) with a yield of 32.1%. LCMS (ESI) m/z: 520 [M+H]$^+$.

Second Step: Preparation of (cis)-4-{[4-ethyl-1-(3,3,3-trifluoropropionyl)pyrrolidin-3-yl]-methyl-amino}-1H-pyrrolo[2,3-b]pyridin-5-carbonitrile H03

Methanol (1 mL) was added into a reaction flask, and then compound 3a (40.0 mg, 0.077 mmol) and sodium hydroxide solution (0.15 mL, 0.15 mmol, 1 mol/L) were added separately. The reaction system was stirred for 12 h at room temperature. After the reaction was completed under TLC monitoring, the reaction system was extracted with ethyl acetate and water for three times. The organic phases were combined, washed with water and saturated sodium chloride, dried with anhydrous sodium sulfate and concentrated to obtain crude products. The crude products were by purified with preparative TLC to obtain the titled compound H03 (20 mg, 0.053 mmol) with a yield of 68.8%. LCMS (ESI) m/z: 380 [M+H]$^+$.

Example 4

Preparation of (cis)-4-({4-methyl-1-[(2,2,2-trifluoroethyl)carbamoyl)]pyrrolidin-3-yl}-methyl-amino)-1H-pyrrolo[2,3-b]pyridin-5-carbonitrile H04

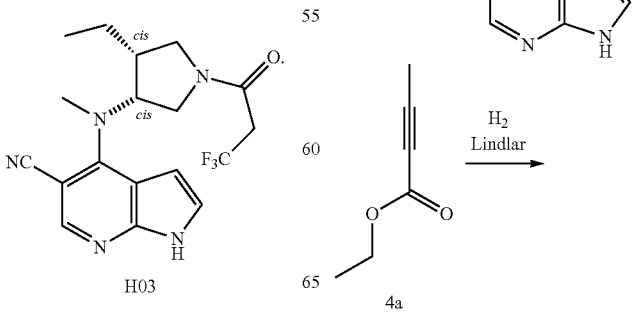

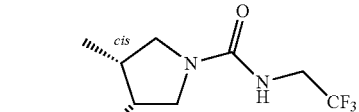

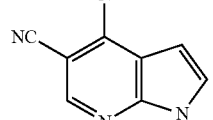

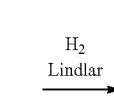

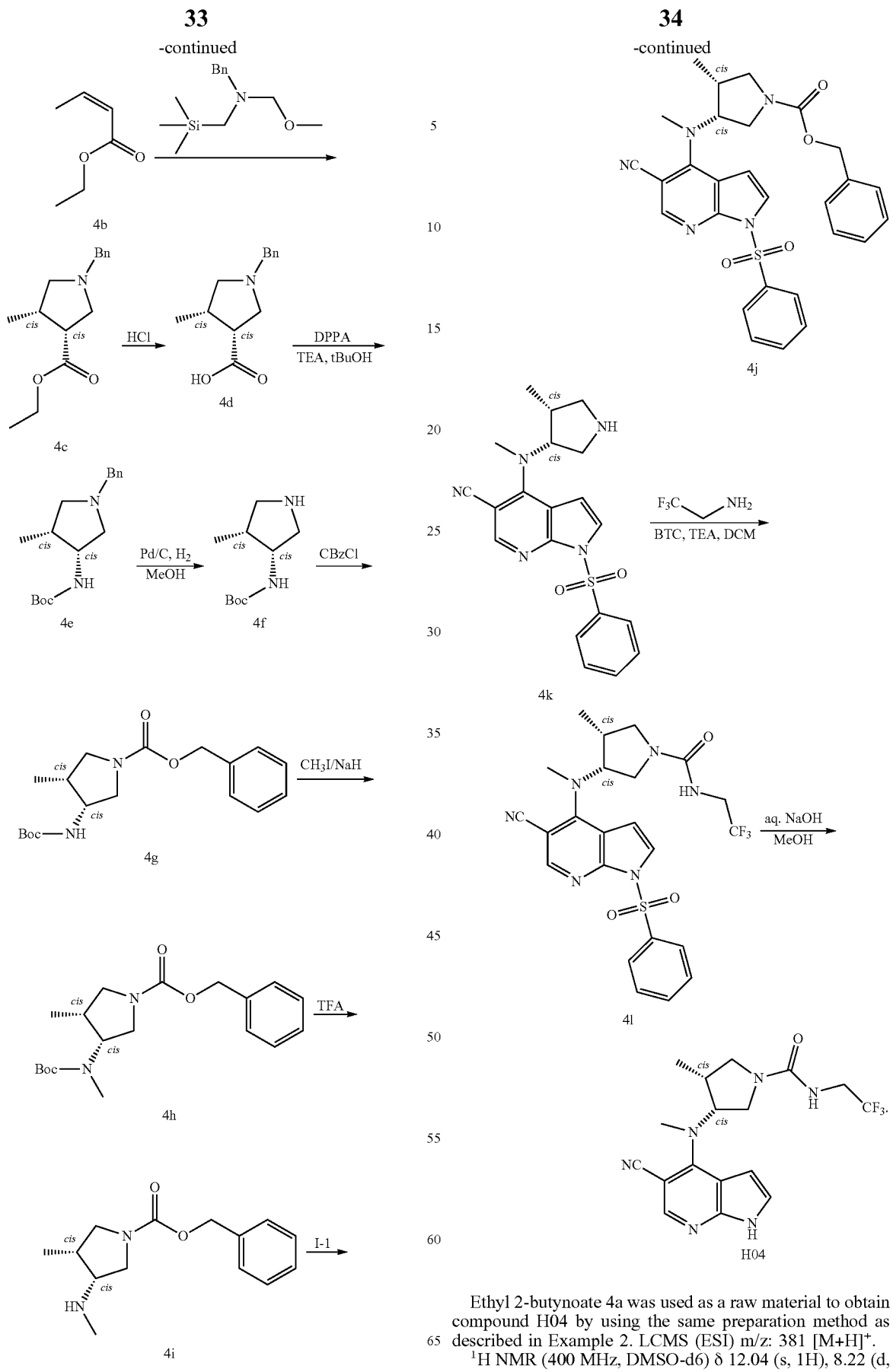
Ethyl 2-butynoate 4a was used as a raw material to obtain compound H04 by using the same preparation method as described in Example 2. LCMS (ESI) m/z: 381 [M+H]+.
 1H NMR (400 MHz, DMSO-d6) δ 12.04 (s, 1H), 8.22 (d, J=1.0 Hz, 1H), 740 (d, J=3.5 Hz, 1H), 6.90 (t, J=6.3 Hz, 1H), 6.62 (d, J=3.5 Hz, 1H), 4.69 (s, 1H), 3.86-3.69 (m, 3H), 3.65-3.52 (m, 2H), 3.11 (m, 4H), 2.68-2.49 (m, 1H), 0.98 (d, 3=6.9 Hz, 3H).

Example 5

Preparation of (cis)-4-{[4-methyl-1-(2-cyanoacetyl)pyrrolidin-3-yl]-methyl-amino}-1H-pyrrolo[2,3-b]pyridin-5-carbonitrile H05

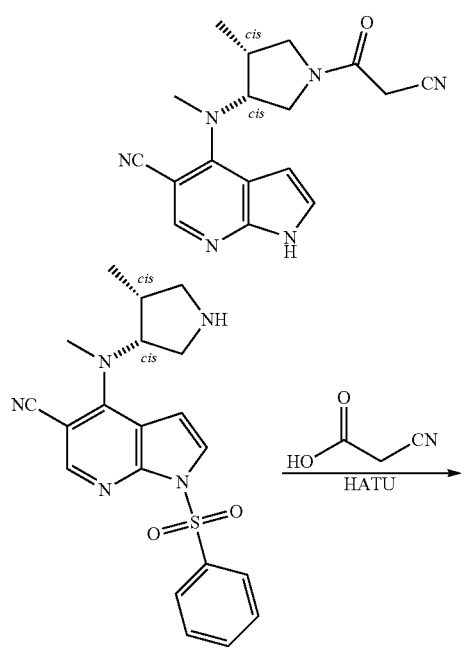

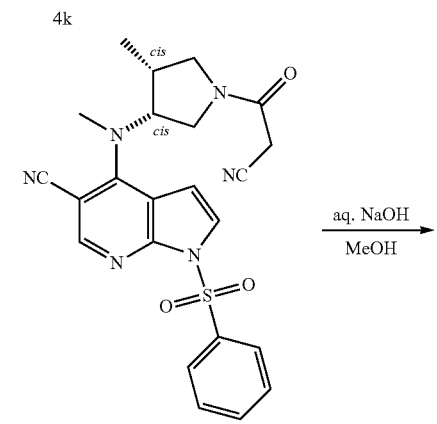

First Step: Preparation of (cis)-1-benzenesulfonyl-4-{[4-methyl-1-(2-cyanoacetyl)pyrrolidin-3-yl]-methyl-amino}-1H-pyrrolo[2,3-b]pyridin-5-carbonitrile 5a Compound 4k (95 mg, 0.24 mol) and dichloromethane (30 mL) were added into a reaction flask, and then triethylamine (24 mg, 0.24 mmol), cyanoacetic acid (20 mg, 0.24 mmol) and HATU (91 mg, 0.24 mmol) were added. The system was stirred for 2 h at room temperature. After the reaction was completed under TLC monitoring, the system was extracted with dichloromethane and water. The organic phase was washed with water and saturated sodium chloride, dried with anhydrous sodium sulfate and concentrated, followed by purification by column chromatography (v/v, petroleum ether/ethyl acetate=4:1-2:1) to obtain the titled compound 5a (50 mg, 0.11 mmol) with a yield of 43.8%. LCMS (ESI) m/z: 463 [M+H]⁺.

Second Step: Preparation of (cis)-4-{[4-methyl-1-(2-cyanoacetyl)pyrrolidin-3-yl]-methyl-amino}-1H-pyrrolo[2,3-b]pyridin-5-carbonitrile H05

Methanol (1 mL) was added into a reaction flask, and then compound 5a (50.0 mg, 0.11 mmol) and sodium hydroxide solution (0.15 mL, 0.15 mmol, 1 mol/L) were added separately. The reaction system was stirred for 12 h at room temperature. After the reaction was completed under TLC monitoring, the reaction system was extracted with ethyl acetate and water for three times. The organic phases were combined, washed with water and saturated sodium chloride, dried with anhydrous sodium sulfate and concentrated to obtain crude products. The crude products were purified by preparative TLC to obtain the titled compound H05 (30 mg, 0.093 mmol) with a yield of 84.5%. LCMS (ESI) m/z: 323 [M+H]⁺.

Example 6

Preparation of (3aR,5R,6aS)-4-{[2-((2S)-2-hydroxypropionyl)-hexahydrocyclopenta[c]pyrrole-5-yl]-methyl-amino}-1H-pyrrolo[2,3-b]pyridin-5-carbonitrile H06

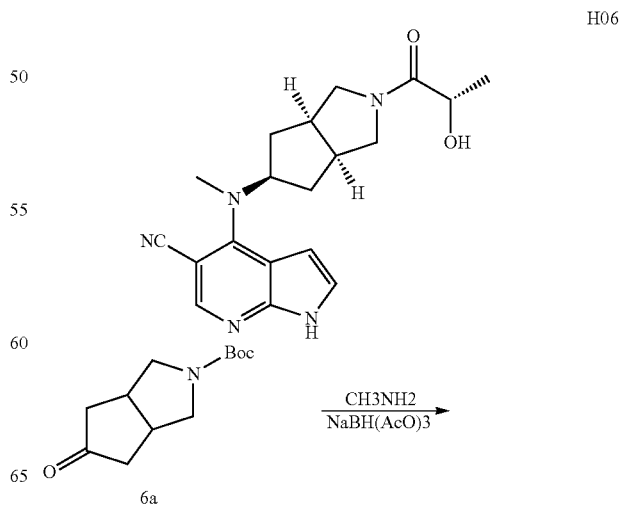

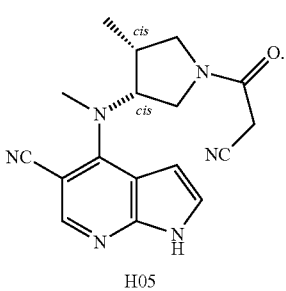

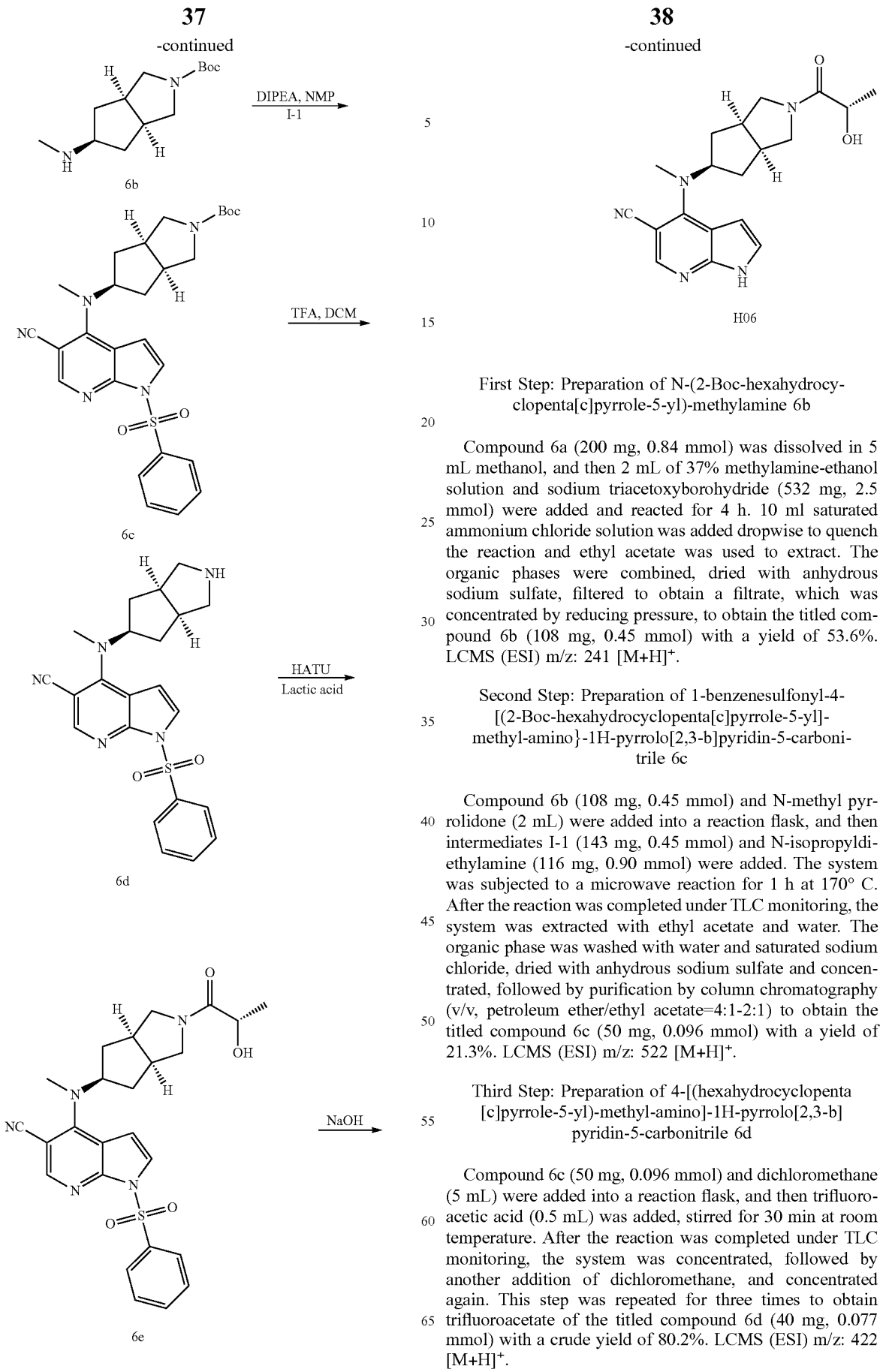

First Step: Preparation of N-(2-Boc-hexahydrocyclopenta[c]pyrrole-5-yl)-methylamine 6b Compound 6a (200 mg, 0.84 mmol) was dissolved in 5 mL methanol, and then 2 mL of 37% methylamine-ethanol solution and sodium triacetoxyborohydride (532 mg, 2.5 mmol) were added and reacted for 4 h. 10 ml saturated ammonium chloride solution was added dropwise to quench the reaction and ethyl acetate was used to extract. The organic phases were combined, dried with anhydrous sodium sulfate, filtered to obtain a filtrate, which was concentrated by reducing pressure, to obtain the titled compound 6b (108 mg, 0.45 mmol) with a yield of 53.6%. LCMS (ESI) m/z: 241 [M+H]+.

Second Step: Preparation of 1-benzenesulfonyl-4-[(2-Boc-hexahydrocyclopenta[c]pyrrole-5-yl]-methyl-amino}-1H-pyrrolo[2,3-b]pyridin-5-carbonitrile 6c Compound 6b (108 mg, 0.45 mmol) and N-methyl pyrrolidone (2 mL) were added into a reaction flask, and then intermediates I-1 (143 mg, 0.45 mmol) and N-isopropyldiethylamine (116 mg, 0.90 mmol) were added. The system was subjected to a microwave reaction for 1 h at 170° C. After the reaction was completed under TLC monitoring, the system was extracted with ethyl acetate and water. The organic phase was washed with water and saturated sodium chloride, dried with anhydrous sodium sulfate and concentrated, followed by purification by column chromatography (v/v, petroleum ether/ethyl acetate=4:1-2:1) to obtain the titled compound 6c (50 mg, 0.096 mmol) with a yield of 21.3%. LCMS (ESI) m/z: 522 [M+H]+.

Third Step: Preparation of 4-[(hexahydrocyclopenta[c]pyrrole-5-yl)-methyl-amino]-1H-pyrrolo[2,3-b]pyridin-5-carbonitrile 6d Compound 6c (50 mg, 0.096 mmol) and dichloromethane (5 mL) were added into a reaction flask, and then trifluoroacetic acid (0.5 mL) was added, stirred for 30 min at room temperature. After the reaction was completed under TLC monitoring, the system was concentrated, followed by another addition of dichloromethane, and concentrated again. This step was repeated for three times to obtain trifluoroacetate of the titled compound 6d (40 mg, 0.077 mmol) with a crude yield of 80.2%. LCMS (ESI) m/z: 422 [M+H]+.

39

Fourth Step: Preparation of 1-benzenesulfonyl-4-{[2-((2S)-2-hydroxypropionyl)-hexahydrocyclopenta[c]pyrrole-5-yl]-methyl-amino}-1H-pyrrolo[2,3-b]pyridin-5-carbonitrile 6e Compound 6e (40 mg, 0.077 mol) and dichloromethane (30 mL) were added into a reaction flask, and then triethylamine (8 mg, 0.077 mmol), sodium L-lactate (9 mg, 0.077 mmol) and HATU (29 mg, 0.077 mmol) were added. The system was stirred for 2 h at room temperature. After the reaction was completed under TLC monitoring, the system was extracted with dichloromethane and water. The organic phase was washed with water and saturated sodium chloride, dried with anhydrous sodium sulfate and concentrated, followed by purification by column chromatography (v/v, petroleum ether/ethyl acetate=4:1-2:1) to obtain the titled compound 6e (30 mg, 0.061 mmol) with a yield of 79.2%. LCMS (ESI) m/z: 494 [M+H]$^+$.

Fifth Step: Preparation of 4-{[2-((2S)-2-hydroxypropionyl)-hexahydrocyclopenta[c] pyrrole-5-yl]-methyl-amino}-1H-pyrrolo[2,3-b]pyridin-5-carbonitrile H06

Methanol (1 mL) was added into a reaction flask, and then compound 6e (30 mg, 0.061 mmol) and sodium hydroxide solution (0.15 mL, 0.15 mmol, 1 mol/L) were added separately. The reaction system was stirred for 12 h at room temperature. After the reaction was completed under TLC monitoring, the reaction system was extracted with ethyl acetate and water for three times. The organic phases were combined, washed with water and saturated sodium chloride, dried with anhydrous sodium sulfate and concentrated to obtain crude products. The crude products were purified by preparative TLC to obtain the titled compound H05 (15 mg, 0.042 mmol) with a yield of 68.9%. LCMS (ESI) m/z: 354 [M+H]$^+$.

$^1$H NMR (400 MHz, DMSO-d$_6$) δ 11.95 (s, 1H), 8.17 (s, 1H), 7.36-7.31 (m, 1H), 6.67 (dd, J=3.6, 2.0 Hz, 1H), 4.85 (dd, J=6.9, 3.0 Hz, 1H), 4.30 (p, J=6.5 Hz, 1H), 3.61-3.57 (m, 1H), 3.56-3.51 (m, 2H), 3.47-3.44 (m, 1H), 3.19 (s, 3H), 2.72-2.55 (m, 2H), 2.17-2.06 (m, 2H), 1.77-0.162 (m, 2H), 1.23-1.15 (m, 3H).

Example 7

(3aR,5s,6aS)-4-({2-[(3-methoxy-1,2,4-thiadiazole-5-yl)carbamoyl]-hexahydrocyclopenta[c]pyrrole-5-yl}-methyl-amino)-1H-pyrrolo[2,3-b]pyridin-5-carbonitrile H07

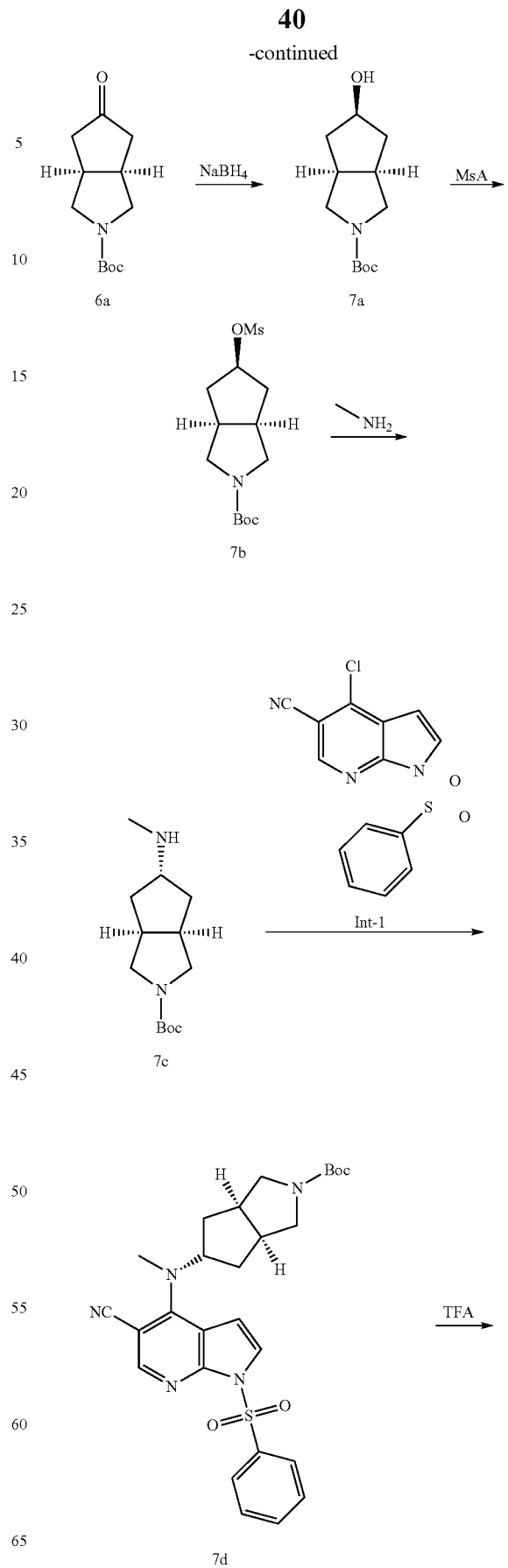

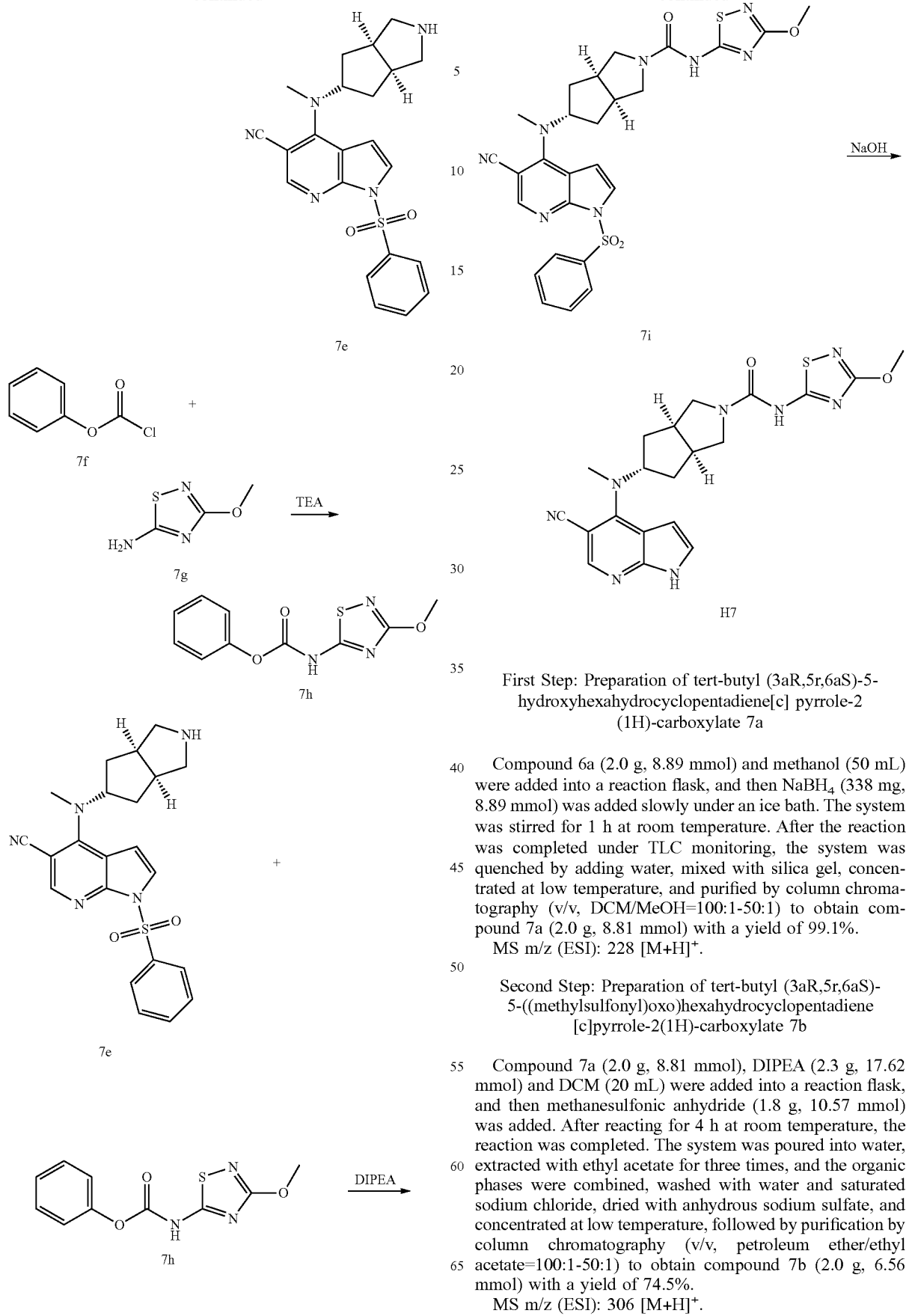

First Step: Preparation of tert-butyl (3aR,5r,6aS)-5-hydroxyhexahydrocyclopentadiene[c] pyrrole-2(1H)-carboxylate 7a Compound 6a (2.0 g, 8.89 mmol) and methanol (50 mL) were added into a reaction flask, and then NaBH$_4$ (338 mg, 8.89 mmol) was added slowly under an ice bath. The system was stirred for 1 h at room temperature. After the reaction was completed under TLC monitoring, the system was quenched by adding water, mixed with silica gel, concentrated at low temperature, and purified by column chromatography (v/v, DCM/MeOH=100:1-50:1) to obtain compound 7a (2.0 g, 8.81 mmol) with a yield of 99.1%.

MS m/z (ESI): 228 [M+H]$^+$.

Second Step: Preparation of tert-butyl (3aR,5r,6aS)-5-((methylsulfonyl)oxo)hexahydrocyclopentadiene[c]pyrrole-2(1H)-carboxylate 7b Compound 7a (2.0 g, 8.81 mmol), DIPEA (2.3 g, 17.62 mmol) and DCM (20 mL) were added into a reaction flask, and then methanesulfonic anhydride (1.8 g, 10.57 mmol) was added. After reacting for 4 h at room temperature, the reaction was completed. The system was poured into water, extracted with ethyl acetate for three times, and the organic phases were combined, washed with water and saturated sodium chloride, dried with anhydrous sodium sulfate, and concentrated at low temperature, followed by purification by column chromatography (v/v, petroleum ether/ethyl acetate=100:1-50:1) to obtain compound 7b (2.0 g, 6.56 mmol) with a yield of 74.5%.

MS m/z (ESI): 306 [M+H]$^+$.

Third Step: Preparation of tert-butyl (3aR,5s,6aS)-5-(methylamino) hexahydrocyclopentadiene[c]pyrrole-2(1H)-carboxylate 7c Compound 7b (1.0 g, 3.28 mmol), methanol amine solution (10 mmol) and methanol (20 mL) were added into a sealed pot. The system was reacted for 8 h at 80° C. After the reaction was completed, the system was concentrated at low temperature, and purified by column chromatography (v/v, DCM/MeOH=100:1-50:1) to obtain compound 7c (700 mg, 2.92 mmol) with a yield of 89.0%.

Fourth Step: Preparation of tert-butyl (3aR,5s,6aS)-5-((5-cyano-1-(phenylsulfonyl)-1H-pyrrolo[2,3-b]pyridin-4-yl)(methyl)amino)hexahydrocyclopentadiene[c]pyrrole-2(1H)-carboxylate 7d Compound 7c (380 mg, 1.58 mmol), DIPEA (408 mg, 3.16 mmol), Int-1 (500 mg, 1.58 mmol) and NMP (5 mL) were added into a reaction flask. The system was subjected to a microwave reaction for 1 h at 150° C. After the reaction was completed, the system was poured into water, extracted with ethyl acetate for three times, and the organic phases were combined, washed with water and saturated sodium chloride, dried with anhydrous sodium sulfate, and concentrated at low temperature, followed by purification by column chromatography (v/v, DCM/MeOH=100:1-50:1) to obtain compound 7d (300 mg, 0.58 mmol) with a yield of 36.7%.

MS m/z (ESI): 522 [M+H]$^+$.

Fifth Step: Preparation of 4-(methyl((3aR,5s,6aS)-octahydrocyclopentadiene[c]pyrrole-5-yl)amino)-1-(phenylsulfonyl)-1H-pyrrolo[2,3-b]pyridin-5-carbonitrile 7e Compound 7d (300 mg, 0.58 mmol), TFA (2 mL) and DCM (5 mL) were added into a reaction flask. The system was reacted for 1 h at room temperature. After the reaction was completed, the system was concentrated directly to obtain compound 7e (200 mg, 0.48 mmol) with a yield of 82.3%.

MS m/z (ESI): 422 [M+H]+.

Sixth Step: Preparation of phenyl (3-methoxy-1,2,4-thiadiazole-5-yl)carbamate 7h Compound 7f (1.2 g, 7.63 mmol), compound 7g (1.0 g, 7.63 mmol) and THF (20 mL) were added into a reaction flask, and then triethylamine (1.5 g, 15.26 mmol) was slowly added dropwise. The system was reacted for 1 h at room temperature. After the reaction was completed, the system was concentrated directly and purified by column chromatography (v/v, DCM/MeOH=100:1-50:1) to obtain compound 7h (90 mg, 0.36 mmol) with a yield of 4.7%.

MS m/z (ESI): 252 [M+H]$^+$.

Seventh Step: Preparation of (3aR,5s,6aS)-5-((5-cyano-1-(phenylsulfonyl)-1H-pyrrolo [2,3-b]pyridin-4-yl)(methyl)amino)-N-(3-methoxy-1,2,4-thiadiazole-5-yl) hexahydrocyclopentadiene[c]pyrrole-2(1H)-carboxamide 7i Compound 7e (50 mg, 0.12 mmol), compound 7h (30 mg, 0.12 mmol), DIPEA (31 mg, 0.24 mmol) and THF (10 mL) were added into a reaction flask. The system was reacted for 2 h at 60° C. After the reaction was completed, the system was concentrated directly and purified by column chromatography (v/v, DCM/MeOH=100:1-50:1) to obtain compound 7i (60 mg, 0.10 mmol) with a yield of 83.3%.

MS m/z (ESI): 579 [M+H]+.

Eighth Step: Preparation of (3aR,5s,6aS)-5-((5-cyano-1H-pyrrolo[2,3-b]pyridin-4-yl)(methyl)amino)-N-(3-methoxy-1,2,4-thiadiazole-5-yl)hexahydrocyclopentadiene[c]pyrrole-2(1H)-carboxamide H7

Compound 7i (60 mg, 0.10 mmol), 2M sodium hydroxide solution (2 mL) and methanol (5 mL) were added into a reaction flask. The system was stirred for 1 h at room temperature. After the reaction was completed under TLC monitoring, the system was adjusted to pH=8-10 with diluted hydrochloric acid, concentrated and purified by column chromatography (v/v, DCM/MeOH=100:1-50:1) to obtain compound H7 (25 mg, 0.057 mmol) with a yield of 57.0%.

MS m/z (ESI): 439 [M+H]+.

$^1$H NMR (400 MHz, DMSO-d6) δ 11.93 (s, 1H), 11.57 (s, 1H), 8.15 (s, 1H), 7.31-7.24 (m, 1H), 6.68-6.61 (m, 1H), 4.79-4.68 (m, 1H), 3.89 (s, 3H), 3.73-3.60 (m, 2H), 3.19 (s, 3H), 3.17-3.15 (m, 2H), 2.96-2.79 (m, 2H), 2.21-2.08 (m, 2H), 1.93-1.80 (m, 2H).

Example 08

(3aR,5s,6aS)-4-({2-[(3-ethyl-1,2,4-thiadiazole-5-yl)carbamoyl]-hexahydrocyclopenta[c] pyrrole-5-yl}-methyl-amino)-1H-pyrrolo[2,3-b]pyridin-5-carbonitrile H08

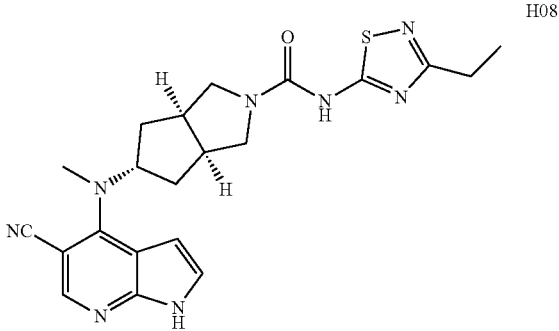 [SMILES: CCc1nsc(NC(=O)N2C[C@H]3C[C@H](N(C)c4c(C#N)cnc5[nH]ccc45)C[C@H]3C2)n1]

Ethyl 3-ethyl-5-amino-1,2,4-thiadiazole was used as a raw material to obtain compound H08 by using the same preparation method as described in Example 7. LCMS (ESI) m/z: 437 [M+H]+.

$^1$H NMR (400 MHz, DMSO-d$_6$) δ 11.89 (s, 1H), 11.42 (s, 1H), 8.12 (s, 1H), 7.26-7.20 (m, 1H), 6.64-6.58 (m, 1H), 4.76-4.65 (m, 1H), 3.73-3.58 (m, 2H), 3.35-3.29 (m, 2H), 3.16 (s, 3H), 2.92-2.78 (m, 2H), 2.69 (q, J=7.5 Hz, 2H), 2.18-2.05 (m, 2H), 1.89-1.78 (m, 2H), 1.20 (t, J=7.6 Hz, 3H).

Example 09

Preparation of 4-{[3-(3-(trifluoromethyl)benzene-sulfonamido)-cyclobutyl-1-yl]-methyl-amino}-1H-pyrrolo[2,3-b]pyridin-5-carbonitrile H09

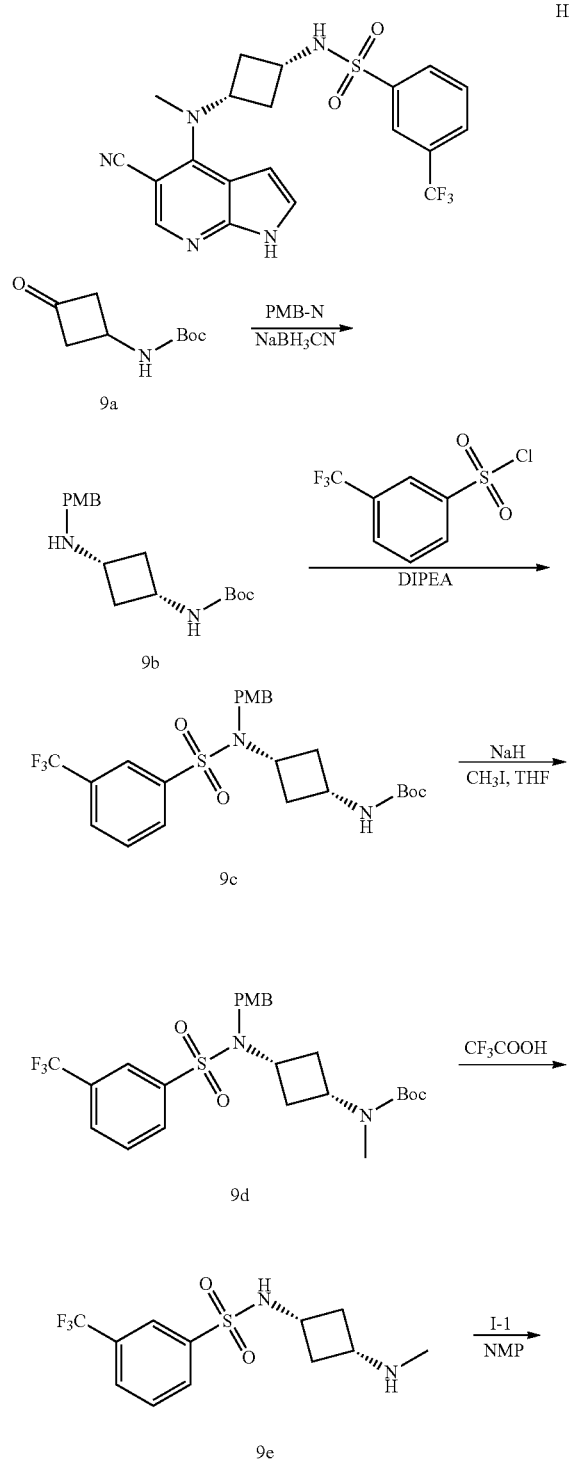

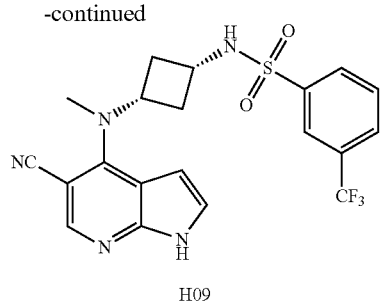

(1) Preparation of tert-butyl (3-((4-methoxybenzyl)amino)cyclobutyl)carbamate 9b Compound tert-butyl (3-oxocyclobutyl)carbamate 9a (1 g, 5.4 mmol), 4-methoxybenzylamine (0.74 g, 5.4 mmol), sodium cyanoborohydride (0.68 g, 10.8 mmol) and 50 mL methanol were added into a reaction flask, stirred for 4 h at room temperature and concentrated to obtain crude products. The crude products were purified by column chromatography (DCM:MeOH=10:1) to obtain white solids, compound 9b tert-butyl (3-((4-methoxybenzyl)amino)cyclobutyl)carbamate (1.3 g) with a yield of 77%. MS m/z (ESI): 307 [M+H]$^+$.

(2) Preparation of tert-butyl (3-((N-(4-methoxybenzyl)-3-(trifluoromethyl)phenyl)sulfonamido)cyclobutyl)carbamate 9c Tert-butyl (3-((4-methoxybenzyl)amino)cyclobutyl)carbamate 9b (250 mg, 0.81 mmol) and DIPEA (313 mg, 2.43 mmol) were dissolved in DCM, and then 3-(trifluoromethyl)phenylsulfonyl chloride (200 mg, 0.81 mmol) was added dropwise. After the addition was completed, this mixture was stirred for 4 h at room temperature, quenched with water, and extracted with DCM. The organic phases were combined, washed with saturated sodium chloride, dried with anhydrous sodium sulfate, filtered and concentrated to obtain crude products. The crude products were purified by column chromatography (PE:EA=3:1) to obtain 200 mg of compound 9c tert-butyl (3-((N-(4-methoxybenzyl)-3-(trifluoromethyl)phenyl)sulfonamido)cyclobutyl)carbamate, which was present as a colorless oily substance, with a yield of 48%.
MS m/z (ESI): 515 [M+H]$^+$ (3) Preparation of tert-butyl (3-((N-(4-methoxybenzyl)-3-(trifluoromethyl)phenyl)sulfonamido)cyclobutyl)(methyl)carbamate 9 d Sodium hydride (7.4 mg, 0.42 mmol) was added into tert-butyl (3-((N-(4-methoxybenzyl)-3-(trifluoromethyl)phenyl)sulfonamido)cyclobutyl)carbamate 9c (110 mg, 0.21 mmol) in THF solution, stirred for 1 h at room temperature, and then iodomethane (60 mg, 0.42 mmol) was added dropwise. This reaction mixture was stirred for 6h at room temperature, quenched with water and extracted with ethyl acetate. The organic phases were combined, washed with saturated sodium chloride, dried with anhydrous sodium sulfate, filtered and concentrated to obtain crude products tert-butyl (3-((N-(4-methoxybenzyl)-3-(trifluoromethyl)phenyl)sulfonamido)cyclobutyl)(methyl)carbamate 9d (100 mg), which was present as a colorless oily substance. The crude products were directly used for a reaction of next step.
MS m/z (ESI): 551 [M+Na]

(4) Preparation of N-(3-(methylamino)cyclobutyl)-3-(trifluoromethyl)benzsulfamide 9e Tert-butyl (3-((N-(4-methoxybenzyl)-3-(trifluoromethyl)phenyl)sulfonamido)cyclobutyl)(methyl)carba mate 9d (100 mg, 0.19 mmol) was dissolved in 2 mL THF, and then trifluoroacetic acid (2 mL) was added. This mixture was stirred for 2 h at room temperature, concentrated and dissolved in DCM again, neutralized with saturated sodium bicarbonate solution. The organic phases were washed with saturated sodium chloride, dried with anhydrous sodium sulfate, filtered and concentrated to obtain crude products. The crude products N-(3-(methylamino)cyclobutyl)-3-(trifluoromethyl)benzsulfamide 9e (50 mg) were directly used for a reaction of next step.

MS m/z (ESI): 309 [M+H]+

(5) N-(3-((5-cyano-1H-pyrrolo[2,3-b]pyridin-4-yl)(methyl)amino)cyclobutyl)-3-(trifluoromethyl)benzsulfamide H09

N-(3-(methylamino)cyclobutyl)-3-(trifluoromethyl)benzsulfamide 9e (50 mg, 0.16 mmol), 4-chloro-1-(phenylsulfonyl)-1H-pyrrolo[2,3-b]pyridin-5-carbonitrile I-1 (50 mg, 0.16 mmol) and DIPEA (62 mg, 0.48 mmol) were dissolved in NMP. This mixture was subjected to a microwave reaction for 2 h at 170° C., cooled, quenched with water and extracted with ethyl acetate. The organic phases were combined, washed with saturated sodium chloride, dried with anhydrous sodium sulfate, filtered and concentrated to obtain crude products. The crude products were purified by column chromatography (DCM:MeOH=10:1) to obtain N-(3-((5-cyano-1H-pyrrolo[2,3-b]pyridin-4-yl)(methyl)amino)cyclobutyl)-3-(trifluoromethyl)benzsulfamide H09 (9.7 mg) with a yield of 13.5%.

MS m/z (ESI): 450 [M+H]+

1H-NMR (400 MHz, Methanol-d4) δ 8.12-8.08 (m, 3H), 7.99-7.90 (m, 2H), 7.77 (t, J=7.9 Hz, 1H), 7.22 (d, J=3.7 Hz, 1H), 6.61 (d, J=3.7 Hz, 1H), 4.27 (tt, J=9.1, 7.0 Hz, 1H), 3.64-3.53 (m, 1H), 3.24 (s, 3H), 2.53 (dtd, J=9.8, 7.1, 2.9 Hz, 2H), 2.07 (qd, =9.0, 2.8 Hz 2H).

Example 10

Preparation of 4-{[3-(3,3,3-trifluoropropanesulfonamido)-cyclobutyl-1-yl]-methyl-amino}-1H-pyrrolo[2,3-b]pyridin-5-carbonitrile H10

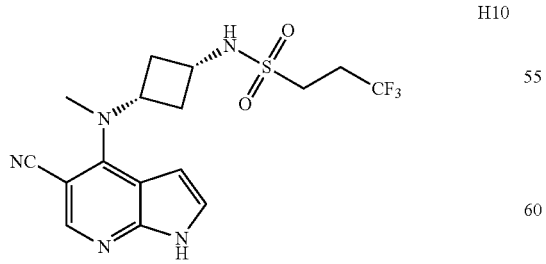

H10

3,3,3-trifluoropropanesulfonyl chloride was used as a raw material to obtain compound H10 by using the same preparation method as described in Example 9. LCMS (ESI) m/z: 388 [M+H]+.

1H NMR (400 MHz, DMSO-d6) δ 11.93 (s, 1H), 8.15 (s, 1H), 7.76 (d, J=8.9 Hz, 1H), 7.32 (t, J=3.1 Hz, 1H), 6.64 (dd, J=3.7, 2.0 Hz, 1H), 4.24 (p, J=8.4 Hz, 1H), 3.55 (h, J=8.6 Hz, 1H), 3.23 (s, 3H), 3.20 (dd, J=7.2, 3.8 Hz, 2H), 2.64 (dt, J=10.8, 7.5 Hz, 4H), 2.25 (dt, J=11.0, 8.6 Hz, 2H).

Example 11

Preparation of 4-{[(3R,4R)-1-(2-cyanoacetyl)-4-methylpiperidin-3-yl]-methyl-amino}-1H-pyrrolo[2,3-b]pyridin-5-carbonitrile H11

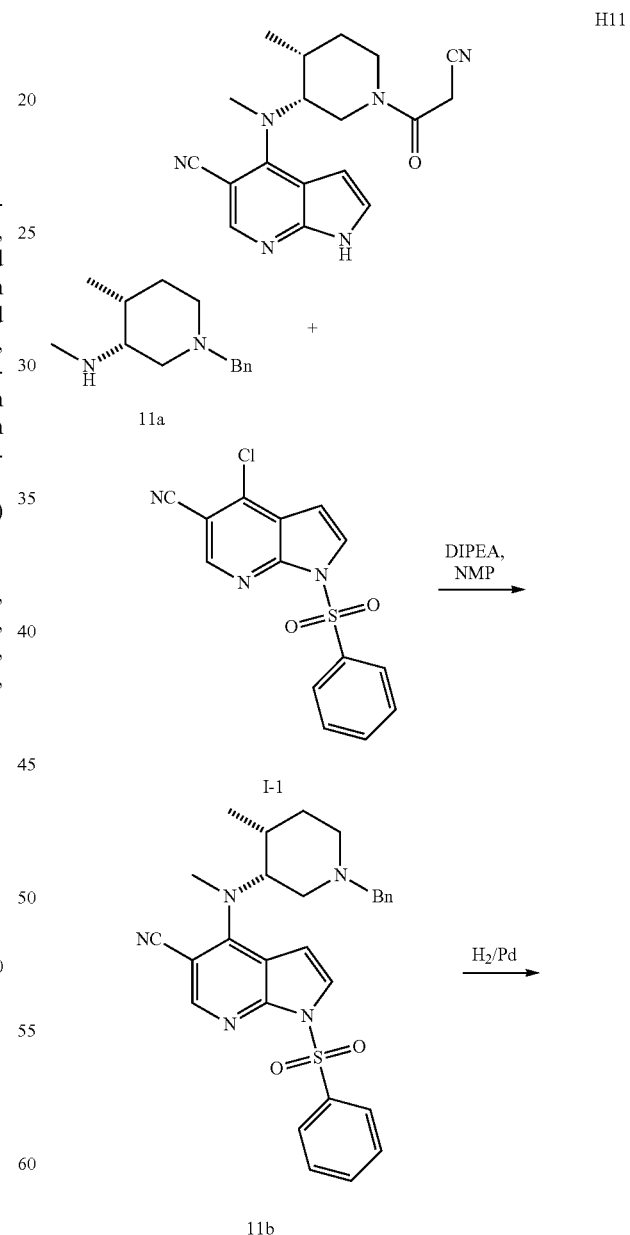

-continued

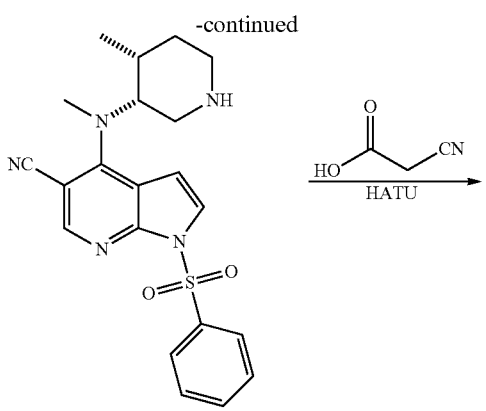

11c

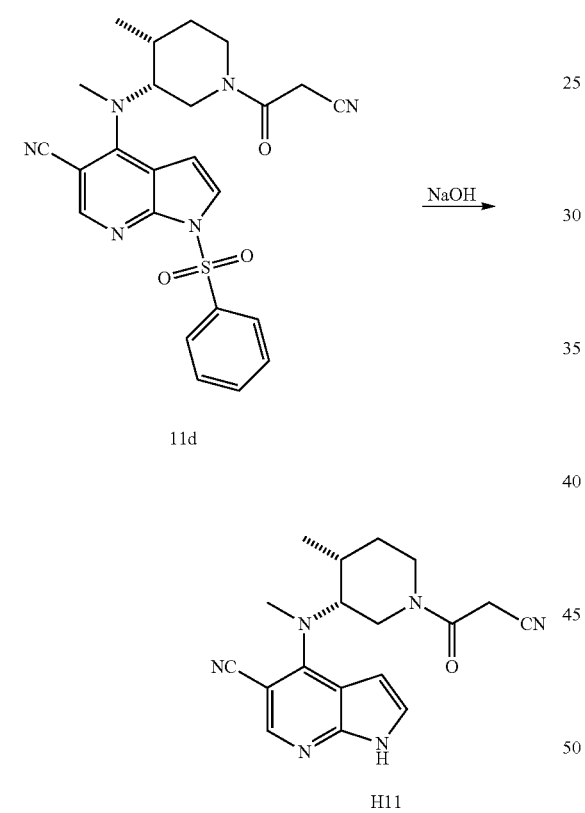

11d

H11

First Step: Preparation of 1-benzenesulfonyl-4-
[((3R,4R)-1-benzyl-4-methylpiperidin-3-yl)-methyl-
amino}-1H-pyrrolo[2,3-b]pyridin-5-carbonitrile 11b Compound 11a (293 mg, 1.35 mmol) and N-methyl pyrrolidone (2 mL) were added into a reaction flask, and then intermediates I-1 (429 mg, 1.35 mmol) and N-isopropyldiethylamine (348 mg, 2.70 mmol) were added. The system was subjected to a microwave reaction for 1 h at 170° C. After the reaction was completed under TLC monitoring, the system was extracted with ethyl acetate and water. The organic phase was washed with water and saturated sodium chloride, dried with anhydrous sodium sulfate and concentrated, followed by purification by column chromatography (v/v, petroleum ether/ethyl acetate=4:1-2:1) to obtain the titled compound 11b (150 mg, 0.30 mmol) with a yield of 22.2%. LCMS (ESI) m/z: 500 [M+H]+.

Second Step: Preparation of 1-benzenesulfonyl-4-
[((3R,4R)-4-methylpiperidin-3-yl)-methyl-amino}-
1H-pyrrolo[2,3-b]pyridin-5-carbonitrile 11c Compound 11b (150 mg, 0.30 mmol) and methanol (10 mL) were added into a reaction flask, and then palladium on carbon was added (30 mg). The system was stirred for 5 h under the protection of hydrogen balloon. After the reaction was completed under TLC monitoring, the system was filtered with kieselguhr, dried by a spin drier (10-15° C.) to obtain the titled compound 11c (100 mg, 0.24 mmol) with a yield of 80.0%. LCMS (ESI) m/z: 410 [M+H]+.

Third Step: Preparation of 1-benzenesulfonyl-4-{
[(3R,4R)-1-(2-cyanoacetyl)-4-methylpiperidin-3-yl]-
methyl-amino}-1H-pyrrolo[2,3-b]pyridin-5-carboni-
trile 11d Compound 11c (100 mg, 0.24 mol) and dichloromethane (30 mL) were added into a reaction flask, and then triethylamine (24 mg, 0.24 mmol), cyanoacetic acid (20 mg, 0.24 mmol) and HATU (91 mg, 0.24 mmol) were added, the system was stirred for 2 h at room temperature. After the reaction was completed under TLC monitoring, the system was extracted with dichloromethane and water. The organic phase was washed with water and saturated sodium chloride, dried with anhydrous sodium sulfate and concentrated, followed by purification by column chromatography (v/v, petroleum ether/ethyl acetate=4:1-2:1) to obtain the titled compound 11d (50 mg, 0.11 mmol) with a yield of 43.8%. LCMS (ESI) m/z: 477 [M+H]+.

Fourth Step: Preparation of 4-{[(3R,4R)-1-(2-cya-
noacetyl)-4-methylpiperidin-3-yl]-methyl-amino}-
1H-pyrrolo[2,3-b]pyridin-5-carbonitrile H11

Methanol (1 mL) was added into a reaction flask, and then compound 11d (50.0 mg, 0.11 mmol) and sodium hydroxide solution (0.15 mL, 0.15 mmol, 1 mol/L) were added separately. The reaction system was stirred for 12 h at room temperature. After the reaction was completed under TLC monitoring, the reaction system was extracted with ethyl acetate and water for three times. The organic phases were combined, washed with water and saturated sodium chloride, dried with anhydrous sodium sulfate and concentrated to obtain crude products. The crude products were purified by preparative TLC to obtain the titled compound H11 (30 mg, 0.089 mmol) with a yield of 80.9%. LCMS (ESI) m/z: 337 [M+H]+.

$^1$H NMR (400 MHz, DMSO-d$_6$) δ 11.40 (s, 1H), 7.91 (s, 1H), 7.10 (s, 1H), 6.83 (s, 1H), 3.88-3.75 (m, 1H), 3.62-3.50 (m, 1H), 3.35-3.31 (m, 1H), 3.29 (s, 3H), 3.25-3.19 (m, 1H), 3.14-3.04 (m, 1H), 2.67 (s, 2H), 1.56-1.46 (m, 1H), 1.19 (s, 2H), 0.97 (d, J=7.1 Hz, 3H).

Example 12

Preparation of (cis)-4-{[3-(3,3,3-trifluoropropane-sulfonamido)-cyclobutyl-1-yl]-amino}-1H-pyrrolo[2,3-b]pyridin-5-carbonitrile H12

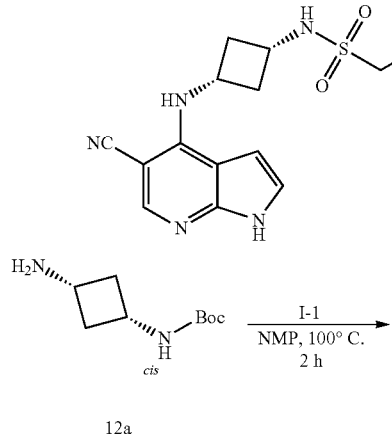

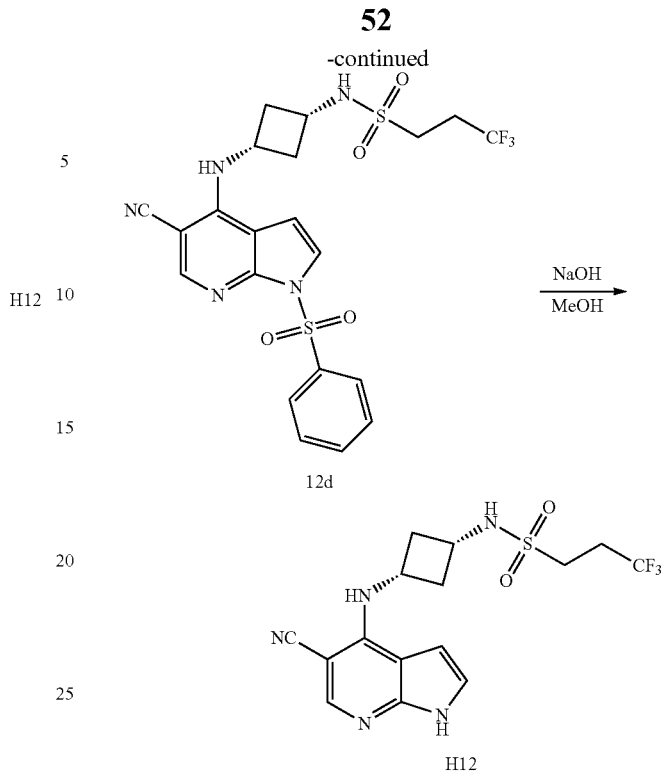

First Step: Preparation of tert-butyl (3-((5-cyano-1-(benzenesulfonyl)-1H-pyrrole[2,3-b] pyridin-4-yl)amino)cyclobutyl) carbamate 12b (Cis)-tert-butyl(3-aminocyclobutyl)carbamate 12a (200 mg, 1.07 mmol), 4-chloro-1-(phenylsulfonyl)-1H-pyrrolo[2,3-b]pyridine-5-carbonitrile I-1 (340 mg, 1.07 mmol) and DIPEA (414 mg, 3.21 mmol) were dissolved in NMP. This mixture was reacted at 100° C. for 2 h, cooled, quenched with water to precipitate taupe solids, filtered and dried to obtain compound tert-butyl (3-((5-cyano-1-(benzenesulfonyl)-1H-pyrrole[2,3-b]pyridin-4-yl)amino)cyclobutyl) carbamate 12b (400 mg) with a yield of 80%.

MS m/z (ESI): 468 [M+H]$^+$

Second Step: Preparation of 4-((3-aminocyclobutyl)amino)-1-(phenylsulfonyl)-1H-pyrrolo[2,3-b]pyridin-5-carbonitrile 12c Tert-butyl (3-((5-cyano-1-(benzenesulfonyl)-1H-pyrrole[2,3-b]pyridine-4-yl)amino)cyclobutyl)carbamate 12b (400 mg, 0.85 mmol) was dissolved in 2 mL THF, and then trifluoroacetic acid (2 mL) was added. This mixture was stirred for 2 h at room temperature, concentrated and dissolved in DCM again, neutralized with saturated sodium bicarbonate solution. The organic phase was washed with saturated sodium chloride, dried with anhydrous sodium sulfate, filtered and concentrated to obtain crude products. The crude products 4-((3-aminocyclobutyl)amino)-1-(phenylsulfonyl)-1H-pyrrolo[2,3-b]pyridin-5-carbonitrile 12c (250 mg) were directly used for a reaction of next step. The yield was 80%.

MS m/z (ESI): 368 [M+H]$^+$

Third Step: Preparation of N-(3-((5-cyano-1-(phenylsulfonyl)-1H-pyrrolo[2,3-b]pyridin-4-yl)amino)cyclobutyl)-3,3,3-trifluoropropane-1-sulfamide 12d 4-((3-aminocyclobutyl)amino)-1-(phenylsulfonyl)-1H-pyrrolo[2,3-b]pyridin-5-carbonitrile 12c (100 mg, 0.27 mmol) and DIPEA (104 mg, 0.81 mmol) were dissolved in DCM, and 3,3,3-trifluoropropane-1-sulfonyl chloride (80 mg, 0.4 mmol) was added slowly at room temperature. After the addition was completed, the mixture was stirred for 2 h at room temperature, quenched with water, extracted with DCM. The organic phases were combined, washed with saturated sodium chloride, dried with anhydrous sodium sulfate, filtered and concentrated to obtain crude products (4) N-(3-((5-cyano-1-(phenylsulfonyl)-1H-pyrrolo[2,3-b] pyridin-4-yl)amino)cyclobutyl)-3,3,3-trifluoropropane-1-sulfamide 12d (100 mg) for a reaction of next step.

MS m/z (ESI): 528 [M+H]+

Fourth Step: Preparation of N-(3-((5-cyano-1H-pyrrolo[2,3-b]pyridin-4-yl)amino)cyclobutyl)-3,3,3-trifluoropropane-1-sulfamide H12

N-(3-((5-cyano-1-(phenylsulfonyl)-1H-pyrrolo[2,3-b] pyridin-4-yl)amino)cyclobutyl)-3,3,3-trifluoropropane-1-sulfamide 12d (100 mg, 0.19 mmol) was dissolved in methanol (4 mL), and then 2 mL of 2 N sodium hydroxide solution was added. This mixture was stirred for 2 h at room temperature, extracted with ethyl acetate. The organic phases were combined, washed with saturated sodium chloride, dried with anhydrous sodium sulfate, filtered and concentrated to obtain crude products. The crude products were purified by column chromatography (DCM: MeOH=10:1) to obtain 36 mg N-(3-((5-cyano-1H-pyrrolo [2,3-b]pyridin-4-yl) amino)cyclobutyl)-3,3,3-trifluoropropane-1-sulfamide H12, which was present as white solids, with a yield of 48%.

MS m/z (ESI): 388 [M+H]+

$^1$H NMR (400 MHz, DMSO-d6) δ 11.77 (s, 1H), 8.03 (s, 1H), 7.75 (d, J=7.6 Hz, 1H), 7.21 (t, J=2.9 Hz, 1H), 7.09 (d, J=6.9 Hz, 1H), 6.76 (dd, J=3.7, 1.9 Hz, 1H), 4.19 (p, J=7.5 Hz, 1H), 3.59 (q, J=8.0 Hz, 1H), 3.25-3.16 (m, 2H), 2.77 (tt, J=8.8, 4.7 Hz, 2H), 2.69-2.58 (m, 2H), 2.14 (dt, J=11.0, 8.4 Hz, 2H).

Example 13

Preparation of (cis)-4-{[3-(3-(trifluoromethyl)benzenesulfonamido)-cyclobutyl-1-yl]-amino}-1H-pyrrolo [2,3-b]pyridin-5-carbonitrile H13

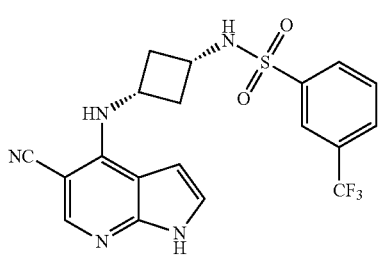

3-trifluoromethylbenzenesulfonyl chloride was used as a raw material to obtain compound H13 by using the same preparation method as described in Example 12. LCMS (ESI) m/z: 436 [M+H]+.

$^1$H NMR (400 MHz, Methanol-d4) δ 8.16-8.10 (m, 2H), 8.00 (s, 1H), 7.95-7.91 (m, 1H), 7.82-7.75 (m, 1H), 7.14 (d, J=3.7 Hz, 1H), 6.66 (d, J=3.6 Hz, 1H), 4.36-4.24 (m, 1H), 3.64 (tt, J=8.9, 7.3 Hz, 1H), 2.69 (dddd, J=9.2, 7.2, 4.6, 2.9 Hz, 2H), 1.94 (qd, J=8.9, 2.9 Hz, 2H).

Example 14

Preparation of (cis)-4-{[3-(propanesulfonamido)-cyclobutyl-1-yl]-methyl-amino}-1H-pyrrolo[2,3-b] pyridin-5-carbonitrile H14

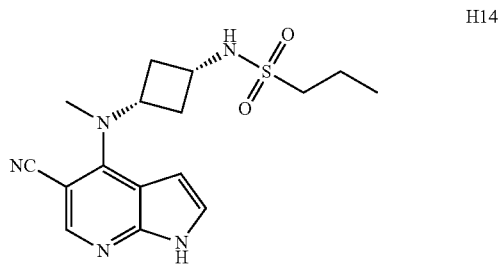 [SMILES: CCCS(=O)(=O)N[C@H]1C[C@@H](N(C)c2c(C#N)cnc3[nH]ccc23)C1]

Propanesulfonyl chloride was used as a raw material to obtain compound H14 by using the same preparation method as described in Example 9. LCMS (ESI) m/z: 348 [M+H]+.

$^1$H NMR (400 MHz, DMSO-d6) δ 11.96 (s, 1H), 8.14 (s, 1H), 7.47 (s, 1H), 7.31 (d, J=3.6 Hz, 1H), 6.64 (d, J=3.6 Hz, 1H), 4.28-4.18 (m, 1H), 3.48 (s, 1H), 2.93-2.84 (m, 2H), 2.68-2.58 (m, 2H), 2.24 (qd, J=9.0, 2.8 Hz, 2H), 1.68-1.56 (m, 2H), 0.94 (t, J=7.4 Hz, 3H).

Example 15

Preparation of (cis)-4-{[3-(3,3,3-trifluoropropane-sulfonamide)-cyclobutyl-1-yl]-methyl-amino}-1H-pyrrolo[2,3-b]pyridin-5-carbonitrile H15

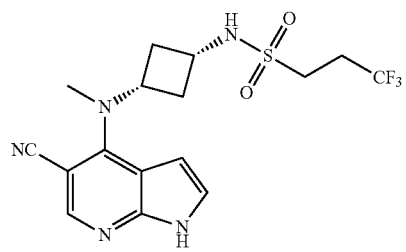

3,3,3-trifluoropropanesulfonyl chloride was used as a raw material to obtain compound H15 by using the same preparation method as described in Example 9.

LCMS (ESI) m/z: 402 [M+H]+.

$^1$H NMR (400 MHz, DMSO-d6) δ 11.93 (s, 1H), 8.15 (s, 1H), 7.76 (d, J=8.9 Hz, 1H), 7.32 (t, J=3.1 Hz, 1H), 6.64 (dd, J=3.7, 2.0 Hz 1H), 4.24 (p, J=8.4 Hz, 1H), 3.55 (h, J=8.6 Hz, 1H), 3.23 (s, 3H), 3.20 (dd, J=7.2, 3.8 Hz, 2H), 2.64 (dt, J=10.8, 7.5 Hz, 4H), 2.25 (dt, J=11.0, 8.6 Hz, 2H).

Example 16

Preparation of (cis)-4-{[3-(4-trifluoromethyl benzenesulfonamido)-cyclobutyl-1-yl]-methyl-amino}-1H-pyrrolo[2,3-b]pyridin-5-carbonitrile H16

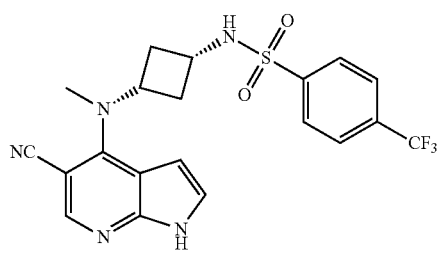

4-trifluoromethylbenzenesulfonyl chloride was used as a raw material to obtain compound H16 by using the same preparation method as described in Example 9. LCMS (ESI) m/z: 450 [M+H]$^+$.

$^1$H NMR (400 MHz, DMSO-d6) δ 7.30 (s, 1H), 7.22 (d, J=8.1 Hz, 2H), 7.06 (d, J=8.3 Hz, 2H), 6.41 (d, J=3.7 Hz, 1H), 5.81 (d, J=3.6 Hz, 1H), 3.50-3.40 (m, 1H), 2.77 (p, J=8.2 Hz, 1H), 2.44 (s, 3H), 1.73 (dtd, J=9.9, 7.2, 3.0 Hz, 2H), 1.33-1.24 (m, 2H).

Example 17

Preparation of (cis)-4-{[3-(4-trifluoromethyl benzenesulfonamido)-cyclobutyl-1-yl]-amino}-1H-pyrrolo[2,3-b]pyridin-5-carbonitrile H17

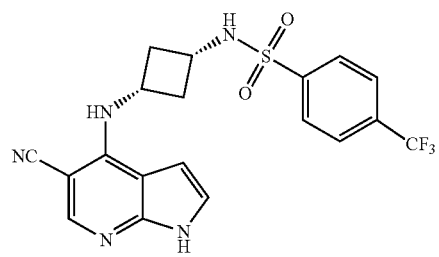

4-trifluoromethylbenzenesulfonyl chloride was used as a raw material to obtain compound H17 by using the same preparation method as described in Example 12. LCMS (ESI) m/z: 436 [M+H]$^+$.

$^1$H NMR (400 MHz, Methanol-d4) δ 8.09-7.97 (m, 3H), 7.88 (dd, J=8.7, 2.7 Hz, 2H), 7.13 (t, J=3.5 Hz, 1H), 6.66 (d, J=3.6 Hz, 1H), 4.34-4.22 (m, 1H), 3.63 (tt, J=9.0, 7.4 Hz, 1H), 2.75-2.65 (m, 2H), 1.96 (qd, J=8.9, 2.9 Hz, 2H).

Example 18

Preparation of (cis)-4-{[3-(benzo[c][1,2,5]oxadiazole-4-sulfonamido)-cyclobutyl-1-yl]-methyl-amino}-1H-pyrrolo[2,3-b]pyridin-5-carbonitrile H18

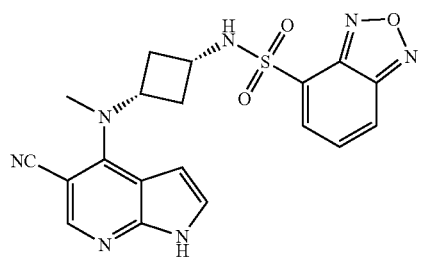

Benzo[c][1,2,5]oxadiazole-4-sulfonyl chloride was used as a raw material to obtain compound H18 by using the same preparation method as described in Example 9. LCMS (ESI) m/z: 424 [M+H]$^+$.

$^1$H NMR (400 MHz, DMSO-d6) δ 11.90 (s, 1H), 8.64 (s, 1H), 8.34 (dd, J=9.1, 0.8 Hz, 1H), 8.12-8.03 (m, 2H), 7.73 (dd, J=9.1, 6.8 Hz, 1H), 7.28 (dd, J=3.7, 2.3 Hz, 1H), 6.55 (dd, J=3.6, 1.9 Hz, 1H), 4.14 (p, J=8.5 Hz, 1H), 3.60 (d, J=8.9 Hz, 1H), 3.13 (s, 3H), 2.37-2.29 (m, 2H), 2.17-2.01 (m, 2H).

Example 19

Preparation of (cis)-4-{[3-(benzo[c][1,2,5]oxadiazole-4-sulfonamido)-cyclobutyl-1-yl]-amino}-1H-pyrrolo[2,3-b]pyridin-5-carbonitrile H19

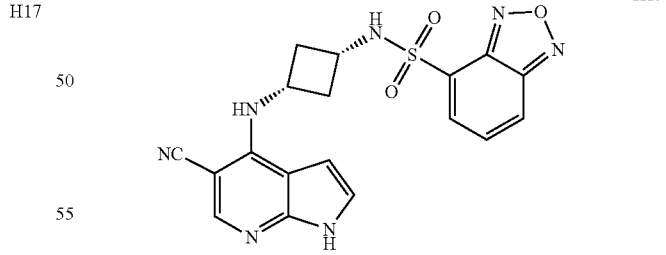

Benzo[c][1,2,5]oxadiazole-4-sulfonyl chloride was used as a raw material to obtain compound H19 by using the same preparation method as described in Example 12. LCMS (ESI) m/z: 410 [M+H]$^+$.

$^1$H NMR (400 MHz, Methanol-d4) δ 8.18 (dd, J=9.1, 0.8 Hz, 1H), 8.10 (dd, J=6.7, 0.8 Hz, 1H), 7.99 (s, 1H), 7.66 (dd, J=9.1, 6.7 Hz, 1H), 7.13 (d, J=3.6 Hz, 1H), 6.64 (d, J=3.6 Hz, 1H), 4.27 (t, J=7.7 Hz, 1H), 3.85-3.74 (m, 1H), 2.67 (dtd, J=10.0, 7.3, 3.0 Hz, 2H), 1.97 (td, J=8.9, 2.9 Hz, 2H).

Example 20
Preparation of (3aR,5s,6aS)-5-((5-cyano-1H-pyrrolo[2,3-b]pyridin-4-yl)amino)-N-(3-methoxy-1,2,4-thiadiazole-5-yl)hexahydrocyclopentadiene[c]pyrrole-2(1H)-carboxamide H20
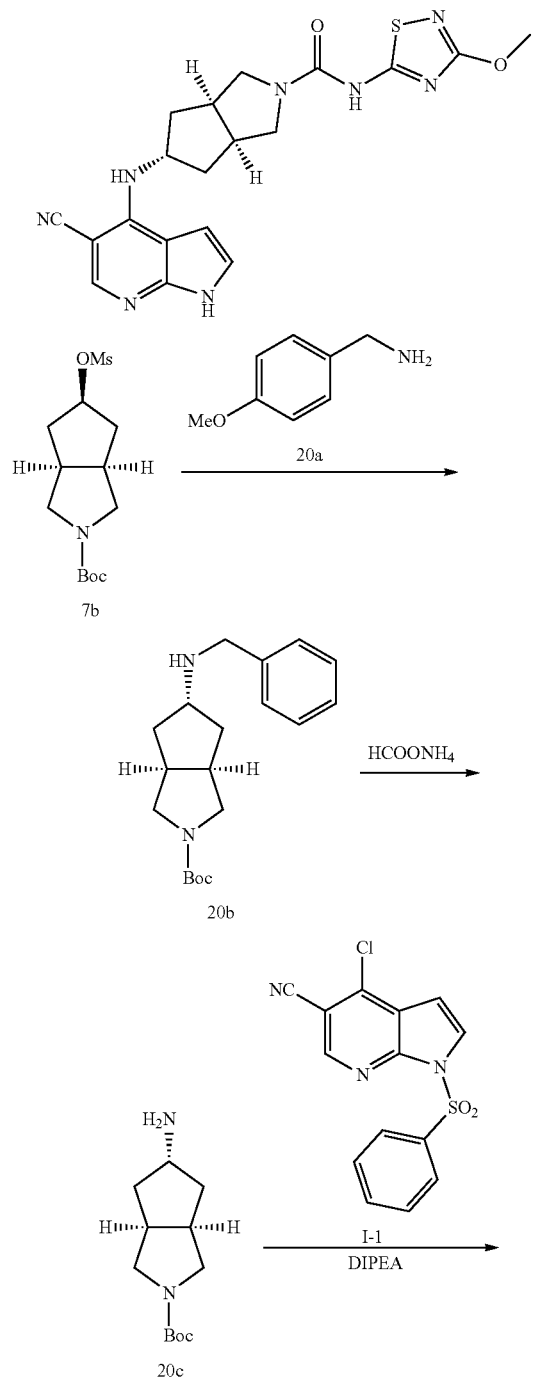
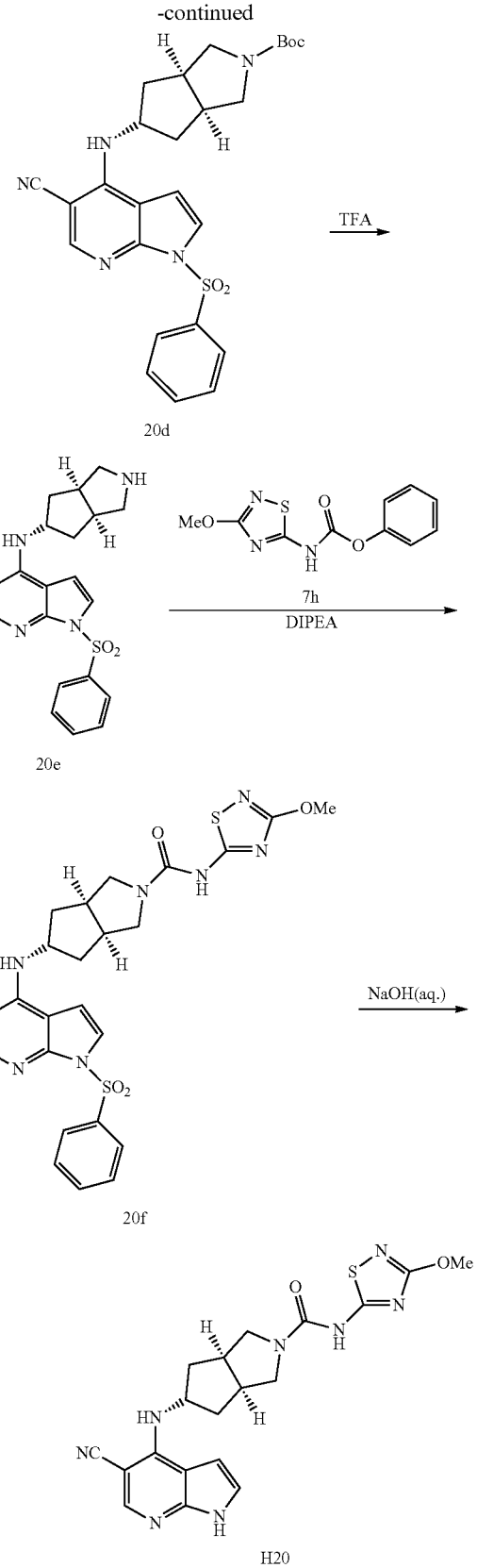

First Step: Preparation of tert-butyl (3aR,5s,6aS)-5-(benzylamino)hexahydrocyclopentadiene[c]pyrrole-2(1H)-carboxylate 20b Compound 7b (500 mg, 1.6 mmol) and compound 20a (0.5 mL, 4.9 mmol) were added into a reaction flask and heated to 80° C. for reacting under a solvent-free condition. After the reaction was completed under TLC monitoring, the system was purified by column chromatography (v/v, DCM/MeOH=100:1-50:1) to obtain compound 20b (400 mg, 1.3 mmol) with a yield of 77.2%.

MS m/z (ESI): 317 [M+H]+.

Second Step: Preparation of tert-butyl (3aR,5s,6aS)-5-aminohexahydrocyclopentadiene[c] pyrrole-2(1H)-carboxylate 20c Compound 20b (350 mg, 1.1 mmol), ammonium formate (1.4 g, 22.1 mmol) and Pd/C (0.7 g) were dissolved in ethanol solvent (15 mL) in a reaction flask and reacted at 80° C. After the reaction was completed under TLC monitoring, the system was purified by column chromatography (v/v, DCM/MeOH=100:1-50:1) to obtain compound 20c (150 mg, 0.66 mmol) with a yield of 59.9%.

MS m/z (ESI): 227 [M+H]+.

Third Step: Preparation of tert-butyl (3aR,5s,6aS)-5-((5-cyano-1-(phenylsulfonyl)-1H-pyrrolo[2,3-b]pyridin-4-yl)amino)hexahydrocyclopentadiene[c]pyrrole-2(1H)-carboxylate 20d Compound 20c (150 mg, 0.66 mmol), DIPEA (1.1 mL, 6.6 mmol), I-1 (421 mg, 1.3 mmol) and NMP (5 mL) were added into a reaction flask. The system was subjected to a reflux reaction for 1.5 h at 140° C. After the reaction was completed, the system was poured into water, extracted with ethyl acetate for three times. The organic phases were combined, washed with water and saturated sodium chloride, dried with anhydrous sodium sulfate, and concentrated at low temperature, followed by purification by column chromatography (v/v, PE/THF=100:1-50:1) to obtain compound 20d (80 mg, 0.16 mmol) with a yield of 23.8%.

MS m/z (ESI): 508 [M+H]+.

Fourth Step: Preparation of 4-(((3aR,5s,6aS)-octahydrocyclopentadiene[c]pyrrole-5-yl)amino)-1-(phenylsulfonyl)-1H-pyrrolo[2,3-b]pyridin-5-carbonitrile 20e Compound 20d (80 mg, 0.16 mmol), TFA (0.1 mL) and DCM (5 mL) were added into a reaction flask. The system was reacted for 1 h at room temperature. After the reaction was completed, the system was concentrated directly to obtain compound 20e (110 mg, 0.27 mmol).

MS m/z (ESI): 408 [M+H]+.

Fifth Step: Preparation of (3aR,5s,6aS)-5-((5-cyano-1-(phenylsulfonyl)-1H-pyrrolo[2,3-b] pyridin-4-yl)amino)-N-(3-methoxy-1,2,4-thiadiazole-5-yl) hexahydrocyclopentadiene[c]pyrrole-2(1H)-carboxamide 20f Compound 20e (110 mg, 0.27 mmol), compound 7h (68 mg, 0.27 mmol), DIPEA (3.0 mL) and THF (5 mL) were added into a reaction flask. The system was reacted for 2 h at 60° C. After the reaction was completed, the system was concentrated directly and purified by column chromatography (v/v, PE/THF=100:1-50:1) to obtain compound 20f (40 mg, 0.07 mmol) with a yield of 26.2%.

MS m/z (ESI): 566 [M+H]+.

Sixth Step: Preparation of (3aR,5s,6aS)-5-((5-cyano-1H-pyrrolo[2,3-b]pyridin-4-yl)amino)-N-(3-methoxy-1,2,4-thiadiazole-5-yl)hexahydrocyclopentadiene[c]pyrrole-2(1H)-carboxamide H20

Compound 20f (40 mg, 0.07 mmol), 2M sodium hydroxide solution (2 mL) and methanol (5 mL) were added into a reaction flask. The system was stirred for 1 h at room temperature. After the reaction was completed under TLC monitoring, the system was adjusted to pH=8-10 with diluted hydrochloric acid, concentrated and purified by column chromatography (v/v, DCM/MeOH=100:1-50:1) to obtain compound H20 (12 mg, 0.03 mmol) with a yield of 39.9%.

MS m/z (ESI): 425 [M+H]+.

$^1$H NMR (400 MHz, DMSO-d6) δ 11.78 (s, 1H), 11.58 (s, 1H), 8.06 (s, 1H), 7.26-7.17 (m, 1H), 6.88-6.70 (m, 2H), 4.75 (q, J=6.9 Hz, 1H), 3.90 (s, 3H), 3.69 (t, J=9.4 Hz, 2H), 3.31-3.35 (m, 2H), 2.91 (m, 2H), 1.99 (d, J=7.8 Hz, 4H).

Example 21

(3aR,5s,6aS)-4-({2-[(3-tert-butyl-1,2,4-thiadiazole-5-yl)carbamoyl]-hexahydrocyclopenta [c]pyrrole-5-yl}-methyl-amino)-1H-pyrrolo[2,3-b]pyridin-5-carbonitrile H21

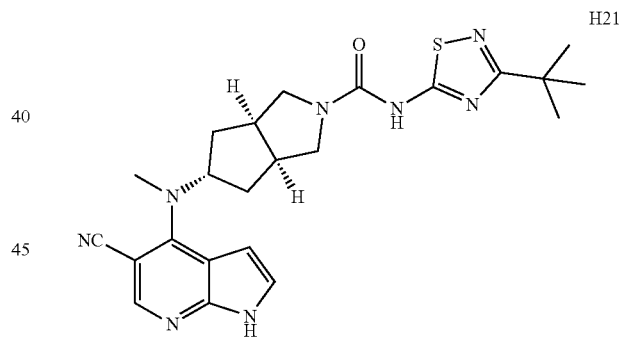

3-tert-butyl-5-amino-1,2,4-thiadiazole was used as a raw material to obtain compound H21 by using the same preparation method as described in Example 7.

MS m/z (ESI): 465 [M+H]+.

$^1$H NMR (400 MHz, DMSO-d$_6$) δ 11.93 (s, 1H), 11.44 (s, 1H), 8.15 (s, 1H), 7.25 (dd, J=3.6, 2.5 Hz, 1H), 6.64 (dd, J=3.7, 2.0 Hz, 1H), 4.73 (t, J=8.1 Hz, 1H), 3.67 (m, 2H), 3.19 (s, 3H), 2.87 (m, 2H), 2.20-2.10 (m, 2H), 1.92-1.82 (m, 2H), 1.31 (s, 9H).

Example 22

Preparation of (3aR,5s,6aS)-4-({2-[(2,2,2-trifluoro-ethyl)-carbamoyl]-hexahydrocyclopenta[c]pyrrole-5-yl}-methyl-amino)-1H-pyrrolo[2,3-b]pyridin-5-carbonitrile H22

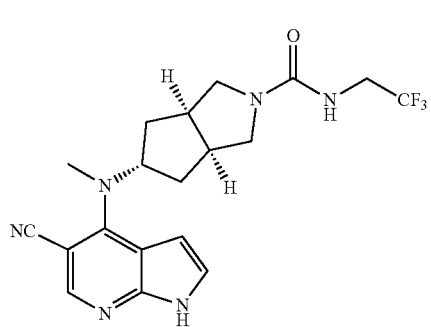

2,2,2-trifluoroethylamine was used as a raw material to obtain compound H22 by using the same preparation method as described in Example 7. LCMS (ESI) m/z: 407 [M+H]+.

¹H NMR (400 MHz, DMSO-d₆) δ 11.90 (s, 1H), 8.12 (s, 1H), 7.30-7.25 (m, 1H), 6.80-6.73 (m, 1H), 6.63-6.58 (m, 1H), 4.75-4.61 (m, 1H), 3.80-3.67 (m, 2H), 3.54-3.44 (m, 2H), 3.15 (s, 3H), 3.09-3.01 (m, 2H), 2.83-2.72 (m, 2H), 2.15-2.02 (m, 2H), 1.84-1.74 (m, 2H).

Example 23

Preparation of (3aR,5S,6aS)-4-{[2-((2S)-2-hydroxy-propionyl)-hexahydrocyclopenta[c]pyrrole-5-yl]-methyl-amino}-1H-pyrrolo[2,3-b]pyridin-5-carbonitrile H23

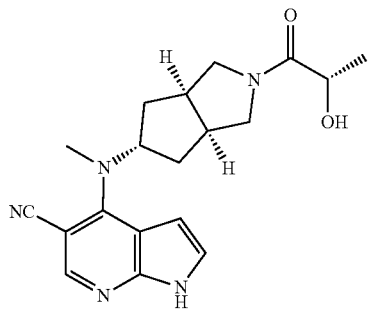

Compound 7e was used as a raw material to obtain compound H23 by using the same preparation method as described in Example 6. LCMS (ESI) m/z: 354 [M+H]+.

¹H NMR (400 MHz, DMSO-d₆) δ 11.91 (s, 1H), 8.13 (s, 1H), 7.29 (s, 1H), 6.62 (s, 1H), 4.74 (t, J=7.2 Hz, 1H), 4.70-4.60 (m, 1H), 4.26-4.17 (m, 1H), 3.80-3.48 (m, 2H), 3.28-3.19 (m, 1H), 3.16 (s, 3H), 2.91-2.67 (m, 2H), 2.16-2.02 (m, 2H), 1.88-1.73 (m, 2H), 1.17-1.03 (m, 3H).

Example 24

Preparation of 4-(methyl((3aR,5s,6aS)-2-((3-(trifluoromethyl)phenyl)sulfonyl)octahydrocyclopentadiene[c]pyrrole-5-yl)amino-1H-pyrrolo[2,3-b]pyridin-5-carbonitrile H24

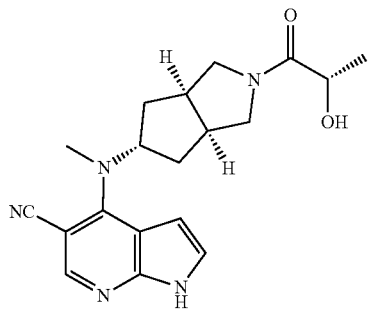

63

-continued

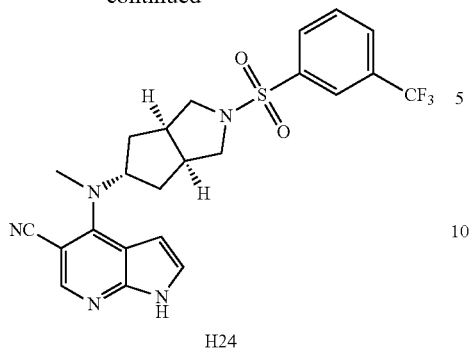

H24

First Step: Preparation of 4-(methyl((3aR,5s,6aS)-2-((3-(trifluoromethyl)phenyl)sulfonyl)octahydrocyclopentadiene[c]pyrrole-5-yl)amino-1-(phenylsulfonyl)-1H-pyrrolo[2,3-b]pyridin-5-carbonitrile 24b Compound 7e (50 mg, 0.12 mmol), compound 24a (30 mg, 0.12 mmol), DIPEA (31 mg, 0.24 mmol) and DCM (10 mL) were added into a reaction flask. The system was reacted for 2 h at room temperature. After the reaction was completed, the system was concentrated directly and purified by column chromatography (v/v, DCM/MeOH=100:1-50:1) to obtain compound 24b (60 mg, 0.095 mmol) with a yield of 79.5%.

MS m/z (ESI): 630 [M+H]+.

Second Step: Preparation of 4-(methyl((3aR,5s,6aS)-2-((3-(trifluoromethyl)phenyl)sulfonyl)octahydrocyclopentadiene[c]pyrrole-5-yl)amino-1H-pyrrolo[2,3-b]pyridin-5-carbonitrile H24

Compound 24b (60 mg, 0.095 mmol), 2M sodium hydroxide solution (2 mL) and methanol (5 mL) were added into a reaction flask. The system was stirred for 1 h at room temperature. After the reaction was completed under TLC monitoring, the system was adjusted to pH=8-10 with diluted hydrochloric acid, concentrated and purified by column chromatography (v/v, DCM/MeOH=100:1-50:1) to obtain compound H24 (25 mg, 0.051 mmol) with a yield of 53.8%.

MS m/z (ESI): 490 [M+H]+.

$^1$H NMR (400 MHz, DMSO-$d_6$) δ 11.92 (s, 1H), 8.16-8.03 (m, 3H), 7.94 (s, 1H), 7.90-7.82 (m, 1H), 7.30-7.24 (m, 1H), 6.55 (dd, J=3.6, 2.0 Hz, 1H), 4.42-4.32 (m, 1H) 3.28-3.22 (m, 2H), 3.09 (s, 3H), 2.90-2.79 (m, 2H), 2.71-2.62 (m, 2H), 2.05-1.94 (m, 2H), 1.70-1.57 (m, 2H).

64

Example 25

Preparation of (3aR,5s,6aS)-N-(4-chloro-3-(trifluoromethyl)phenyl)-5-((5-cyano-1H-pyrrolo[2,3-b]pyridin-4-yl)(methyl)amino)hexahydrocyclopentadiene[c]pyrrole-2(1H)-carboxamide H25

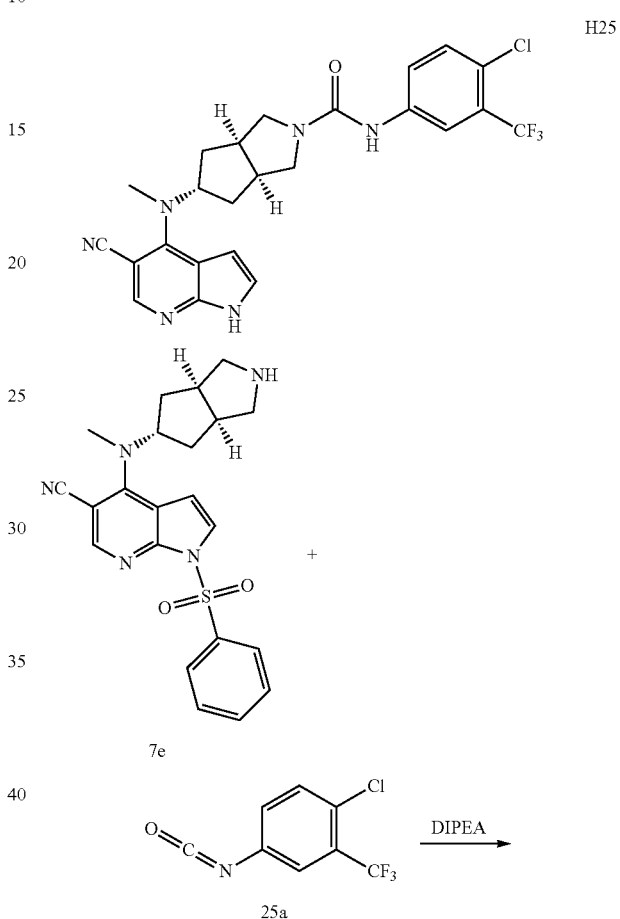

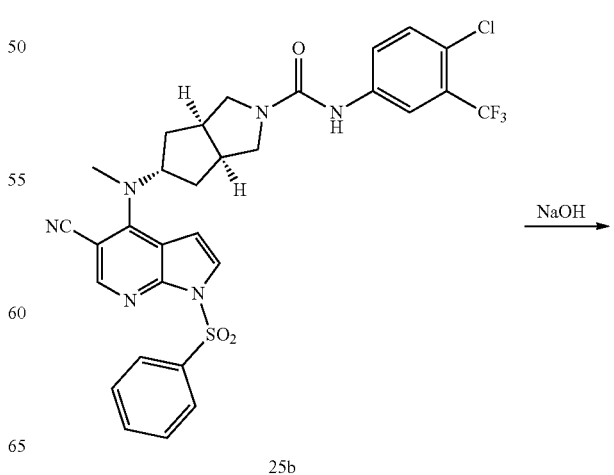

-continued

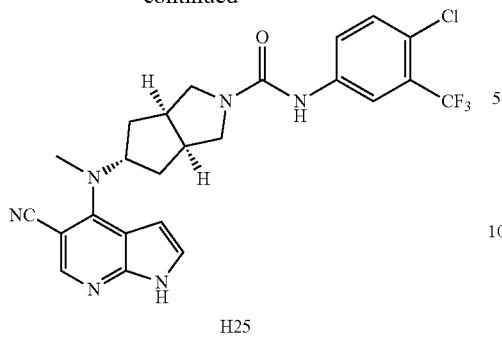

H25

First Step: Preparation of (3aR,5s,6aS)-N-(4-chloro-3-(trifluoromethyl)phenyl)-5-((5-cyano-1-(phenylsulfonyl)-1H-pyrrolo[2,3-b]pyridin-4-yl)(methyl)amino)hexahydrocyclopentadiene[c]pyrrole-2(1H)-carboxamide 25b Compound 7e (50 mg, 0.12 mmol), compound 25a (27 mg, 0.12 mmol), DIPEA (31 mg, 0.24 mmol) and DCM (10 mL) were added into a reaction flask. The system was reacted for 2 h at room temperature. After the reaction was completed, the system was concentrated directly and purified by column chromatography (v/v, DCM/MeOH=100:1-50:1) to obtain compound 24b (50 mg, 0.078 mmol) with a yield of 64.8%.

MS m/z (ESI): 643 [M+H]+.

Second Step: Preparation of (3aR,5s,6aS)-N-(4-chloro-3-(trifluoromethyl)phenyl)-5-((5-cyano-1H-pyrrolo[2,3-b]pyridin-4-yl)(methyl)amino)hexahydrocyclopentadiene[c]pyrrole-2(1H)-carboxamide H25

Compound 25b (50 mg, 0.078 mmol), 2M sodium hydroxide solution (2 mL) and methanol (5 mL) were added into a reaction flask. The system was stirred for 1 h at room temperature. After the reaction was completed under TLC monitoring, the system was adjusted to pH=8-10 with diluted hydrochloric acid, concentrated and purified by column chromatography (v/v, DCM/MeOH=100:1-50:1) to obtain compound H25 (20 mg, 0.040 mmol) with a yield of 51.1%.

MS m/z (ESI): 503 [M+H]+.

$^1$H NMR (400 MHz, DMSO-d$_6$) δ 11.90 (s, 1H), 8.60 (s, 1H), 8.12 (s, 1H), 8.08 (d, J=2.4 Hz, 1H), 7.83-7.77 (m, 1H), 7.52 (d, J=8.9 Hz, 1H), 7.28-722 (m, 1H), 6.68-6.60 (m, 1H), 4.77-4.68 (m, 1H), 3.68-3.57 (m, 2H), 3.26-3.21 (m, 2H), 3.17 (s, 3H), 2.89-2.77 (m, 2H), 2.17-2.08 (m, 2H), 1.89-1.80 (m, 2H).

Example 26

Preparation of (3aR,5s,6aS)-5-((5-cyano-1H-pyrrolo[2,3-b]pyridin-4-yl)(methyl)amino)-N-(3-cyclopropyl-1,2,4-thiadiazol-5-yl)hexahydrocyclopentadiene[c]pyrrole-2(1H)-carboxamide H26

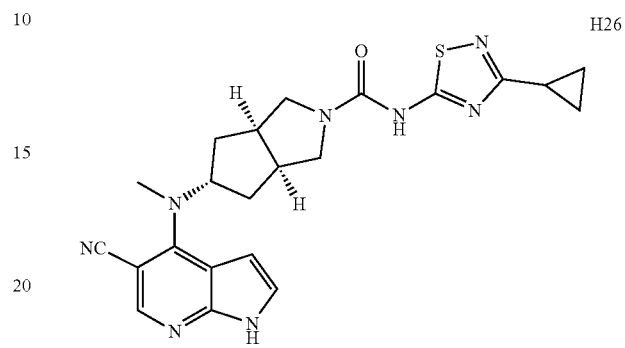

3-cyclopropyl-5-amino-1,2,4-thiadiazole was used as a raw material to obtain compound H26 by using the same preparation method as described in Example 7.

MS m/z (ESI): 449 [M+H]+.

$^1$H NMR (400 MHz, DMSO-d$_6$) δ 11.95 (s, 1H), 11.45 (s, 1H), 8.15 (s, 1H), 7.31-7.24 (m, 1H), 6.64 (dd, J=3.5, 1.8 Hz, 1H), 4.78-4.68 (m, 1H), 3.74-3.61 (m, 2H), 3.34-3.28 (m, 2H), 3.19 (s, 3H), 2.95-2.78 (m, 2H), 2.20-2.05 (m, 3H), 1.91-1.81 (m, 2H), 1.00-0.85 (m, 4H).

Example 27

Preparation of 4-(methyl((3aR,5s,6aS)-2-((3,3,3-trifluoropropyl)sulfonyl)octahydrocyclopentadiene[c]pyrrole-5-yl)amino-1H-pyrrolo[2,3-b]pyridin-5-carbonitrile H27

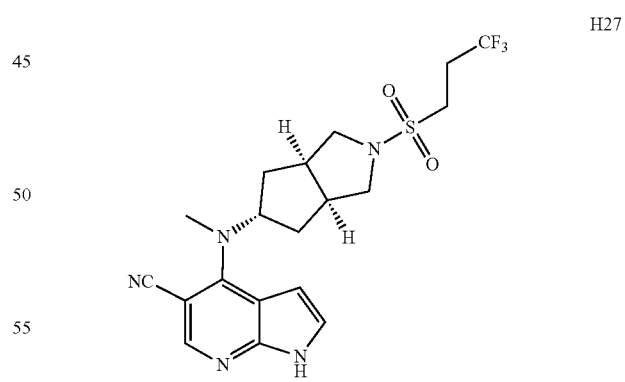

3,3,3-trifluoropropanesulfonyl chloride was used as a raw material to obtain compound H27 by using the same preparation method as described in Example 24.

MS m/z (ESI): 442 [M+H]+.

$^1$H NMR (400 MHz, DMSO-d$_6$) δ 11.92 (s, 1H), 8.13 (s, 1H), 7.33-7.26 (m, 1H), 6.65 (dd, J=3.4, 2.0 Hz, 1H), 4.70-4.61 (m, 1H), 3.50-3.42 (m, 2H), 3.36-3.30 (m, 2H), 3.15 (s, 3H), 3.09-3.02 (m, 2H), 2.88-2.79 (m, 2H), 2.72-2.62 (m, 2H), 2.15-2.02 (m, 2H), 1.83-1.72 (m, 2H).

Example 28

Preparation of 4-(((3aR,5s,6aS)-2-((3-fluorophenyl)sulfonyl)octahydrocyclopentadiene[c]pyrrole-5-yl)(methyl)amino-1H-pyrrolo[2,3-b]pyridin-5-carbonitrile H28

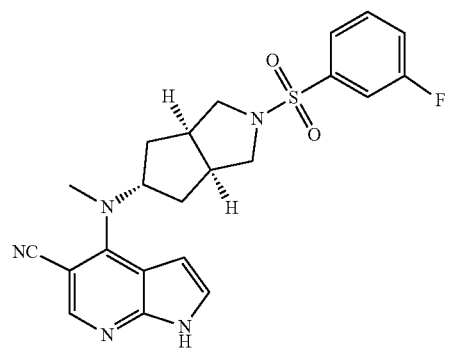

H28

3-trifluorobenzenesulfonyl chloride was used as a raw material to obtain compound H28 by using the same preparation method as described in Example 24.

MS m/z (ESI): 440 [M+H]+.

$^1$H NMR (400 MHz, DMSO-d$_6$) δ 11.92 (s, 1H), 8.10 (s, 1H), 7.71-7.62 (m, 1H), 7.62-7.50 (m, 3H), 7.32-7.25 (m, 1H), 6.54 (dd, J=3.6, 2.0 Hz, 1H), 4.42-4.32 (m, 1H), 3.28-3.22 (m, 2H, 3.09 (s, 3H) 2.87-2.75 (m, 2H), 2.72-2.60 (m, 2H), 2.06-1.92 (m, 2H), 1.68-1.54 (m, 2H).

Example 29

Preparation of (cis)-1-(3-((5-cyano-1H-pyrrolo[2,3-b]pyridin-4-yl)(methyl)amino)cyclobutyl)-3-(3-methoxy-1,2,4-thiadiazole-5-yl)urea H29

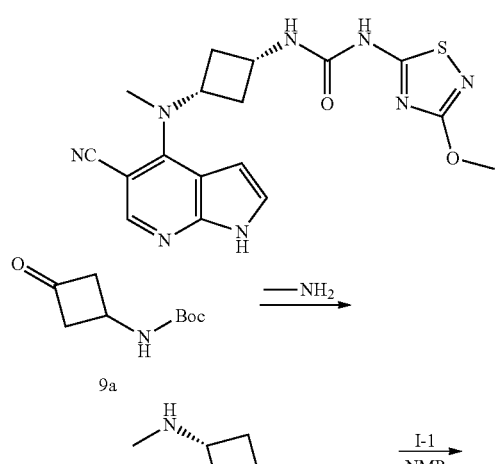

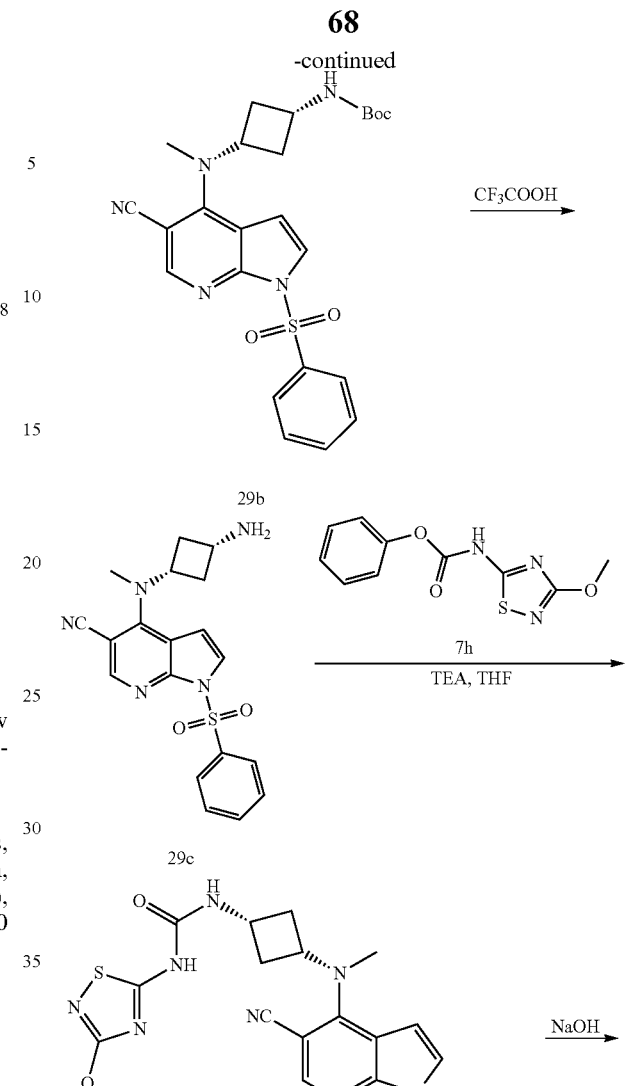

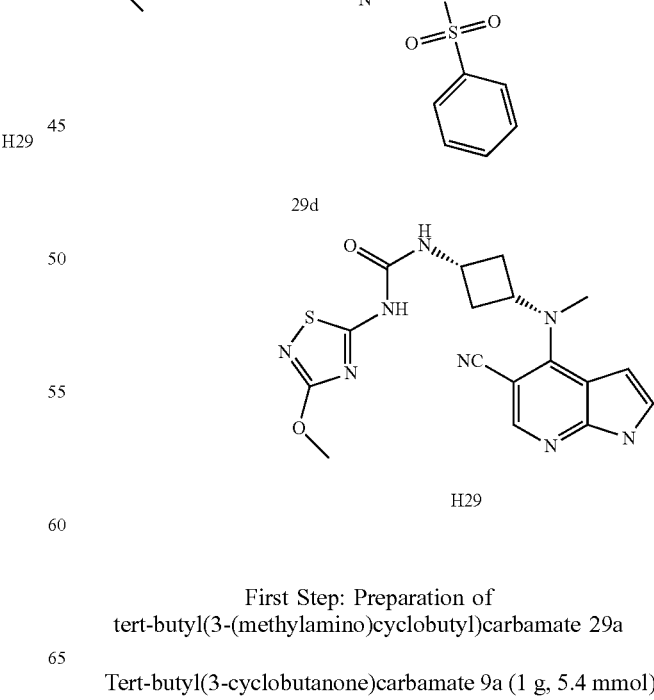

First Step: Preparation of tert-butyl(3-(methylamino)cyclobutyl)carbamate 29a

Tert-butyl(3-cyclobutanone)carbamate 9a (1 g, 5.4 mmol) and methylamine hydrochloride (0.55 g, 8.1 mmol) were dissolved in acetic acid, and then sodium borohydride (0.4 g, 10.8 mmol) was added. This mixture was stirred overnight at room temperature, quenched with water, neutralized with saturated sodium bicarbonate aqueous solution, extracted with DCM for 5 times. The organic phases were combined, washed with saturated sodium chloride, dried with anhydrous sodium sulfate, filtered and concentrated to obtain crude products. The crude products were purified by column chromatography (DCM:MeOH=8:1) to obtain tert-butyl(3-(methylamino)cyclobutyl)carbamate 29a (400 mg) with a yield of 37%.

MS m/z (ESI): 201 [M+H]+.

Second Step: Preparation of tert-butyl(3-(methylamino)cyclobutyl)carbamate 29b

Tert-butyl(3-(methylamino)cyclobutyl)carbamate 29a (300 mg, 1.5 mmol), 4-chloro-1-(phenylsulfonyl)-1H-pyrrolo[2,3-b]pyridin-5-carbonitrile I-1 (475 mg, 1.5 mmol) and DIPEA (580 mg, 4.5 mmol) were dissolved in NMP. This mixture was stirred for 2 h at 170° C., cooled, quenched with water and extracted with ethyl acetate. The organic phases were combined, washed with saturated sodium chloride, dried with anhydrous sodium sulfate, filtered and concentrated to obtain crude products. The crude products were purified by column chromatography (PE:EA=1:1) to obtain tert-butyl(3-(methylamino)cyclobutyl)carbamate 29b (400 mg), which was present as orange solids, with a yield of 55%.

MS m/z (ESI): 482 [M+H]+.

Third Step: Preparation of 4-((3-aminocyclobutyl)(methyl)amino)-1-(phenylsulfonyl)-1H-pyrrolo[2,3-b]pyridin-5-carbonitrile 29c Tert-butyl(3-(methylamino)cyclobutyl) carbamate 29b (400 mg, 0.83 mmol) was dissolved in 2 mL DCM, and then trifluoroacetic acid (2 mL) was added. This mixture was stirred for 2 h at room temperature, concentrated and dissolved in DCM again, neutralized with saturated sodium bicarbonate solution. The organic phases were washed with saturated sodium chloride, dried with anhydrous sodium sulfate, filtered and concentrated to obtain crude products 4-((3-aminocyclobutyl)(methyl)amino)-1-(phenylsulfonyl)-1H-pyrrolo[2,3-b]pyridin-5-carbonitrile 29c (200 mg) which was directly used for a reaction of next step.

MS m/z (ESI): 382 [M+H]+.

Fourth Step: Preparation of 1-(3-((5-cyano-1-(phenylsulfonyl)-1H-pyrrolo[2,3-b]pyridin-4-yl)(methyl)amino)cyclobutyl)-3-(3-methoxy-1,2,4-thiadiazole-5-yl)urea 29d 4-((3-aminocyclobutyl)(methyl)amino)-1-(phenylsulfonyl)-1H-pyrrolo[2,3-b]pyri din-5-carbonitrile 29c (150 mg, 0.39 mmol), phenyl (3-methoxy-1,2,4-thiadiazole-5-yl) carbamate 7h (100 mg, 0.39 mol) and DIPEA (150 mg, 1.17 mmol) were dissolved in THF. This mixture was stirred for 1 h at 60° C. and concentrated to obtain crude products. The crude products were purified by column chromatography (DCM:MeOH=20:1) to obtain (2) 1-(3-((5-cyano-1-(phenylsulfonyl)-1H-pyrrolo[2,3-b]pyridin-4-yl)(methyl)amino) cyclobutyl)-3-(3-methoxy-1,2,4-thiadiazole-5-yl)urea 29d (100 mg) with a yield of 47%.

MS m/z (ESI): 539 [M+H]+.

Fifth Step: Preparation of 1-(3-((5-cyano-1H-pyrrolo[2,3-b]pyridin-4-yl)(methyl)amino)cyclobutyl)-3-(3-methoxy-1,2,4-thiadiazole-5-yl)urea H29

1-(3-((5-cyano-1-(phenylsulfonyl)-1H-pyrrolo[2,3-b]pyridin-4-yl)(methyl)amino)cyclobutyl)-3-(3-methoxy-1,2,4-thiadiazole-5-yl)urea 29d (100 mg, 0.18 mmol) was dissolved in methanol (4 mL), and then 2 mL of 2 N sodium hydroxide solution was added. This mixture was stirred for 2 h at room temperature, extracted with ethyl acetate. The organic phases were combined, washed with saturated sodium chloride, dried with anhydrous sodium sulfate, filtered and concentrated to obtain crude products. The crude products were purified by column chromatography (DCM:MeOH=10:1) to obtain 1-(3-((5-cyano-1H-pyrrolo[2,3-b]pyridin-4-yl)(methyl)amino)cyclobutyl)-3-(3-methoxy-1,2,4-thiadiazole-5-yl)urea H29 (15 mg) with a yield of 21%.

MS m/z (ESI): 399 [M+H]+.

$^1$H NMR (400 MHz, DMSO-d6) δ 11.92 (s, 1H), 11.39 (s, 1H), 8.15 (s, 1H), 7.41-7.24 (m, 2H), 6.65 (dd, J=3.6, 2.0 Hz, 1H), 4.28 (p, J=8.2 Hz, 1H), 3.94-3.87 (m, 1H), 3.27 (s, 3H), 2.58 (d, J=8.6 Hz, 2H), 2.32 (dt, J=11.9, 9.1 Hz, 2H).

Example 30

Preparation of (3aR,5s,6aS)-4-({2-[(3-isopropyl-1,2,4-thiadiazole-5-yl)carbamoyl]-hexahydrocyclopenta[c]pyrrole-5-yl}-methyl-amino)-1H-pyrrolo[2,3-b]pyridin-5-carbonitrile H30

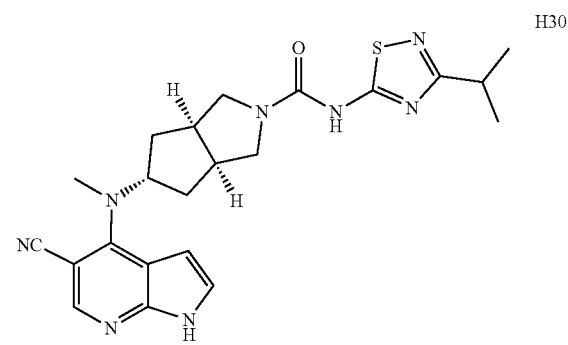 [SMILES: CC(C)c1nsc(NC(=O)N2C[C@H]3C[C@H](N(C)c4c(C#N)cnc5[nH]ccc45)C[C@H]3C2)n1]

3-isopropyl-5-amino-1,2,4-thiadiazole was used as a raw material to obtain compound H30 by using the same preparation method as described in Example 7.

MS m/z (ESI): 451 [M+H]+.

$^1$H NMR (400 MHz, DMSO-d$_6$) δ 11.90 (s, 1H), 11.44 (s, 1H), 8.11 (s, 1H), 7.28-7.15 (m, 1H), 6.61 (dd, J=3.7, 2.0 Hz, 1H), 4.70 (m, 1H), 3.63 (m, 2H), 3.31 (m, 2H), 3.16 (s, 3H), 2.98 (p, J=7.0 Hz, 1H), 2.84 (s, 2H), 2.22-2.01 (m, 2H), 1.83 (dd, J=13.2, 7.6 Hz, 2H), 1.21 (d, 6H).

Example 31

Preparation of (3aR,5s,6aS)-4-({2-[(1-ethyl-1H-1,2,4-triazole-3-yl)-carbamoyl]-hexahydrocyclopenta[c]pyrrole-5-yl}-methyl-amino)-1H-pyrrolo[2,3-b]pyridin-5-carbonitrile H31

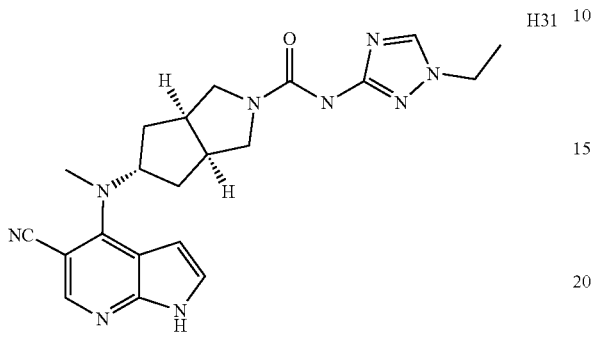

1-ethyl-3-amino-1H-1,2,4-triazole was used as a raw material to obtain compound H31 by using the same preparation method as described in Example 7.

MS m/z (ESI): 420 [M+H]+.

$^1$H NMR (400 MHz, DMSO-d$_6$) δ 11.95 (s, 1H), 8.58 (s, 1H), 8.28 (s, 1H), 8.16 (s, 1H), 7.37-7.30 (m, 1H), 6.67 (dd, J=3.4, 0.9 Hz, 1H), 4.81-4.70 (m, 1H), 4.08 (q, J=7.3 Hz, 2H), 3.65-3.54 (m, 2H), 3.19 (s, 3H), 3.19-3.13 (m, 2H), 2.91-2.75 (m, 2H), 2.21-2.07 (m, 2H), 1.91-1.77 (m, 2H), 1.35 (t, J=7.3 Hz, 31H).

Example 32

Preparation of (3aR,5s,6aS)-4-({2-[(3-cyclopropyl-1,2,4-oxadiazole-5-yl)carbamoyl]-hexahydrocyclopenta[c]pyrrole-5-yl}-methyl-amino)-1H-pyrrolo[2,3-b]pyridin-5-carbonitrile H32

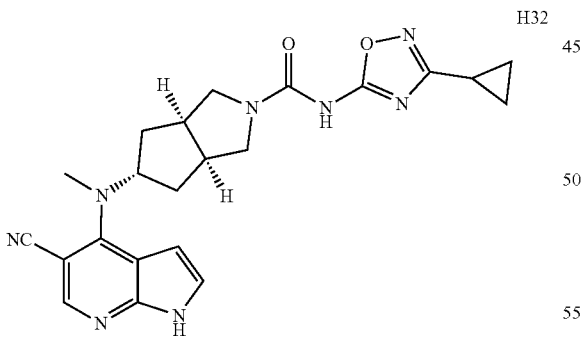

3-cyclopropyl-5-amino-1,2,4-oxadiazole was used as a raw material to obtain compound H32 by using the same preparation method as described in Example 7.

MS m/z (ESI): 433 [M+H]+.

$^1$H NMR (400 MHz, DMSO-d$_6$) δ 11.91 (s, 1H), 10.68 (s, 1H), 8.12 (s, 1H), 7.30-7.22 (m, 1H), 6.66-6.57 (m, 1H), 4.75-4.63 (m, 1H), 3.69-3.49 (m, 2H), 3.29-3.20 (m, 2H), 3.15 (s, 3H), 2.88-2.71 (m, 2H), 2.17-2.03 (m, 2H), 2.01-1.89 (m, 1H), 1.87-1.71 (m, 2H), 1.02-0.86 (m, 2H), 0.85-0.72 (m, 2H).

Example 33

(3aR,5s,6aS)-4-({2-[(3-dimethylamino-1,2,4-thiadiazole-5-yl)carbamoyl]-hexahydrocyclopenta[c]pyrrole-5-yl}-methyl-amino)-1H-pyrrolo[2,3-b]pyridin-5-carbonitrile H33

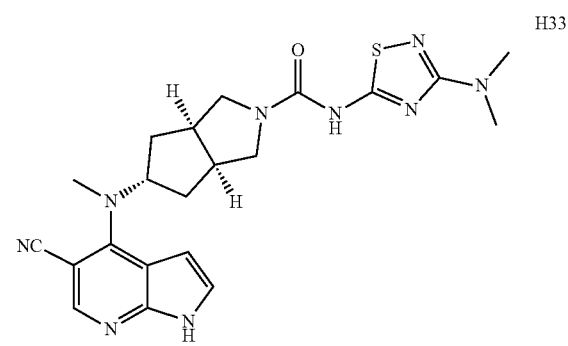

Preparation of 3-(N,N-dimethylamino)-5-amino-1,2,4-thiadiazole was used as a raw material to obtain compound H33 by using the same preparation method as described in Example 7.

MS m/z (ESI): 452 [M+H]+.

$^1$H NMR (400 MHz, DMSO-d$_6$) δ 11.92 (s, 1H), 1.22 (s, 1H), 8.15 (s, 1H), 7.32-7.26 (m, 1H), 6.69-6.63 (m, 1H), 4.77-4.70 (m, 1H), 3.72-3.59 (m, 2H), 3.29 (s, 3H), 3.19 (s, 3H), 3.01 (s, 3H), 2.93-2.81 (m, 2H), 2.20-2.09 (m, 2H), 2.07-1.93 (m, 2H), 1.92-1.79 (m, 2H).

Example 34

Preparation of 4-((1-((3-(trifluoromethyl)phenyl)sulfonyl)piperidin-4-yl)amino)-2,3-dihydro-1H-pyrrolo[2,3-b]pyridin-4-carbonitrile H34

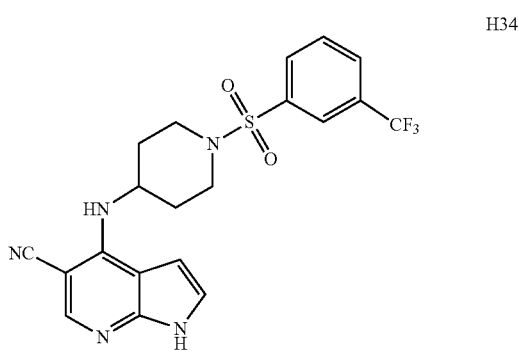 [SMILES: N#Cc1cnc2[nH]ccc2c1NC1CCN(S(=O)(=O)c2cccc(C(F)(F)F)c2)CC1]

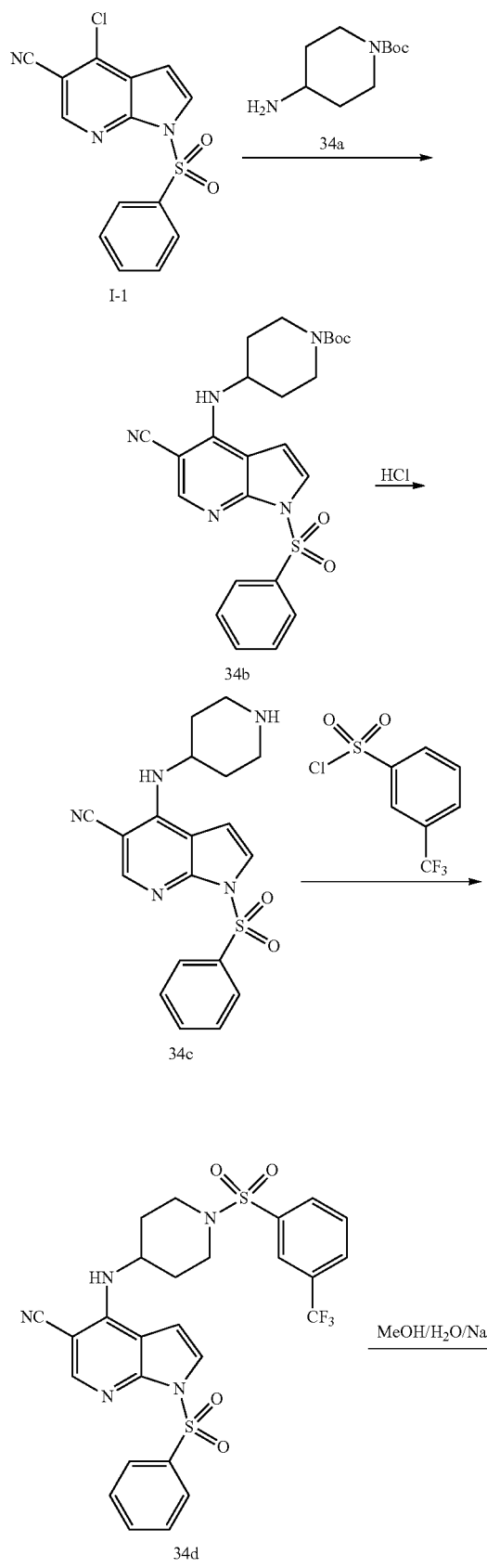

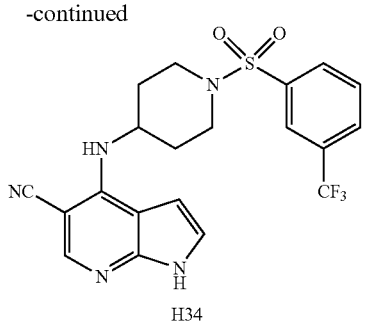

H34

First Step: Preparation of tert-butyl 4-((5-cyano-1-(benzenesulfonyl)-2,3-dihydro-1H-pyrrole[2,3-b]pyridin-4-yl)amino)piperidin-1-carboxylic ester 34b 4-chloro-1-(phenylsulfonyl)-2,3-dihydro-1H-pyrrolo[2,3-b]pyridin-5-carbonitrile I-1 (500 mg, 1.6 mmol, 1.0 eq) and tert-butyl 4-aminopiperidin-1-carboxylate 34a (0.96 g, 4.8 mmol, 3.0 eq) were added in NMP (5 ml), and then DIPEA (0.53 ml, 3.2 mmol, 2.0 eq) was added. The system was subjected to a microwave reaction for 1 h at 100° C., cooled to room temperature, diluted with water (20 ml), extracted with ethyl acetate (50 ml). The organic layers were washed with brine (10 ml), concentrated and purified by flash column (PE-PE/EA=2:1) to obtain white solids 34b (750 mg).

MS m/z (ESI): 482 [M+1]$^+$

Second Step: Preparation of 1-(phenylsulfonyl)-4-(piperidin-4-yl-amino)-2,3-dihydro-1H-pyrrolo[2,3-b]pyridin-5-carbonitrile 34c Compound 34b (750 mg, 1.6 mmol, 1.0 eq) was added into 2N of HCl/EA (30 ml), reacted overnight at room temperature, filtered and dried in vacuum to obtain white solids 34c (600 mg).

MS m/z (ESI): 382 [M+1]$^+$

Third Step: Preparation of 1-(phenylsulfonyl)-4-((1-((3-(trifluoromethyl)phenyl) sulfonyl) piperidin-4-yl)amino)-2,3-dihydro-1H-pyrrolo[2,3-b]pyridin-5-carbonitrile 34d Compound 34c (100 mg, 0.26 mmol, 1.0 eq) and TEA (53 mg, 0.52 mmol, 2.0 eq) were dissolved in anhydrous DCM (10 ml). 3-trifluoromethylbenzenesulfonyl chloride (64 mg, 0.26 mmol, 1.0 eq) was added dropwise to DCM solution (5 ml). After the addition was completed, the system was reacted for 1 h at room temperature. Then, the system was quenched with water (10 ml) and layered. The organic layers were dried with anhydrous sodium sulfate, concentrated and purified by flash column to obtain white solids 34d (160 mg).

MS m/z (ESI): 590 [M+1]$^+$

Fourth Step: Preparation of 4-((1-((3-(trifluoromethyl)phenyl)sulfonyl)piperidin-4-yl)amino)-2,3-dihydro-1H-pyrrolo[2,3-b]pyridin-5-carbonitrile H34

Compound 34d (160 mg, 0.27 mmol, 1.0 eq) was dissolved in a mixed solvent of methanol (3 ml) and THF (3 ml), and then 2N of NaOH (0.7 ml, 1.4 mmol, 5.0 eq) was added and reacted for 2 h at room temperature to obtain a reaction liquid. The reaction liquid was stirred directly and purified by flash column (DCM-DCM/MeOH=20:1) to obtain white solid H34 (56 mg).

MS m/z (ESI): 450 [M+1]$^+$ $^1$H NMR (400 MHz, DMSO-d$_6$) δ 11.80 (s, 1H), 8.18-8.08 (m, 2H), 8.04 (s, 1H), 8.01-7.91 (m, 2H), 7.21 (dd, J=3.5, 2.5 Hz, 1H), 6.75-6.65 (m, 2H), 4.07 (s, 1H), 3.76 (d, J=11.8 Hz, 2H), 2.54 (d, J=10.2 Hz, 2H), 2.05 (d, J=11.3 Hz, 2H), 1.75 (qd, =12.2, 4.0 Hz, 2H).

Example 35

Preparation of 4-((1-((3-(trifluoromethyl)phenyl)sulfonyl)piperidin-4-yl)-methyl-amino)-2,3-dihydro-1H-pyrrolo[2,3-b]pyridin-5-carbonitrile H35

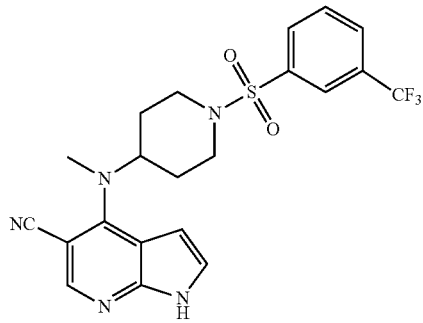

H35

Tert-buty 4-(methylamino)-piperidin-1-carboxylate was used as a raw material to obtain compound H35 by using the same preparation method as described in Example 34.

MS m/z (ESI): 464 [M+1]$^+$ $^1$H NMR (400 MHz, DMSO-d$_6$) δ 8.13 (q, J=8.0 Hz, 3H), 8.00 (s, 1H), 7.93 (t, J=7.9 Hz, 1H), 7.32 (t, J=3.0 Hz, 1H), 6.61-6.55 (m, 1H), 3.90 (dd, J=44.8, 11.8 Hz, 3H), 3.14 (s, 3H), 2.45 (d, J=11.4 Hz, 2H), 2.03 (q, J=11.1 Hz, 3H), 1.85 (d, J=12.3 Hz, 2H).

Example 36

Preparation of 3-((5-cyano-1H-pyrrolo[2,3-b]pyridin-4-yl)amino)-N-(2,2,2-trifluoroethyl) pyrrolidin-1-carboxamide H36

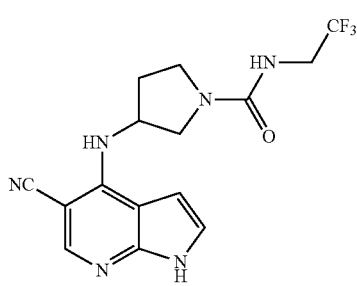

H36

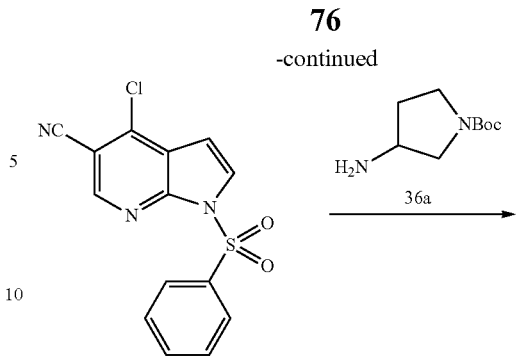

I-1

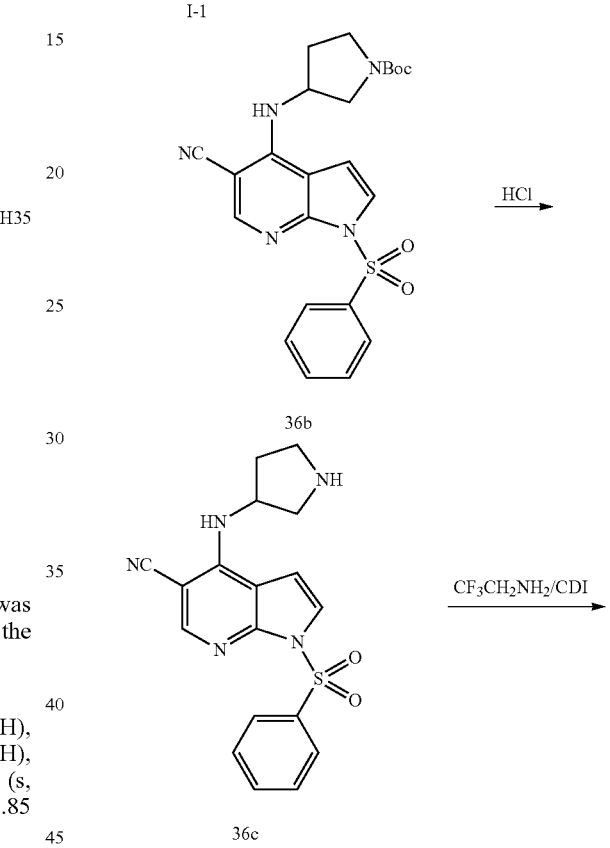

36b

36c

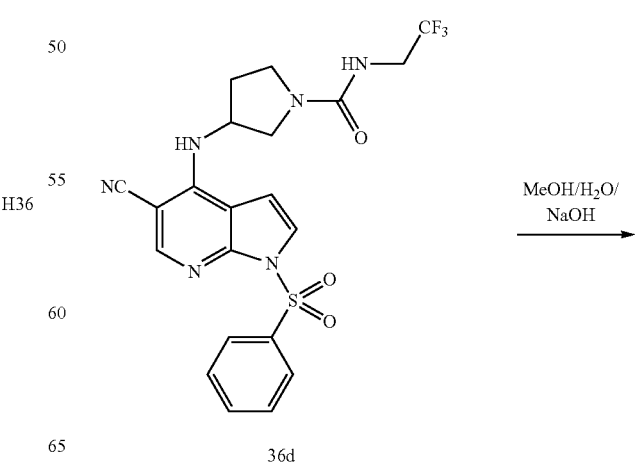

36d

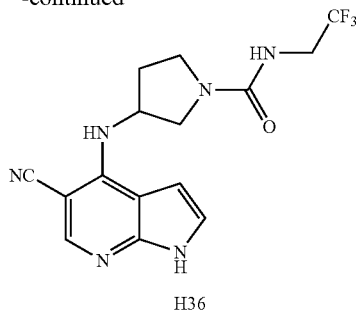

H36

First Step: Preparation of tert-butyl 3-((5-cyano-1-(benzenesulfonyl)-1H-pyrrole[2,3-b]pyridin-4-yl)amino)pyrrolidin-1-carboxylic ester 36b 4-chloro-1-(phenylsulfonyl)-2,3-dihydro-1H-pyrrolo[2,3-b]pyridin-5-carbonitrile I-1 (350 mg, 1.1 mmol, 1.0 eq) and tert-butyl-3-aminopyrrolidine-1-carboxylate 36a (0.20 g, 1.1 mmol, 1.0 eq) were added in NMP (5 ml), and then DIPEA (0.28 ml, 2.2 mmol, 2.0 eq) was added. The system was reacted for 5 h at 100° C., cooled to room temperature, diluted with water (20 ml), and extracted with ethyl acetate (50 ml). The organic layers were washed with brine (10 ml), concentrated and purified by flash column (PE-PE/EA=1:1) to obtain white solids 36b (330 mg).

MS m/z (ESI): 468 [M+1]$^+$

Second Step: Preparation of 1-(phenylsulfonyl)-4-(pyrrolidin-3-yl-amino)-1H-pyrrolo[2,3-b]pyridin-5-carbonitrile 36c Compound 36b (150 mg, 0.32 mmol, 1.0 eq) was added into 2N of HCl/EA (10 ml), reacted overnight at room temperature, filtered and dried in vacuum to obtain white solids 36c (120 mg).

MS m/z (ESI): 368 [M+1]$^+$

Third Step: Preparation of 3-((5-cyano-1-(phenylsulfonyl)-1H-pyrrolo[2,3-b]pyridin-4-yl) amino)-N-(2,2,2-trifluoroethyl)pyrrolidin-1-carboxamide 36d Trifluoroethylamine (63 mg, 0.64 mmol, 2.0 eq) was dissolved in anhydrous THF (10 ml), and then CDI (0.10 g, 0.64 mmol, 2.0 eq) was added. The system was reacted for 4 h at room temperature to obtain a reaction liquid. Compound 36c (120 mg, 0.32 mmol, 1.0 eq) and TEA (97 mg, 0.96 mmol, 3.0 eq) were dissolved in anhydrous THF (5 ml). This solution was pipetted to the above reaction liquid one time and subjected to a reflux reaction for 2 h. The solvent was dried under reduced pressure, and ethyl acetate (30 ml) was added. The system was washed with water (10 ml) and brine (10 ml) in sequence, dried with anhydrous sodium sulfate, concentrated and purified by flash column (DCM-DCM/MeOH=20:1) to obtain white solids 36d (150 mg).

MS m/z (ESI): 493 [M+1]$^+$

Fourth Step: Preparation of 3-((5-cyano-1H-pyrrolo[2,3-b]pyridin-4-yl)amino)-N-(2,2,2-trifluoroethyl)pyrrolidin-1-carboxamide H36

Compound 36d (150 mg, 0.30 mmol, 1.0 eq) was dissolved in a mixed solvent of MeOH/THF (5 ml/5 ml), and then 2N of NaOH (0.8 ml, 1.5 mmol, 5.0 eq) was added and reacted for 4 h at room temperature to obtain a reaction liquid. The reaction liquid was concentrated and purified by flash column (DCM-DCM/MeOH=10:1) to obtain white solids H36 (40 mg).

MS m/z (ESI): 353 [M+1]$^+$ $^1$H NMR (400 MHz, DMSO-d$_6$) δ 11.85 (s, 1H), 8.10 (s, 1H), 7.26 (dd, J=3.6, 2.4 Hz, 1H), 7.03 (d, J=7.1 Hz, 1H), 6.89 (t, J=6.2 Hz, 1H, 6.80 (dd, J=3.6, 2.0 Hz, 1H), 4.82 (s, 1H), 3.86-3.72 (m, 2H), 3.66 (dd, J=10.7, 6.2 Hz, 1H), 3.56-3.36 (m, 3H), 2.30-2.05 (m, 2H).

Example 37

Preparation of 3-((5-cyano-1H-pyrrolo[2,3-b]pyridin-4-yl)methyl-amino)-N-(2,2,2-trifluoroethyl)pyrrolidin-1-carboxamide H37

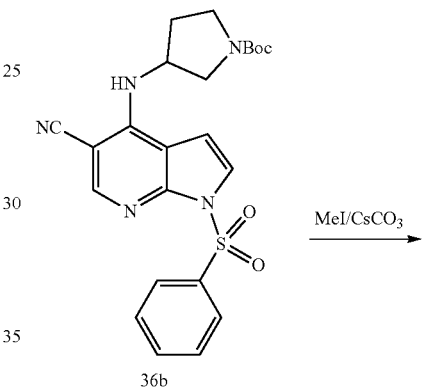

36b

MeI/CsCO$_3$ →

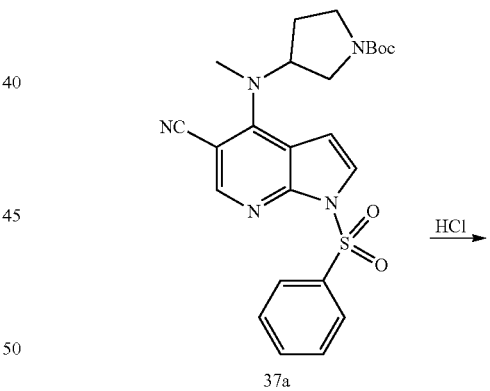

37a

HCl →

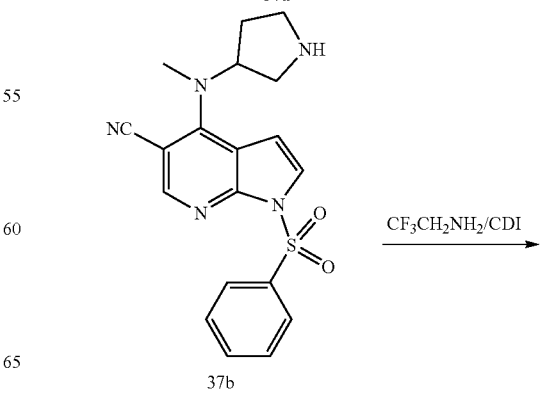

37b

CF$_3$CH$_2$NH$_2$/CDI →

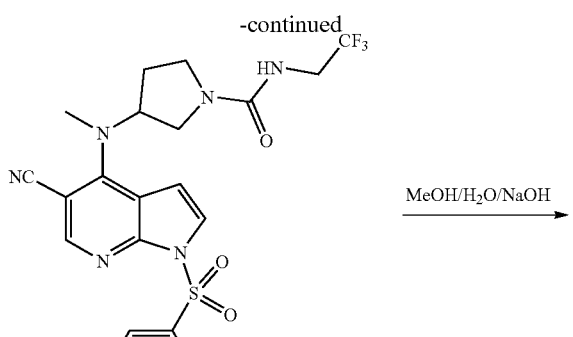

37c

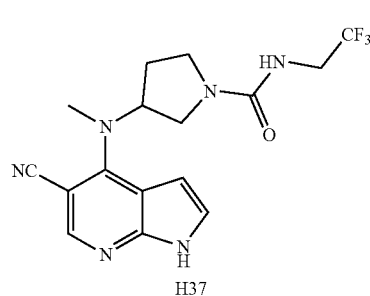

H37

First Step: Preparation of tert-butyl-3-((5-cyano-1-(benzenesulfonyl)-1H-pyrrole[2,3-b]pyridin-4-yl)(methyl)amino)pyrrolidin-1-carboxylate 37a Compound 36b (150 mg, 0.32 mmol, 1.0 eq) and cesium carbonate (0.21 g, 0.64 mmol, 2.0 eq) were added in DMF (10 ml) and CH$_3$I (108 mg, 0.76 mmol, 2.5 eq) was added dropwise. The system was reacted overnight at room temperature to obtain a reaction liquid. The reaction liquid was diluted with water (50 ml) and extracted with ethyl acetate (30 ml×2). The organic phases were combined, washed with brine (25 ml×3), concentrated and purified by flash column (DCM-DCM/MeOH=50:1) to obtain white foamed solids 37a (120 mg).
MS m/z (ESI): 482 [M+1]$^+$ Second Step: Preparation of 4-(methyl(pyrrolidin-3-yl)amino)-1-(phenylsulfonyl)-1H-pyrrolo[2,3-b]pyridin-5-carbonitrile 37b Compound 37a (120 mg, 0.25 mmol, 1.0 eq) was added into 2N of HCl/EA (20 ml), reacted overnight at room temperature, filtered and dried in vacuum to obtain white solids 37b (90 mg).
MS m/z (ESI): 382 [M+1]$^+$ Third Step: Preparation of 3-((5-cyano-1-(phenylsulfonyl)-1H-pyrrolo[2,3-b]pyridin-4-yl)(methyl)amino)-N-(2,2,2-trifluoroethyl)pyrrolidin-1-carboxamide 37c Trifluoroethylamine (50 mg, 0.50 mmol, 2.0 eq) was dissolved in anhydrous THF (10 ml), and then CDI (81 g, 0.50 mmol, 2.0 eq) was added. The system was reacted for 4 h at room temperature to obtain a reaction liquid. Compound 37b (90 mg, 0.25 mmol, 1.0 eq) and TEA (76 mg, 0.75 mmol, 3.0 eq) were dissolved in anhydrous THF (5 ml).

This solution was pipetted to the above reaction liquid one time and subjected to a reflux reaction for 2 h. The solvent was dried under reduced pressure, and ethyl acetate (30 ml) was added. The system was washed with water (10 ml) and brine (10 ml) in sequence, dried with anhydrous sodium sulfate, concentrated and purified by flash column (DCM-DCM/MeOH=50:1) to obtain white solids 37c (110 mg).
MS m/z (ESI): 507 [M+1]$^+$ Fourth Step: Preparation of 3-((5-cyano-1H-pyrrolo[2,3-b]pyridin-4-yl)amino)-N-(2,2,2-trifluoroethyl)pyrrolidin-1-carboxamide H37

Compound 37c (110 mg, 0.22 mmol, 1.0 eq) was dissolved in a mixed solvent of MeOH/THF (5 ml/5 ml), and then 2N of NaOH (0.6 ml, 1.1 mmol, 5.0 eq) was added and reacted for 4 h at room temperature to obtain a reaction liquid. The reaction liquid was concentrated and purified by flash column (DCM-DCM/MeOH=15:1) to obtain white solids H37 (47 mg).
MS m/z (ESI): 367 [M+1]$^+$
$^1$H NMR (400 MHz, DMSO-d$_6$) δ 12.04 (s, 1H), 8.23 (s, 1H), 7.40 (dd, J=3.7, 2.3 Hz, 1H), 6.92 (1, J=6.3 Hz, 1H), 6.69 (dd, J=3.6, 1.8 Hz, 1H), 4.76 (q, J=7.5 Hz, 1H), 3.90-3.72 (m, 2H), 3.67 (dd, J=10.7, 7.7 Hz, 1H) 3.60-3.40 (m, 2H), 3.31-3.24 (m, 1H), 3.21 (s, 3H), 2.19 (m, 2H).

Example 38

Preparation of (3aR,5s,6aS)-5-((5-cyano-1H-pyrrolo[2,3-b]pyridin-4-yl)(methyl)amino)-N-(3-hydroxy-1,2,4-thiadiazole-5-yl)hexahydrocyclopentadiene[c]pyrrole-2(1H)-carboxamide H38

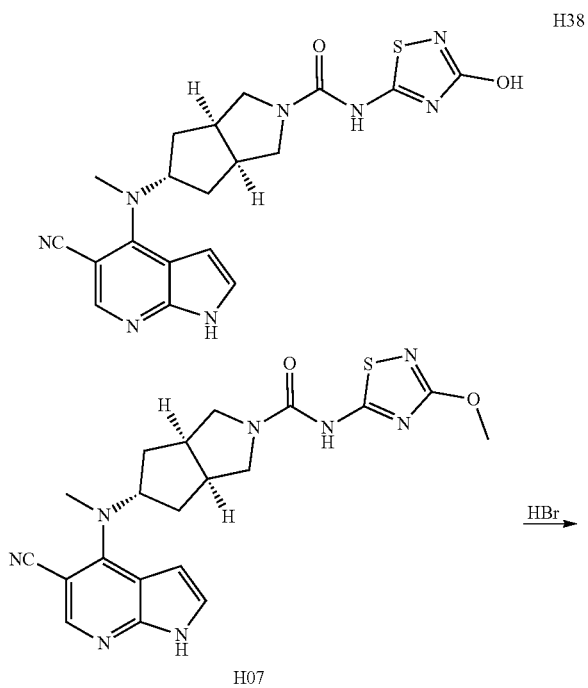

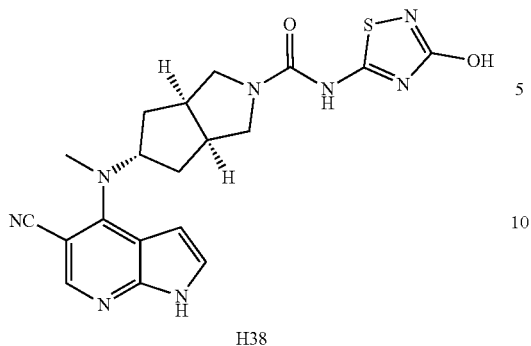

Compound H07 (100 mg, 0.23 mmol) and HBr/AcOH solution (5 mL) were added into a reaction flask and stirred for 1 h at 80° C. The system was poured into water, neutralized to be alkalescent, extracted with ethyl acetate for three times. The organic phases were combined, washed with water and saturated sodium chloride, dried with anhydrous sodium sulfate and concentrated at low temperature, followed by purification by column chromatography (v/v, DCM/MeOH=100:1-50:1) to obtain compound H38 (10 mg, 0.024 mmol) with a yield of 10.4%.

MS m/z (ESI): 425 [M+H]+.

$^1$H NMR (400 MHz, DMSO-d$_6$) δ 12.12 (brs, 1H), 11.91 (s, 1H), 9.19 (brs, 1H), 8.12 (s, 1H), 7.29-7.21 (m, 1H), 6.64-6.56 (m, 1H), 4.74-4.65 (m, 1H), 3.78-3.56 (m, 2H), 3.16 (s, 5H), 2.87-2.76 (m, 2H), 2.14-2.05 (m, 2H), 1.86-1.78 (m, 2H).

Example 39

Preparation of 6-(5-cyano-1H-pyrrolo[2,3-b]pyridin-4-yl)-N-(2,2,2-trifluoroethyl)-3,6-diazabicyclo[3.2.0]heptane-3-carboxamide H39

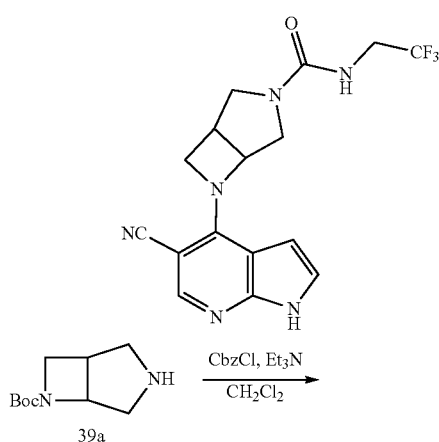

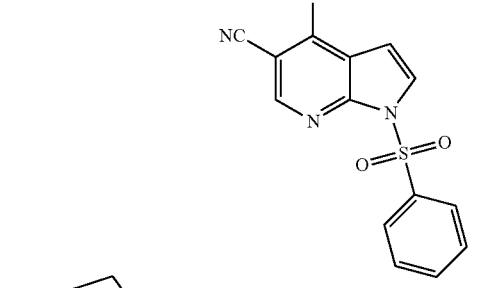

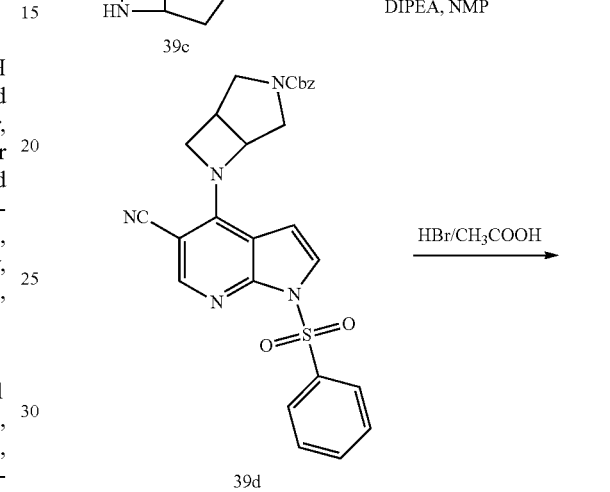

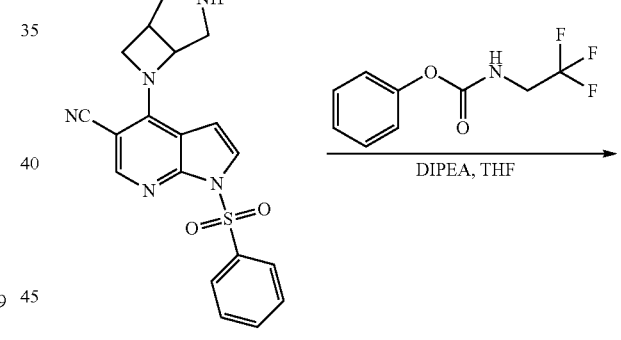

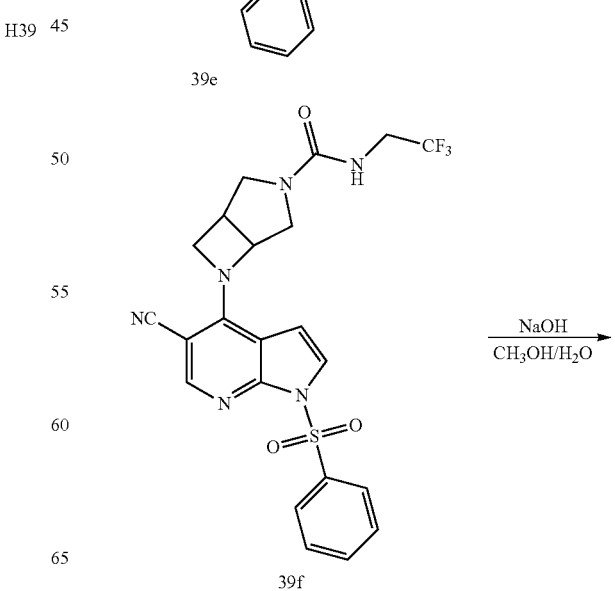

-continued

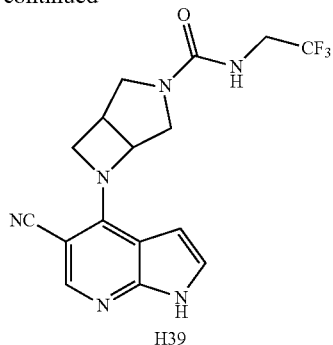

H39

First Step: 3-benzyl 6-(tert-butyl)-3,6-diazabicyclo[3.2.0]heptane-3,6-dicarboxylate 39b Compound 39a (300 mg, 1.5 mmol) and dichloromethane (20 mL) were added into a reaction flask, and then triethylamine (303 mg, 3 mmol) and benzyl chloroformate (306 mg, 1.8 mmol) were added in sequence to obtain a reaction liquid. The reaction liquid was stirred for 2 h at room temperature and washed with water. The organic phases were dried by a spin drier, mixed with silica gel, concentrated at low temperature, and purified by column chromatography to obtain compound 39b (470 mg, 1.4 mmol) with a yield of 94%.

MS m/z (ESI): 355 [M+23]+

Second Step: benzyl 3,6-diazabicyclo[3.2.0]heptane-3-carboxylate 39c

Compound 39b (470 mg, 1.4 mmol) was dissolved in dichloromethane (5 mL), and then trifluoroacetic acid (1 mL) was added to obtain a reaction liquid. The reaction liquid was stirred for 2 h at room temperature, then concentrated and dried by a spin drier to obtain compound 39c (328 mg, 1.4 mmol) with a yield of 100%.

MS m/z (ESI): 233 [M+H]+.

Third Step: benzyl 6-(5-cyano-1-(phenylsulfonyl)-1H-pyrrolo[2,3-b]pyridin-4-yl)-3,6-diazabicyclo[3.2.0]heptane-3-carboxylate 39d Compound I-1 (200 mg, 0.63 mmol), compound 39c (146 mg, 0.63 mmol) DIPEA (162 mg, 1.26 mmol) and NMP (5 mL) were added into a reaction flask. The system was subjected to a microwave reaction for 2 h at 170° C. After the reaction was completed, the system was poured into water, extracted with ethyl acetate for three times. The organic phases were combined, washed with water and saturated sodium chloride, dried with anhydrous sodium sulfate, and concentrated at low temperature, followed by purification by column chromatography (v/v, DCM/MeOH=100:1-50:1) to obtain compound 39d (200 mg, 0.39 mmol) with a yield of 62%.

MS m/z (ESI): 514 [M+H]+.

Fourth Step: 4-(3,6-diazabicyclo[3.2.0]heptane-6-yl)-1-(phenylsulfonyl)-1H-pyrrolo[2,3-b]pyridin-5-carbonitrile 39e Compound 1e (180 mg, 0.35 mmol) and 40% hydrobromic acid-acetic acid solution (3 mL) were added into a reaction flask to obtain a reaction liquid. The reaction liquid was stirred for 20 minutes at room temperature, then concentrated and dried by a spin drier to obtain compound 39e (133 mg, 0.35 mmol) with a yield of 100%.

MS m/z (ESI): 380 [M+H]+.

Fifth Step: 6-(5-cyano-1-(phenylsulfonyl)-1H-pyrrolo[2,3-b]pyridin-4-yl)-N-(2,2,2-trifluoroethyl)-3,6-diazabicyclo[3.2.0]heptane-3-carboxamide 39f Compound 39e (133 mg, 0.35 mmol), N-(3,3,3-trifluoroethyl)phenyl carbamate (77 mg, 0.35 mmol), DIPEA (90 mg, 0.70 mmol) and THF (10 mL) were added into a reaction flask. The system was reacted for 2 h at 60° C. After the reaction was completed, the system was concentrated directly and purified by column chromatography (v/v, DCM/MeOH=100:1-50:1) to obtain compound 39f (130 mg, 0.26 mmol) with a yield of 74%.

MS m/z (ESI): 505 [M+H]+.

Sixth Step: 6-(5-cyano-1H-pyrrolo[2,3-b]pyridin-4-yl)-N-(2,2,2-trifluoroethyl)-3,6-diazabicyclo[3.2.0]heptane-3-carboxamide H39

Compound 39f (130 mg, 0.26 mmol), 2M sodium hydroxide solution (2 mL) and methanol (5 mL) were added into a reaction flask. The system was stirred for 1 h at room temperature. After the reaction was completed under TLC monitoring, the system was adjusted to pH=8-10 with diluted hydrochloric acid, concentrated and purified by column chromatography (v/v, DCM/MeOH=100:1-50:1) to obtain compound H39 (10 mg, 0.027 mmol) with a yield of 11%.

MS m/z (ESI): 365 [M+H]+.

$^1$H NMR (400 MHz, DMSO-d$_6$) δ 11.85 (s, 1H), 8.01 (s, 1H), 7.26-7.11 (m, 2H), 6.45 (s, 1H), 5.37 (dd, J=6.9, 4.5 Hz, 1H), 4.59 (t, J=8.6 Hz, 1H), 4.19 (dd, J=8.9, 4.4 Hz, 1H), 4.04 (d, J=12.4 Hz, 1H), 3.87-3.63 (m, 3H), 3.19 (ddd, J=23.2, 11.9, 5.5 Hz, 2H), 1.96 (q J=7.1, 6.7 Hz, 1H).

Example 40

Preparation of (3S,4S)-4-({4-methyl-1-[(2,2,2-trifluoroethyl)carbamoyl)]pyrrolidin-3-yl} amino)-1H-pyrrolo[2,3-b]pyridin-5-carbonitrile H40

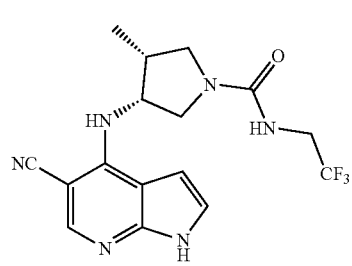

H40

(3S,4S)-(4-methyl-pyrrolidin-3-yl)tert-butyl carbamate was used as a raw material to obtain compound H40 by using the same preparation method as described in Example 1.

MS m/z (ESI): 367 [M+H]+.

1H NMR (400 MHz, DMSO-d6) δ 11.86 (s, 1H), 8.11 (s, 1H), 7.28 (t, J=3.0 Hz, 1H), 6.94-6.80 (m, 2H), 6.70 (d, J=8.8 Hz, 1H), 4.87 (dq, J=10.9, 5.7 Hz, 1H), 3.81 (ddd, J=9.4, 6.3, 2.8 Hz, 2H), 3.71 (dd, J=10.8, 6.5 Hz, 1H), 3.60-3.48 (m, 2H), 3.26 (dd, J=10.2, 7.3 Hz, 1H), 2.61 (p, J=6.9 Hz, 1H), 0.98 (d, J=6.9 Hz, 3H).

Example 41

Preparation of (3aR,5s,6aS)-5-((5-cyano-1H-pyrrolo[2,3-b]pyridin-4-yl)(methyl)amino)-N-(3-(methylamino)-1,2,4-thiadiazole-5-yl)hexahydrocyclopentadiene[c]pyrrole-2(1H)-carboxamide H41

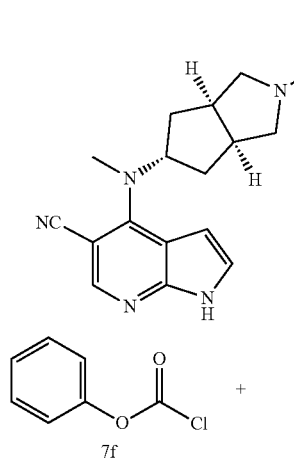

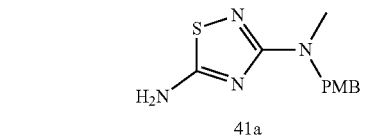

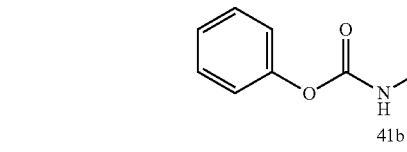

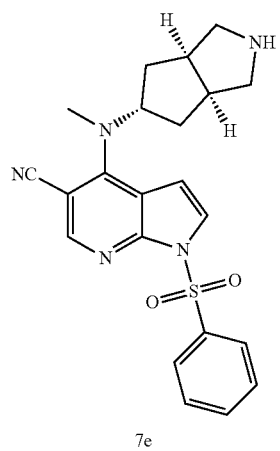

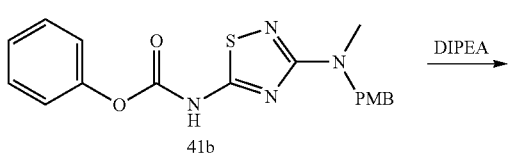

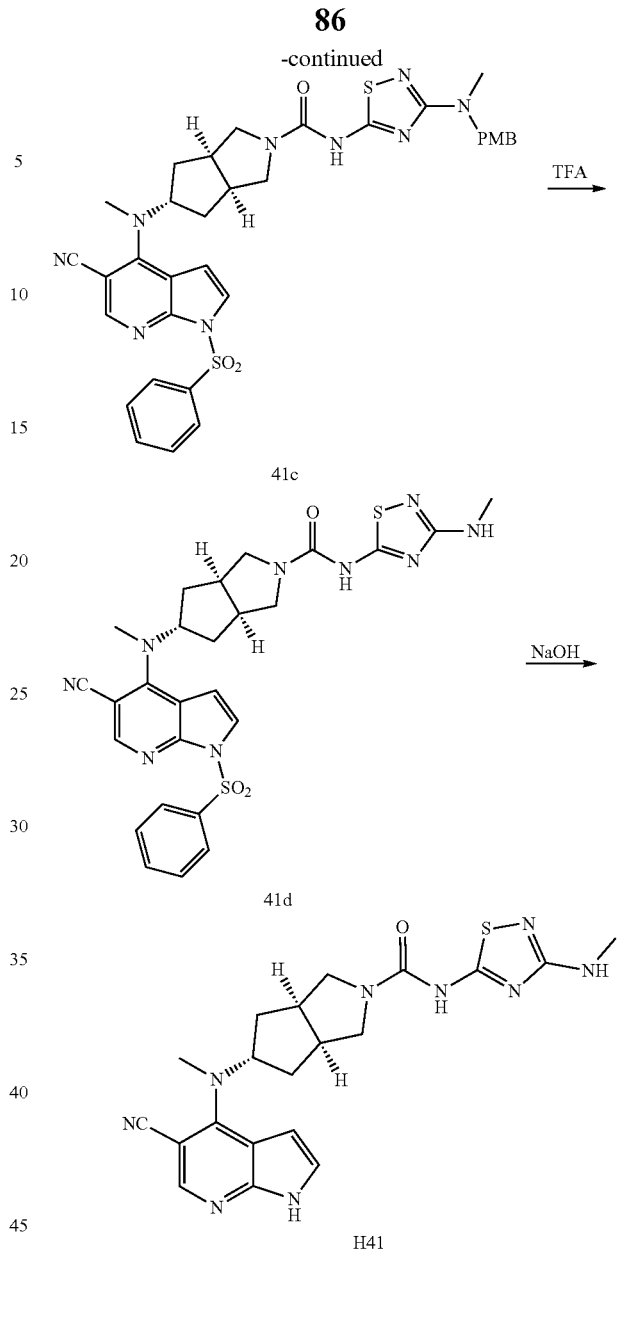

First Step: phenyl(3-((4-methoxyphenyl)(methyl)amino)-1,2,4-thiadiazole-5-yl)carbamate 41b Compound 41a (267 mg, 1.71 mmol), compound 92a (388 mg, 1.55 mmol) and DCM (20 mL) were added into a reaction flask, and then triethylamine (313 mg, 3.10 mmol) was slowly added dropwise at an ice bath. The system was reacted for 2 h at that temperature. After the reaction was completed, water was added. The system was extracted with DCM, dried, concentrated and purified by column chromatography (v/v, DCM/MeOH=100:1-50:1) to obtain compound 41b (450 mg, 1.22 mmol) with a yield of 78.7%.
MS m/z (ESI): 371 [M+H]+.

Second Step: (3aR,5s,6aS)-5-((5-cyano-1-(phenylsulfonyl)-1H-pyrrolo[2,3-b]pyridin-4-yl)(methyl)amino)-N-(3-((4-methoxyphenyl(methyl)amino)-1,2,4-thiadiazole-5-yl) hexahydrocyclopentadiene[c]pyrrole-2(1H)-carboxamide 41c Compound 7e (50 mg, 0.12 mmol), compound 41b (44 mg, 0.12 mmol), DIPEA (31 mg, 0.24 mmol) and THE (10 mL) were added into a reaction flask. The system was reacted for 2 h at 60° C. After the reaction was completed, the system was concentrated directly and purified by column chromatography (v/v, DCM/MeOH=100:1-50:1) to obtain compound 41c (56 mg, 0.08 mmol) with a yield of 66.7%.

MS m/z (ESI): 698 [M+H]+.

Third Step: (3aR,5s,6aS)-5-((5-cyano-1-(phenylsulfonyl)-1H-pyrrolo[2,3-b]pyridin-4-yl)(methyl)amino)-N-(3-(methylamino)-1,2,4-thiadiazole-5-yl)hexahydrocyclopentadiene[c]pyrrole-2(1H)-carboxamide 41d Compound 41c (56 mg, 0.08 mmol), TFA (2 mL) and DCM (10 mL) were added into a reaction flask. The system was reacted for 0.5 h at room temperature. After the reaction was completed, the system was concentrated directly and purified by column chromatography (v/v, DCM/MeOH=100:1-50:1) to obtain compound 41d (40 mg, 0.07 mmol) with a yield of 86.7%.

MS m/z (ESI): 578 [M+H]+.

Fourth Step: (3aR,5s,6aS)-5-((5-cyano-1H-pyrrolo[2,3-b]pyridin-4-yl)(methyl)amino)-N-(3-(methylamino)-1,2,4-thiadiazole-5-yl)hexahydrocyclopentadiene[c]pyrrole-2(1H)-carboxamide H41

Compound 41d (40 mg, 0.07 mmol), 2M sodium hydroxide solution (2 mL) and methanol (5 mL) were added into a reaction flask. The system was stirred for 1 h at room temperature. After the reaction was completed under TLC monitoring, the system was adjusted to pH=8-10 with diluted hydrochloric acid, concentrated and purified by column chromatography (v/v, DCM/MeOH=100:1-50:1) to obtain compound H41 (10 mg, 0.023 mmol) with a yield of 32.90%.

MS m/z (ESI): 438 [M+H]+.
1H NMR (400 MHz, DMSO-d6) δ 11.90 (s, 1H), 11.13 (s, 1H), 8.12 (s, 1H), 7.28-7.19 (m, 1H), 6.65-6.59 (m, 1H), 6.56-6.44 (m, 1H), 4.73-4.64 (m, 1H), 3.67-3.56 (m, 2H), 3.29-3.23 (m, 2H), 3.16 (s, 3H), 2.88-2.77 (m, 2H), 2.71 (s, 3H), 2.16-2.05 (m, 2H), 1.88-1.78 (m, 2H).

Example 42

(3aR,5s,6aS)-5-((5-cyano-1H-pyrrolo[2,3-b]pyridin-4-yl)(methyl)amino)-N-(3-hydroxymethyl-1,2,4-thiadiazole-5-yl)hexahydrocyclopentadiene[c]pyrrole-2(1H)-carboxamide H42

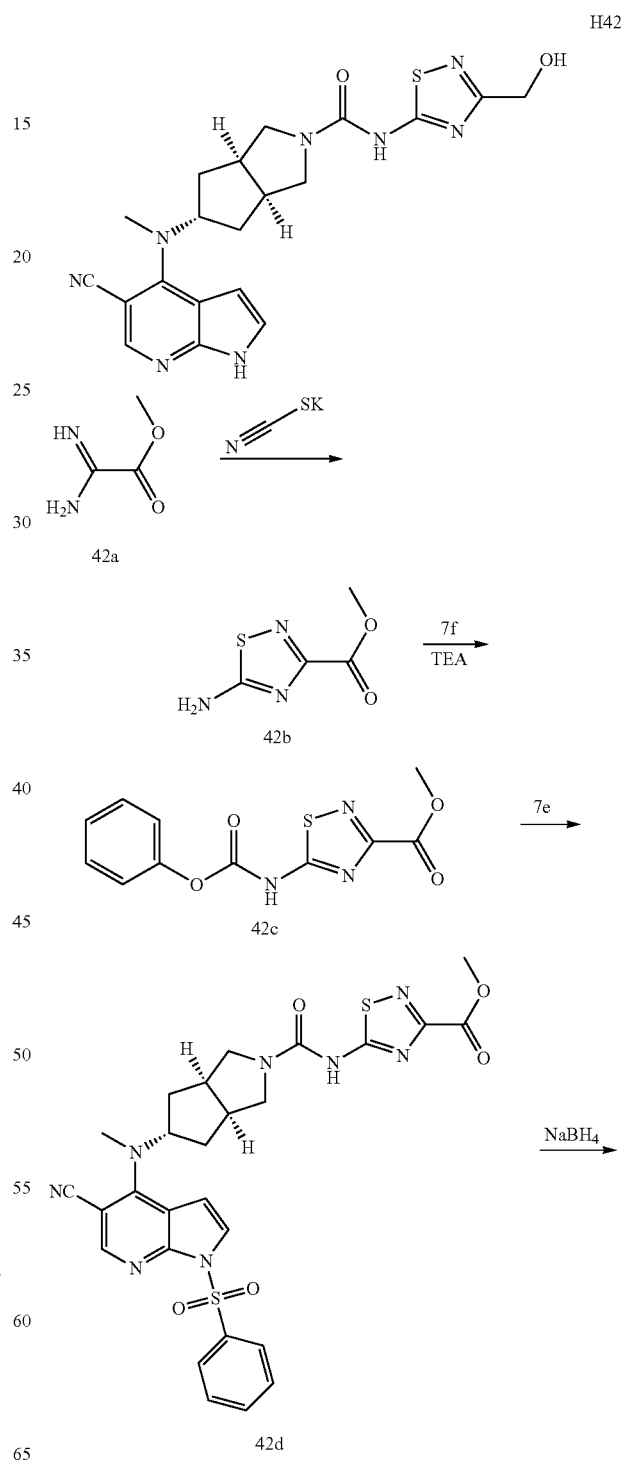

-continued

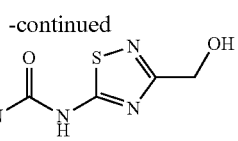

42e

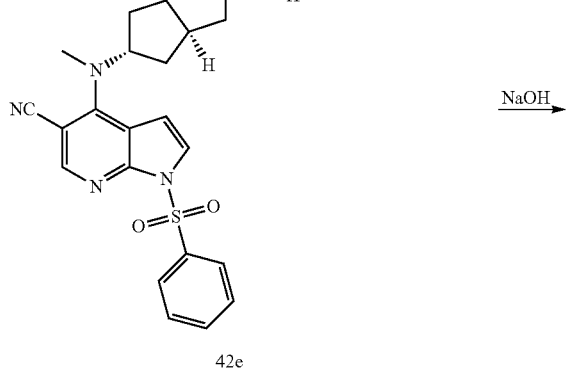

H42

First Step: methyl 5-amino-1,2,4-thiadiazole-3 carboxylate 42b

Compound 42a (1.0 g, 9.79 mmol), potassium thioisocyanate (1.0 g, 10.3 mmol) and methanol (20 mL) were added into a reaction flask, cooled to −5° C. and then sodium methoxide (1.0 g, 18.5 mmol) was slowly added. The system was reacted for 3 h at −5° C., and then heated to room temperature slowly. After the reaction was completed, the system was concentrated directly and purified by column chromatography (v/v, DCM/MeOH=100:1-10:1) to obtain compound 42b (300 mg, 1.88 mmol) with a yield of 19.3%.
MS m/z (ESI): 160.1 [M+H]+.

Second Step: methyl 5-((phenoxyformyl)amino-1,2,4-thiadiazole-3 carboxylate 42c

Compound 42b (200 mg, 1.26 mmol), compound 7f (300 mg, 1.92 mmol) and dichloromethane (10 mL) were added into a reaction flask, and then triethylamine (300 mg, 2.96 mmol) was slowly added dropwise. The system was reacted for 1 h at room temperature. After the reaction was completed, the system was concentrated directly and purified by column chromatography (v/v, DCM/MeOH=100:1-20:1) to obtain compound 42c (130 mg, 0.465 mmol) with a yield of 36.9%.
MS m/z (ESI): 280.1 [M+H]+.

Third Step: methyl 5-((3aR,5s,6aS)-5-((5-cyano-1-p-toluenesulfonyl-1H-pyrrolo[2,3-b]pyridin-4-yl)(methyl)amino)hexahydrocyclopentadiene[c]pyrrole-2-formamido)-1,2,4-thiadiazole-3-carboxylate 42d Compound 42c (100 mg, 0.358 mmol), compound 7e (80 mg, 0.184 mmol), DIPEA (100 mg, 0.774 mmol) and THF (10 mL) were added into a reaction flask. The system was reacted for 2 h at 60° C. After the reaction was completed, the system was concentrated directly and purified by column chromatography (v/v, DCM/MeOH=100:1-10:1) to obtain compound 42d (100 mg, 0.161 mmol) with a yield of 87.5%.
MS m/z (ESI): 607.4 [M+H]+.

Fourth Step: (3aR,5s,6aS)-5-((5-cyano-1-p-toluenesulfonyl-1H-pyrrolo[2,3-b]pyridin-4-yl)(methyl)amino)-N-(3-hydroxymethyl-1,2,4-thiadiazole-5-yl)hexahydrocyclopentadiene[c]pyrrole-2(1H)-carboxamide 42e Compound 42d (90 mg, 0.145 mmol), sodium borohydride (200 mg, 5.29 mmol) and methanol (10 mL) were added into reaction flask. The system was reacted for 2 h at room temperature. After the reaction was completed, the system was concentrated directly and purified by column chromatography (v/v, DCM/MeOH=100:1-5:1) to obtain compound 42e (60 mg, 0.101 mmol) with a yield of 62.7%.
MS m/z (ESI): 579.3 [M+H]+.

Fifth Step: (3aR,5s,6aS)-5-((5-cyano-1H-pyrrolo[2,3-b]pyridin-4-yl)(methyl)amino)-N-(3-hydroxymethyl-1,2,4-thiadiazole-5-yl)hexahydrocyclopentadiene[c]pyrrole-2(1H)-carboxamide H42

Compound 42e (60 mg, 0.101 mmol), 2M sodium hydroxide solution (2 mL) and methanol (5 mL) were added into a reaction flask. The system was stirred for 1 h at room temperature. After the reaction was completed, the system was adjusted to pH=8-10 with diluted hydrochloric acid, concentrated and purified by column chromatography (v/v, DCM/MeOH=100:1-5:1) to obtain compound H42 (25 mg, 0.057 mmol) with a yield of 56.4%.
MS m/z (ESI): 439.3 [M+H]+.
$^1$H NMR (400 MHz, DMSO-d$_6$) δ 11.92 (s, 1H), 11.55 (s, 1H), 8.11 (s, 1H), 7.25-7.21 (m, 1H), 6.63-6.59 (m, 1H), 5.51-5.22 (m, 1H), 4.75-4.64 (m, 1H), 4.45 (s, 2H), 3.71-3.59 (m, 2H), 3.32-3.24 (m, 2H), 3.16 (s, 3H), 2.92-2.77 (m, 2H), 2.17-2.05 (m, 2H), 1.88-1.79 (m, 2H).

Example 43

(3aR,5s,6aS)-5-((5-cyano-1H-pyrrolo[2,3-b]pyridin-4-yl)(methyl)amino)-N-(3-methoxy-1,2,4-oxadiazole-5-yl)hexahydrocyclopentadiene[c]pyrrole-2(1H)-carboxamide H43

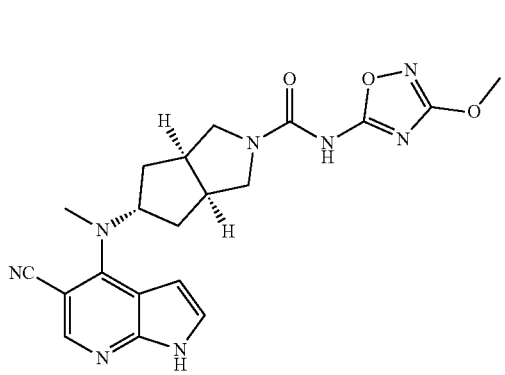

3-methoxy-5-amino-1H-1,2,4-oxadiazole was used as a raw material to obtain compound H43 by using the same preparation method as described in Example 7.

MS m/z (ESI): 423 [M+H]+.

Example 44

(3aR,5s,6aS)-5-((5-cyano-1H-pyrrolo[2,3-b]pyridin-4-yl)(methyl)amino)-N-(3-(2-amino-2-methyl-propoxy)-1,2,4-thiadiazole-5-yl)hexahydrocyclopentadiene[c]pyrrole-2(1H)-carboxamide H44

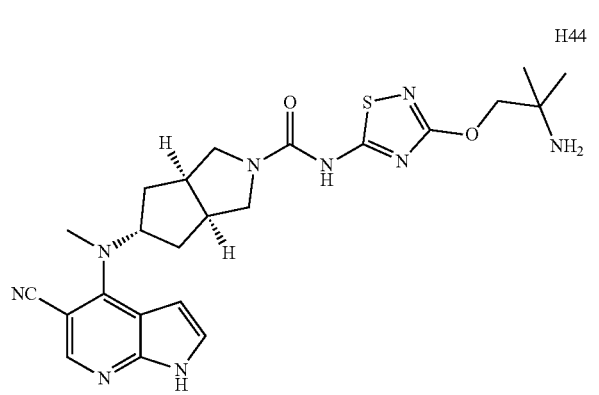 [SMILES: CN(c1c(C#N)cnc2[nH]ccc12)[C@H]1C[C@@H]2CN(C(=O)Nc3nc(OCC(C)(C)N)ns3)C[C@@H]2C1]

3-(2-amino-2-methyl-propoxy)-5-amino-1H-1,2,4-oxadiazole was used as a raw material to obtain compound H44 by using the same preparation method as described in Example 7.

MS m/z (ESI): 496 [M+H]+.

Example 45

(3aR,5s,6aS)-5-((5-cyano-1H-pyrrolo[2,3-b]pyridin-4-yl)(methyl)amino)-N-(3-(2-hydroxy-2-methyl-propoxy)-1,2,4-thiadiazole-5-yl)hexahydrocyclopentadiene[c]pyrrole-2(1H)-carboxamide H45

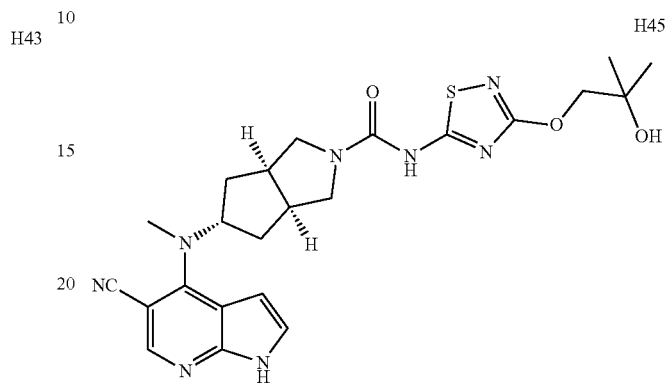

3-(2-hydroxy-2-methyl-propoxy)-5-amino-1H-1,2,4-oxadiazole was used as a raw material to obtain compound H45 by using the same preparation method as described in Example 7.

MS m/z (ESI): 497 [M+H]+.

Example 46

Preparation of (cis)-4-{[3-(propanesulfonamido)-cyclobutyl-1-yl]-amino}-1H-pyrrolo [2,3-b]pyridin-5-carbonitrile H46

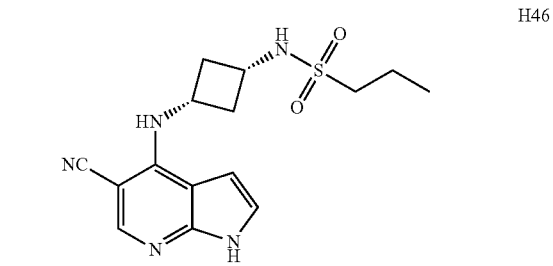 [SMILES: CCCS(=O)(=O)N[C@H]1C[C@@H](Nc2c(C#N)cnc3[nH]ccc23)C1]

Propanesulfonyl chloride was used as a raw material to obtain compound H46 by using the same preparation method as described in Example 12. LCMS (ESI) m/z: 334 [M+H]$^+$.

$^1$H NMR (400 MHz, DMSO-d6) δ 11.76 (s, 1H), 8.03 (s, 1H), 7.42 (d, J=8.3 Hz, 1H), 7.20 (dd, J=3.5, 2.4 Hz, 1H), 7.06 (d, J=6.9 Hz, 1H), 6.77 (dd, J=3.5, 1.9 Hz, 1H), 4.25-4.12 (m, 1H), 3.52 (h, J=8.4 Hz, 1H), 2.95-2.83 (m, 2H), 2.75 (dtd, J=9.8, 7.2, 2.9 Hz, 2H), 2.12 (qd, J=8.8, 2.9 Hz, 2H), 1.70-1.53 (m, 2H), 0.94 (t, J=7.4 Hz, 3H).

Example 47

(3aR,5s,6aS)-5-((5-cyano-1H-pyrrolo[2,3-b]pyridin-4-yl)(methyl)amino)-N-(3-ethoxy-1,2,4-oxadiazole-5-yl)hexahydrocyclopentadiene[c]pyrrole-2(1H)-carboxamide H47

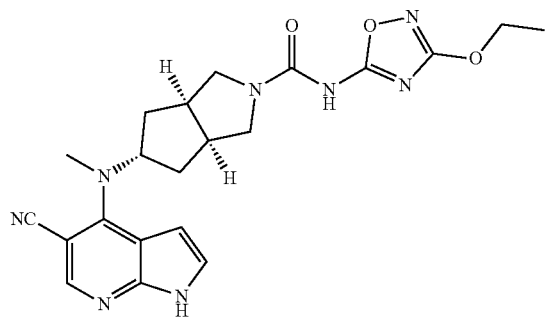

3-ethoxy-5-amino-1H-1,2,4-oxadiazole was used as a raw material to obtain compound H47 by using the same preparation method as described in Example 7.

MS m/z (ESI): 437 [M+H]+.

$^1$H NMR (400 MHz, DMSO-d$_6$) δ 11.95 (s, 1H), 10.78 (s, 1H), 8.16 (s, 1H), 7.31 (t, J=3.0 Hz, 1H), 6.66 (dd, J=3.7, 1.9 Hz, 1H), 4.73 (t, J=8.1 Hz, 1H), 4.24 (q, J=7.0 Hz, 2H), 3.61 (d, J=9.8 Hz, 2H), 3.29 (d, J=12.1 Hz, 2H), 3.19 (s, 3H), 2.91-2.79 (m, 2H), 2.21-2.09 (m, 2H), 1.85 (dd, J=13.3, 7.6 Hz, 2H), 1.33 (t, J=7.0 Hz, 3H).

Example 48

(3aR,5s,6aS)-5-((5-cyano-1H-pyrrolo[2,3-b]pyridin-4-yl)(methyl)amino)-N-(5-ethoxy-1,2,4-oxadiazole-3-yl)hexahydrocyclopentadiene[c]pyrrole-2(1H)-carboxamide H48

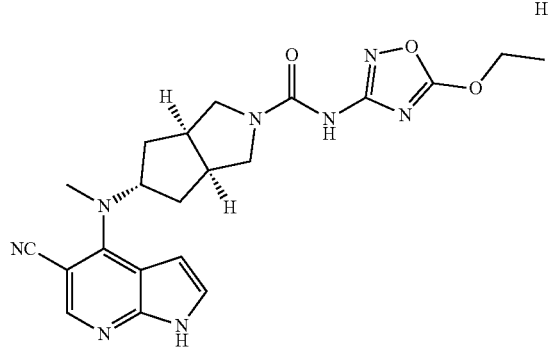

5-ethoxy-3-amino-1H-1,2,4-oxadiazole was used as a raw material to obtain compound H48 by using the same preparation method as described in Example 7.

MS m/z (ESI): 437 [M+H]+.

$^1$H NMR (400 MHz, DMSO-d$_6$) δ 11.93 (s, 1H), 10.32 (s, 1H), 8.16 (s, 1H), 7.31 (dd, J=3.6, 2.5 Hz, 1H), 6.65 (dd, J=36, 2.0 Hz, 1H), 4.83-4.63 (m, 1H), 4.09 (q, J=7.1 Hz, 2H), 3.70 (dd, J=10.7, 7.9 Hz, 2H), 3.35 (d, J=4.3 Hz, 2H), 3.20 (s, 3H), 2.96 (h, J=3.4 Hz, 2H), 2.17 (dt, J=12.7, 8.2 Hz, 2H), 1.91 (ddd, =13.5, 7.2, 2.0 Hz, 2H), 1.20 (t, J=7.1 Hz, 3H).

Example 49

(3aR,5s,6aS)-5-((5-cyano-1H-pyrrolo[2,3-b]pyridin-4-yl)amino)-N-(3-cyclopropyl-1,2,4-thiadiazole-5-yl)hexahydrocyclopentadiene[c]pyrrole-2(1H)-carboxamide H49

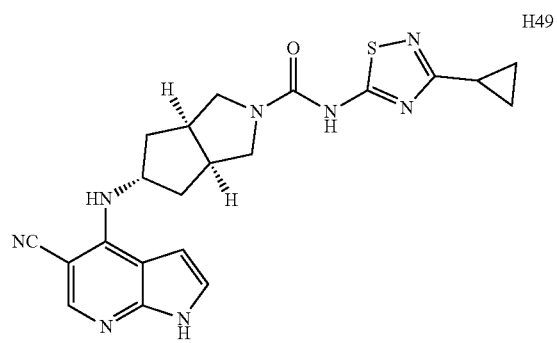 [SMILES: N#Cc1cnc2[nH]ccc2c1N[C@H]1C[C@@H]2CN(C(=O)Nc3nc(C4CC4)ns3)C[C@@H]2C1]

3-cyclopropyl-5-amino-1H-1,2,4-thiadiazole was used as a raw material to obtain compound H49 by using the same preparation method as described in Example 20.

MS m/z (ESI): 435 [M+H]+.

$^1$H NMR (400 MHz, DMSO-d$_6$) δ 11.74 (s, 1H), 11.41 (s, 1H), 8.02 (s, 1H), 7.17-7.13 (m, 1H), 6.79 (d, J=8.4 Hz, 1H), 6.71 (dd, J=3.5, 2.0, 1H), 4.75-4.66 (m, 1H), 3.65-3.55 (m, 2H), 3.37-3.31 (m, 2H), 2.92-2.80 (m, 2H), 2.10-2.03 (m, 1H), 1.99-1.87 (m, 4H), 0.95-0.86 (m, 4H).

Example 50

Preparation of (3aR,5s,6aS)-5-((5-trifluoromethyl-1H-pyrrolo[2,3-b]pyridin-4-yl)amino)-N-(3-methoxy-1,2,4-thiadiazole-5-yl)hexahydrocyclopentadiene[c]pyrrole-2(1H)-carboxamide H50

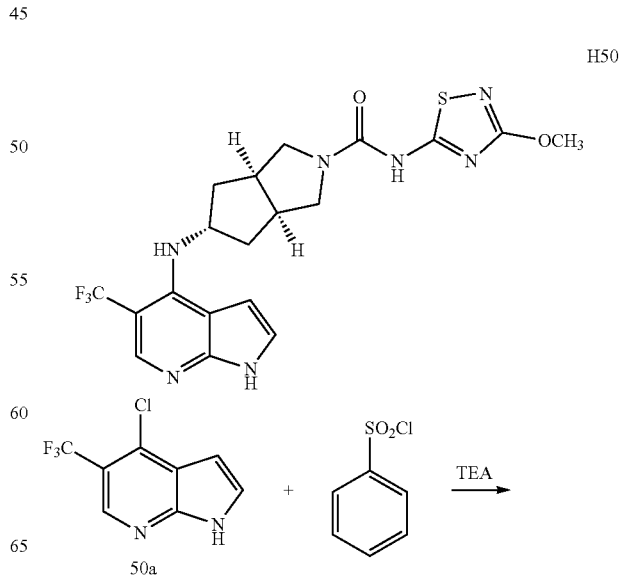

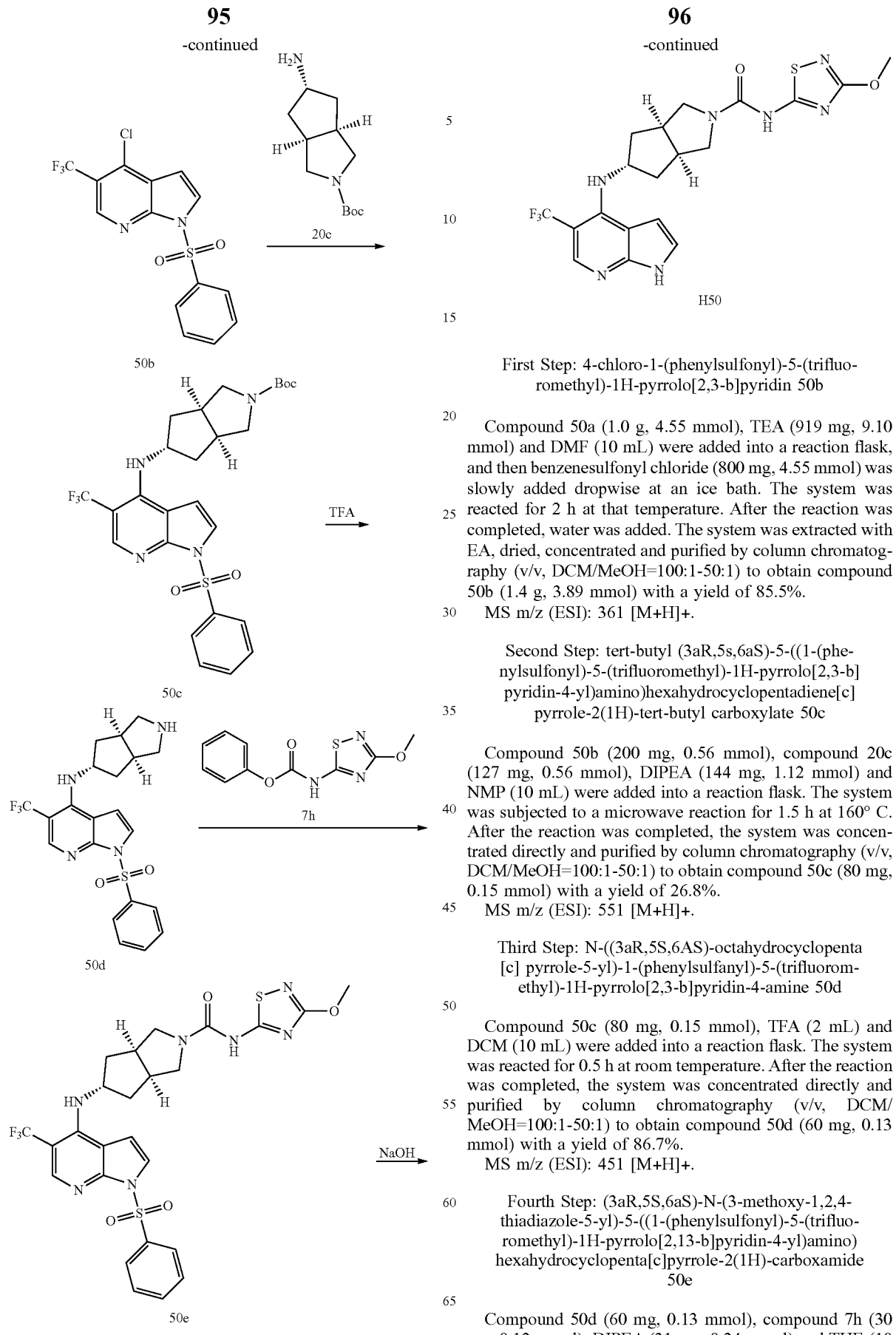

First Step: 4-chloro-1-(phenylsulfonyl)-5-(trifluoromethyl)-1H-pyrrolo[2,3-b]pyridin 50b Compound 50a (1.0 g, 4.55 mmol), TEA (919 mg, 9.10 mmol) and DMF (10 mL) were added into a reaction flask, and then benzenesulfonyl chloride (800 mg, 4.55 mmol) was slowly added dropwise at an ice bath. The system was reacted for 2 h at that temperature. After the reaction was completed, water was added. The system was extracted with EA, dried, concentrated and purified by column chromatography (v/v, DCM/MeOH=100:1-50:1) to obtain compound 50b (1.4 g, 3.89 mmol) with a yield of 85.5%.

MS m/z (ESI): 361 [M+H]+.

Second Step: tert-butyl (3aR,5s,6aS)-5-((1-(phenylsulfonyl)-5-(trifluoromethyl)-1H-pyrrolo[2,3-b]pyridin-4-yl)amino)hexahydrocyclopentadiene[c]pyrrole-2(1H)-tert-butyl carboxylate 50c Compound 50b (200 mg, 0.56 mmol), compound 20c (127 mg, 0.56 mmol), DIPEA (144 mg, 1.12 mmol) and NMP (10 mL) were added into a reaction flask. The system was subjected to a microwave reaction for 1.5 h at 160° C. After the reaction was completed, the system was concentrated directly and purified by column chromatography (v/v, DCM/MeOH=100:1-50:1) to obtain compound 50c (80 mg, 0.15 mmol) with a yield of 26.8%.

MS m/z (ESI): 551 [M+H]+.

Third Step: N-((3aR,5S,6AS)-octahydrocyclopenta[c]pyrrole-5-yl)-1-(phenylsulfanyl)-5-(trifluoromethyl)-1H-pyrrolo[2,3-b]pyridin-4-amine 50d Compound 50c (80 mg, 0.15 mmol), TFA (2 mL) and DCM (10 mL) were added into a reaction flask. The system was reacted for 0.5 h at room temperature. After the reaction was completed, the system was concentrated directly and purified by column chromatography (v/v, DCM/MeOH=100:1-50:1) to obtain compound 50d (60 mg, 0.13 mmol) with a yield of 86.7%.

MS m/z (ESI): 451 [M+H]+.

Fourth Step: (3aR,5S,6aS)-N-(3-methoxy-1,2,4-thiadiazole-5-yl)-5-((1-(phenylsulfonyl)-5-(trifluoromethyl)-1H-pyrrolo[2,13-b]pyridin-4-yl)amino)hexahydrocyclopenta[c]pyrrole-2(1H)-carboxamide 50e Compound 50d (60 mg, 0.13 mmol), compound 7h (30 mg, 0.12 mmol), DIPEA (31 mg, 0.24 mmol) and THF (10 mL) were added into a reaction flask. The system was reacted for 2 h at 60° C. After the reaction was completed, the system was concentrated directly and purified by column chromatography (v/v, DCM/MeOH=100:1-50:1) to obtain compound 50e (40 mg, 0.07 mmol) with a yield of 53.8%.

MS m/z (ESI): 608 [M+H]+.

Fifth Step: (3aR,5S,6aS)-N-(3-methoxy-1,2,4-thiadiazole-5-yl)-5-((5-(trifluoromethyl)-1H-pyrrolo[2,3-b]piperidinopyridin-4-yl)amino)hexahydrocyclopenta[c]pyrrole-2(1H)-carboxamide H50

Compound 102f (40 mg, 0.07 mmol), 2M sodium hydroxide solution (2 mL) and methanol (5 mL) were added into a reaction flask. The system was stirred for 1 h at room temperature. After the reaction was completed under TLC monitoring, the system was adjusted to pH=8-10 with diluted hydrochloric acid, concentrated and purified by column chromatography (v/v, DCM/MeOH=100:1-50:1) to obtain compound H50 (20 mg, 0.04 mmol) with a yield of 57.10%.

MS m/z (ESI): 468 [M+H]+.

¹H NMR (400 MHz, DMSO-d₆) δ 11.66 (s, 1H), 11.56 (s, 1H), 8.04 (s, 1H), 7.22-7.16 (m, 1H), 6.60 (dd, J=3.6, 1.8 Hz, 1H), 5.31 (d, J=9.7 Hz, 1H), 4.70-4.62 (m, 1H), 3.86 (s, 3H), 3.61 (d, J=7.0 Hz, 2H), 3.41-3.34 (m, 2H), 2.88-2.75 (m, 2H), 2.03-1.83 (m, 4H).

Example 51

(3aR,5S,6aS)-5-((5-cyano-1H-pyrrolo[2,3-b]pyridin-4-yl)(methyl)amino)-N-(3-(2-methoxyethoxy)-1,2,4-thiadiazole-5-yl)hexahydrocyclopenta[c]pyrrole-2(1H)-carboxamide H51

H51

3-(2-methoxyethoxy)-5-amino-1,2,4-thiadiazole was used as a raw material to obtain compound H51 by using the same preparation method as described in Example 7.

MS m/z (ESI): 483 [M+H]+.

¹H NMR (400 MHz, DMSO-d₆) δ 11.90 (s, 1H), 11.52 (s, 1H), 8.12 (s, 1H), 7.27-7.22 (m, 1H), 6.62 (dd, J=3.6, 2.0 Hz, 1H), 4.75-4.66 (m, 1H), 4.36-4.26 (m, 2H), 3.71-3.52 (m, 4H), 3.35-3.27 (m, 2H), 3.25 (s, 3H), 3.16 (s, 3H), 2.91-2.77 (m, 2H), 2.18-2.07 (m, 2H), 1.90-1.77 (m, 2H).

Example 52

(3aR,5S,6aS)-5-((5-cyano-1H-pyrrolo[2,3-b]pyridin-4-yl)amino)-N-(3-(2-methoxyethoxy)-1,2,4-thiadiazole-5-yl)hexahydrocyclopenta[c]pyrrole-2(1H)-carboxamide H52

H52

3-(2-methoxyethoxy)-5-amino-1,2,4-thiadiazole was used as a raw material to obtain compound H52 by using the same preparation method as described in Example 20.

MS m/z (ESI): 469 [M+H]+.

¹H NMR (400 MHz, DMSO-d₆) δ 11.74 (s, 1H), 11.53 (s, 1H), 8.02 (s, 1H), 7.18-7.13 (m, 1H), 6.79 (d, J=7.3 Hz, 1H), 6.72 (dd, J=3.5, 2.0 Hz, 1H), 4.76-4.67 (m, 1H), 4.36-4.29 (m, 2H), 3.71-3.56 (m, 4H), 3.36-3.29 (m, 2H), 3.26 (s, 3H), 2.93-2.81 (m, 2H), 2.01-1.90 (m, 4H).

Example 53

Methyl 5-((3aR,5s,6as)-5-((5-cyano-1H-pyrrole[2,3-b]pyridin-4-yl)(methyl)amino) octahydrocyclopenta[c]pyrrole-2-formamido)-1,2,4-thiadiazole-3-carboxylate H53

H53

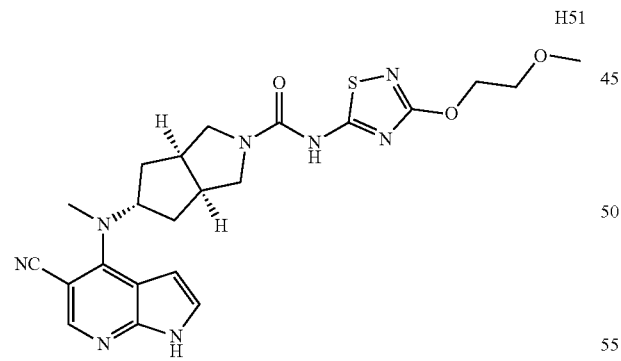

53a

TEA, DCM

-continued

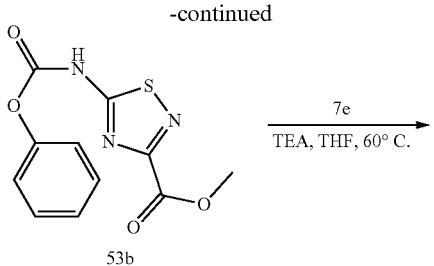

53b

→ 7e
TEA, THF, 60° C.

Example 54

(3aR,5s,6aS)-5-((5-cyano-1H-pyrrole[2,3-b]pyridin-4-yl)(methyl)amino)-N-(3-((dimethylamino)methyl)-1,2,4-thiadiazole-5-yl)hexahydrocyclopenta[c]pyrrole-2(1H)-carboxamide H54

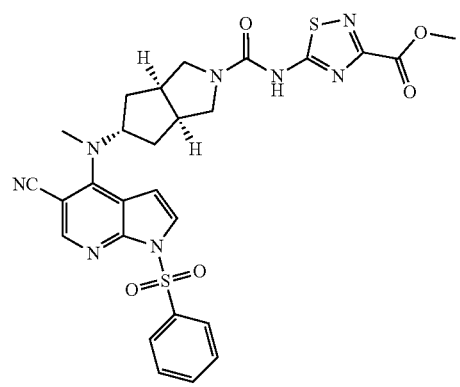

53c

→ K₂CO₃

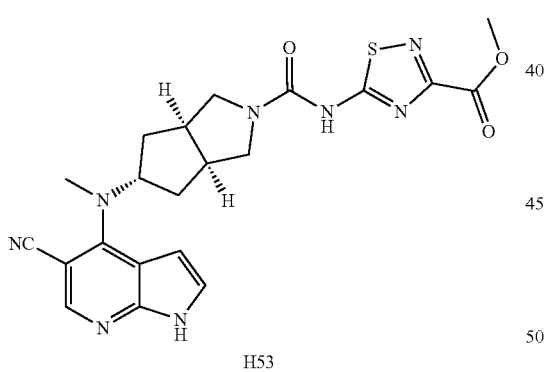

H53

Methyl 5-amino-1,2,4-thiadiazole-3-carboxylate was used as a raw material to obtain compound H53 by using the same preparation method as described in Example 7.

MS m/z (ESI): 467 [M+H]⁺

¹H NMR (400 MHz, DMSO-d6) δ12.03 (s, 1H), 11.89 (s, 1H), 8.11 (s, 1H), 7.23 (dd, J=3.7, 2.5 Hz, 1H), 6.62 (dd, J=3.7, 2.0 Hz, 1H), 4.71 (q, J=8.2 Hz, 1H), 3.82 (s, 3H), 3.72-3.60 (m, 2H), 3.40-3.30 (m, 2H), 3.16 (s, 31H), 2.90-2.75 (m, 2H), 2.12 (dt, J=12.8, 8.3 Hz, 2H), 1.90-1.78 (m, 2H).

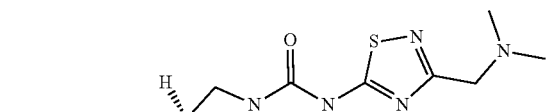

H54

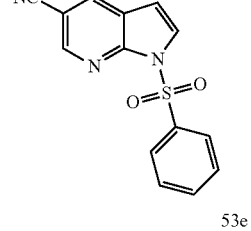

53e

→ NaBH₄

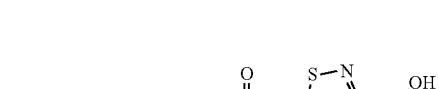

54a

→ Dess-Martin

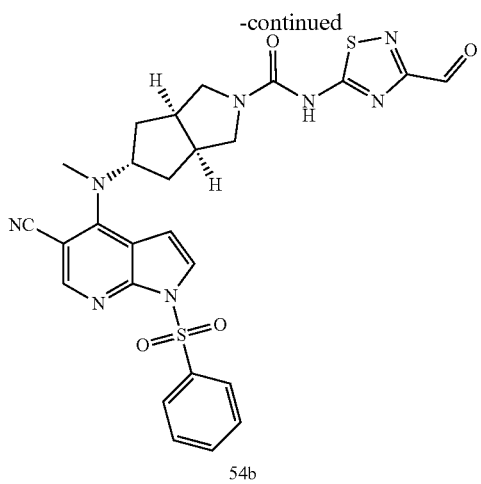

Second Step: (3aR,5s,6aS)-5-((5-cyano-1-(benzenesulfonyl)-1H-pyrrolo[2,3-b]pyridin-4-yl)(methyl)amino)-N-(3-formyl-1,2,4-thiadiazole-5-yl)hexahydrocyclopenta[c]pyrrole-2(1H)-carboxamide 54b Compound 54a (200 mg, 0.34 mmol) and Dess-Martin (293 mg, 0.68 mmol) were dispersed in DCM (14 mL). This mixture was stirred for 2 h at room temperature to obtain a reaction liquid. The reaction liquid was washed with saturated NaHCO₃ solution and Na₂SO₃ solution. The organic phases were dried and concentrated to obtain crude products 54b, which were used for a reaction of next step.

Third Step: (3aR,5s,6aS)-5-((5-cyano-1-(benzenesulfonyl)-1H-pyrrolo[2,3-b]pyridin-4-yl)(methyl)amino)-N-(3-((dimethylamino)methyl)-1,2,4-thiadiazole-5-yl)hexahydrocyclopenta[c]pyrrole-2(1H)-carboxamide 54c Compound 54b (100 mg, 0.17 mmol) and hydrochloride of dimethylamine (28 mg, 0.34 mmol) were dispersed in THF (10 mL), and sodium acetic acidborohydride (72 mg, 0.34 mmol) was added in batches. This mixture was stirred for 2 h at room temperature and concentrated to obtain crude products. The crude products were purified by column chromatography (DCM:MeOH=10:1) to obtain compound 54c (30 mg), which was present as white solids, with a yield of 29%.

Fourth Step: (3aR,5s,6aS)-5-((5-cyano-1H-pyrrole[2,3-b]pyridin-4-yl)(methyl)amino)-N-(3-((dimethylamino)methyl)-1,2,4-thiadiazole-5-yl)hexahydrocyclopenta[c]pyrrole-2(1H)-carboxamide H54

Compound 54c (30 mg, 0.05 mmol) was dissolved in methanol (5 mL), and potassium carbonate (34 mg, 0.25 mmol) was added. This mixture was stirred for 2 h at room temperature, and filtered to obtain a filtrate, which was concentrated to obtain crude products. The crude products were purified by column chromatography to obtain compound H54 (3.5 mg), which was present as white solids, with a yield of 15%.

MS m/z (ESI): 466 [M+H]⁺

¹H NMR (400 MHz, Methanol-d4) δ 8.11 (s, 1H), 7.18 (d, J=3.7 Hz, 1H), 6.69 (d, J=3.7 Hz, 1H), 4.90 (s, 2H), 3.73 (dd, J=11.1, 8.1 Hz, 2H), 3.59 (s, 2H), 3.49-3.40 (m, 3H), 3.01 (s, 3H), 2.31 (s, 6H), 2.27 (t, J=8.9 Hz, 2H), 2.00 (dd, J=13.6, 7.7 Hz, 3H).

Example 55

(3aR,5s,6aS)-5-((5-cyano-1H-pyrrole[2,3-b]pyridin-4-yl)amino)-N-(3-((dimethylamino)methyl)-1,2,4-thiadiazole-5-yl)hexahydrocyclopenta[c]pyrrole-2(1H)-carboxamide H55

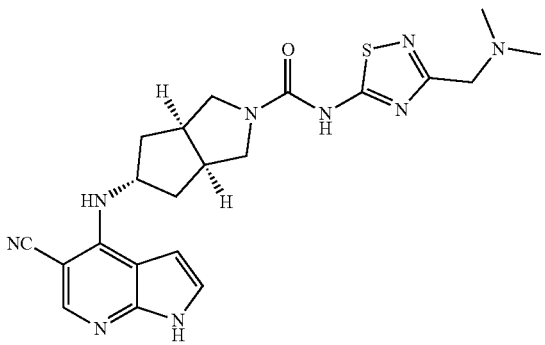

First Step: (3aR,5s,6aS)-5-((5-cyano-1-(benzenesulfonyl)-1H-pyrrolo[2,3-b]pyridin-4-yl)(methyl)amino)-N-(3-(hydroxymethyl)-1,2,4-thiadiazole-5-yl)hexahydrocyclopenta[c]pyrrole-2(1H)-carboxamide 54a Compound 53e (400 mg, 0.66 mmol) was dispersed in THF (20 mL), and sodium borohydride (376 mg, 9.9 mmol) was added in batches. This mixture was stirred for 6 h at room temperature and concentrated to obtain crude products. The crude products were purified by column chromatography (DCM:MeOH=15:1) to obtain compound 54a (250 mg), which was present as gray solids, with a yield of 65%.

Compound 20e was used as a raw material to obtain compound H55 by using the same preparation method as described in Example 54.

MS m/z (ESI): 452 [M+H]+

$^1$H NMR (400 MHz, Methanol-d4) δ 8.03 (s, 1H), 7.13 (d, J=3.7 Hz, 1H), 6.70 (d, J=3.6 Hz, 1H), 4.90-4.75 (m, 1H), 3.75 (dd, J=11.0, 8.1 Hz, 2H), 3.60 (s, 2H), 3.50-3.45 (m, 2H), 3.04 (s, 2H), 2.32 (s, 6H), 2.20-2.06 (m, 4H).

Example 56

(3aR,5S,6aS)-5-((5-cyano-1H-pyrrole[2,3-b]pyridin-4-yl)(methyl)amino)-N-(3-methoxymethyl)-1,2,4-thiadiazole-5-yl)hexahydrocyclopenta[c]pyrrole-2(1H)-carboxamide H56

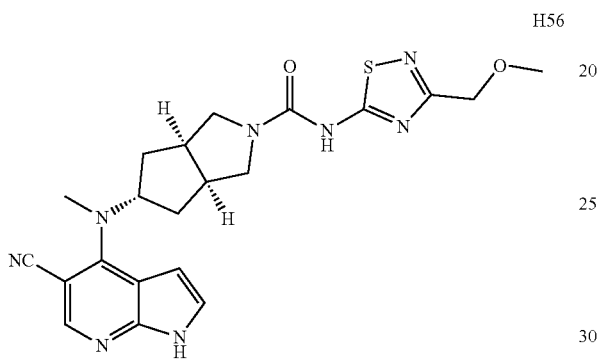

3-(methoxymethyl)-5-amino-1,2,4-thiadiazole was used as a raw material to obtain compound H56 by using the same preparation method as described in Example 7.

MS m/z (ESI): 453 [M+H]+.

1H NMR (400 MHz, DMSO-d6) δ 11.90 (s, 1H), 11.61 (s, 1H), 8.12 (s, 1H), 7.23 (dd, J=3.6, 2.5 Hz, 1H), 6.62 (dd, J=3.6, 2.0 Hz, 1H), 4.71 (q, J=8.0 Hz, 1H), 4.41 (s, 2H), 3.65 (m, 2H), 3.37 (m, 2H), 3.28 (s, 3H), 3.17 (s, 3H), 2.85 (s, 2H), 2.12 (dt, J=13.4, 8.4 Hz, 2H), 1.84 (dd, J=13.3, 7.5 Hz, 2H).

Example 57

(3aR,5s,6aS)-5-((5-cyano-1H-pyrrole[2,3-b]pyridin-4-yl)amino)-N-(3-methoxymethyl)-1,2,4-thiadiazole-5-yl)hexahydrocyclopenta[c]pyridin-2(1H)-carboxamide H57

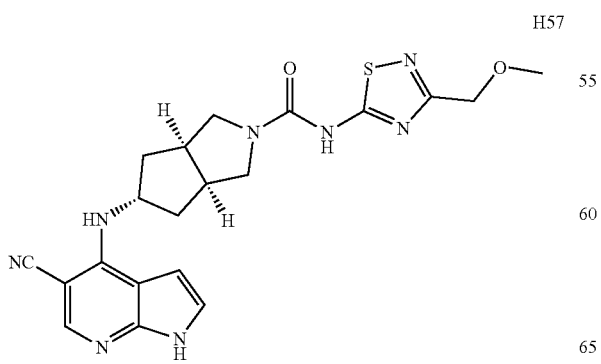

3-(methoxymethyl)-5-amino-1,2,4-thiadiazole was used as a raw material to obtain compound H57 by using the same preparation method as described in Example 20.

MS m/z (ESI): 439 [M+H]+

$^1$H NMR (400 MHz, DMSO-d6) δ 11.74 (s, 1H) 1.163 (s, 1H), 8.02 (d, J=2.1 Hz, 1H), 7.21-7.13 (m, 1H), 6.79 (d, J=7.8 Hz, 1H), 6.72 (dd, J=3.6, 2.0 Hz, 1H), 4.72 (q, J=6.8 Hz, 1H), 4.41 (s, 2H), 3.70-3.64 (m, 2H), 3.38-3.30 (m, 2H), 3.28 (s, 3H), 2.92-2.85 (m, 2H), 1.99-1.92 (m, 4H).

Example 58

N-(3-((5-cyano-1H-pyrrolo[2,3-b]pyridin-4-yl)amino)-4-ethylcyclopentyl)benzo[c][1,2,5] oxadiazole-4-sulfamide H58

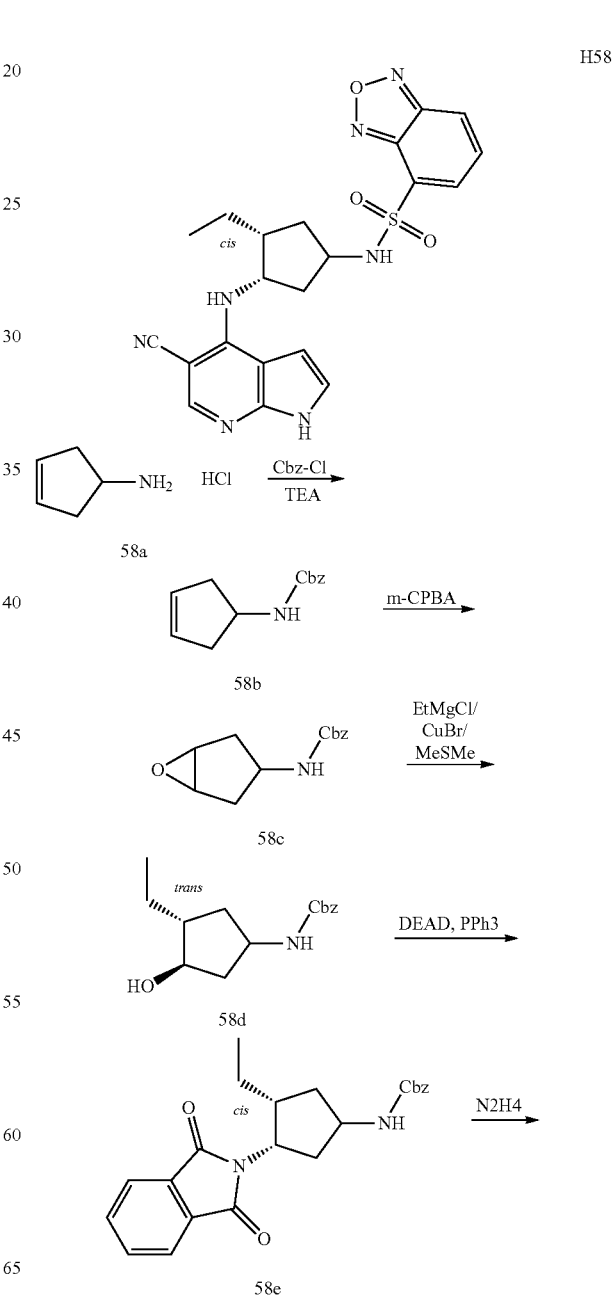

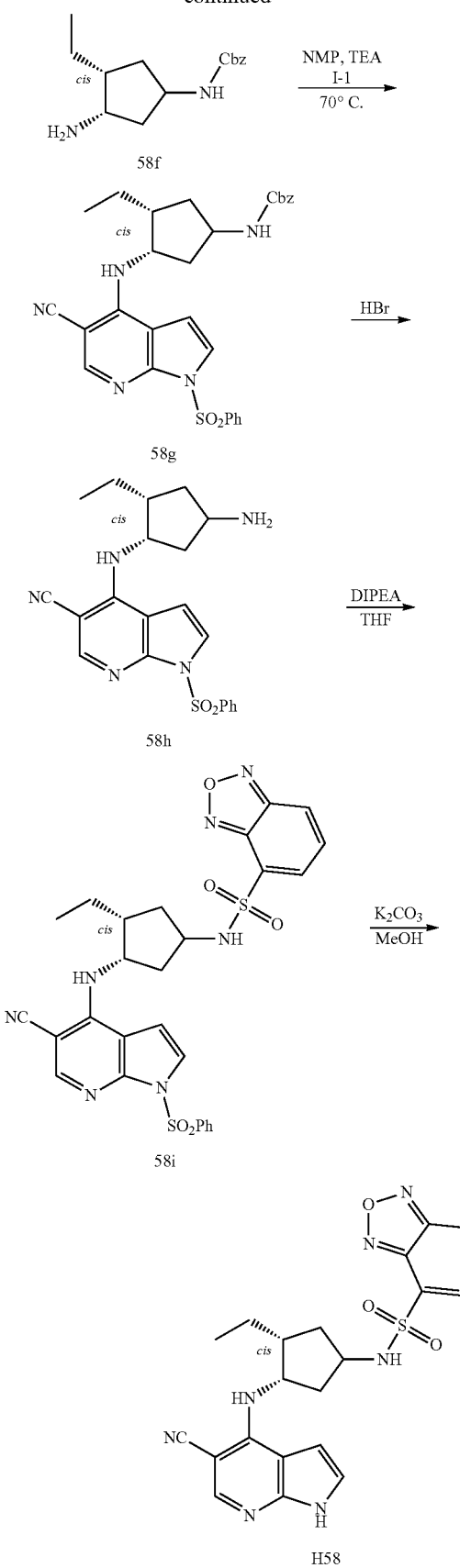

First Step: benzylcyclopentyl-3-ene-1-yl-carbamate 58b

Compound 58a (5 g, 41.6 mmol) and triethylamine (12.6 g, 124.8 mmol) were dissolved in DCM, and CBZ-Cl (7.8 g, 45.8 mmol) was slowly added dropwise. The mixture was stirred for 2 h at room temperature, quenched with water and extracted with DCM. The organic phases were washed with water, dried and concentrated to obtain crude products. The crude products were purified with column chromatography (PE:EA=3:1) to obtain compound 58b (4 g), which was present as white solids, with a yield of 44%.

MS m/z (ESI): 218 [M+H]$^+$

Second Step: benzyl (6-oxabicyclic[3.1.0]hexane-3-yl)carbamate 58c

Compound 58b (2 g, 9.2 mmol) was dissolved in DCM (60 mL), and m-CPBA (2.3 g, 13.8 mmol) was added in batches at room temperature. The mixture was stirred for 2 h at room temperature, and filtered to obtain a filtrate, which was washed with saturated sodium bicarbonate solution and sodium thiosulfate solution. The organic phases were separated, and the aqueous phase was extracted with DCM. The organic phases were combined, dried and concentrated to obtain crude products 58c, which were used directly for a reaction of next step.

Third Step: benzyl ((3R,4R)-3-ethyl-4-hydroxylcyclopentyl)carbamate 58d

Compound 58c (2 g, 8.5 mmol) and CuBr-DMS (17 mg, 0.085 mmol) were dissolved in anhydrous THF, and ethylmagnesium bromide (21 ml, 42.5 mmol) was slowly added dropwise under the protection of nitrogen at −60° C. The reaction temperature was kept below −50° C. and this mixture was stirred for 2 h. The cold reaction mixture was added into saturated ammonium chloride solution and quenched, extracted with EA, and an organic phase was washed with water, dried and concentrated to obtain crude products. The crude products were purified by column chromatography (PE:EA=2:1) to obtain 58d (1.9 g), which was present as yellowish solids, with a yield of 84%.

Fourth Step: benzyl ((3S,4R)-3-(1,3-dioxoisoindolinone-2-yl)-4-ethylcyclopentyl) carbamate 58e Compound 58d (1.9 g, 7.2 mmol), phthalimide (1.27 g, 8.6 mmol) and triphenyl phosphine (2.25 g, 8.6 mmol) were dissolved in anhydrous THF, and DIAD (1.7 g, 8.6 mmol) was slowly added dropwise at an ice bath, then heated to room temperature and stirred for 4 h, quenched with water and extracted with EA. The organic phase was washed with water, dried and concentrated to obtain crude products. The crude products were purified by column chromatography (PE:EA=1:1) to obtain compound 58e (2.8 g), which was present as white solids, with a yield of 98%.

Fifth Step: benzyl ((3S,4R)-3-amino-4-ethylcyclopentyl)carbamate 58f

Compound 58e (3 g, 7.6 mmol) was dissolved in ethanol, and hydrazine hydrate (2.4 g, 76 mmol) was added. This reaction mixture was stirred under reflux for 2 hours, cooled, and filtered to obtain a filtrate, which was concentrated to obtain crude products. The crude products were purified by column chromatography (DCM:MeOH=10:1) to obtain compound 58f (1 g), which was present as a colorless oily substance, with a yield of 50%.

Sixth Step: benzyl ((3S,4R)-3-((5-cyano-1-(benzenesulfonyl)-1H-pyrrole[2,3-b]pyridin-4-yl)amino)-4-ethylcyclopentyl)carbamate 58g Compounds 58f (1 g, 2.8 mmol) and I-1 (0.96 g, 3 mmol) were dissolved in NMP, and DIPEA (1.5 g, 11.4 mmol) was added. This mixture was stirred for 2 h at 75° C., cooled, poured into water and extracted with EA. The organic phase was washed with water for three times, dried and concentrated to obtain crude products. The crude products were purified by column chromatography (PE:EA=1:1) to obtain compound 58g (1.2 g), which was present as yellowish solids, with a yield of 73%.

Seventh Step: 4-(((1S,2R)-4-amino-2-ethylcyclopentyl)amino)-1-(phenylsulfonyl)-1H-pyrrolo[2,3-b]pyridin-5-carbonitrile 58h Compound 58g (1.2 g, 2.2 mmol) was dissolved in HBr in acetic acid solution. This mixture was stirred for 2 h at room temperature, and concentrated to obtain crude products 58h, which were used directly fro a reaction of next step.

Eighth Step: N-((3S,4R)-3-((5-cyano-1-(phenylsulfonyl)-1H-pyrrolo[2,3-b]pyridin-4-yl) amino)-4-ethylcyclopentyl)benzo[c][1,2,5]oxadiazole-4-sulfamide 58i Compound 58h (100 mg, 0.24 mmol) and triethylamine (72 mg, 0.72 mmol) were dissolved in THF, and benzo[c][1,2,5]oxadiazole-4-sulfonyl chloride (64 mg, 0.29 mmol) was slowly added. This mixture was stirred for 2 h at room temperature, quenched with water and extracted with EA. The organic phase was washed with water, dried and concentrated to obtain crude products. The crude products were purified by column chromatography to obtain 58i (40 mg), which was present as yellowish solids, with a yield of 28%.

Ninth Step: N-((3S,4R)-3-((5-cyano-1H-pyrrolo[2,3-b]pyridin-4-yl)amino)-4-ethylcyclopentyl)benzo[c][1,2,5]oxadiazole-4-sulfamide H58

Compound 58i (40 mg, 0.06 mmol) and potassium carbonate (41 mg, 0.3 mmol) were dissolved in methanol, stirred for 1 h at room temperature and filtered to obtain a filtrate, which was concentrated to obtain crude products. The crude products were purified by column chromatography (DCM:MeOH=10:1) to obtain compound H58 (18.3 mg), which was present as yellowish solids, with a yield of 67%.

MS m/z (ESI): 452 [M+H]$^+$ $^1$H NMR (400 MHz, DMSO-d6) δ 11.75 (s, 1H), 8.44 (s, 1H), 8.32 (d, J=9.1 Hz, 1H), 8.06 (dd, J=6.7, 0.7 Hz, 1H), 8.00 (s, 1H), 7.73 (dd, J=9.1, 6.8 Hz, 1H), 7.19 (d, J=3.5 Hz, 1H), 6.69 (d, J=3.5 Hz, 1H), 6.37 (d, J=9.1 Hz, 1H), 4.67 (p, J=7.4 Hz, 1H), 3.94 (s, 1H), 2.10-1.96 (m, 2H), 1.87-1.76 (m, 1H), 1.65-1.56 (m, 2H), 1.32-1.14 (m, 1H), 1.10-1.02 (m, 1H), 0.63 (t, J=7.4 Hz, 3H).

Example 59

N-(3-((5-cyano-1H-pyrrolo[2,3-b]pyridin-4-yl)amino)-4-ethylcyclopentyl)-4,4,4-trifluorobutanamide H59

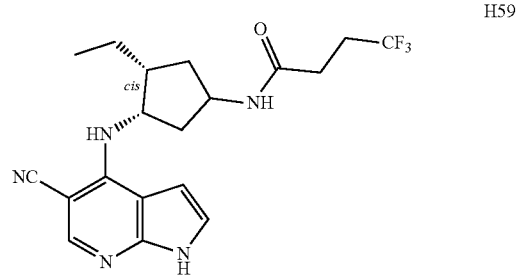 [SMILES: CC[C@@H]1CC(NC(=O)CCC(F)(F)F)C[C@@H]1Nc1c(C#N)cnc2[nH]ccc12]

4,4,4-trifluorobutylryl chloride was used as a raw material to obtain compound H59 by using the same preparation method as described in Example 58.

MS m/z (ESI): 394 [M+H]$^+$ $^1$H NMR (400 MHz, DMSO-d6) δ 11.77 (s, 1H), 8.11 (d, J=7.1 Hz, 1H), 8.03 (s, 1H), 7.23-7.17 (m, 1H), 6.79 (s, 1H), 6.47 (d, J=9.3 Hz, 1H), 4.81-4.71 (m, 1H), 4.25-4.15 (m, 1H), 2.48-2.30 (m, 4H), 2.16 (dt, J=13.8, 7.3 Hz, 2H), 1.86 (ddt, J=38.3, 15.4, 7.0 Hz, 2H), 1.67 (dq, J=12.1, 6.9, 5.5 Hz, 1H), 1.37 (dt, J=13.2, 6.2 Hz, 1H), 1.20 (t, J=8.4 Hz, 1H), 0.77 (t, J=7.4 Hz, 3M).

Example 60

N-(3-((5-cyano-1H-pyrrolo[2,3-b]pyridin-4-yl)amino)-4-ethylcyclopentyl)-3-(trifluoromethyl)benzsulfamide H60

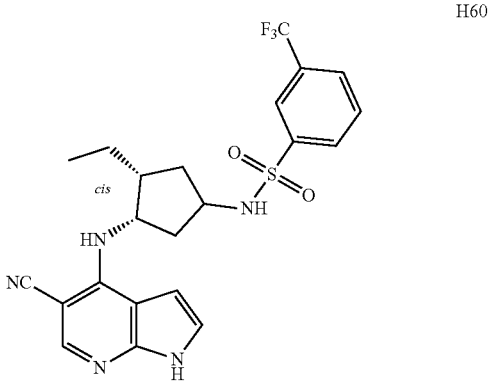 [SMILES: CC[C@@H]1CC(NS(=O)(=O)c2cccc(C(F)(F)F)c2)C[C@@H]1Nc1c(C#N)cnc2[nH]ccc12]

3-trifluoromethylbenzenesulfonyl chloride was used as a raw material to obtain compound H60 by using the same preparation method as described in Example 58.

MS m/z (ESI): 478 [M+H]$^+$ $^1$H NMR (400 MHz, DMSO-d6) δ 11.75 (s, 1H), 8.13-8.05 (m, 3H), 8.02 (d, J=8.9 Hz, 2H), 7.84 (t, J=7.8 Hz, 1H), 7.19 (t, J=3.0 Hz, 1H), 6.71 (dd, J=3.6, 0.9 Hz, 1H), 6.43 (d, J=9.1 Hz, 1H), 4.69 (q, J=7.6 Hz, 1H), 3.73 (d, J=6.5 Hz,

1H), 2.12 (q, J=7.5 Hz, 1H), 1.99 (dt, J=13.6, 6.9 Hz, 1H), 1.89-1.77 (m, 1H), 1.64-1.55 (m, 2H), 1.33-1.19 (m, 1H), 1.07 (m, 1H), 0.65 (t, J=7.4 Hz, 3H).

Example 61

1-((3S,4R)-3-((5-cyano-1H-pyrrolo[2,3-b]pyridin-4-yl)amino)-4-ethylcyclopentyl)-3-(3-methoxy-1,2,4-thiadiazole-5-yl)urea H61

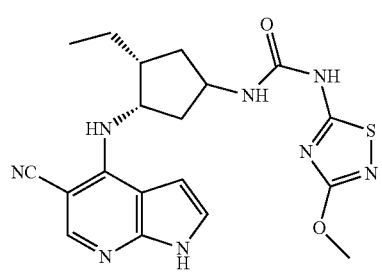

H61

Compound 7h was used as a raw material to obtain compound H61 by using the same preparation method as described in Example 58.

MS m/z (ESI): 427 [M+H]+

$^1$H NMR (400 MHz, DMSO-d6) δ 11.78 (s, 1H), 11.05 (s, 1H), 8.04 (s, 1H), 7.21 (dd, J=3.6, 2.4 Hz, 1H), 7.06 (s, 1H), 6.79 (dd, J=3.7, 2.0 Hz, 1H), 6.51 (s, 1H), 4.78 (p, J=7.2 Hz, 1H), 4.24-4.15 (m, 1H), 3.84 (s, 3H), 2.22 (dt, J=13.9, 7.2 Hz, 2H), 1.99 (ddd, J=13.0, 7.4, 4.6 Hz, 1H), 1.88 (dt, J=13.3, 7.7 Hz, 1H), 1.74 (ddd, J=12.6, 7.4, 4.4 Hz, 1H), 1.44-1.29 (m, 1H), 1.25-1.12 (m, 1H), 0.78 (t, J=7.4 Hz, 31H).

Example 62

4-((4-((((3-hydroxy-3-methylpyrrolidin-1-yl)sulfonyl)methyl)cyclohexyl)(methyl)amino)-1H-pyrrolo[2,3-b]pyridin-5-carbonitrile H62

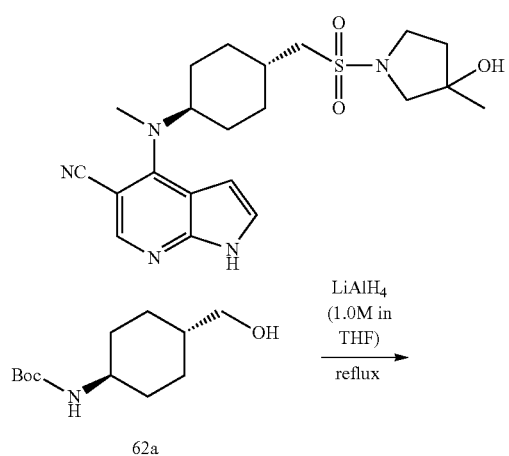

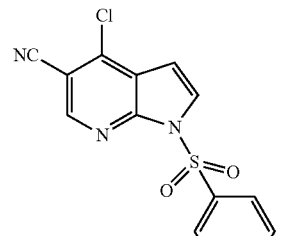

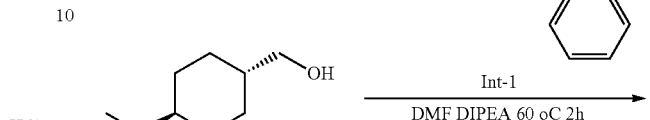

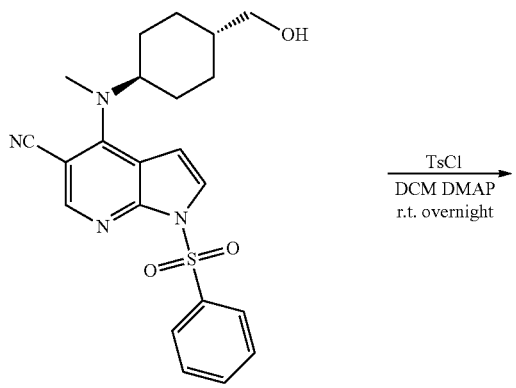

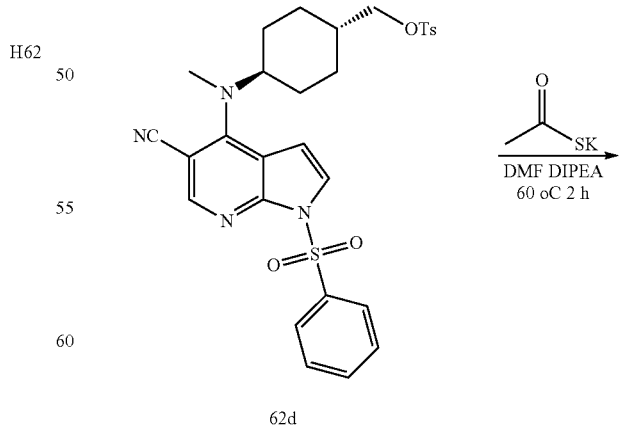

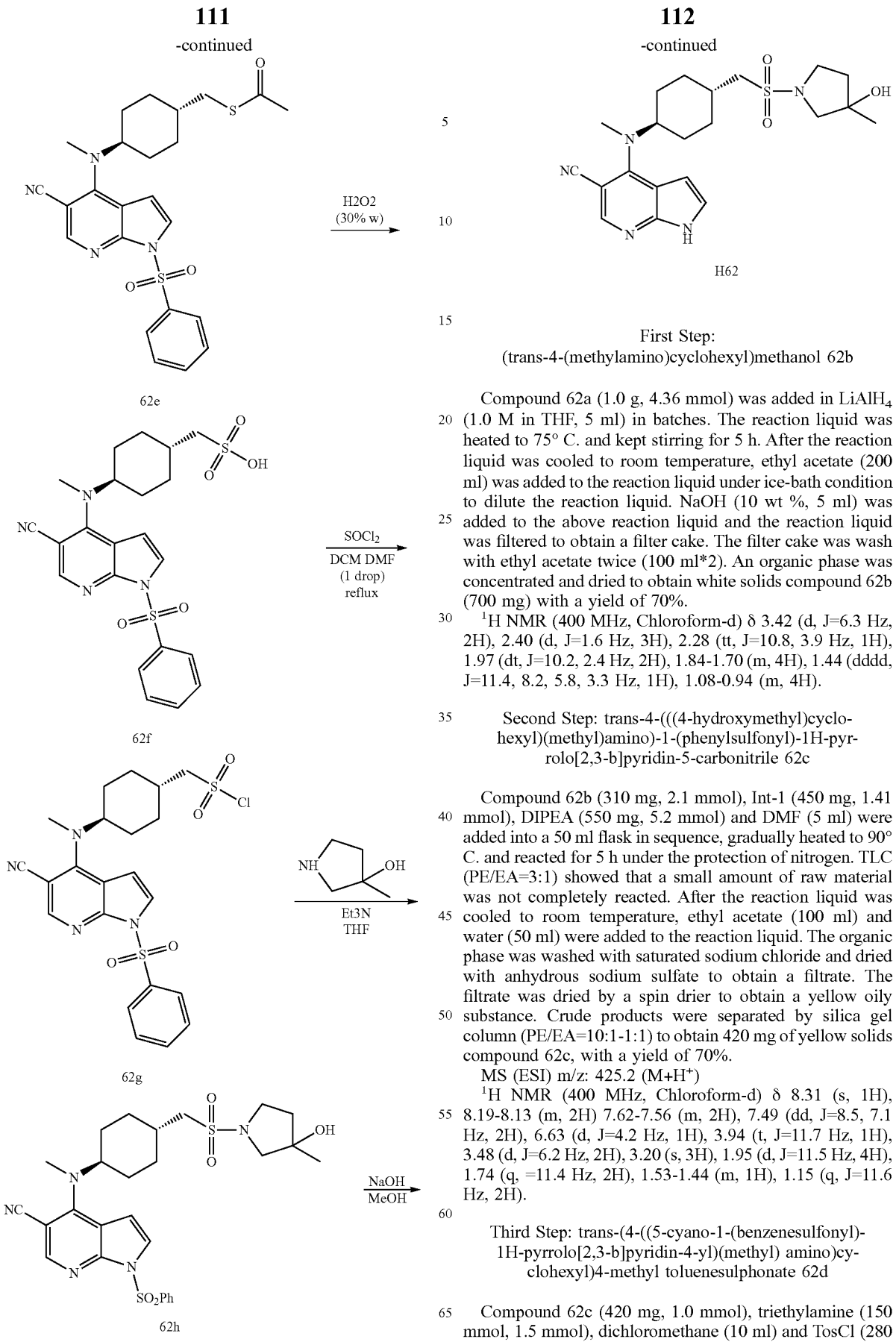

First Step: (trans-4-(methylamino)cyclohexyl)methanol 62b

Compound 62a (1.0 g, 4.36 mmol) was added in LiAlH₄ (1.0 M in THF, 5 ml) in batches. The reaction liquid was heated to 75° C. and kept stirring for 5 h. After the reaction liquid was cooled to room temperature, ethyl acetate (200 ml) was added to the reaction liquid under ice-bath condition to dilute the reaction liquid. NaOH (10 wt %, 5 ml) was added to the above reaction liquid and the reaction liquid was filtered to obtain a filter cake. The filter cake was wash with ethyl acetate twice (100 ml*2). An organic phase was concentrated and dried to obtain white solids compound 62b (700 mg) with a yield of 70%.

$^1$H NMR (400 MHz, Chloroform-d) δ 3.42 (d, J=6.3 Hz, 2H), 2.40 (d, J=1.6 Hz, 3H), 2.28 (tt, J=10.8, 3.9 Hz, 1H), 1.97 (dt, J=10.2, 2.4 Hz, 2H), 1.84-1.70 (m, 4H), 1.44 (dddd, J=11.4, 8.2, 5.8, 3.3 Hz, 1H), 1.08-0.94 (m, 4H).

Second Step: trans-4-(((4-hydroxymethyl)cyclohexyl)(methyl)amino)-1-(phenylsulfonyl)-1H-pyrrolo[2,3-b]pyridin-5-carbonitrile 62c Compound 62b (310 mg, 2.1 mmol), Int-1 (450 mg, 1.41 mmol), DIPEA (550 mg, 5.2 mmol) and DMF (5 ml) were added into a 50 ml flask in sequence, gradually heated to 90° C. and reacted for 5 h under the protection of nitrogen. TLC (PE/EA=3:1) showed that a small amount of raw material was not completely reacted. After the reaction liquid was cooled to room temperature, ethyl acetate (100 ml) and water (50 ml) were added to the reaction liquid. The organic phase was washed with saturated sodium chloride and dried with anhydrous sodium sulfate to obtain a filtrate. The filtrate was dried by a spin drier to obtain a yellow oily substance. Crude products were separated by silica gel column (PE/EA=10:1-1:1) to obtain 420 mg of yellow solids compound 62c, with a yield of 70%.

MS (ESI) m/z: 425.2 (M+H⁺)

$^1$H NMR (400 MHz, Chloroform-d) δ 8.31 (s, 1H), 8.19-8.13 (m, 2H) 7.62-7.56 (m, 2H), 7.49 (dd, J=8.5, 7.1 Hz, 2H), 6.63 (d, J=4.2 Hz, 1H), 3.94 (t, J=11.7 Hz, 1H), 3.48 (d, J=6.2 Hz, 2H), 3.20 (s, 3H), 1.95 (d, J=11.5 Hz, 4H), 1.74 (q, =11.4 Hz, 2H), 1.53-1.44 (m, 1H), 1.15 (q, J=11.6 Hz, 2H).

Third Step: trans-(4-((5-cyano-1-(benzenesulfonyl)-1H-pyrrolo[2,3-b]pyridin-4-yl)(methyl) amino)cyclohexyl)4-methyl toluenesulphonate 62d Compound 62c (420 mg, 1.0 mmol), triethylamine (150 mmol, 1.5 mmol), dichloromethane (10 ml) and TosCl (280 mg, 1.5 mmol) were added into a 25 ml flask in sequence at room temperature, stirred to react overnight to obtain a reaction liquid. TLC (PE/EA=3:1) showed that raw materials were completely reacted. Ethyl acetate (100 ml) and water (50 ml) were added to the reaction liquid. The organic phase was washed with saturated sodium chloride and dried with anhydrous sodium sulfate to obtain a filtrate. The filtrate was dried by spin to obtain crude products. The crude products were separated by preparative plate (PE/EA=2:1) to obtain 500 mg of white solids compound 62d, with a yield of 86%.

MS (ESI) m/z: 396.2 (M+H$^+$)

$^1$H NMR (400 MHz, Chloroform-d) δ 8.29 (s, 1H), 8.18-8.13 (m, 2H), 7.78-7.73 (m, 2H), 7.59 (dd, J=8.4, 5.8 Hz, 2H), 7.49 (t, J=7.7 Hz, 2H), 7.33 (d, J=8.1 Hz, 2H), 6.60 (d, J=4.1 Hz, 1H), 3.88 (s, 1H), 3.81 (d, J=6.4 Hz, 2H), 3.16 (s, 3H), 2.44 (s, 3H), 1.90 (t, J=14.5 Hz, 4H), 1.67 (s, 3H), 1.17-1.05 (m, 2H).

Fourth Step: trans-((4-((5-cyano-1-(benzenesulfonyl)-1H-pyrrolo[2,3-b]pyridin-4-yl)(methyl)amino)cyclohexyl)methyl)thioacetate 62e Compound 62d (500 mg, 0.86 mmol), potassium thioacetate (200 mg, 1.73 mmol) and DMF (5 ml) were added into a 50 ml flask in sequence. The reaction liquid was heated to 60° C. and stirred for 2 h. TLC (PE/EA=3:1) showed that raw materials were completely reacted. Ethyl acetate (100 ml) and water (50 ml) were added to the reaction liquid. The organic phase was washed with saturated sodium chloride solution once and dried with anhydrous sodium sulfate to obtain a filtrate. The filtrate was dried by a spin drier to obtain white solids compound 62e (350 mg), with a yield of 84%.

LCMS (ESI-MS) m/z: 483.3 (M+H$^+$).

$^1$H NMR (400 MHz, Chloroform-d) δ 8.30 (s, 1H), 8.16 (d, J=7.7 Hz, 2H), 7.59 (dd, J=9.2, 5.7 Hz, 2H), 7.49 (t, J=7.7 Hz, 2H), 6.61 (d, J=4.1 Hz, 1H), 3.92 (s, 1H), 3.16 (s, 3H), 2.79 (d, J=6.6 Hz, 2H), 2.32 (d, J=0.8 Hz, 3H), 1.94 (t, J=16.3 Hz, 4H), 1.68 (d, J=11.7 Hz, 3H), 1.16 (q, J=12.1 Hz, 2H).

Fifth Step: trans-(4-((5-cyano-1-(benzenesulfonyl)-1H-pyrrolo[2,3-b]pyridin-4-yl)(methyl)amino)cyclohexyl)methanesulfonic acid 62f Compound 62e (250 mg, 0.51 mmol) was dissolved in formic acid (3.0 ml) under an ice-bath condition to obtain a reaction liquid. Hydrogen peroxide (30% aq, 0.5 ml) solution was added in the above reaction liquid dropwise. The reaction liquid was stirred to react overnight at room temperature. LCMS showed that a small amount of raw material remained. Saturated sodium sulfite solution (20 ml) was slowly added in the reaction liquid dropwise under an ice-bath condition to quench the reaction. Starch KI test paper detected that hydrogen peroxide was completely quenched. (Dichloromethane:methanol=10:1, 50 ml×4) was added in the reaction liquid, and the organic phase was concentrated to dryness to obtain crude products. Crude products were separated by silica gel column (dichloromethane:methanol=20:1-8:1) to obtain white solids 62f (200 mg), with a yield of 80%.

MS (ESI) m/z: 489.2 (M+H$^+$)

$^1$H NMR (400 MHz, DMSO-d6) δ 8.24 (s, 1H), 8.08-8.01 (m, 2H), 7.76-7.67 (m, 2H), 7.64-7.57 (m, 2H), 6.86 (d, J=4.2 Hz, 1H), 3.89-3.79 (m, 1H), 3.13 (s, 31H), 2.28 (d, J=6.2 Hz, 2H), 2.03 (d, J=13.0 Hz, 2H), 1.72 (q, J=6.3 Hz, 5H), 1.07-0.94 (m, 2H).

Sixth Step: trans-(4-((5-cyano-1-(benzenesulfonyl)-1H-pyrrolo[2,3-b]pyridin-4-yl)(methyl)amino)cyclohexyl)methylsulfonyl chloride 62g Compound 62f (200 mg, 0.4 mmol) was dispersed in dichloromethane (30 ml) to obtain a reaction liquid. Thionyl chloride (1.0 ml, 13.4 mmol) was added in the above reaction liquid, and a drop of DMF was added. The reaction liquid was subjected to a reflux reaction under the protection of nitrogen for 2 h. LCMS showed that the reaction was complete substantially. The reaction liquid was directly adjusted to pH=8 with saturated sodium bicarbonate solution without purification under an ice-bath condition to obtain crude products 62g, which were used for a reaction of next step.

LCMS (ESI-MS) m/z: 507.2 (M+H$^+$)

Seventh Step: trans-4-((4-((((3-hydroxy-3-methylpyrrolidin-1-yl)sulfonyl)methyl)cyclohexyl)(methyl)amino)-1-(phenylsulfonyl)-1H-pyrrolo[2,3-b]pyridin-5-carbonitrile 62h Et$_3$N (303.3 mg, 3.0 mmol) was added in compound Int-2 (202.2 mg, 2.0 mmol) in THF solution under an ice-bath condition, and then compound 62g (0.4 mmol) was added dropwise to obtain a reaction liquid. The reaction liquid was kept reacting at the ice bath for 1 h. LCMS showed that raw material was reacted completely. Dichloromethane (50 ml) and water (20 ml) were added in the reaction liquid. The organic phase was dried and concentrated to obtain yellow compound 62h (100 mg), with a yield of 44%.

LCMS (ESI-MS) m/z: 572.3 (M+H$^+$)

Eighth Step: 4-((trans-4-((((3-hydroxy-3-methylpyrrolidin-1-yl)sulfonyl)methyl)cyclohexyl)(methyl)amino)-1H-pyrrolo[2,3-b]pyridin-5-carbonitrile H62

Compound 62h (100 mg, 0.2 mmol) was dissolved in methanol (3 ml), and NaOH (200 uL, 0.6 mmol, 4 M in water) was added to obtain a reaction liquid. The reaction liquid was stirred for 2 h at room temperature. The reaction liquid was separated by TLC (DCM/MeOH=15:1) silica gel preparative plate to obtain white solids compound H62 (21 mg), with a yield of 24%.

MS (ESI) m/z: 432.3 (M+H$^+$).

$^1$H NMR (400 MHz, DMSO-d$_6$) δ 11.88 (s, 1H), 8.10 (s, 1H), 7.28 (dd, J=3.6, 2.5 Hz, 1H), 6.56 (dd, J=3.6, 2.0 Hz, 1H), 4.83 (s, 1H), 3.93 (q, J=6.4, 5.6 Hz, 1H), δ 3.34 (dd, J=10.0, 7.6 Hz, 1H), 3.29-3.24 (m, 1H), 3.20-3.03 (m, 5H), 3.00-2.85 (m, 2H), 2.06-1.90 (m, 3H), 1.88-1.68 (m, 8H, 24 (s, 3H).

Example 63

Trans-4-(methyl((1r,4r)-4-(((4-methylpiperazin-1-yl)sulfonyl)methyl)cyclohexyl)amino)-1H-pyrrolo[2,3-b]pyridin-5-carbonitrile H63

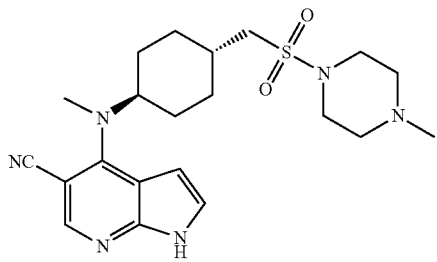

N-methylpiperazine was used as a raw material to obtain compound H63 by using the same preparation method as described in Example 62.

MS (ESI) m/z: 431.3 (M+H$^+$).

$^1$H NMR (400 MHz, DMSO-d$_6$) δ 11.98 (s, 1H), 8.20 (s, 1H), 7.38 (dd, J=3.6, 2.5 Hz, 1H), 6.66 (dd, J=3.6, 2.0 Hz, 1H), 4.06-3.96 (m, 1H), 3.26 (s, 3H), 3.20 (t, J=4.9 Hz, 4H), 3.01 (d, J=6.4 Hz, 2H), 2.44 (t, J=4.7 Hz, 4H), 2.27 (s, 3H), 2.10 (d, J=13.0 Hz, 2H), 1.99-1.87 (m, 5H), 1.39-1.24 (m, 2H).

Example 64 trans-4-((4-(((3-(2-methoxyethoxy)piperidin-1-yl)sulfonyl)methyl)cyclopentyl)(methyl)amino)-1H-pyrrolo[2,3-b]pyridin-5-carbonitrile H64

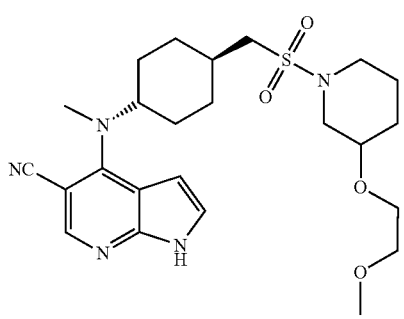

3-(2-methoxyethoxy)piperidine was used as a raw material to obtain compound H64 by using the same preparation method as described in Example 62.

MS m/z (ESI): 490 [M+H]+.

$^1$H NMR (400 MHz, DMSO-d$_6$) δ 11.88 (s, 1H), 8.10 (s, 1H), 7.32-7.25 (m, 1H), 6.56 (dd, J=3.5, 2.0 Hz, 1H), 3.95-3.87 (m, 1H), 3.57-3.16 (m, 13H), 3.10-2.85 (m, 4H), 2.06-1.97 (m, 2H), 1.89-1.74 (m, 6H), 1.72-1.65 (m, 1H), 1.43-1.34 (m, 2H), 1.27-1.20 (m, 2H).

Example 65

4-((trans-4-(((3-isobutoxypiperidin-1-yl)sulfonyl)methyl)cyclohexyl)(methyl)amino)-1H-pyrrolo[2,3-b]pyridin-5-acetonitrile H65

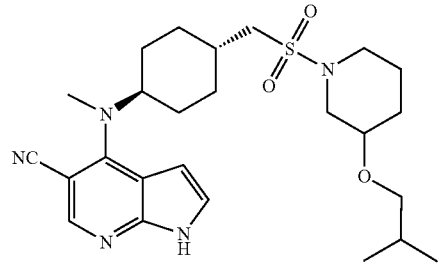

3-(2-methylpropoxy)piperidine was used as a raw material to obtain compound H65 by using the same preparation method as described in Example 62.

MS m/z (ESI): 488 [M+H]+.

$^1$H NMR (400 MHz, DMSO-d$_6$) δ11.88 (s, 1H), 8.11 (s, 1H), 7.31-7.25 (m, 1H), 6.59-6.52 (m, 1H), 3.95-3.87 (m, 1H), 3.45-3.38 (m, 1H), 3.34-3.29 (m, 1H), 3.27-3.18 (m, 2H), 3.18-3.11 (m, 4H), 2.99-2.80 (m, 4H), 2.04-1.96 (m, 2H), 1.91-1.74 (m, 6H), 1.75-1.66 (m, 2H), 1.44-1.33 (m, 2H), 1.27-1.20 (m, 2H), 0.82 (s, 6H).

Example 66

4-((trans-4-(((trans-3-(hydroxymethyl)-4-methylpyrrolidin-1-yl)sulfonyl)methyl)cyclohexyl)(methyl)amino)-1H-pyrrolo[2,3-b]pyridin-5-carbonitrile H66

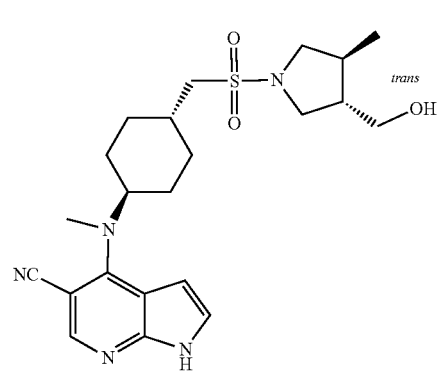

Trans-3-(hydroxymethyl)-4-methylpyrrolidine was used as a raw material to obtain compound H66 by using the same preparation method as described in Example 62.

MS (ESI) m/z: 446 (M+H)$^+$.

$^1$H NMR (400 MHz, DMSO-d6) δ 11.88 (s, 1H), 8.10 (s, 1H), 7.28 (dd, J=3.6, 2.5 Hz, 1H), 6.56 (dd, J=3.6, 2.0 Hz, 1H), 4.64 (t, J=5.2 Hz, 1H), 3.95-3.87 (m, 1H), 3.49-3.40 (m, 2H), 3.40-3.30 (m, 2H), 3.16 (s, 3H), 3.03 (dd, J=9.9, 8.1 Hz, 1H), 2.94 (d, J=6.4 Hz, 2H), 2.78 (dd, J=9.6, 8.6 Hz, 1H), 2.06-1.95 (m, 3H), 1.89-1.73 (m, 6H), 1.29-1.20 (m, 2H), 0.95 (d, J=6.5 Hz, 3H).

Example 67

4-(methyl-(trans-4-(((3-((methylamino)methyl)pyrrolidin-1-yl)sulfonyl)methyl)cyclohexyl)amino)-1H-pyrrolo[2,3-b]pyridin-5-carbonitrile H67

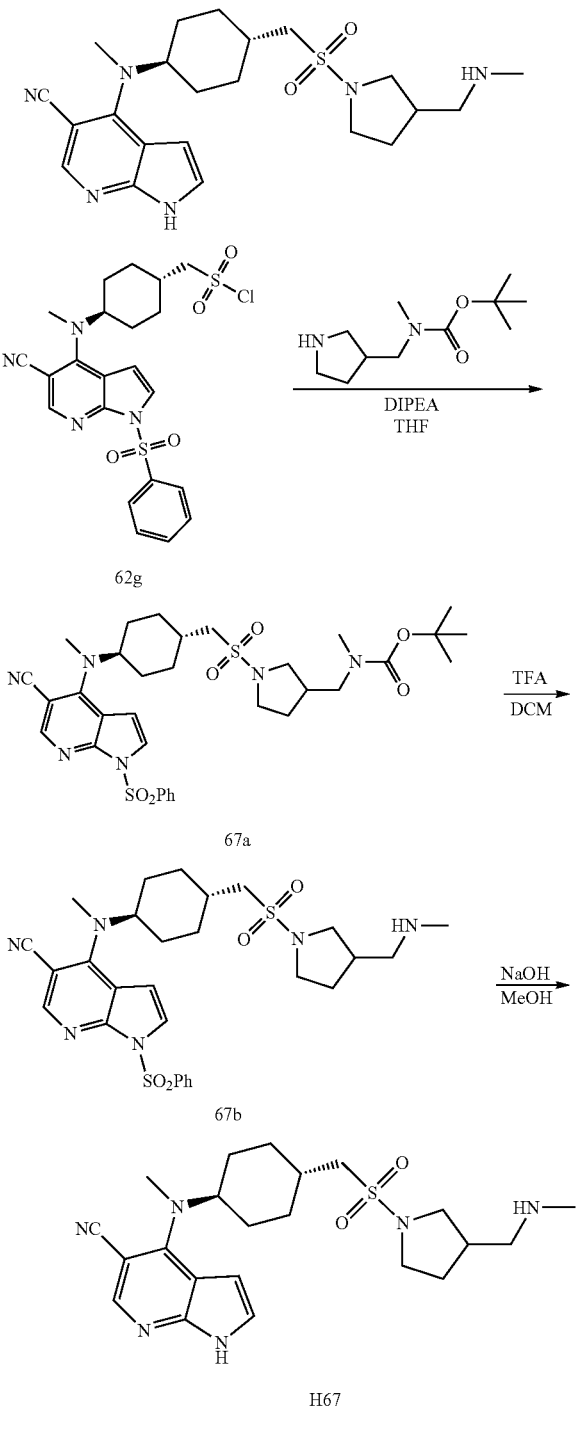

First Step: 4-(methyl(trans-4-(((3-((N-Boc-methylamino)methyl)pyrrolidin-1-yl)sulfonyl)methyl)cyclohexyl)amino)-1-(phenylsulfonyl)-1H-pyrrolo[2,3-b]pyridin-5-carbonitrile 67a DIEA (387.9 mg, 3.0 mmol) was added in compound 3-((N-Boc-methylamino)methyl)pyrrolidine (214.2 mg, 1.0 mmol) in THE solution under an ice-bath condition, and then compound 62a (0.4 mmol) was added dropwise. The system was naturally raised to room temperature to react overnight. LCMS showed that raw material was reacted completely. Dichloromethane (50 ml) and water (20 ml) were added in above reaction liquid. The organic phase was dried and concentrated to obtain yellow compound 67a (200 mg), with a yield of 73%.

MS (ESI) m/z: 685.4 (M+H⁺)

Second Step: 4-(methyl(trans-4-(((3-((methylamino)methyl)pyrrolidin-1-yl)sulfonyl)methyl)cyclohexyl)amino)-1-(phenylsulfonyl)-1H-pyrrolo[2,3-b]pyridin-5-carbonitrile 67b Compound 67a (200 mg, 0.3 mmol) was dissolved in dichloromethane (3 ml), and TFA (100 μL, 1.2 mmo) was added to obtain a reaction liquid. The reaction liquid was stirred for 1 h at room temperature. The reaction liquid was concentrated directly to obtain crude products compound 67b (150 mg), with a yield of 86%, which were subjected to a reaction of next step.

Third Step: 4-(methyl-(trans-4-(((3-((methylamino)methyl)methyl)pyrrolidinobutyl-1-yl)sulfonyl)methyl)cyclohexyl)amino)-1H-pyrrolo[2,3-b]pyridin-5-carbonitrile H67

Compound 67b (150 mg, 0.2 mmol) was dissolved in methanol (3 ml), and NaOH (200 uL, 0.6 mmol, 4 M in water) was added to obtain a reaction liquid. The reaction liquid was stirred for 2 h at room temperature. The reaction liquid was separated by TLC (DCM/MeOH=15:1) silica gel preparative plate to obtain white solids compound H67 (30 mg), with a yield of 34%.

MS (ESI) m/z: 445.3 (M+H⁺).

$^1$H NMR (400 MHz, DMSO-$d_6$) δ 11.89 (s, 1H), 8.10 (s, 1H), 7.28 (d, J=3.6 Hz, 1H), 6.56 (d, J=3.7 Hz, 1H), 4.02-3.79 (m, 1H), 3.35-3.16 (m, 7H), 2.98-2.93 (m, 2H), 2.60-2.50 (m, 2H), 2.35 (d, J=7.2 Hz, 1H), 2.30 (s, 3H), 2.06-1.98 (m, 2H), 1.97-1.90 (m, 1H), 1.87-1.73 (m, 5H), 1.56 (dq, J=12.4, 8.1 Hz, 1H), 1.21 (d, J=13.3 Hz, 3H).

Example 68

4-((trans-4-(((3-(methoxymethyl)pyrrolidin-1-yl)sulfonyl)methyl)cyclohexyl)(methyl)amino)-1H-pyrrolo[2,3-b]pyridin-5-carbonitrile H68

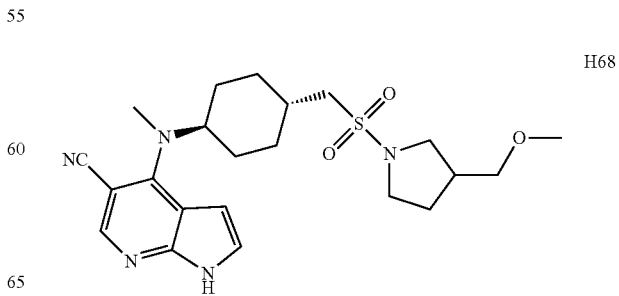

3-(methoxymethyl)piperidine was used as a raw material to obtain compound H68 by using the same preparation method as described in Example 62.

MS (ESI-MS) m/z: 446 (M+H⁺).

¹H NMR (400 MHz, DMSO-d₆) δ 11.88 (s, 1H), 8.10 (s, 1H), 7.38-7.21 (m, 1H), 6.56 (s, 1H), 3.92 (s, 1H), 3.51-3.10 (m, 12H) 2.93 (dd, J=11.2, 6.8 Hz, 2H), 2.46 (s, 2H), 2.1-1.71 (m, 6H), 1.57 (dd, J=12.8, 7.5 Hz, 1H), 1.32-1.20 (m, 3H).

Example 69

4-((trans-4-(((3-(hydroxymethyl)pyrrolidin-1-yl)sulfonyl)methyl)cyclohexyl)(methyl)amino)-1H-pyrrolo[2,3-b]pyridin-5-carbonitrile H69

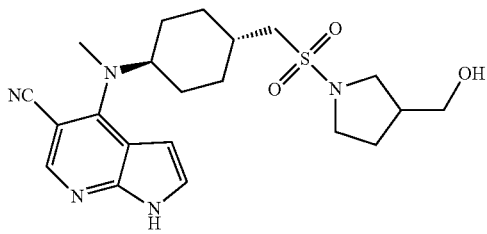

3-(hydroxymethyl)piperidine was used as a raw material to obtain compound H69 by using the same preparation method as described in Example 62.

MS (ESI) m/z: 432 (M+H⁺).

¹H NMR (400 MHz, DMSO-d₆) δ 11.93 (s, 1H), 8.14 (s, 1H), 7.32 (dd, J=3.6, 2.5 Hz, 1H), 6.60 (dd, J=3.7, 2.0 Hz, 1H), 4.73 (t, J=5.3 Hz, 1H), 3.95 (dt, J=10.1, 4.7 Hz, 1H), 3.44-3.21 (m, 8H), 3.08-2.91 (m, 3H), 2.32 (p, J=7.0 Hz, 1H), 2.14-1.98 (m, 2H), 1.88 (dddd, J=24.3, 10.4, 7.5, 2.8 Hz, 5H), 1.63 (dt, J=12.4, 7.7 Hz, 1H), 1.46-1.09 (m, 3H).

Example 70

4-((cis-(3-(((3-((2-methoxyethoxy)piperidin-1-yl)sulfonyl)methyl)cyclopentyl)(methyl)amino)-1H-pyrrolo[2,3-b]pyridin-5-carbonitrile H70

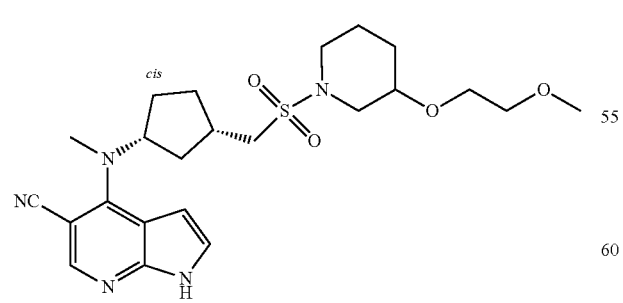

Cis-3-(methylamino)-cyclopentyl-methanol was used as a raw material to obtain compound H70 by using the same preparation method as described Example 64.

MS m/z (ESI): 476 [M+H]+.

¹H NMR (400 MHz, DMSO-d₆) δ 11.91 (s, 1H), 8.12 (s, 1H), 7.33-7.27 (m, 1H), 6.67-6.60 (m, 1H), 4.65-4.49 (m, 1H), 3.58-3.15 (m, 15H), 2.99-2.82 (m, 2H), 2.30-2.10 (m, 2H), 2.01-1.76 (m, 41H), 1.76-1.59 (m, 2H), 1.59-1.33 (m, 3H).

Example 71

4-((cis-3-(((3-((hydroxymethyl)pyrrolidin-1-yl)sulfonyl)methyl)cyclopentyl)(methyl)amino)-1H-pyrrolo[2,3-b]pyridin-5-carbonitrile H71

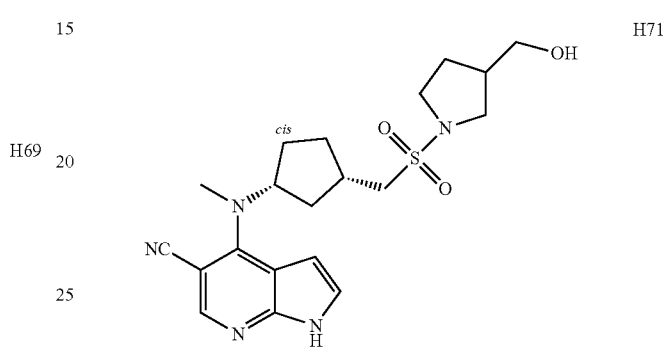

3-(hydroxymethyl)piperidine was used as a raw material to obtain compound H71 by using the same preparation method as described in Example 70.

MS (ESI) m/z: 418

¹H NMR (400 MHz, DMSO-d6) δ 11.90 (s, 1H), 8.12 (s, 1H), 7.30 (dd, J=3.6, 2.4 Hz, 1H), 6.64 (dd, J=3.6, 1.8 Hz, 1H), 4.69 (t, J=5.3 Hz, 1H), 4.57 (p, J=7.6 Hz, 1H), 3.41-3.17 (m, 10H), 2.97 (dd, J=9.8, 6.8 Hz, 1H), 2.29-2.17 (m, 3H), 1.98-1.78 (m, 3H), 1.74-1.44 (m, 3H).

Example 72

(R)-7-((5-cyano-1H-pyrrolo[2,3-b]pyridin-4-yl)amino)-N-(2,2,2-trifluoroethyl)-5-azaspiro[2.4]heptane-5-carboxamide H72

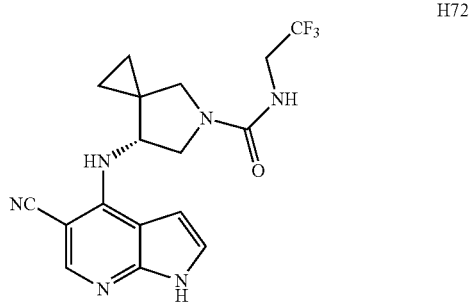 [SMILES: N#Cc1cnc2[nH]ccc2c1N[C@H]1CN(C(=O)NCC(F)(F)F)CC12CC2]

(R)-(5-azaspiro[2.4]heptane-7-yl)tert-butyl carbamate was used as a raw material to obtain compound H72 by using the same preparation method as described in Example 2.

MS m/z (ESI): 379 [M+1]⁺

¹H NMR (400 MHz, DMSO-d₆) δ 11.85 (s, 1H), 8.09 (s, 1H), 7.27 (dd, J=3.6, 2.5 Hz, 1H), 6.89 (t, J=6.3 Hz, 1H), 6.82 (dd, J=3.5, 2.0 Hz, 1H), 6.71 (d, J=7.6 Hz, 1H), 4.45 (s,

1H), 3.84-3.68 (m, 4H), 3.63 (dd, J=10.9, 2.9 Hz, 1H), 3.21 (d, J=10.2 Hz, 1H), 0.87 (dd, J=9.2, 4.5 Hz, 1H), 0.77 (dd, J=9.7, 5.5 Hz, 1H), 0.69 (d, J=6.3 Hz, 2H).
Example 73
(cis)-3-isopropyl-4-(imidazo[4,5-d]pyrrolo[2,3-b]pyridin-1(6H)-yl)-N-(2,2,2-trifluoroethyl) pyrrolidin-1-carboxamide H73
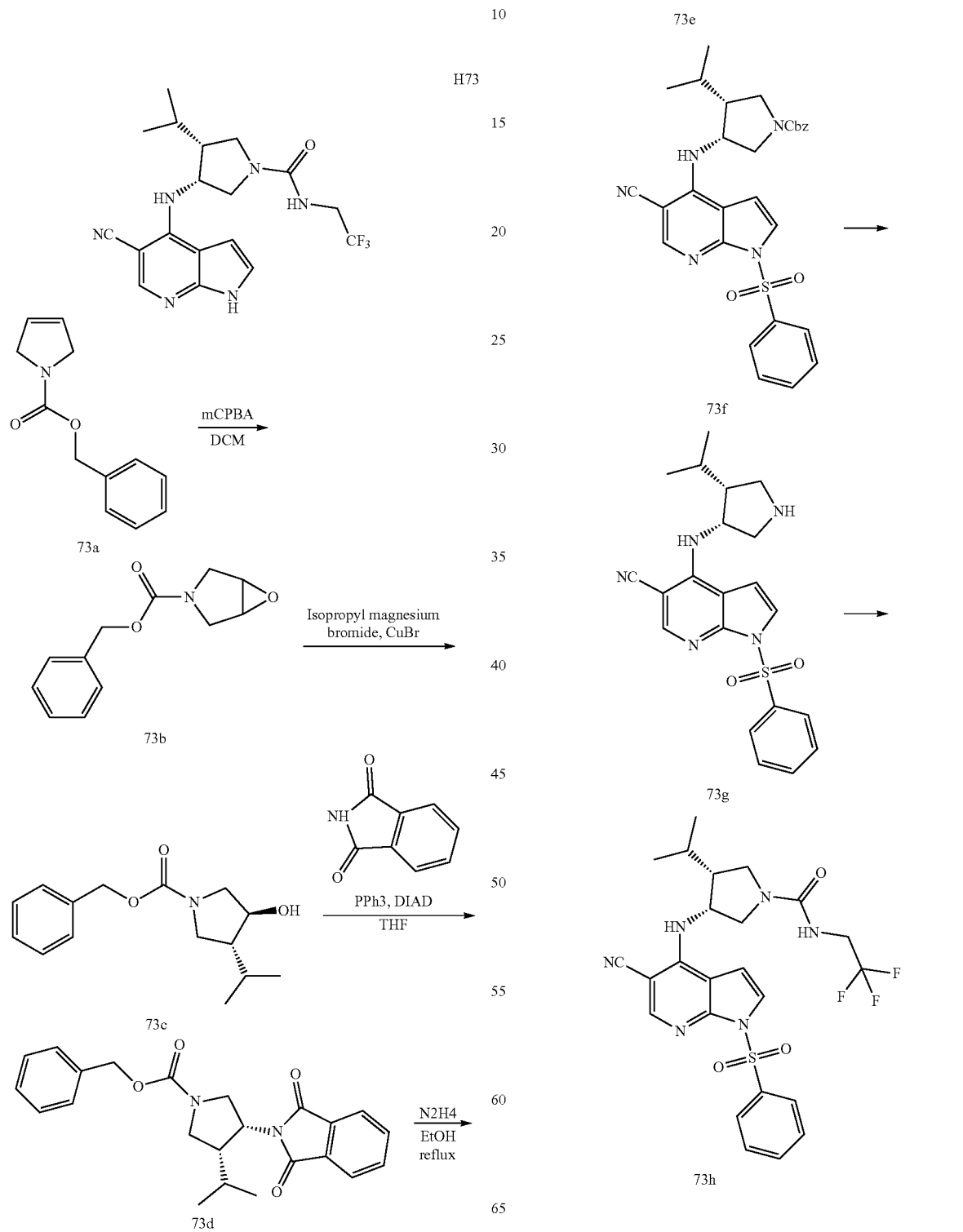

-continued

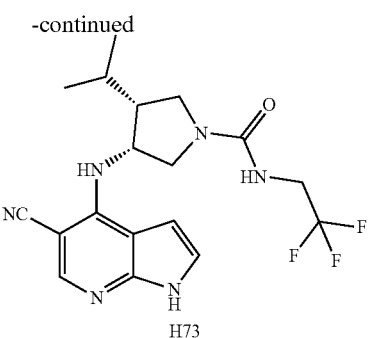

H73

First Step: benzyl 6-oxa-3-azabicyclo[3.1.0]hexyl-3-carboxylate 73b

Compound 73a (17 g, 83.6 mmol) was dissolved in 120 mL dichloromethane, and m-CPBA (29.4 g, 167.2 mmol) was added in batches under an ice bath for reacting overnight at room temperature. After the reaction was completed, the reaction solution was filtered to obtain a filtrate. A sodium hydrogen sulfite solution was added in the filtrate and stirred for 0.5 h, extracted with EA and separated by column chromatography (PE:EA=10:1) to obtain compound 73b (10 g), with a yield of 56%.

MS (ESI) m/z: 242 (M+Na$^+$).

Second Step: benzyl (trans)-3-isopropyl-4-hydroxypyrrolidin-1-carboxylate 73c Compound 73b (2.19 g, 10.0 mmol) was dissolved in 20 mL anhydrous THF, and CuBr (150 mg, 1.0 mmol) was added, substituted by hydrogen for three times, and then cyclopropyl magnesium bromide (30 mL, 90 mmol, 3 M in THF) was added dropwise under a dry ice bath of ethyl acetate, and naturally heated to room temperature to react overnight. After the reaction was completed, the system was quenched with ammonium chloride solution, extracted with EA and separated by column chromatography (PE:EA=3:1) to obtain compound 73c (1.6 g), with a yield of 60%.

MS (ESI) m/z: 264 (M+H$^+$)

Third Step: benzyl (cis)-3-isopropyl-4-(1,3-dioxoisoindol-2-yl)pyrrolidin-1-carboxylate 73d Compound 73c (1.6 g, 6.08 mmol) was dissolved in 10 mL anhydrous tetrahydrofuran, and PPh$_3$ (1.91 g, 7.3 mmol) and phthalimide (1.07 g, 7.3 mmol) were added. The system was substituted by nitrogen for three times. DIAD (1.91 g, 7.3 mmol) was added under an ice bath and naturally heated to room temperature to react overnight. After the reaction was completed, water was added. The system was extracted with EA and the organic phases were collected. Then the system was separated by column chromatography (PE:EA=3:1) to obtain crude products 73d (3.0 g).

MS (ESI-MS) m/z: 393 (M+H$^+$).

Fourth Step: benzyl (cis)-3-amino-4-isopropylpyrrolidin-1-carboxylate 73e

Compound 73d (3.0 g, crude products) was dissolved in 10 mL ethanol, and hydrazine hydrate (979.2 mg, 30.6 mmol) was added, heated to 80° C. and reacted for 2 h. After the reaction was completed, saturated NaCl solution was added. The system was extracted with DCM, and organic phases were collected. Then the system was separated by column chromatography (DCM:MeOH=95:5) to obtain compound 73e (1.2 g).

MS (ESI) m/z: 263 (M+H$^+$)

Fifth Step: (cis)-3-isopropyl-4-((5-cyano-1-(benzenesulfonyl)-1H-pyrrole[2,3-b]pyridin-4-yl)amino) pyrrolidin-1-benzyl formate 73f Compound 73e (496 g, 1.89 mmol) was dissolved in 5 mL NMP, and then Int-1 (300 mg, 0.94 mmol) and DIEA (364 mg, 2.82 mmol) were added, heated to 130° C. and reacted for 3 h. After the reaction was completed, water was added to wash NMP, and the system was extracted with DCM, then separated by column chromatography (DCM:MeOH=98:2) to obtain compound 73f (100 mg).

MS (ESI) m/z: 544 (M+H$^+$).

Sixth Step: 4-(((cis)-4-isopropylpyrrolidin-3-yl) amino)-1-(phenylsulfonyl)-1H-pyrrolo[2,3-b]pyridin-5-carbonitrile 73g Compound 73f (100 mg, crude products) was dissolved in 5 mL dichloromethane, and hydrogen bromide in glacial acetic acid solution (1 ml) was added, stirred and reacted for 2 h at room temperature. After the reaction was completed, the system was mixed with silica gel, and subjected to column chromatography (DCM:MeOH=10:1) to obtain compound 73g (50 mg), which was present as an oily substance.

MS (ESI) m/z: 410 (M+H$^+$).

Seventh Step: (cis)-3-((5-cyano-1-(phenylsulfonyl)-1H-pyrrolo[2,3-b]pyridin-4-yl)amino)-4-isopropyl-N-(2,2,2-trifluoroethyl)pyrrolidin-1-carboxamide 73h Compound 73g (50 mg, 0.12 mmol) was dissolved in THF, and phenyl (2,2,2-trifluoroethyl)carbamate (50 mg, 0.122 mmol) and potassium carbonate (25 mg, 0.18 mmol) were added to perform a reflux reaction for 4 h to obtain a reaction liquid. After the reaction was completed, the reaction liquid was used directly for next step.

MS (ESI) m/z: 535 (M+H$^+$).

Eighth Step: (cis)-3-((5-cyano-1H-pyrrolo[2,3-b] pyridin-4-yl)amino)-4-isopropyl-N-(2,2,2-trifluoroethyl)pyrrolidin-1-carboxamide H73

Compound 73h (50 mg, 0.09 mmol) was dissolved in 2 mL methanol, and 2N sodium hydroxide (2 mL) was added, stirred for 1 h at room temperature. After the reaction was completed, the system was extracted with EA, and the organic phase was dried by a spin drier, concentrated, followed by column chromatography (DCM:MeOH=15:1) to obtain compound H73 (20 mg).

MS (ESI) m/z: 395 (M+H$^+$).

$^1$H NMR (400 MHz, Methanol-d$_4$) δ 8.10 (s, 1H), 7.23 (d, J=3.7 Hz, 1H), 6.73 (d, J=3.7 Hz, 1H), 3.87-3.66 (m, 5H), 3.42 (t, J=10.9 Hz, 1H), 3.33 (s, 1H), 2.30 (d, J=23.2 Hz, 1H), 1.94-1.81 (m, 1H), 1.03 (d, J=6.5 Hz, 3H), 0.93 (d, J=6.5 Hz, 3H).

Example 74
(cis)-3-((5-cyano-1H-pyrrolo[2,3-b]pyridin-4-yl)amino)-4-cyclopropyl-N-isobutyl pyrrolidin-1-carboxamide H74
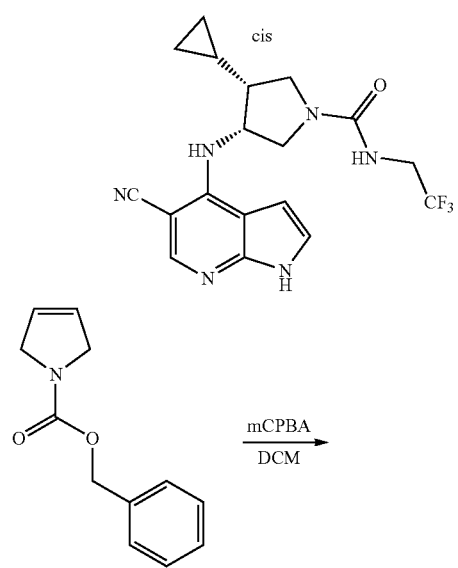
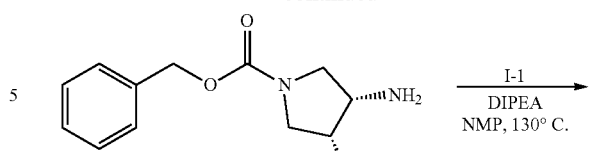
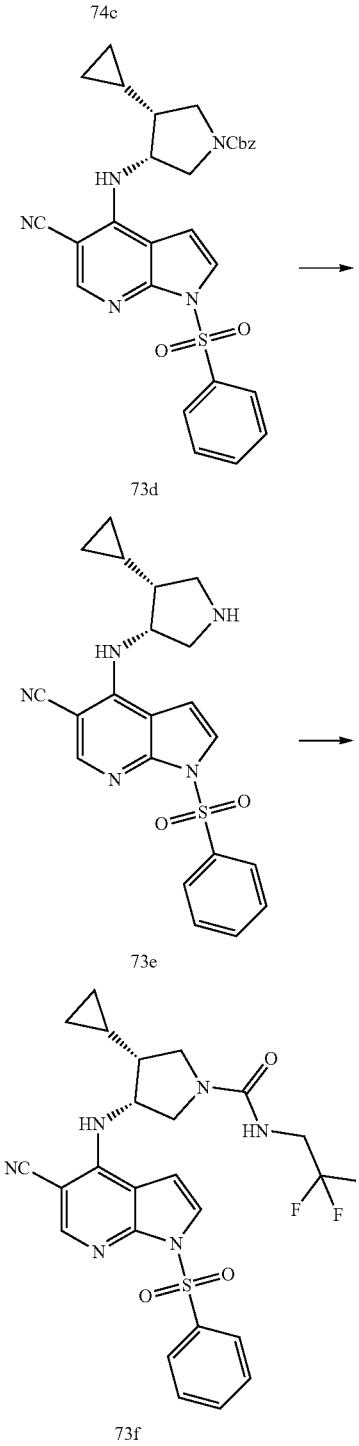

-continued

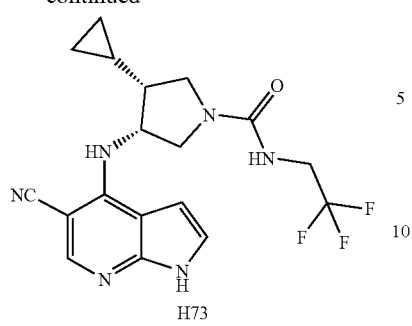

H73

Cyclopropyl magnesium bromide was used as a raw material to obtain compound H74 by using the same preparation method as described in Example 73.

MS (ESI) m/z: 393 (M+H⁺).

¹H NMR (400 MHz, DMSO-d₆) δ 11.83 (s, 1H), 8.09 (s, 1H), 7.25 (dd, J=3.6, 2.4 Hz, 1H), 6.89-6.79 (m, 2H), 6.62 (d, J=8.7 Hz, 1H), 4.87 (q, J=6.6, 6.1 Hz, 1H), 3.82-3.65 (m, 3H), 3.54-3.42 (m, 3H), 1.80 (p, J=6.8 Hz, 1H), 0.81 (tq, J=9.5, 5.1, 4.6 Hz, 1H), 0.38 (ddt, J=22.2, 8.3, 4.2 Hz, 2H), 0.18-0.04 (m, 2H).

Example 75

(cis)-3-((5-cyano-1H-pyrrolo[2,3-b]pyridine-4-yl)amino)-4-ethyl-N-isobutylpyrrolidin-1-carboxamide
H75

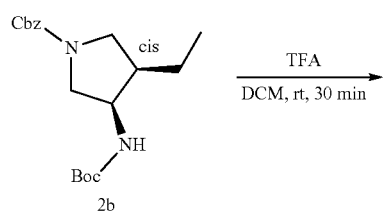

H75

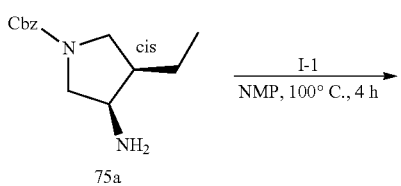

-continued

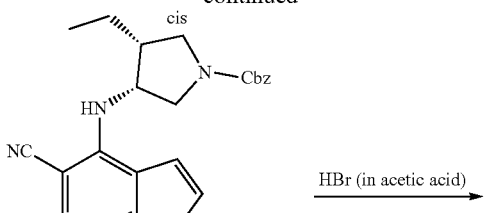

75b

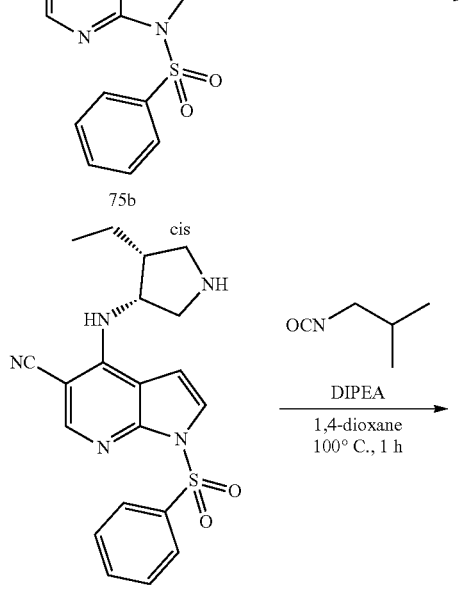

75c

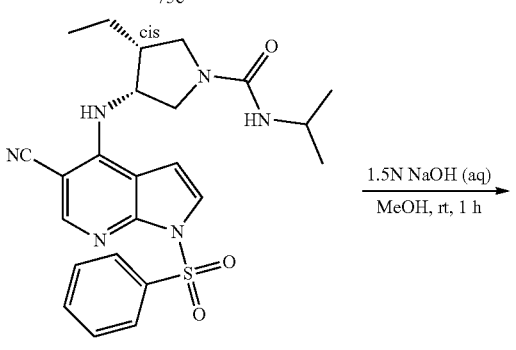

75d

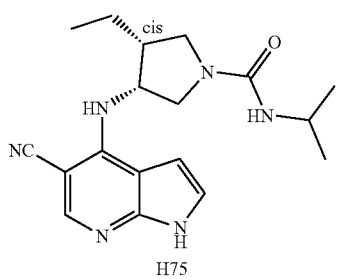

H75

First Step:
(cis)-N-carbobenzoxy-4-ethylpyrrolidin-3-amino
75a

Compound 2b (184 mg, 0.53 mmol) was dissolved in 5 mL dichloromethane and 2 mL TFA was added. After the addition was completed, the mixture was stirred for 0.5 h at room temperature to react. After the reaction was completed, the system was dried by a spin drier to remove solvent, thereby obtaining crude products 75a, which was used directly for next step.

MS (ESI) m/z: 249 (M+H⁺)

Second Step: (cis)-3-((5-cyano-1-(benzenesulfonyl)-1H-pyrrole[2,3-b]pyridin-4-yl)amino)-4-ethylpyrrolidin-1-benzyl formate 75b Compound 75a (0.53 mmol) was dissolved in 5 mL NMP, and compound I-1 (168 mg, 0.53 mmol) was added. After the addition was completed, the mixture was stirred for 2 h at 100° C. to react under LCMS monitoring. After the reaction was completed, DCM/H₂O was layered. DCM layer was collected, dried, filtered and separated by preparative TLC (PE/EA=4/1). Then target compound 75b (175 mg) was obtained, which was white solids, with a yield of 63%.

MS (ESI) m/z: 530 (M+H⁺)

Third Step: (cis)-4-((4-ethylpyrrolidin-3-yl)-amino-1-(benzenesulfonyl)-1H-pyrrole[2,3-b]pyridin-5-carbonitrile 75c Compound 75b (175 mg, 0.33 mmol) was dissolved in 10 mL dichloromethane and 5 mL HBr (in acetic acid) was added. After the addition was completed, the mixture was stirred for 0.5 h at room temperature to react. After the reaction was completed, the mixture was dried by a spin drier to remove solvent, freeze-dried with acetonitrile-water, thereby obtaining compound 75c, which was used directly for next step.

MS (ESI) m/z: 396 (M+H⁺)

Fourth Step: (cis)-4-((4-ethylpyrrolidin-3-yl)-amino-1-(benzenesulfonyl)-1H-pyrrole[2,3-b]pyridin-5-carbonitrile 75d Compound 75c (80 mg) was dissolved in 5 mL of 1,4-dioxane, and then isopropyl isocyanate (20 mg) and 0.5 mL DIPEA were added and reacted for 1 h at 100° C. After the reaction was completed, the system was dried by a spin drier to remove solvent and separated by preparative TLC (DCM/MeOH=20/1) to obtain target compound 75d (60 mg), which was a colorless jelly, with a yield of 62%.

LCMS (ESI-MS) m/z: 481.3 (M+H⁺).

Fifth Step: (cis)-3-((5-cyano-1H-pyrrolo[2,3-b]pyridin-4-yl) amino)-4-ethyl-N-isobutylpyrrolidin-1-carboxamide H75

Compound 75d (60 mg, 0.125 mmol) was dissolved in 5 mL methanol, and 2 mL sodium hydroxide solution was added. The mixture was stirred for 1 h at room temperature to react. After the reaction was completed, dichloromethane and water were layered. Dichloromethane layer was dried by a spin drier to remove solvent, followed by preparative separation to obtain target compound H75 (38 mg), which was white solids, with a yield of 62%.

MS (ESI) m/z: 341 (M+H⁺).
¹H NMR (400 MHz, MeOD) δ=11.82 (s, 1H), 8.08 (s, 1H), 7.24 (s, 1H), 8.82 (s, 1H), 6.49-6.51 (m, 1H), 5.80-5.82 (d, J=7.6 Hz, 1H), 4.77-4.79 (m, 1H), 3.67-3.76 (m, 1H), 3.59-3.52 (m, 3H), 3.22-3.27 (t, J=10 Hz, 1H), 2.32-2.37 (m, 1H), 1.44-1.50 (m, 1H), 1.30-1.38 (m, 1H), 1.02 (s, 3H), 1.01 (s, 3H), 0.80-0.83 (t, J=7.6 Hz, 3H).

Example 76

4-(((cis)-4-ethyl-1-((3,3,3-trifluoropropyl)sulfonyl)pyrrolidin-3-yl)amino)-1H-pyrrolo[2,3-b]pyridin-5-carbonitrile H76

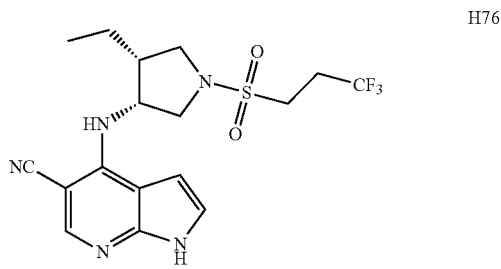 [SMILES: CC[C@@H]1CN(S(=O)(=O)CCC(F)(F)F)C[C@@H]1Nc1c(C#N)cnc2[nH]ccc12]

3,3,3-trifluoropropanesulfonyl chloride was used as a raw material to obtain compound H76 by using the same preparation method as described in Example 75.

MS m/z (ESI): 416 [M+H]+.
¹H NMR (400 MHz, DMSO-d₆) δ 11.90 (s, 1H), 8.12 (s, 1H), 7.28-7.19 (m 1H), 6.65-6.59 (m, 1H), 6.56-6.44 (m, 1H), 4.73-4.64 (m, 1H), 3.67-3.23 (m, 6H), 2.72-2.60 (m, 2H), 2.51-2.37 (m, 1H), 1.60-1.22 (m, 2H), 0.88-0.78 (t, 3H).

Example 77

4-(((cis)-4-ethyl-1-(4,4,4-trifluorobutyryl)pyrrolidin-3-yl)amino)-1H-pyrrolo[2,3-b]pyridin-5-carbonitrile H77

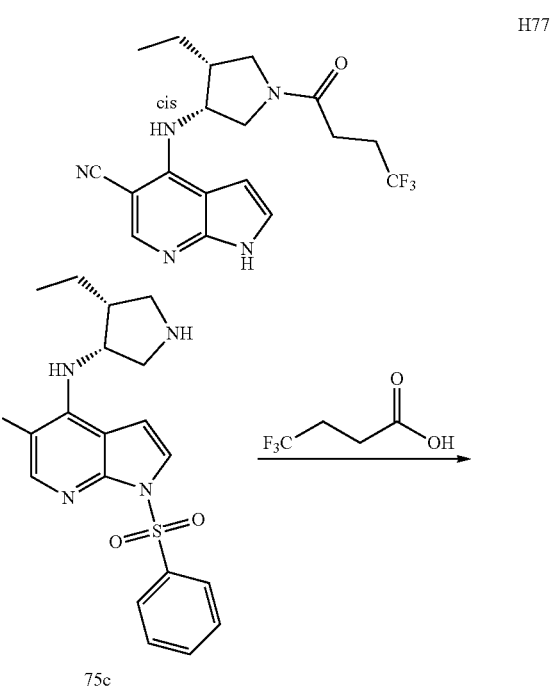

-continued

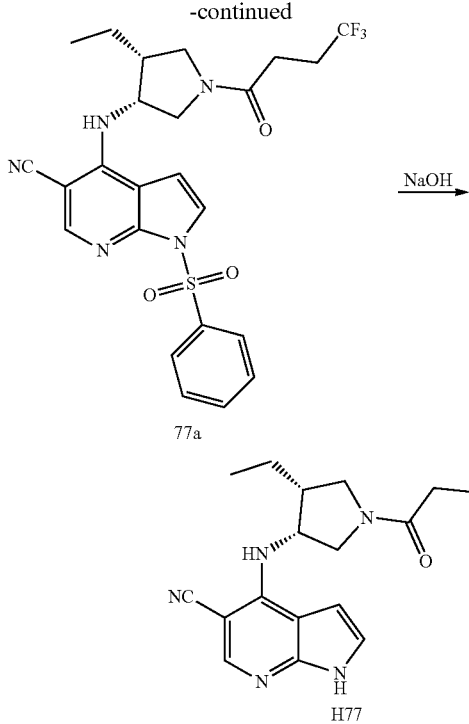

77a

H77

First Step: 4-(((cis)-4-ethyl-1-(4,4,4-trifluorobutyryl)pyrrolidin-3-yl)amino)-1-(benzenesulfonyl)-1H-pyrrolo[2,3-b]pyridin-5-acetonitrile 77a Compound 75c (100 mg, 0.25 mmol), compound 4,4,4-trifluorobutyric acid (36 mg, 0.25 mmol), EDCI (48 mg, 0.25 mmol), HOBT (34 mg, 0.25 mmol), DIPEA (65 mg, 0.50 mmol) and DCM (20 mL) were added into a flask. The system was reacted for 2 h at room temperature. After the reaction was completed, the system was concentrated directly and purified by column chromatography (v/v, DCM/MeOH=100:1-50:1) to obtain compound 77a (100 mg, 0.19 mmol) with a yield of 76.0%.

MS m/z (ESI): 520 [M+H]+.

Second Step: 4-(((cis)-4-ethyl-1-(4,4,4-trifluorobutyryl)pyrrolidin-3-yl)amino)-1H-pyrrolo [2,3-b]pyridin-5-acetonitrile H77

Compound 75a (100 mg, 0.19 mmol), 2M sodium hydroxide solution (2 mL) and methanol (5 mL) were added into a reaction flask. The system was stirred for 1 h at room temperature. After the reaction was completed under TLC monitoring, the system was adjusted to pH=8-10 with diluted hydrochloric acid, concentrated and purified by column chromatography (v/v, DCM/MeOH=100:1-50:1) to obtain compound H77 (50 mg, 0.13 mmol) with a yield of 68.4%.

MS m/z (ESI): 380 [M+H]+.

$^1$H NMR (600 MHz, DMSO-d$_6$) δ 11.87 (d, J=7.0 Hz, 1H), 8.12 (s, 1H), 7.31-7.24 (m, 1H), 6.83 (d, J=26.2 Hz, 1H), 6.57 (dd, J=74.5, 8.9 Hz, 1H), 4.99-4.76 (m, 1H), 3.92-3.38 (m, 4H), 2.64-2.30 (m, 5H), 1.58-1.25 (m, 2H), 0.83 (t, =7.4 Hz, 3H).

Example 78

4-((4-ethyl-1-(2-cyanoacetyl)pyrrolidin-3-yl)amino)-1H-pyrrolo[2,3-b]pyridin-5-carbonitrile H78

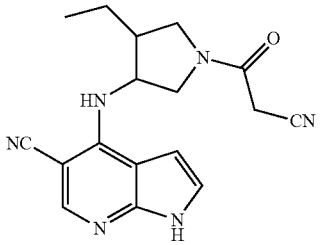

H78

2-Cyanoacetic acid was used as a raw material to obtain compound H78 by using the same preparation method as described in Example 77.

MS m/z (ESI): 323 [M+H]+.

$^1$H NMR (400 MHz, DMSO-d$_6$) δ 11.91-11.79 (m, 1H), 8.08 (d, J=6.8 Hz, 1H), 7.28-7.22 (m, 1H), 6.84-6.75 (m, 1H), 6.66-6.50 (m, 1H), 4.94-4.77 (m, 1H), 4.01-3.83 (m, 2H), 3.68-3.56 (m, 2H), 3.49-3.30 (m, 2H), 2.49-2.31 (m, 1H), 1.64-1.23 (m, 2H), 0.90-0.76 (m, 3H).

Example 79

(cis)-3-((5-cyano-1H-pyrrolo[2,3-b]pyridin-4-yl)amino)-4-ethyl-N-isobutylpyrrolidin-1-carboxamide H79

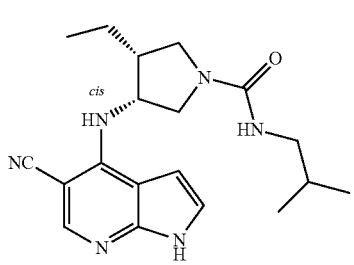

H79

Isobutyl isocyanate was used as a raw material to obtain compound H79 by using the same preparation method as described in Example 75.

LCMS (ESI-MS) m/z: 502.1 (M+H$^+$).

$^1$H NMR (400 MHz, DMSO-d$_6$) δ 11.82 (s, 1H), 8.07 (d, J=6.7 Hz, 1H), 7.23 (td, J=3.5, 2.5 Hz, 1H), 6.92-6.75 (m, 2H), 6.14 (t, J=5.8 Hz, 1H), 4.44 (p, J=7.6 Hz, 1H), 3.76 (dd, J=10.3, 7.1 Hz, 1H), 3.64-3.54 (m, 1H), 3.54-3.42 (m, 1H), 3.31-3.12 (m, 1H), 2.95 (dd, J=10.3, 8.3 Hz, 1H), 2.79 (t, J=6.4 Hz, 2H), 2.30 (s, 1H), 1.72-1.40 (m, 2H), 1.40-1.18 (m, 1H), 0.91-0.75 (m, 9H).

Example 80

4-(((cis)-4-ethyl-1-(3-methoxy-1,2,4-thiadiazole-5-aminocarbonyl)pyrrolidin-3-yl)amino)-1H-pyrrolo[2,3-b]pyridin-5-carbonitrile H80

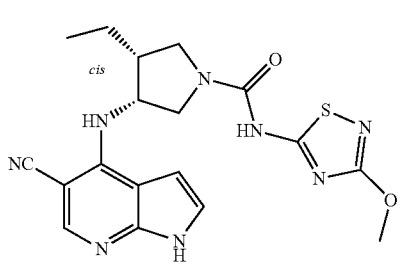

Compound 7h was used as a raw material to obtain compound H80 by using the same preparation method as described in Example 75.

MS m/z (ESI): 413 [M+H]+.

¹H NMR (400 MHz, DMSO-d₆) δ 11.84 (s, 1H), 11.63 (s, 1H), 8.08 (s, 1H), 7.29-7.21 (m, 1H), 6.85-6.78 (m, 1H), 6.77-6.67 (m, 1H), 4.99-4.82 (m, 1H), 3.86 (s, 3H), 3.77-3.61 (m, 2H), 3.58-3.30 (m, 2H), 2.41-2.27 (m, 1H), 1.62-1.26 (m, 2H), 0.82 (1, J=7.4 Hz, 3H).

Example 81

4-(((cis)-1-(3-cyanopropionyl)-4-ethylpyrrolidin-3-yl)amino)-1H-pyrrolo[2,3-b]pyridin-5-carbonitrile H81

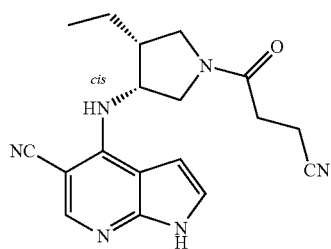

3-Cyanopropionic acid was used as a raw material to obtain compound H81 by using the same preparation method as described in Example 77.

MS m/z (ESI): 337 [M+1]+

¹H NMR (400 MHz, DMSO-d₆) δ 11.84 (s, 1H), 8.09 (s, 1H), 7.25 (qd, J=3.6, 2.4 Hz, 1H), 6.80 (ddt, J=15.9, 4.6, 2.3 Hz, 1H), 6.59 (dd, J=48.2, 9.0 Hz, 1H), 4.85-4.75 (m, 1H), 3.75-3.51 (m, 3H), 2.75-2.25 (m, 4H), 1.59-1.27 (m, 2H), 0.84 (ddt, J=17.6, 10.2, 7.4 Hz, 3H).

Example 82

3-((5-cyano-1H-pyrrolo[2,3-b]pyridin-4-yl)amino)-4-ethyl-N-(cyclopropylmethyl)pyrrolidin-1-carboxamide H82

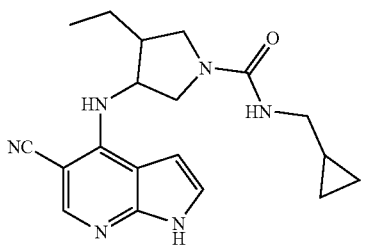

Cyclopropylmethyl isocyanate was used as a raw material to obtain compound H82 by using the same preparation method as described in Example 75.

MS (ESI) m/z: 353 (M+H)⁺.

¹H NMR (400 MHz, DMSO-d6) δ 11.83 (s, 1H), 8.07 (d, J=6.3 Hz, 1H), 7.23 (q, J=2.9 Hz, 1H), 6.47-6.92 (m, 2H), 6.22 (t, J=5.7 Hz, 1H), 4.83-4.37 (m, 1H), 3.85-3.39 (m, 3H), 3.27-3.13 (m, 1H), 2.99-2.82 (m, 2H), 2.41-2.27 (m, 1H), 1.61-1.42 (m, 1H), 1.40-1.26 (m, 1H), 1.20 (d, J=3.6 Hz, 1H), 0.88 (q, J=7.5 Hz, 2H), 0.82 (t, J=7.4 Hz, 2H), 0.41-0.24 (m, 2H), 0.21-0.04 (m, 2H).

Example 83

3-((5-cyano-1-H-pyrrolo[2,3-b]pyridin-4-yl)amino)-4-ethyl-N-(2,2,3,3,3-pentafluoropropyl)-pyrrolidin-1-carboxamide H83

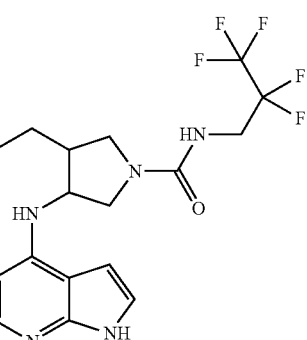

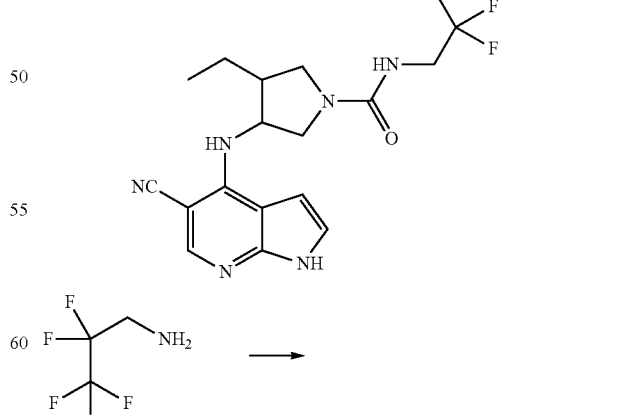

83a

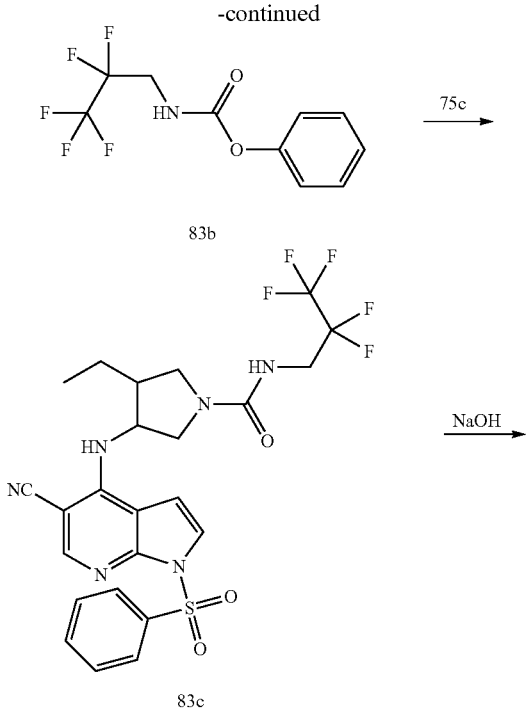

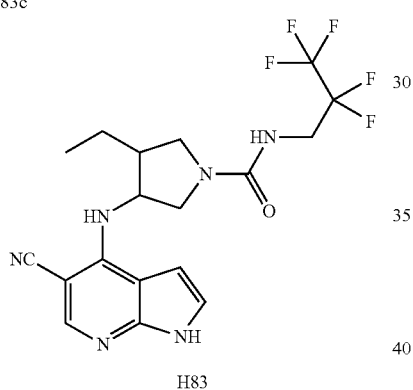

H83

First Step: 2,2,3,3,3-pentafluoropropylphenyl carbamate 83b

Phenyl chloroformate (1.5 g, 9.6 mmol) was gradually added in 2,2,3,3,3-pentafluoropropylamino (1 g, 6.7 mmol) and triethylamine (2 g, 20 mmol) in DCM (20 mL) dropwise at an ice bath, stirred for 1 h at room temperature, concentrated and separated by column chromatography (DCM:MeOH=20:1) to obtain compound 83b (1.3 g), with a yield of 72.0%.

$^1$H NMR (400 MHz, DMSO-$d_6$) δ 7.50-7.41 (m, 1H), 7.38-7.28 (m, 2H), 7.26-7.16 (m, 2H), 7.10-7.04 (m, 1H), 3.42-3.32 (m, 1H), 3.27 (d, J=7.2 Hz, 1H).

Second Step: 3-((5-cyano-1-(benzenesulfonyl)-1H-pyrrolo[2,3-b]pyridin-4-yl)amino)-4-ethyl-N-(2,2,3,3,3-pentafluoropropyl)-pyrrolidin-1-carboxamide 83c Compound 75c (200 mg, 0.51 mmol) was dissolved in 10 mL THF, and then compound 83b (1.4 g, 1.49 mmol) and DIEA (300 mg, 2.33 mmol) were added, heated to 60° C. and reacted for 4 h. After the reaction was completed, the system was concentrated and separated by preparative TLC to obtain compound 83c (120 mg), with a yield of 41.6%.

MS (ESI) m/z: 571 (M+H)$^+$.

Third Step: 3-((5-cyano-1-H-pyrrolo[2,3-b]pyridin-4-yl)amino)-4-ethyl-N-(2,2,3,3,3-pentafluoropropyl)-pyrrolidin-1-carboxamide H83

Compound 83c (120 mg, 0.21 mmol) was dissolved in 5 mL methanol, and NaOH (2 mL, 6 M in water) was added and reacted for 1 h at room temperature. After the reaction was completed, the system was diluted with water (30 mL), extracted with DCM (10 mL×3). The organic phases were combined, dried with anhydrous Na$_2$SO$_4$, filtered, concentrated and separated by comparative TLC to obtain H83 (35 mg) with a yield of 38.7%.

MS (ESI) m/z: 431 (M+H)$^+$.

$^1$H NMR (400 MHz, DMSO-d6) δ11.83 (s, 1H), 8.08 (d, J=6.2 Hz, 1H), 7.24 (dd, J=3.5, 2.4 Hz, 1H), 6.55-6.77 (m, 3H), 4.42-4.85 (m, 1H), 3.90-3.75 (m, 2H), 3.64 (dd, J=10.9, 5.6 Hz, 1H), 3.58-3.46 (m, 1H), 2.92-3.42 (m, 2H), 2.27-2.43 (m, 1H), 1.61-1.49 (m, 1H), 1.21-1.46 (m, 1H), 0.84 (dt, J=20.1, 7.4 Hz, 3H).

Example 84

(cis)-3-((5-cyano-1H-pyrrolo[2,3-b]pyridin-4-yl)amino)-N-cyclopropyl-4-ethylpyrrolidin-1-carboxamide H84

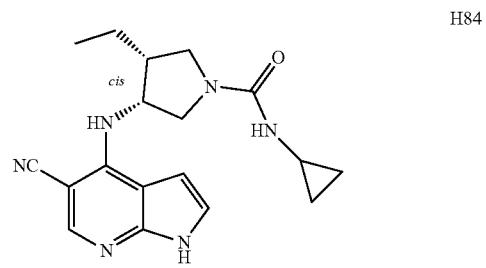 [SMILES: CC[C@@H]1CN(C(=O)NC2CC2)C[C@@H]1Nc1c(C#N)cnc2[nH]ccc12]

H84

Cyclopropylamine was used as a raw material to obtain compound H84 by using the same preparation method as described in Example 83.

LCMS (ESI-MS) m/z: 339.2 (M+H$^+$).

$^1$H NMR (400 MHz, DMSO-$d_6$) δ 11.84 (d, J=5.4 Hz, 1H), 8.08 (d, J=6.3 Hz, 1H), 7.23 (q, J=3.1 Hz, 1H), 6.81 (ddd, J=13.1, 3.6, 2.0 Hz, 1H), 6.53 (d, J=8.8 Hz, 1H), 6.25 (d, J=2.6 Hz, 1H), 4.78 (dtd, J=8.8, 5.7, 2.8 Hz, 1H), 4.42 (p, J=7.5 Hz, 1H), 3.62-3.51 (m, 1H), 3.51-3.40 (m, 1H), 3.27-3.10 (m, 1H), 2.93 (dd, J=10.3, 8.2 Hz, 1H), 2.40-2.19 (m, 1H), 1.61-1.41 (m, 1H), 1.38-1.24 (m, 1H), 0.83 (dt, J=20.5, 7.4 Hz, 3H), 0.48 (dt, J=6.7, 3.3 Hz, 2H), 0.38-0.30 (m, 2H).

Example 85

(cis)-3-((5-cyano-1H-pyrrolo[2,3-b]pyridin-4-yl)amino)-4-ethyl-N-(3-methylbutane-2-yl) pyrrolidin-1-carboxamide H85

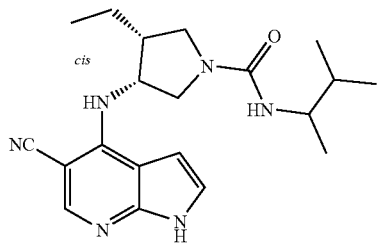

3-Methylbutane-2-ylamine was used as a raw material to obtain compound H85 by using the same preparation method as described in Example 83.

LCMS (ESI-MS) m/z: 369 (M+H⁺).

1H NMR (400 MHz, DMSO-d6) δ 11.82 (d, J=7.0 Hz, 1H), 8.07 (d, J=7.1 Hz, 1H), 7.23 (td, J=3.5, 2.4 Hz, 1H), 6.96-6.77 (m, 1H), 6.49 (d, J=13.5 Hz, 1H), 5.70 (d, J=8.5 Hz, 1H), 4.79 (s, 1H), 3.58 (d, J=16.5 Hz, 1H), 3.52-3.38 (m, 2H), 3.21 (s, 1H), 2.95 (ddd, J=21.9, 10.3, 8.6 Hz, 1H), 2.40-2.21 (m, 1H), 1.68-1.53 (m, 1H), 1.52-1.42 (m, 1H), 1.41-1.26 (m, 1H), 0.99-0.92 (m, 3H), 0.90-0.73 (m, 9H).

Example 86

(cis)-3-((5-cyano-1H-pyrrolo[2,3-b]pyridin-4-yl)amino)-4-ethyl-N-neopentyl-pyrrolidin-1-carboxamide H86

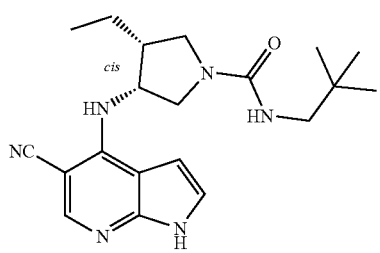

Neoamylamine was used as a raw material to obtain compound H86 by using the same preparation method as described in Example 83.

LCMS (ESI-MS) m/z: 369.3 (M+H⁺).

¹H NMR (400 MHz, DMSO-d₆) δ 11.83 (s, 1H), 8.08 (s, 1H), 7.24 (dd, J=3.6, 2.4 Hz, 1H), 6.82 (dd, J=3.6, 2.0 Hz, 1H), 6.46 (d, J=8.7 Hz, 1H), 5.96 (t, J=6.3 Hz, 1H), 4.80 (dt, J=6.0, 3.2 Hz, 1H), 3.61 (dd, J=10.9, 5.7 Hz, 1H), 3.50 (ddd, J=10.9, 9.6, 5.4 Hz, 1H), 3.30-3.22 (m, 2H), 2.93-2.76 (m, 2H), 2.43-2.26 (m, 1H), 1.54-1.41 (m, 1H), 1.40-1.26 (m, 1H), 0.82 (t, J=7.4 Hz, 3H), 0.77 (s, 9H).

Example 87

3-((5-cyano-1H-pyrrolo[2,3-b]pyridin-4-yl)amino)-N-(2,2-difluoroethyl)-4-ethylpyrrolidin-1-carboxamide H87

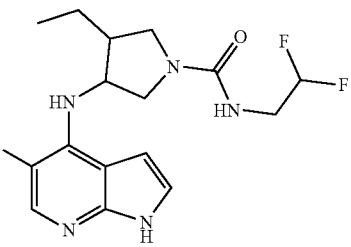

2,2-difluoroethylamine was used as a raw material to obtain compound H87 by using the same preparation method as described in Example 83.

LCMS (ESI-MS) m/z: 363.2 (M+H⁺).

¹H NMR (400 MHz, DMSO-d₆) δ 11.83 (s, 1H), 8.08 (d, J=5.8 Hz, 1H), 7.24 (q, J=2.6 Hz, 1H), 6.96-6.71 (m, 1H), 6.70-6.45 (m, 2H), 6.25-5.53 (m, 1H), 4.81 (d, J=7.5 Hz, 1H), 4.52-3.73 (m, 1H), 3.62 (ddd, J=9.8, 6.6, 3.4 Hz, 1H), 3.55-3.44 (m, 1H), 3.37 (ddd, J=14.3, 11.4, 6.6 Hz, 2H), 3.10 (ddd, J=85.1, 10.3, 7.5 Hz, 1H), 2.35 (ddt, J=22.3, 14.6, 7.5 Hz, 1H), 1.63-1.42 (m, 1H), 1.40-1.20 (m, 1H), 0.84 (dt, J=20.8, 7.4 Hz, 3H).

Example 88

4-(((cis)-1-(2-cyanoethyl)-4-ethylpyrrolidin-3-yl)amino)-1H-pyrrolo[2,3-b]pyridin-5-carbonitrile H88

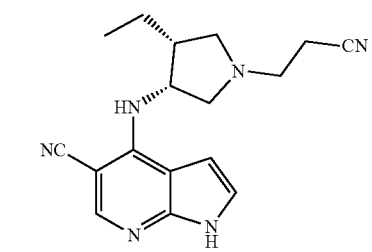

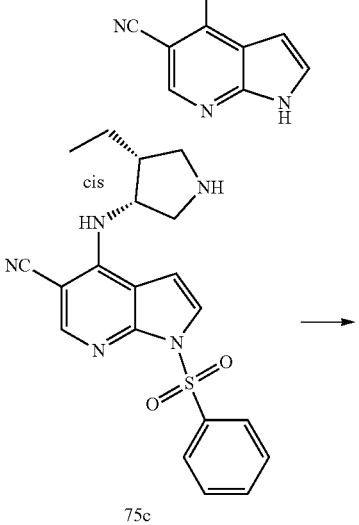

75c

139

-continued

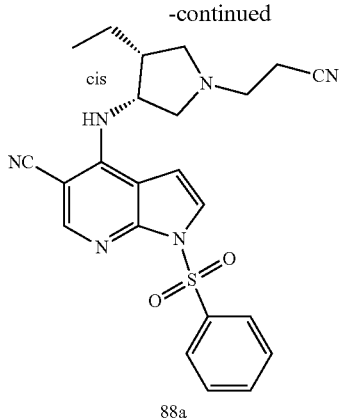

88a

↓

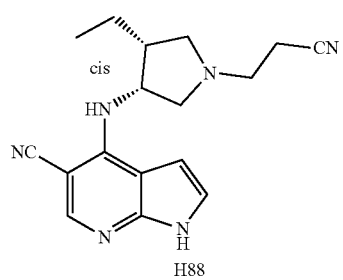

H88

First Step: 4-(((cis)-1-(2-cyanoethyl)-4-ethylpyrrolidin-3-yl)amino)-1-(benzenesulfonyl)-1H-pyrrolo[2,3-b]pyridin-5-carbonitrile 88a

Compound 75c (110 mg, 0.28 mmol, 1.0 eq), acrylonitrile (45 mg, 0.84 mmol, 3.0 eq) and DIPEA (0.11 g, 0.84 mmol, 3.0 eq) were added in anhydrous MeOH (10 ml) and reacted for 2 h at room temperature. The system was concentrated and purified by flash column to obtain a colorless oily substance 88a (99 mg).

MS m/z (ESI): 449 [M+1]$^+$

Second Step: 4-(((cis)1-(2-cyanoethyl)-4-ethylpyrrolidin-3-yl)amino)-1H-pyrrolo[2,3-b] pyridin-5-carbonitrile H88

Compound 88a (99 mg, 0.22 mmol, 1.0 eq) was dissolved in a mixed solvent of methanol (4 ml) and THF (4 ml), and then 2N of NaOH (0.55 ml, 1.1 mmol, 5.0 eq) was added and reacted for 2 h at room temperature to obtain a reaction liquid. The reaction liquid was mixed directly and purified by flash column (DCM-DCM/MeOH=15:1) to obtain white solid H88 (36 mg).

MS m/z (ESI): 309 [M+1]$^+$ $^1$H NMR (400 MHz, DMSO-d$_6$) δ 11.78 (s, 1H), 8.04 (s, 1H), 7.20 (dd, J=3.5, 2.4 Hz, 1H), 6.79-6.73 (m, 1H), 6.58 (s, 1H), 4.77 (d, J=7.9 Hz, 1H), 3.20 (t, J=8.1 Hz, 1H), 3.04 (t, J=8.0 Hz, 1H), 2.67 (m, 4H), 2.56-2.49 (m, 1H), 2.28 (p, J=7.9, 7.5 Hz, 1H), 2.18 (t, J=8.8 Hz, 1H), 1.36-1.22 (m, 2H), 0.76 (t, J=7.4 Hz, 3H).

140

Example 89

(cis)-3-((5-cyano-1H-pyrrolo[2,3-b]pyridin-4-yl)amino)-N-(2,2-difluoropropyl)-4-ethylpyrrolidin-1-carboxamide H89

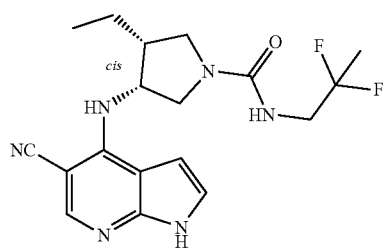

H89

2,2-difluoropropylamine was used as a raw material to obtain compound H89 by using the same preparation method as described in Example 83.

LCMS (ESI-MS) m/z: 377.2 (M+H$^+$).

$^1$H NMR (400 MHz, DMSO-d$_3$) δ 11.86 (s, 1H), 8.11 (s, 1H), 7.27 (dd, J=3.6, 2.4 Hz, 1H), 6.85 (dd, J=3.6, 2.0 Hz, 1H), 6.58 (q, J=6.1 Hz, 2H), 4.84 (dq, J=9.0, 2.7 Hz, 1H), 3.66-3.32 (m, 6H), 2.40 (q, J=6.6 Hz, 1H), 1.53 (m, 4H), 1.38 (ddd, J=13.8, 8.7, 7.1 Hz, 1H), 0.85 (t, J=7.4 Hz, 3H).

Example 90

7-((5-cyano-1H-pyrrolo[2,3-b]pyridin-4-yl)amino)-5,6,7,8-tetrahydroimidazo[1,2-a]pyridin-2-carbonitrile H90

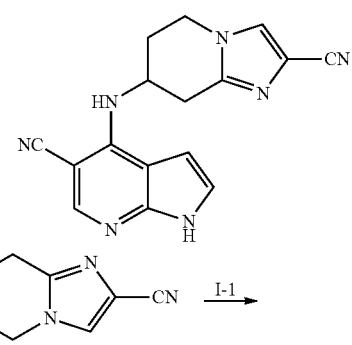

H90

90a

I-1 →

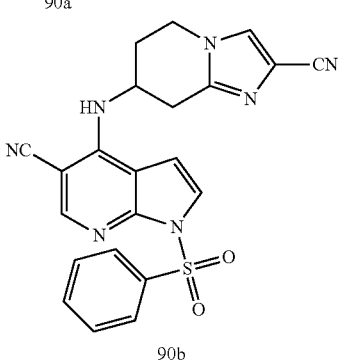

90b

→

-continued

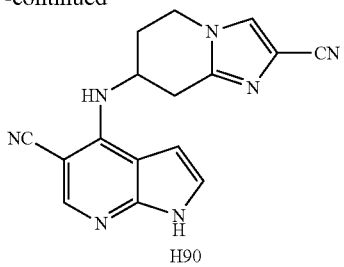

H90

First Step: 7-((5-cyano-1-(benzenesulfonyl)-1H-pyrrolo[2,3-b]pyridin-4-yl)amino)-5,6,7,8-tetrahydroimidazo[1,2-a]pyridin-2-carbonitrile 90b Compound 90a (290 mg, 1.8 mmol, 1.0 eq) and compound I-1 (0.57 g, 1.8 mmol, 1.0 eq) were dissolved in NMP (5 ml), and DIPEA (1.2 g, 9.0 mmol, 5.0 eq) was added and reacted for 4 h at 110° C. The system was diluted with ethyl acetate (30 ml), washed with brine (20 ml×4), concentrated and purified with flash column (DCM-DCM/MeOH=10:1) to obtain yellow solids 90b (20 mg).

MS m/z (ESI): 444 [M+H]+

Second Step: 7-((5-cyano-1H-pyrrolo[2,3-b]pyridin-4-yl)amino)-5,6,7,8-tetrahydroimidazo[1,2-a]pyridin-2-carbonitrile H90

Compound 90b (20 mg, 0.05 mmol, 1.0 eq) was dissolved in a mixed solvent of methanol (5 ml) and THE (5 ml), and then 2N of NaOH (0.13 ml, 0.25 mmol, 5.0 eq) was added and reacted for 1 h at room temperature to obtain a reaction liquid. The reaction liquid was dried under reduced pressure and purified by preparative plate (DCM-DCM/MeOH=15:1) to obtain white solids H90 (5 mg).

MS m/z (ESI): 304 [M+H]+

$^1$H NMR (400 MHz, DMSO-d$_6$) δ 11.84 (s, 1H), 8.05 (d, J=22.6 Hz, 2H), 7.24 (dd, J=3.6, 2.4 Hz, 1H), 6.99 (d, J=8.4 Hz, 1H), 6.74 (dd, J=3.6, 2.0 Hz, 1H), 4.76-4.62 (m, 1H), 4.23-4.02 (m, 2H), 3.23-2.98 (m, 2H), 2.34-2.01 (m, 2H).

Example 91

(cis)-3-cyclopropyl-N-(2,2,2-trifluoroethyl)-4-((5-(trifluoromethyl)-1H-pyrrolo[2,3-b]pyridin-4-yl)amino)pyrrolidin-1-carboxamide H91

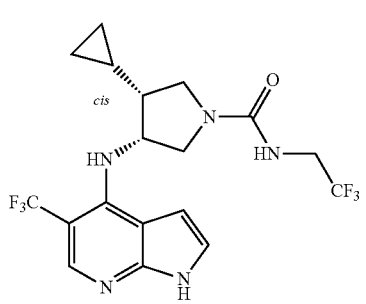

H91

-continued

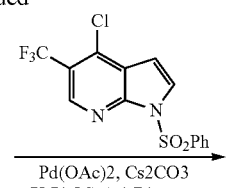

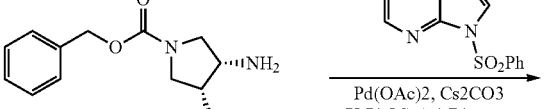

74c

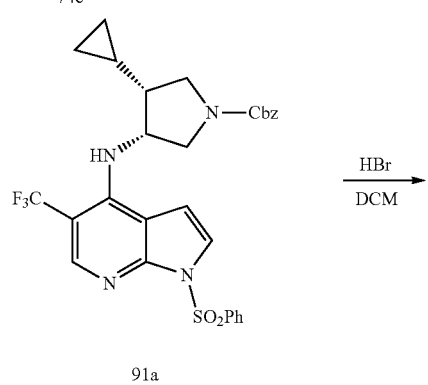

91a

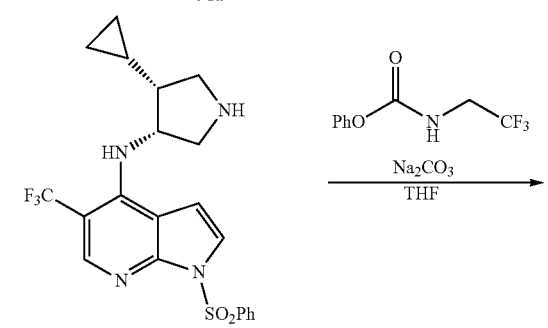

91b

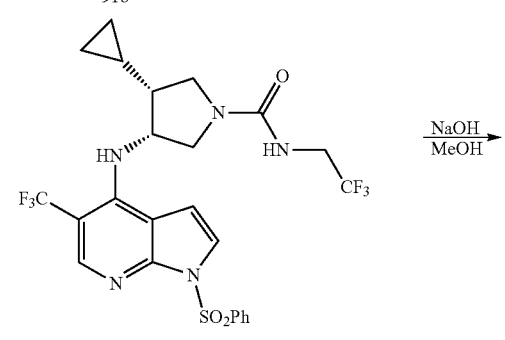

91c

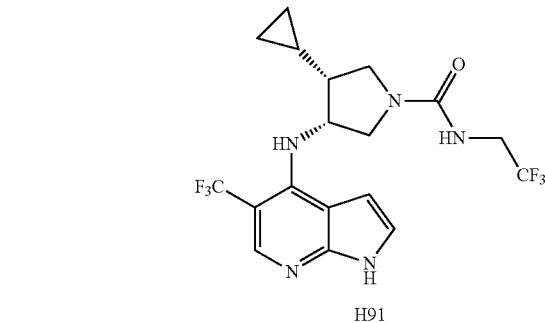

H91

143

Fifth Step: (cis)-3-isopropyl-4-((1-(benzenesulfo-nyl)-5-(trifluoromethyl)-1H-pyrrole[2,3-b]pyridin-4-yl)amino)pyrrolidin-1-benzyl formate 91a Compound 74c (546.6 mg, 2.1 mmol) was dissolved 3 mL of 1,4-dioxane, and 1-benzenesulfonyl-4-chloro-5-trifluoromethyl-1H-pyrrole[2,3-b]pyridine (500 mg, 1.4 mmol), Cs₂CO₃ (1.3 g, 4.2 mmol) and X-PhOS (162 mg, 0.28 mmol) were added. The system was substituted by nitrogen for three times, and then palladium acetate (62.9 mg, 0.28 mmol) was added, heated and subjected to a reflux reaction for 3 h. After the reaction was completed, water was added. The system was extracted with EA and the organic phases were collected. Then the system was separated by column chromatography (PE:EA=5:1) to obtain 91a (460 mg), with a yield of 56%.

LCMS (ESI-MS) m/z: 585.3 (M+H+).

Second Step: N-((cis)-4-cyclopropylpyrrolidin-3-yl)-1-(phenylsulfanyl)-5-(trifluoromethyl)-1H-pyr-rolo[2,3-b]pyridin-4-amine 91b Compound 91a (460 mg, 0.8 mmol) was dissolved in 2 mL dichloromethane, and then HBr (1 mL) was added and reacted for 1 h at room temperature. After the reaction was completed, the system was concentrated and lyophilized directly to obtain crude products 91b (300 mg) with a yield of 83%.

LCMS (ESI-MS) m/z: 451.2 (M+H+).

Third Step: (cis)-3-cyclopropyl-4-((1-(phenylsulfo-nyl)-5-(trifluoromethyl)-1H-pyrrolo [2,3-b]pyridin-4-yl)amino))-N-(2,2,2-trifluoroethyl)pyrrolidin-1-carboxamide 91c Compound 91b (300 mg, 0.6 mmol) was dissolved in 5 mL THF, and then compound Int-2 (263 mg, 1.2 mmol) and Na₂CO₃ (191 mg, 1.8 mmol) were added, heated to 70° C. and reacted for 3 h. After the reaction was completed, the system was concentrated and separated by preparative TLC to obtain compound 91c (150 mg), with a yield of 43%.

LCMS (ESI-MS) m/z: 576.3 (M+H+).

Fourth Step: (cis)-3-cyclopropyl-N-(2,2,2-trifluoroethyl)-4-((5-(trifluoromethyl)-1H-pyrrolo [2,3-b]pyridin-4-yl)amino)pyrrolidin-1-carboxamide H91

Compound 91c (150 mg, 0.26 mmol) was dissolved in 2 mL methanol, and NaOH (1 mL, 1.5 mmol, 4 M in water) was added and reacted for 1 h at room temperature. After the reaction was completed, water was added. The system was extracted with DCM, concentrated and separated by preparative TLC to obtain compound H91 (23 mg) with a yield of 20%.

LCMS (ESI-MS) m/z: 436.3 (M+H+).

1H NMR (400 MHz, DNMSO-d6) δ 11.77 (s, 1H), 8.10 (s, 1H), 7.32 (dd, J=3.6, 2.4 Hz, 1H), 6.84 (t, J=6.3 Hz, 1H), 6.71 (dd, J=3.8, 1.8 Hz, 1H), 5.51 (d, J=7.9 Hz, 1H), 4.82 (t, J=6.8 Hz, 1H), 3.85-3.63 (m, 3H), 3.54 (dd, J=10.3, 7.0 Hz, 1.1), 3.37-3.31 (m, 2H), 1.85 (s, 1H), 0.79 (dt, J=13.9, 5.6 Hz, 1H), 0.48 (dd, J=8.1, 1.7 Hz, 2H), 0.28-0.01 (m, 2H).

144

Example 92

(cis)-3-ethyl-N-(2,2,2-trifluoroethyl)-4-((5-(trifluoromethyl)-1H-pyrrolo[2,3-b]pyridin-4-yl)amino)pyrrolidin-1-carboxamide H92

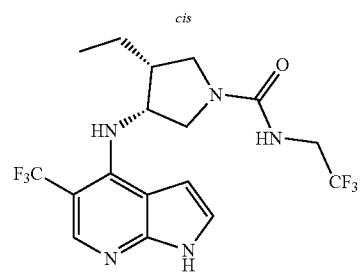

Ethyl magnesium bromide was used as a raw material to obtain compound H92 by using the same preparation method as described in Example 91.

LCMS (ESI-MS) m/z: 481.3 (M+H⁺).

¹H NMR (400 MHz, DMSO-d₆) δ 11.79 (s, 1H), 8.09 (s, 1H), 7.32 (dd, J=3.7, 2.4 Hz, 1H), 6.84 (t, J=6.3 Hz, 1H), 6.65 (dd, J=3.7, 1.8 Hz, 1H), 5.06-4.98 (m, 1H), 4.76 (s, 1H), 3.79-3.56 (m, 4H), 3.48 (m, 1H), 3.07 (t, J=10.2 Hz, 1H), 2.42 (m, 1H), 1.47-1.34 (m, 2H), 0.86 (t, J=7.3 Hz, 3H).

Example 93

(cis)-3-ethyl-N-(cyanmethyl)-4-((5-(trifluoromethyl)-1H-pyrrolo[2,3-b]pyridin-4-yl)amino)pyrrolidin-1-carboxamide H93

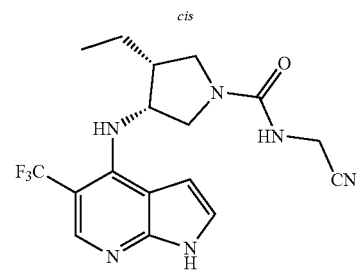

N-(cyanomethyl)phenyl carbamate was used as a raw material to obtain compound H93 by using the same preparation method as described in Example 92.

LCMS (ESI-MS) m/z: 481.3 (M+H⁺).

¹H NMR (400 MHz, DMSO-d₆) δ 11.80 (s, 1H) 8.09 (s, 1H), 7.32 (dd, J=3.7, 2.5 Hz, 1H), 6.93 (t, J=5.7 Hz, 1H), 6.65 (dd, J=3.7, 1.9 Hz, 1H), 5.05 (d, J=7.7 Hz, 1H), 4.77 (s, 1H), 3.95 (d, J=5.5 Hz, 2H), 3.66-3.56 (m, 2H), 3.44 (d, J=11.1 Hz, 1H), 3.06 (t, J=10.1 Hz, 1H), 2.43-2.40 (m, 1H), 1.46-1.35 (m, 2H), 0.85 (t, J=7.3 Hz, 3H).

BIOLOGICAL TEST EXAMPLES

Example 1 Inhibition Test of the Compounds of the Invention on the JAK Kinase

1. Test Purpose

Inhibition test on activity of JAK kinase in vitro was carried out by the following methods.

1.1 Kits and Test Liquids

JAK1 LANCE® Ultra assay, JAK2 LANCE® Ultra assay and JAK3 LANCE® Ultra assay were used to carry out the test separately, and kits of the above assays were supplied by PerkinElmer.

A reaction system of JAK1 LANCE®Ultra kinase assay comprises 2 nM JAK1 (Intech, PV4775), 50 nM ULight™-JAK-1 peptide (substrate, PerkinElmer, TRF0121-M) and 38 uM ATP (Sigma, A7699). A reaction system of JAK2 LANCE®Ultra kinase assay comprises 0.03 nM JAK2 (Intech, PV4288), 50 nM ULight™-JAK-1 peptide (substrate, PerkinElmer, TRF0121-M) and 12 uM ATP (Sigma, A7699). A reaction system of JAK3 LANCE®Ultra kinase assay comprises 0.08 nM JAK3 (Intech, PV4080), 50 nM ULight™-JAK-1 peptide (substrate, PerkinElmer, TRF0121-M) and 4 uM ATP (Sigma, A7699).

Buffers of an enzymatic reaction is 50 mM 4-hydroxyethylpiperazine ethane sulfonic acid (pH7.5) Intech, 15630130), 10 mM magnesium chloride (Sigma, 63020), 1 mM edetic acid (Intech, 1842C505), 2 mM dithiothreitol (Intech, 43815) and 0.01% BRIJ-35 (Intech, B4184). JAK1, JAK2 and JAK3 kinase, ATP and substrates were dissolved and diluted with buffers.

A test liquid was 2 nM Eu-W1024 anti-phosphotyrosine (PerkinElmer, AD0069). A stop buffer was 10 mM edetic acid (Intech, 1842C505).

1.2 Formulation of the Compound

Test compounds H01-H93 were dissolved in dimethyl sulfoxide, respectively, from 0.017 nM to 1 μM in triplicate dilutions for a total of 11 gradient concentrations.

Test Procedure 2.5 μl of an 8-fold solution of the compound and 5 μl of a 4-fold solution of JAK1 or JAK2 or JAK3 kinase were added into a 384-well plate, respectively, and reacted for 10 minutes at room temperature. 2.5 μl of an 8-fold solution of ULight™-JAK-1 peptide/ATP was added and reacted for 90 minutes at room temperature. Finally, 5 μl of 4-fold edetic acid stop buffer and 5 μl of 4-fold test liquid of Eu-W1024 anti-phosphotyrosine were added and incubated for 60 minutes. Luminescence values were read in an ENVISION Multi-Mode Plate Reader (PE, 2105-0010).

1.4 Test Result

According to the formula: percentage of inhibition rate= (maximum value−transform value)/(maximum value−minimum value)×100, inhibition rate of each compound at various concentrations was calculated. The maximum value was the reference value of dimethyl sulfoxide added into the well plate, the minimum value was the blank value, and the transform value is the value obtained by the well of each compound. The $IC_{50}$ values of the corresponding compounds were then obtained by fitting by using the XLFit fitting tool in excel.

2. Test Result and Conclusion $IC_{50}$ of the compounds of the invention on inhibiting the activities of JAK1-3 kniases was shown in the following table. The data showed that the compounds of the invention have different inhibiting effects on JAK1-3 kinases. The compounds of the invention showed better inhibiting activity on JAK1 and better selectivity on JAK family compared with JAK2 and JAK3, which indicated that the compounds of the invention have good specificity for target, strong pharmaceutical effect and less adverse reaction induced by other targets in the same family.

TABLE 1

$IC_{50}$ of the compounds of the invention on inhibiting the activities of JAK1-3 kniases

| Test compound number | $IC_{50}$ (nM) | | | JAK2/JAK1 |
|---|---|---|---|---|
| | JAK1 | JAK2 | JAK3 | |
| H01 | 0.79 | 6.70 | 50.00 | 8.48 |
| H02 | 0.98 | 7.50 | 66.00 | 7.65 |
| H03 | 2.86 | 22.00 | 133.00 | 7.69 |
| H04 | 5.96 | 18.00 | 186.00 | 3.02 |
| H05 | 7.86 | 12.33 | 256.00 | 1.56 |
| H06 | 6.68 | 29.86 | 96.00 | 4.47 |
| H07 | 0.53 | 4.96 | 47.00 | 9.35 |
| H08 | 0.39 | 3.00 | 63.00 | 7.69 |
| H09 | 3.86 | 26.50 | 156.00 | 6.86 |
| H10 | 4.98 | 36.00 | 143.00 | 7.22 |
| H11 | 1.28 | 9.86 | 77.00 | 7.70 |
| H12 | 0.56 | 7.63 | 66.00 | 13.63 |
| H13 | 2.96 | 21.00 | 58.90 | 7.09 |
| H14 | 1.78 | 9.95 | 34.20 | 5.59 |
| H15 | 2.36 | 16.60 | 244.00 | 7.03 |
| H16 | 9.16 | 132.00 | 633.00 | 14.41 |
| H17 | 5.00 | 13.00 | 27.00 | 2.60 |
| H18 | 0.65 | 5.70 | 40.00 | 8.80 |
| H19 | 2.00 | 15.00 | 99.00 | 7.50 |
| H20 | 5.80 | 36.00 | 161.00 | 6.20 |
| H21 | 9.40 | 46.00 | 223.00 | 15.40 |
| H22 | 0.35 | 5.80 | 58.00 | 16.40 |
| H23 | 7.16 | 135.00 | 533.00 | 18.85 |
| H24 | 5.10 | 12.60 | 28.00 | 2.40 |
| H25 | 0.56 | 6.70 | 58.00 | 11.96 |
| H26 | 2.60 | 18.00 | 101.00 | 6.92 |
| H27 | 5.60 | 33.00 | 171.00 | 5.89 |
| H28 | 9.50 | 135.00 | 220.00 | 14.21 |
| H29 | 0.36 | 6.80 | 60.00 | 18.89 |
| H30 | 0.57 | 6.40 | 76.00 | 11.23 |
| H31 | 13.00 | 32.00 | 77.00 | 2.46 |
| H32 | 5.00 | 13.00 | 27.00 | 2.60 |
| H33 | 0.65 | 5.70 | 40.00 | 8.77 |
| H34 | 2.00 | 15.00 | 99.00 | 7.50 |
| H35 | 8.40 | 120.00 | 172.00 | 14.86 |
| H36 | 7.50 | 65.00 | 160.00 | 8.67 |
| H37 | 5.60 | 48.00 | 356.00 | 8.57 |
| H38 | 6.40 | 30.00 | 440.00 | 4.69 |
| H39 | 0.35 | 21.00 | 150.00 | 60.00 |
| H40 | 2.60 | 15.60 | 144.00 | 6.00 |
| H41 | 0.73 | 6.70 | 96.00 | 9.17 |
| H42 | 3.60 | 21.30 | 263.00 | 5.92 |
| H43 | 2.40 | 20.00 | 125.00 | 8.33 |
| H44 | 0.67 | 15.60 | 80.00 | 23.28 |
| H45 | 5.90 | 50.00 | 77.00 | 8.47 |
| H46 | 1.13 | 9.80 | 68.00 | 8.67 |
| H47 | 2.67 | 20.00 | 130.00 | 7.49 |
| H48 | 0.86 | 7.40 | 56.00 | 8.60 |
| H49 | 5.43 | 15.00 | 178.00 | 2.76 |
| H50 | 4.65 | 33.00 | 137.00 | 7.10 |
| H51 | 6.89 | 30.94 | 101.00 | 4.49 |
| H52 | 0.79 | 7.95 | 69.00 | 10.06 |
| H53 | 0.64 | 4.00 | 68.00 | 6.25 |
| H54 | 3.64 | 24.80 | 148.00 | 6.81 |
| H55 | 2.59 | 17.70 | 253.00 | 6.83 |
| H56 | 1.43 | 10.03 | 82.00 | 7.01 |
| H57 | 0.89 | 6.40 | 48.00 | 7.19 |
| H58 | 2.74 | 19.00 | 55.70 | 6.93 |
| H59 | 2.06 | 11.60 | 39.60 | 5.63 |
| H60 | 5.60 | 35.00 | 153.00 | 6.25 |
| H61 | 8.23 | 126.00 | 589.00 | 15.31 |
| H62 | 5.80 | 16.00 | 40.00 | 2.76 |
| H63 | 1.42 | 7.30 | 64.00 | 5.14 |
| H64 | 2.50 | 18.00 | 113.00 | 7.20 |
| H65 | 3.20 | 21.00 | 124.00 | 6.56 |
| H66 | 8.90 | 126.00 | 197.00 | 14.16 |
| H67 | 0.67 | 9.50 | 76.00 | 14.18 |

TABLE 1-continued

IC$_{50}$ of the compounds of the invention on inhibiting the activities of JAK1-3 kniases

| Test compound number | IC$_{50}$ (nM) | | | |
|---|---|---|---|---|
| | JAK1 | JAK2 | JAK3 | JAK2/JAK1 |
| H68 | 6.87 | 122.00 | 386.00 | 17.76 |
| H69 | 0.81 | 7.30 | 90.00 | 9.01 |
| H70 | 6.70 | 13.90 | 47.00 | 2.07 |
| H71 | 1.13 | 9.80 | 70.00 | 8.67 |
| H72 | 10.30 | 29.00 | 75.00 | 2.82 |
| H73 | 4.90 | 30.00 | 157.00 | 6.12 |
| H74 | 9.10 | 128.00 | 180.00 | 14.07 |
| H75 | 2.60 | 17.30 | 89.00 | 6.65 |
| H76 | 0.95 | 7.80 | 91.00 | 8.21 |
| H77 | 4.20 | 49.00 | 273.00 | 11.67 |
| H78 | 6.00 | 16.00 | 42.00 | 2.67 |
| H79 | 0.96 | 6.50 | 59.00 | 6.77 |
| H80 | 2.90 | 18.60 | 152.00 | 6.41 |
| H81 | 9.30 | 117.00 | 162.00 | 12.58 |
| H82 | 8.90 | 69.00 | 172.00 | 7.75 |
| H83 | 3.70 | 34.00 | 146.00 | 9.19 |
| H84 | 6.90 | 38.00 | 387.00 | 5.51 |
| H85 | 5.47 | 15.66 | 48.00 | 2.86 |
| H86 | 1.41 | 29.00 | 169.00 | 20.57 |
| H87 | 5.10 | 45.00 | 73.00 | 8.82 |
| H88 | 0.86 | 7.90 | 112.00 | 9.19 |
| H89 | 2.90 | 19.70 | 241.00 | 6.79 |
| H90 | 0.76 | 5.71 | 68.00 | 7.51 |
| H91 | 0.92 | 18.70 | 96.00 | 20.33 |
| H92 | 8.21 | 14.90 | 258.00 | 1.81 |
| H93 | 0.64 | 7.10 | 79.00 | 11.09 |
| Tofacitinib | 6.4 | 2.1 | 0.39 | 0.32 |

Example 2 Inhibiting Test of the Compounds of the Invention on Cell Proliferation 1. Test Purpose and Method Inhibiting test of the compounds of the invention on proliferation of Blast T cell and TF-1 cell (American type culture collection) was carried out by the following method.

1.1 Formulation of the Compound

The tested compounds H01, H02, H03, H07, H08, H09, H11, H12, H14, H15, H18, H19, H22, H25, H26, H29, H30, H33, H34, H39, H40, H41, H43, H44, H50, H58, H62, H70, H85, and H92 were dissolved in dimethyl sulfoxide from 0.0006 to 10 µM in quadruplicate dilutions.

1.2 Cell Proliferation Test of IL-2 Stimulated Blast T Cell

A culture medium included RPMI 1640 culture medium (Grand Turk Island Biotechnology Company™, 11875093), 10% fetal calf serum (Aosibina, 0986180), 55 µM 2-mercaptoethanol and 1% penicillin-streptomycin (Grand Turk Island Biotechnology Company, 1902422). Nunc™ Edge 2.0 96-well flat bottom (Cat. No. 167425).

Healthy human PBMC cells (drawn blood from healthy human) were isolated, and CD4$^+$T cells were isolated using the EasySep™ human CD4 T cell isolation kit (Stemcell, 19052). 10 µg/ml polyhydroxyalkanoate was added to stimulate and obtain cells with a density of 2×10$^6$/mL, which were incubated for 3 days. The cells were washed with phosphate buffer for three times and IL-2 (100 u/ml) was added to stimulate for 1 week. Cells were suspended using the culture medium and seeded at 5×10$^4$ cell/well density into 96-well plates, and incubated for 1 h with the prepared test compound or DMSO control at various concentrations from 0.0006 to 10 µM diluted by 4-fold volume. After incubation with 20 u/ml of IL-2 (50 µl/well without reference well) for 72 hours, Celltiter Glo® reagent (Promega, G7571) was added and mixed for 5 minutes, then incubated for 30 minutes at room temperature. The luminescence value was read on SpectraMax L (Molecular Device). Equation: inhibition rate=1−(the value−minimum value)/(maximum value−minimum value) was used to calculate inhibition rate of each concentration, wherein the value is the luminescence value of each well, maximum value is reference value of dimethyl sulfoxide well and minimum value is the value without IL-2 stimulation. The IC$_{50}$ values of the corresponding compounds were then obtained by fitting by using the XLFit fitting tool in excel.

1.3 TF-1 Cell Proliferation Test

A culture medium included RPMI 1640 culture medium (Grand Turk Island Biotechnology Company™-11875093), 10% fetal calf serum (Aosibina, 0986180) and 1% penicillin-streptomycin (Grand Turk Island Biotechnology Company, 1902422).

TF-1 cells were incubated with culture medium containing 2 ng/mL of human granulocyte macrophage colony stimulating factor to reach a density of 4.0×10$^5$ cells/mL, then incubated with culture medium without human granulocyte macrophage colony stimulating factor for 24 h, centrifuged in 1000 rpm for 5 minutes, and suspended using the culture medium containing 2 ng/mL of human granulocyte macrophage colony stimulating factor and seeded at 5000 cell/well density into 96-well plates. The above test compounds at various concentrations formulated in 1.1 or dimethyl sulfoxide control were added and incubated for 72 h, and then Celltiter Glo® reagent (Promega, G7571) was added. The luminescence value was read on Microplate Reader (Molecular Device). Equation: inhibition rate=1−(the value−minimum value)/(maximum value−minimum value) was used to calculate inhibition rate of each concentration, wherein the value is the luminescence value of each well, maximum value is reference value of dimethyl sulfoxide well and minimum value is the value without IL-2 stimulation. The IC$_{50}$ values of the corresponding compounds were then obtained by fitting by using the XLFit fitting tool in excel.

2. Test Result and Conclusion

IC$_{50}$ of the compounds of the invention on inhibiting proliferation of Blast T cell and TF-1 cell was shown in following table. The data showed that IC$_{50}$ value of the compounds of the invention on proliferation of T cell was 13-50 nM, and IC$_{50}$ value on proliferation of TF-1 cell was 70-2500 nM. It was clear that the compounds of the invention had good inhibiting effect on proliferation of T cell and poor inhibiting effect on proliferation of TF-1 cell, which indicated that the compounds of the invention had strong activity on JAK1 and weak activity on JAK2 and had good selectivity. It had better pharmaceutical effect on animals and less adverse reaction.

TABLE 2

IC$_{50}$ of the compounds of the invention on inhibiting proliferation of Blast T cell and TF-1 cell

| Compound number | IC$_{50}$ (µM) | |
|---|---|---|
| | T cell | TF-1 cell |
| H01 | 0.013 | 0.67 |
| H02 | 0.48 | 1.34 |
| H03 | 0.027 | 0.76 |
| H07 | 0.024 | 0.073 |
| H08 | 0.026 | 1.30 |
| H09 | 0.036 | 1.56 |
| H11 | 0.013 | 0.68 |
| H12 | 0.011 | 1.67 |

TABLE 2-continued

IC$_{50}$ of the compounds of the invention on inhibiting proliferation of Blast T cell and TF-1 cell

| Compound number | IC$_{50}$ (μM) | |
|---|---|---|
| | T cell | TF-1 cell |
| H14 | 0.017 | 0.63 |
| H15 | 0.014 | 0.073 |
| H18 | 0.040 | 1.56 |
| H19 | 0.024 | 2.30 |
| H22 | 0.019 | 1.76 |
| H25 | 0.020 | 0.73 |
| H26 | 0.027 | 1.98 |
| H29 | 0.016 | 0.87 |
| H30 | 0.018 | 1.23 |
| H33 | 0.023 | 1.10 |
| H34 | 0.044 | 1.54 |
| H39 | 0.015 | 0.69 |
| H40 | 0.036 | 1.24 |
| H41 | 0.055 | 1.64 |
| H43 | 0.043 | 1.44 |
| H44 | 0.014 | 0.73 |
| H50 | 0.034 | 0.85 |
| H58 | 0.041 | 0.98 |
| H62 | 0.029 | 1.32 |
| H70 | 0.048 | 1.53 |
| H85 | 0.032 | 1.47 |
| H92 | 0.027 | 0.91 |
| Tofacitinib | 0.065 | 0.047 |

Example 3 Pharmacodynamics Test of the Compounds of the Invention on Paw Swelling in Mice 1. Abstract The inhibiting effects of compounds H01, H07, H11, H12, H14, H15, H22, H25, H29, H30, H33, H39 and H44 on paw swelling in mice were determined after intragastric administration by using male ICR mice (ShanghaiSippr-BK laboratory animal Co. Ltd.), aged 8 weeks and weighing 22-24 g as test animals. The anti-inflammatory pharmacodynamics characteristic of the compounds of the invention was discussed.

2. Test Scheme
2.1 Compounds for Tests

Compounds H01, H07, H11, H12, H14, H15, H22, H25, H29, H30, H33, H39, and H44.
2.2 Formulation of the Compound A certain amount of compounds were taken and dissolved in 4% Tween 80/0.5% hydroxy propyl methyl cellulose solution. A volume of intragastric administration in mice was 10 ml/kg.
2.3 Operation Mice were given 10 mg/kg compounds H01, H07, H11, H12, H14, H15, H22, H25, H29, H30, H33, H39, and H44 and the positive drug indomethacin (Diamond Reagent Co., Ltd., China) by intragastric administration at the dosages shown in the table below and 20 μL 1% (W/V) carrageenan was injected subcutaneously into the plantar 0.5 h later. A paw volume was measured with a paw swelling meter before and at different time points after modeling (0.5 h, 1 h and 2 h). According to the formula: paw swelling rate=(paw volume after administration−basic paw volume)/basic paw volume×100, the inhibiting effect of the compounds on paw volume was calculated. The basic paw volume was a paw volume before administration.

3. Test Result and Conclusion

Data in the following table showed that 10 mg/kg compounds of the invention could relieve paw swelling rate of mice caused by carrageenan, especially over 1-2 h after administration, which indicated that the compounds of the invention had a certain anti-acute inflammatory effect and had better effect on inhibiting paw swelling rate than indometacin.

Example 3 Pharmacodynamics Effect of the Compounds of the Invention on Paw Swelling in Mice

| Compound number | Dosage (mg/kg) | Paw swelling_0.5 h (%) | Paw swelling rate_1 h (%) | Paw swelling rate_2 h (%) |
|---|---|---|---|---|
| Control group | 0 | 36.43 ± 2.56 | 49.24 ± 2.7 | 61.57 ± 3.41 |
| Indomethacin | 10 | 32.91 ± 3.22 | 42.21 ± 4.64 | 55.10 ± 2.21 |
| H01 | 10 | 33.99 ± 1.69 | 40.93 ± 1.64 | 41.56 ± 5.23 |
| H07 | 10 | 37.02 ± 1.35 | 42.33 ± 2.20 | 41.24 ± 3.36 |
| H11 | 10 | 30.22 ± 2.62 | 39.76 ± 1.20 | 40.25 ± 5.47 |
| H12 | 10 | 38.45 ± 4.37 | 45.64 ± 3.58 | 41.66 ± 5.38 |
| H14 | 10 | 39.03 ± 4.53 | 40.65 ± 2.51 | 39.00 ± 4.25 |
| H15 | 10 | 36.02 ± 1.37 | 43.33 ± 2.30 | 43.24 ± 4.36 |
| H22 | 10 | 31.22 ± 2.62 | 41.76 ± 1.20 | 42.25 ± 5.67 |
| H25 | 10 | 37.45 ± 4.37 | 44.64 ± 3.68 | 44.66 ± 5.58 |
| H29 | 10 | 33.03 ± 4.23 | 41.65 ± 2.21 | 40.10 ± 4.32 |
| H30 | 10 | 33.12 ± 1.38 | 43.43 ± 2.12 | 44.52 ± 4.37 |
| H33 | 10 | 30.78 ± 2.62 | 31.76 ± 1.86 | 41.75 ± 5.67 |
| H39 | 10 | 30.45 ± 1.74 | 26.44 ± 3.68 | 38.99 ± 5.58 |
| H44 | 10 | 31.03 ± 2.43 | 42.65 ± 2.21 | 41.56 ± 3.32 |

Example 4 Effects Test of the Compounds of the Invention on Paw Swelling in Mice 1. Abstract The inhibiting effects of compounds H13, H14, H09, H11 and compounds of Example 12 on paw swelling in mice were determined after intragastric administration by using Sprague-Dawley (SD) mice (ShanghaiSippr-BK laboratory animal Co. Ltd.), aged 6-7 weeks and weighing 160-180 g as test animals. The anti-inflammatory pharmacodynamics characteristic of the compounds of the invention was discussed.

2. Test Scheme
2.1 Compounds for Tests

Compounds H01, H07, H11, H12, H14, H15, H22, H25, H29, H30, H33, H39, and H44.
2.2 Formulation of the Compound A certain amount of compounds were taken and dissolved in 4% Tween 80/0.5% hydroxy propyl methyl cellulose solution.
2.3 Operation Mice were given compounds H01, H07, H11, H12, H14, H15, H22, H25, H29, H30, H33, H39, and H44 and the positive drug indomethacin (Diamond Reagent Co., Ltd., China) by intragastric administration at the dosages shown in the table below and 0.1 ml 0.03% (W/V) concanavalin was injected subcutaneously into the plantar 0.5 h later. A paw volume was measured with a paw swelling meter before modeling and 1 h, 2 h, 4 h and 6 h after modeling. According to the formula: paw swelling rate=(paw volume after administration−basic paw volume)/basic paw volume×100, the inhibiting effect of the compounds on paw volume was calculated. The basic paw volume was a paw volume before administration.

3. Test Result and Conclusion

Data in the following table showed that 10 mg/kg compounds of the invention could relieve the paw swelling in mice induced by concanavalin, which indicated that the compounds of the invention had a certain anti-acute inflammation effect and some compounds had a better anti-acute inflammation effect after 4 h than indometacin.

Example 4 Pharmacodynamics Effect of the Compounds of the Invention on Paw Swelling in Mice

| Compound number | Dosage (mg/kg) | Paw swelling rate_1 h (%) | Paw swelling rate_2 h (%) | Paw swelling rate_4 h (%) | Paw swelling rate_6 h (%) |
|---|---|---|---|---|---|
| Control group | 0 | 39.90 ± 3.00 | 51.90 ± 6.00 | 51.90 ± 4.000 | 41.80 ± 4.00 |
| Indomethacin | 10 | 34.00 ± 2.30 | 44.80 ± 3.00 | 42.70 ± 2.00 | 36.20 ± 2.00 |
| H01 | 10 | 25.70 ± 1.50 | 25.20 ± 2.40 | 31.20 ± 3.10 | 30.20 ± 3.10 |
| H07 | 10 | 25.20 ± 2.10 | 32.10 ± 1.70 | 22.30 ± 4.20 | 21.30 ± 4.20 |
| H11 | 10 | 23.50 ± 2.40 | 25.80 ± 3.30 | 31.00 ± 2.10 | 32.00 ± 2.10 |
| H12 | 10 | 28.90 ± 2.00 | 23.10 ± 3.00 | 24.00 ± 2.90 | 24.00 ± 3.00 |
| H14 | 10 | 32.10 ± 5.20 | 25.90 ± 5.00 | 25.50 ± 4.00 | 25.10 ± 4.20 |
| H15 | 10 | 24.50 ± 2.50 | 25.90 ± 3.40 | 32.00 ± 2.30 | 31.00 ± 2.30 |
| H22 | 10 | 29.80 ± 2.00 | 29.10 ± 3.00 | 31.00 ± 2.90 | 31.00 ± 2.90 |
| H25 | 10 | 32.10 ± 5.20 | 26.90 ± 5.00 | 24.50 ± 4.00 | 24.50 ± 4.00 |
| H29 | 10 | 23.70 ± 1.60 | 23.20 ± 2.60 | 32.20 ± 3.50 | 29.20 ± 3.50 |
| H30 | 10 | 24.40 ± 2.40 | 25.20 ± 3.40 | 26.00 ± 2.30 | 24.50 ± 2.30 |
| H33 | 10 | 27.80 ± 2.00 | 29.20 ± 3.10 | 30.10 ± 2.90 | 30.10 ± 2.90 |
| H39 | 10 | 31.10 ± 2.30 | 25.60 ± 4.00 | 26.30 ± 3.30 | 25.30 ± 3.30 |
| H44 | 10 | 23.80 ± 1.60 | 24.80 ± 2.50 | 24.20 ± 2.90 | 23.50 ± 2.90 |

Example 5 Effects Test of the Compounds of the Invention on Rheumatoid Arthritis in Mice 1. Abstract The effects of compounds H07, H12, H14, H25, H30, H39 and H44 on rheumatoid arthritis in mice were determined after long term administration by using Lewis male mice (Beijing Vital River Laboratory Animal Technology Co., Ltd.), aged 5-6 weeks and weighing 160 g as test animals. The anti-inflammatory pharmacodynamics characteristic of the compounds of the invention was discussed.

2. Test Scheme 2.1 Compounds for Tests

Compounds H07, H12, H14, H25, H30, H39, and H44.

2.2 Formulation of the Compound

A certain amount of compounds were taken and dissolved in 4% Tween 80/0.5% hydroxy propyl methyl cellulose solution. A volume of intragastric administration of mice was 10 ml/kg.

2.3 Operation

Collagen type II was dissolved in 0.1M acetic acid and kept in a 4° C. refrigerator overnight at a collagen concentration of 4 mg/mL. Same volume of incomplete Freund adjuvant (Sigma, USA) was added in collagen before injection in test, which was emulsified high speed homogenizer (30000 rpm) to prepare a collagen emulsion. This procedure was carried out on ice.

Mice were immunologically injected with the collagen emulsion by two separate times for modeling on days 1 and 7 (the day before modeling was day 0). 0.1 ml of collagen emulsion prepared as above was injected intradermally into a root of tail at a single point, and 0.2 ml was injected intradermally into back at two points. The animals were subjected to clinical score and paw volume test from day 10 to day 14 after modeling. Animals successfully modeled (average clinical score≥3 points/animal) were assigned to each administration group, with each group included 10 animals. They were administrated intragastrically with above compounds or resolvents at a dosage of 10 mg/kg twice/day, and administrated intragastrically with methotrexate (2 mg/kg, Sigma, USA) every three days, until day 27. During the test, the mice were scored twice a week, and the paw volume and body weight were measured twice.

According to the different degrees of lesions (redness and joint deformation), the scores were ranged from 0 to 4 points, with the highest score of 4 points for each limb and 16 points for each animal. Scoring standards are as follows: 0, no redness; 1, slight redness on mid legs (tarsals) or ankles; 2, slight redness from ankles to mid legs (tarsals); 3, medium redness from ankles to tarsometatarsal joints; 4, severe redness from toes or fingers to ankles or wrist joints.

3. Test Result and Conclusion

Data in the following table showed that the compounds of the invention with the dosage of 10 mg/kg could decrease the clinical score of arthritis in mice and paw swelling volume after one week of intragastric administration. Animals could move normally after two weeks of administration, and the progress of arthritis was remarkably relieved. Therefore the compound was superior to methotrexate which was a front-line clinical medicine.

TABLE 5

Scores of the compounds of the invention on rheumatoid arthritis models

| Group | Score | | | | | | |
|---|---|---|---|---|---|---|---|
| | Day 0 | Day 13 | Day 14 | Day 18 | Day 21 | Day 25 | Day 27 |
| Model control group | 0.00 ± 0.00 | 3.50 ± 0.52 | 4.40 ± 0.52 | 6.50 ± 0.45 | 9.80 ± 0.84 | 11.00 ± 1.15 | 12.20 ± 0.95 |
| Methotrexate | 0.00 ± 0.00 | 3.10 ± 0.43 | 3.60 ± 0.37 | 4.10 ± 0.47 | 6.45 ± 0.23 | 8.87 ± 0.21 | 9.65 ± 0.13 |
| H07 | 0.00 ± 0.00 | 3.10 ± 056 | 4.10 ± 0.41 | 3.10 ± 0.30 | 3.00 ± 0.11 | 2.00 ± 0.25 | 1.00 ± 0.17 |

TABLE 5-continued

Scores of the compounds of the invention on rheumatoid arthritis models

| Group | Day 0 | Day 13 | Day 14 | Day 18 | Day 21 | Day 25 | Day 27 |
|---|---|---|---|---|---|---|---|
| H12 | 0.00 ± 0.00 | 3.40 ± 0.39 | 3.90 ± 0.61 | 2.90 ± 0.67 | 1.23 ± 0.29 | 0.60 ± 0.17 | 0.50 ± 0.14 |
| H14 | 0.00 ± 0.00 | 3.30 ± 0.32 | 4.10 ± 0.50 | 3.20 ± 0.73 | 3.20 ± 0.61 | 2.20 ± 0.45 | 1.10 ± 0.27 |
| H25 | 0.00 ± 0.00 | 2.90 ± 0.48 | 3.40 ± 0.27 | 2.13 ± 0.21 | 1.10 ± 0.10 | 0.93 ± 0.18 | 0.74 ± 0.34 |
| H30 | 0.00 ± 0.00 | 3.20 ± 0.37 | 4.00 ± 0.45 | 3.50 ± 0.50 | 2.83 ± 0.29 | 2.00 ± 0.27 | 1.20 ± 0.27 |
| H39 | 0.00 ± 0.00 | 3.10 ± 0.44 | 4.10 ± 0.50 | 3.0 ± 0.37 | 2.33 ± 0.31 | 2.20 ± 0.52 | 1.10 ± 0.27 |
| H44 | 0.00 ± 0.00 | 2.80 ± 0.45 | 3.40 ± 0.27 | 2.13 ± 0.21 | 1.70 ± 0.10 | 0.83 ± 0.48 | 0.64 ± 0.34 |

Example 6 Pharmacokinetic Test of the Compounds of the Invention

1. Abstract

Drug concentrations of compounds H01, H07, H11, H12, H14, H15, H22, H25, H29, H30, H33, H39 and H44 intragastrically administrated in plasma by using LC/MS/MS method at various time points were determined by using Sprague-Dawley (SD) mice, aged 7-8 weeks and weighing 180-220 g as test animals. Pharmacokinetic behavior of the compounds of the invention in mice was studied and its pharmacokinetic characteristics were evaluated.

2. Test Scheme 2.1 Compounds for Tests

Compounds H01, H07, H11, H12, H14, H15, H22, H25, H29, H30, H33, H39, H44.

2.2 Formulation of the Compound

A certain amount of compounds was taken and dissolved in 50% PEG400/water to prepare a uniform solution.

2.3 Operation

Mice were administered intragastrically with the above compounds with a dosage of 5 mg/kg. Blood (0.2 ml) was taken from orbits before administration and 0.083 h, 0.25 h, 0.5 h, 1.0 h, 2.0 h, 4.0 h, 6.0 h, 8.0 h, 12.0 h and 24.0 h after administration. The blood was placed in anticoagulant tubes containing dipotassium ethylene glycol diethyl ether diamine tetraacetic acid, centrifugated at 6000 rpm at 4° C. for 10 minutes to separate plasma and saved at −80° C.

50 μL plasma at various time was taken and 150 μL acetonitrile solution containing internal standard tolbutamide (Sigma, USA) was added, mixed and stirred for 5 minutes. After centrifugation for 5 minutes at 12,000 rpm, 100 μL supernatant was taken, mixed with 200 μL water, following by sample injection and analysis.

2.4 Liquid Chromatogram Condition and Analysis Software

Liquid chromatogram system was LC-20AD UFLC High Performance Liquid Chromatography system. Mass spectrum system was AB Sciex API4000 triple quadrupole mass spectrometer equipped with Electron Spray Ionization (ESI) (Applied Biosystems, Canada). A software for controlling liquid chromatography-mass spectrometry and quantitative analysis was Anna Rust 1.6 (Applied Biosystems, Canada). Pharmacokinetic parameters were analyzed by WinNonlin (version 5.2, Pharsight, Mountain View, Canada) non-compartment model.

2.5 Standards and Preparation of Quality Control Solution

The test compound was dissolved in dimethyl sulfoxide to prepare a stock solution with a concentration of 1 mg/mL. The solution was diluted with 50% acetonitrile to obtain a series of standard working solutions with concentrations of 10 μg/mL, 3 μg/mL, 1 μg/mL, 0.3 μg/mL, 0.1 μg/mL, 0.03 μg/mL and 0.01 μg/mL, and a series of standard quality control solutions with concentrations of 8 μg/mL, 0.5 μg/mL, 0.03 μg/mL. 5 μL standard solution was mixed with 45 μL blank plasma substrate uniformly to obtain standard solutions of each concentration of a standard curve (1000 ng/mL, 500 ng/mL, 200 ng/mL, 100 ng/mL, 10 ng/mL, 5 ng/mL, 2 and 1 ng/mL) and quality control solutions (plasma samples: 800 ng/mL, 50 and 3 ng/mL).

Internal standard tolbutamide solid powder was dissolved in dimethyl sulfoxide to prepare a 1 mg/mL stock solution. The stock solution was diluted with 100% acetonitrile to obtain 200 ng/mL solution as a protein precipitation solution.

3. Test Result

TABLE 6

Results of pharmacokinetic parameters of the compounds of the invention

| | Dosag 5 mg/kg | | |
|---|---|---|---|
| Compound | Plasma concentration ($C_{max}$, ng/ml) | Area under the curve ($AUC_{0-24}$, ng/ml · h) | half life ($T_{1/2}$, h) |
| H01 | 578.00 ± 72.00 | 1720.00 ± 220.00 | 2.13 ± 0.27 |
| H07 | 578.00 ± 43.00 | 1918.00 ± 20.00 | 4.62 ± 0.87 |
| H11 | 428.00 ± 32.00 | 2620.00 ± 10.00 | 8.53 ± 0.67 |
| H12 | 644.00 ± 82.00 | 1020.00 ± 266.00 | 4.23 ± 0.47 |
| H14 | 438.00 ± 24.00 | 915.00 ± 240.00 | 2.11 ± 0.16 |
| H15 | 518.00 ± 24.00 | 1515.00 ± 241.00 | 5.11 ± 0.16 |
| H22 | 213.00 ± 22.00 | 757.00 ± 169.00 | 3.11 ± 0.64 |
| H25 | 501.00 ± 17.00 | 1273.00 ± 231.00 | 4.67 ± 0.23 |
| H29 | 522.00 ± 23.00 | 1529.00 ± 176.00 | 4.43 ± 0.32 |
| H30 | 433.00 ± 16.00 | 923.00 ± 263.00 | 2.47 ± 0.46 |
| H33 | 440.00 ± 89.00 | 1821.00 ± 173.00 | 8.64 ± 0.23 |
| H39 | 574.00 ± 64.00 | 1556.00 ± 230.00 | 4.65 ± 0.15 |
| H44 | 619.00 ± 39.00 | 1680.00 ± 120.00 | 4.17 ± 0.45 |

Data from the above table showed a pharmacokinetic feature that the compounds of the invention had a better pharmacokinetic absorption.

Example 7 Inhibiting Effect Test of the Compounds on hERG Potassium Channel Current 1. Abstract Effects of compounds H07, H12, H14, H25, H30, H39 and H44 on hERG potassium channel were detected by applying electrophysiological manual patch clamp to study an initial cardiac safety of the compounds of the invention.

2. Test Scheme 2.1 Formulation of the Compound

Test compounds were dissolved in dimethyl sulfoxide to prepare mother solutions (10 mM, 3.3 mM, 1.1 mM and 0.37 mM). Next an extracellular fluid was used for secondary dilution so that the test solution had final concentrations of 30 μM, 10 μM, 3.3 μM, 1.1 μM and 0.37 μM.

2.2 Preparation of Solvents

Extracellular fluids: 130 mM sodium chloride, 4 mM potassium chloride, 1.8 mM calcium chloride, 1 mM magnesium chloride, 10 mM glucose, 10 mM 4-hydroxyethylpiperazine ethane sulfonic acid (pH 7.4)

Intracellular fluid: 130 mM potassium chloride, 1 mM magnesium chloride, 5 mM ethylene glycol diethyl ether diamine tetraacetic acid, 5 mM triphosadenine and 10 mM 4-hydroxyethylpiperazine ethane sulfonic acid (pH7.2)

Compositions of a cell culture medium: Dulbecco's modified eagle medium (Grand Turk Island Biotechnology Company, 11330032), 15% fetal calf serum (Sigma, A15-101, USA), 1% penicillin-streptomycin (Biowest, L0022-100).

2.3 Test Scheme of Electrophysiological Manual Patch Clamp System

HEK293 cells overexpressing hERG potassium channel (from Dr. Mohamed Boutjdir's laboratory, School of Medicine, New York University—PharmaCore Labs, Inc.) were incubated in a medium consisting of Dulbecco's modified eagle medium/15% fetal calf serum/1% penicillin-streptomycin in a 5% CO2 incubator at 37° C. In the test, the cells were transferred to a cell bath embedded into a inverted microscope platform, and extracellular fluid was perfused. After stabilization for 5 minutes, the cells were precipitated and then the test could start. Membrane currents were recorded by using HEKA EPC-10 patch clamp amplifier and PATCHMASTER acquisition system (HEKA Instrument Co., Ltd., D-67466 Lambrcht, Palatinate, Germany). All tests were completed at room temperature (22-24° C.). P-97 microelectrode puller (Sutter Instrument Company, Novato, Canada 94949) was used to straighten the electrodes (BF150-110-10). The inner diameter of the electrode was 1-1.5 mm, and the water resistance after internal liquid filling was 2-4 MΩ.

Tests were carried out in whole-cell recording mode, with current values recorded according to the electrophysiological stimulation protocol below. First, the membrane voltage was clamped at −80 mV, and the cells were stimulated with +20 mV for two seconds to activate hERG potassium channel, which was then repolarized to −50 mV for five seconds, producing an outward tail current with a stimulation frequency of every 15 seconds. The current value was a peak value of the tail current. In the test, the channel current was recorded in the whole-cell recording mode. First, extracellular fluid (about 2 ml per minute) was perfused and recorded continuously, and then the current was allowed to stabilize (current decay (run-down) was less than 5% within 5 minutes). At this time, the peak value of the tail current was the control current value. Subsequently, the extracellular fluid containing the drug to be tested was perfused and recorded continuously until the inhibiting effect of drug on hERG current reached a stable state, at which time the peak value of the tail current was the current value after adding drugs. After a stable situation was achieved, if hERG current recovered after perfusing and washing with extracellular fluid, perfusion could be continued to test other concentrations or drugs. The solution containing the drugs to be tested was perfused in descending order of concentration and the current values were recorded. PATCHMASTER V2X60 (HEKA Instrument Co., Ltd., D-67466 Lambrcht, Palatinate, Germany) was used to collect data. ORANGE 8.5 (ORANGE Laboratory Company, Northampton, UK) software was used for the analysis and statistics.

3. Result $IC_{50}$ of the compounds of the invention for inhibiting hERG current was shown in Table 7 below. Data from the table showed the compounds of the invention had a weak effect on inhibiting hERG current and better safety.

TABLE 7

| Inhibiting effect of the compounds of the invention on hERG current | |
|---|---|
| Compound | $IC_{50}$ (μM) |
| H07 | >30 |
| H12 | >30 |
| H14 | >30 |
| H25 | >30 |
| H30 | >30 |
| H39 | >30 |
| H44 | >30 |

Example 8 Acute Toxicity Test of the Compounds of the Invention

1. Abstract

ICR mice (Beijing Vital River Laboratory Animal Technology Co., Ltd.), 20-22 g and aged 8 weeks, half male and half female, were orally administered with the compounds of Example H07, Example H12, Example H14, Example H25, Example H30, Example H39 and Example H34 once for continuous observation for 14 days, including state observation on the edge of a cage, daily body weight weighing, and endpoint histopathological observation.

2. Test Scheme 2.1 Compounds for Tests

Compounds of Example H07, Example H12, Example H14, Example H25, Example H30, Example H39 and Example H34.

2.2 Formulation of the Compound

A certain amount of compounds were taken and dissolved in 0.5% hydroxy propyl methyl cellulose to prepare a uniform solution.

2.3 Operation

Up-down method was used to observe acute toxicity of mice after oral administration once. There were 10 mice per dosage group. The dosage of administration was 100 mg/kg, 300 mg/kg and 1000 mg/kg, and the volume of administration was 10 ml/kg.

2.4 Test Statistics $LD_{50}$ was calculated using Bliss software based on a death rate of animal of each dosage.

2.5 Test Result

After continuous observation for 14 days, all the animals in the administration group survived, and their weights increased normally without any abnormal performance. After the 14-day observation period, all the animals were euthanized and underwent gross anatomical examination. No obvious abnormality was found on body surfaces and no visible lesion was found in the thoracic cavity, enterocoelia, pelvic cavity and cranial cavity.

Under the test conditions, the $LD_{50}$ of the compounds of the invention after oral administration to mice was more than 1000 mg/kg, which indicated the safety was good.

The above examples are only preferred embodiments of the present invention, and are not intended to limit the present invention. Any modifications, equivalent substitutions, improvements made within the spirit and principles of the present invention shall be included in the scope of protection of the present invention.

The invention claimed is:

1. A compound of formula (II), tautomers, mesomers, racemates, enantiomers, diastereoisomers, or mixtures thereof, pharmaceutically acceptable salts, polymorphs, solvates, or isotope derivatives thereof,

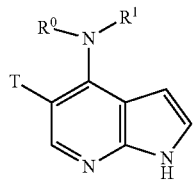

(II)

wherein,
T is —CN;
$R^0$ is hydrogen or $C_{1-3}$ alkyl;
$R^1$ is

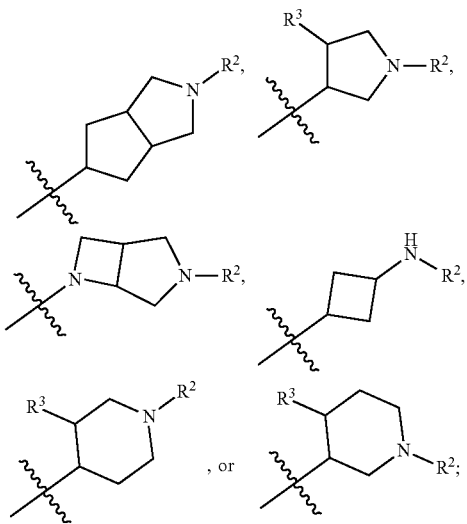

$R^2$ is —C(O)$R^4$, —C(O)N$R^5R^6$, or —S(O)$_2R^4$;
$R^3$ is —H or —$C_{1-4}$ alkyl, wherein the —$C_{1-4}$ alkyl is optionally substituted by the following groups: —OH, —$C_{1-3}$ alkyl, —O—$C_{1-4}$ alkyl, —NH$_2$, halogen, phenyl or cyano;
$R^4$ is —$C_{1-5}$ alkyl, 4- to 6-membered heterocyclyl, 5- to 10-membered heteroaryl, or phenyl, wherein the —$C_{1-5}$ alkyl is optionally substituted by the following groups: —OH, —$C_{1-3}$ alkyl, —$C_{5-6}$ cycloalkyl, 4- to 6-membered heterocyclyl, 5- to 10-membered heteroaryl, —O—$C_{1-4}$ alkyl, —NH$_2$, halogen, CF$_3$, phenyl or cyano;
wherein the phenyl of $R^4$ is optionally substituted by $R^e$;
$R^5$ is hydrogen or —$C_{1-3}$ alkyl;
$R^6$ is —$C_{1-4}$ alkyl, —$C_{3-6}$ cycloalkyl, 4- to 6-membered heterocyclyl, phenyl,

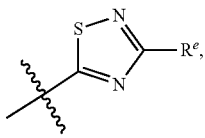 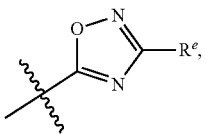

-continued

[triazole structure with $R^f$]

—CHF$_2$ or —CH$_2$CF$_2$CF$_3$, wherein the —$C_{1-4}$ alkyl is optionally substituted by the following groups: —OH, —$C_{1-3}$ alkyl, 4- to 6-membered heterocyclyl, 5- to 10-membered heteroaryl, —O—$C_{1-4}$ alkyl, —NH$_2$, halogen, CF$_3$, phenyl or cyano; wherein phenyl is optionally substituted by $R^e$ or $R^g$, or $R^e$ and $R^g$;
$R^e$ and $R^g$ are each independently halogen, —$C_{1-4}$ alkyl, alkoxy, 3- to 6-membered cycloalkyl, —N$R^cR^d$, —(CH$_2$)$_n$—OH, —(CH$_2$)$_n$—CF$_3$, or —(CH$_2$)$_n$—CN, wherein the —$C_{1-4}$ alkyl, alkoxy or cycloalkyl is optionally monosubstituted or disubstituted by the following groups: halogen, —OH, —NH$_2$, —$C_{1-3}$ alkyl, —O—$C_{1-4}$ alkyl, CF$_3$, phenyl or cyano;
$R^f$ is —$C_{1-4}$ alkyl or 3- to 6-membered cycloalkyl, wherein the —$C_{1-4}$ alkyl or cycloalkyl is optionally substituted by the following substituents: halogen, —OH, —NH$_2$, —$C_{1-3}$ alkyl, —O—$C_{1-4}$ alkyl, CF$_3$, phenyl or cyano;
$R^c$ and $R^d$ are each independently hydrogen, —$C_{1-3}$ alkyl, —$C_{1-4}$ alkylene-OH, —$C_{1-4}$ alkylene-CF$_3$, —$C_{2-4}$ alkylene-OCH$_3$, 3- to 6-membered cycloalkyl or 4- to 6-membered heterocyclyl; and
n is 0, 1, 2, 3 or 4.

2. The compound or tautomers, mesomers, racemates, enantiomers, diastereoisomers, or mixtures thereof, pharmaceutically acceptable salts, polymorphs, solvates, or isotope derivatives thereof according to claim 1, wherein
$R^4$ is —$C_{1-5}$ alkyl, 4- to 6-membered heterocyclyl, 5- to 10-membered heteroaryl, or phenyl, wherein the —$C_{1-5}$ alkyl is optionally substituted by the following groups: —OH, —$C_{1-3}$ alkyl, —O—$C_{1-4}$ alkyl, —NH$_2$, halogen, CF$_3$, phenyl or cyano;
wherein the phenyl of $R^4$ is optionally substituted by $R^e$;
$R^6$ is —$C_{1-4}$ alkyl, —$C_{3-6}$ cycloalkyl, 4- to 6-membered heterocyclyl, or phenyl, wherein the phenyl is optionally substituted by $R^e$ or $R^g$, or $R^e$ and $R^g$; wherein the —$C_{1-4}$ alkyl is optionally substituted by the following groups: —OH, —$C_{1-3}$ alkyl, 4- to 6-membered heterocyclyl, 5- to 10-membered heteroaryl, —O—$C_{1-4}$ alkyl, —NH$_2$, halogen, CF$_3$, phenyl or cyano; and
$R^f$ is —$C_{1-4}$ alkyl or 3- to 6-membered cycloalkyl, wherein the —$C_{1-4}$ alkyl or cycloalkyl is optionally substituted by the following substituents: halogen, —OH, or —$C_{1-3}$ alkyl.

3. The compound or tautomers, mesomers, racemates, enantiomers, diastereoisomers, or mixtures thereof, pharmaceutically acceptable salts, polymorphs, solvates, or isotope derivatives thereof according to claim 1, wherein
$R^6$ is —(CH$_2$)$_n$—CH$_2$CF$_3$, —(CH$_2$)$_n$—CF$_2$CF$_3$, —(CH$_2$)$_n$—CH$_2$CN, 4- to 6-membered heterocyclyl or phenyl, wherein the phenyl is optionally substituted by $R^e$ or $R^g$, or $R^e$ and $R^g$;
$R^f$ is —$C_{1-4}$ alkyl, wherein the —$C_{1-4}$ alkyl is optionally substituted by halogen or —OH; and
Rc and Rd are each independently hydrogen, —C1-3 alkyl, —C1-4 alkylene-OH or —C2-4 alkylene-OCH3;
n is 0, 1, 2 or 3.

4. The compound or tautomers, mesomers, racemates, enantiomers, diastereoisomers, or mixtures thereof, pharmaceutically acceptable salts, polymorphs, solvates, or isotope derivatives thereof according to claim 3, wherein $R^3$ is H, —CH$_3$, or —CH$_2$CH$_3$;

$R^4$ is methyl, ethyl, propyl, —(CH$_2$)$_n$—CH$_2$CN, —(CH$_2$)$_n$—CH$_2$CF$_3$, —CH(OH)—(CH$_2$)$_n$—CH$_3$,

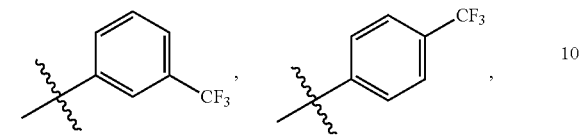

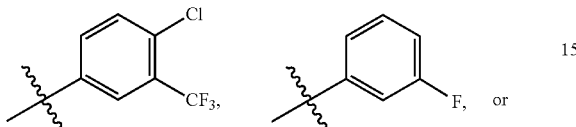

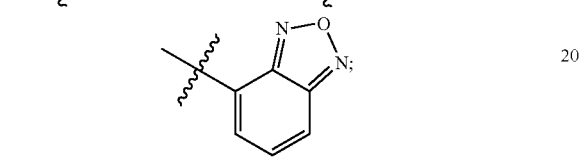

$R^5$ is H;

$R^6$ is —(CH$_2$)$_n$—CH$_2$CF$_3$, —(CH$_2$)$_n$—CF$_2$CF$_3$, —(CH$_2$)$_n$—CH$_2$CN,

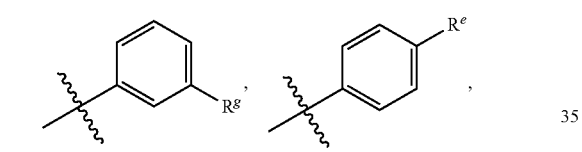

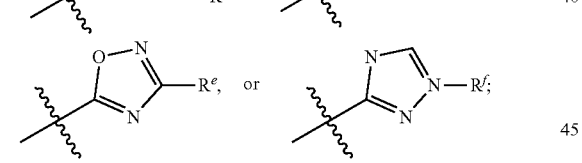

$R^e$ and $R^g$ are each independently —F, —Cl, methyl, ethyl, propyl, —CH(CH$_3$)—(CH$_2$)$_n$CH$_3$, —CH$_2$CH(CH$_3$)$_2$, —CH(CH$_3$)CH(CH$_3$)$_2$, —CH$_2$C(CH$_3$)$_3$, —C(CH$_3$)$_2$—(CH$_2$)$_n$CH$_3$, —O—(CH$_2$)$_n$CH$_3$, —O—(CH$_2$)$_n$CH$_2$—O—CH$_3$, —(CH$_2$)$_n$OCH$_3$, —O—(CH$_2$)$_n$—CH$_2$—C(CH$_3$)$_2$—OH, —O—(CH$_2$)$_n$—CH$_2$—C(CH$_3$)$_2$—NH$_2$, C$_{3-6}$ cycloalkyl, —(CH$_2$)$_n$—OH, —(CH$_2$)$_n$—CF$_3$, —(CH$_2$)$_n$—CHF$_2$, or —(CH$_2$)$_n$—CN;

$R^f$ is methyl, ethyl or propyl;

$R^c$ and $R^d$ are each independently —H, methyl, ethyl or propyl; and n is 0 or 1.

5. The compound or tautomers, mesomers, racemates, enantiomers, diastereoisomers, or mixtures thereof, pharmaceutically acceptable salts, polymorphs, solvates, or isotope derivatives thereof according to claim 1, wherein the compound is:

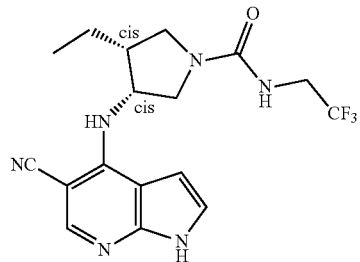

H01

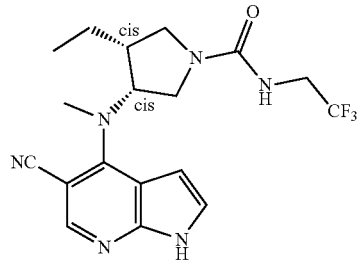

H02

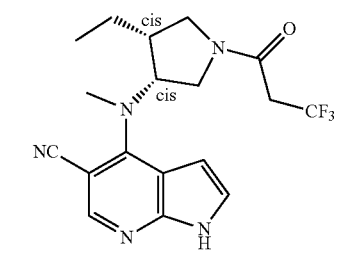

H03

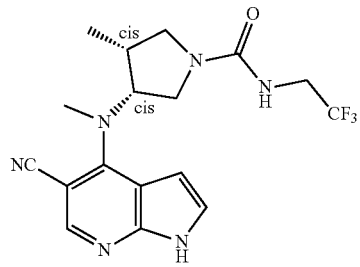

H04

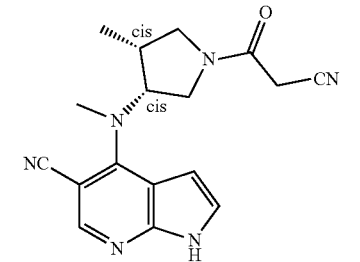

H05

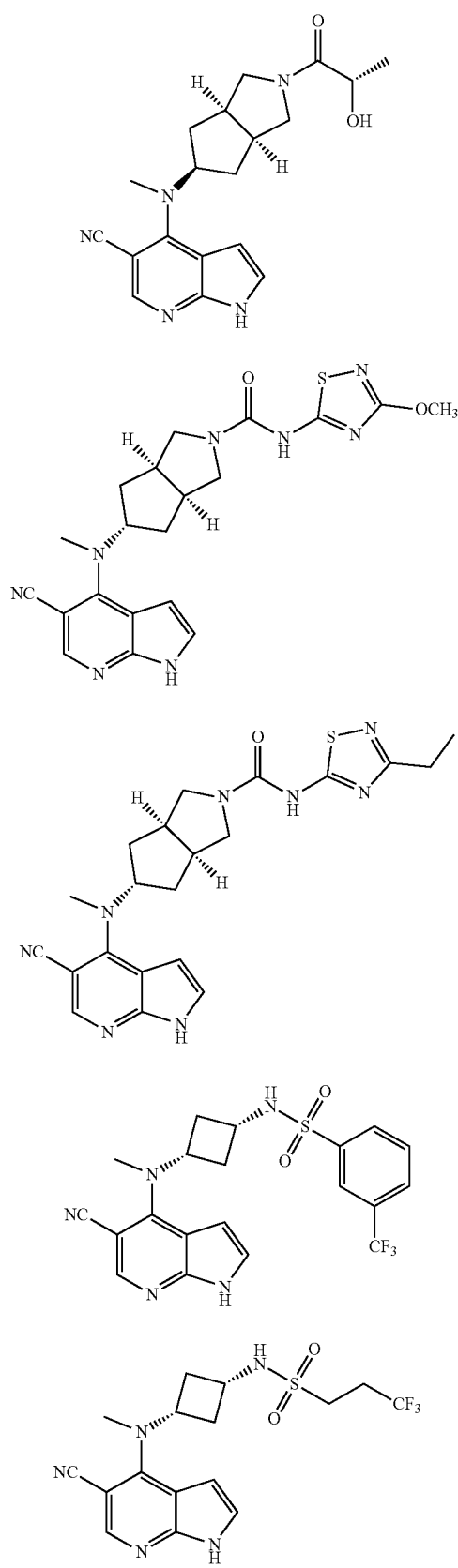
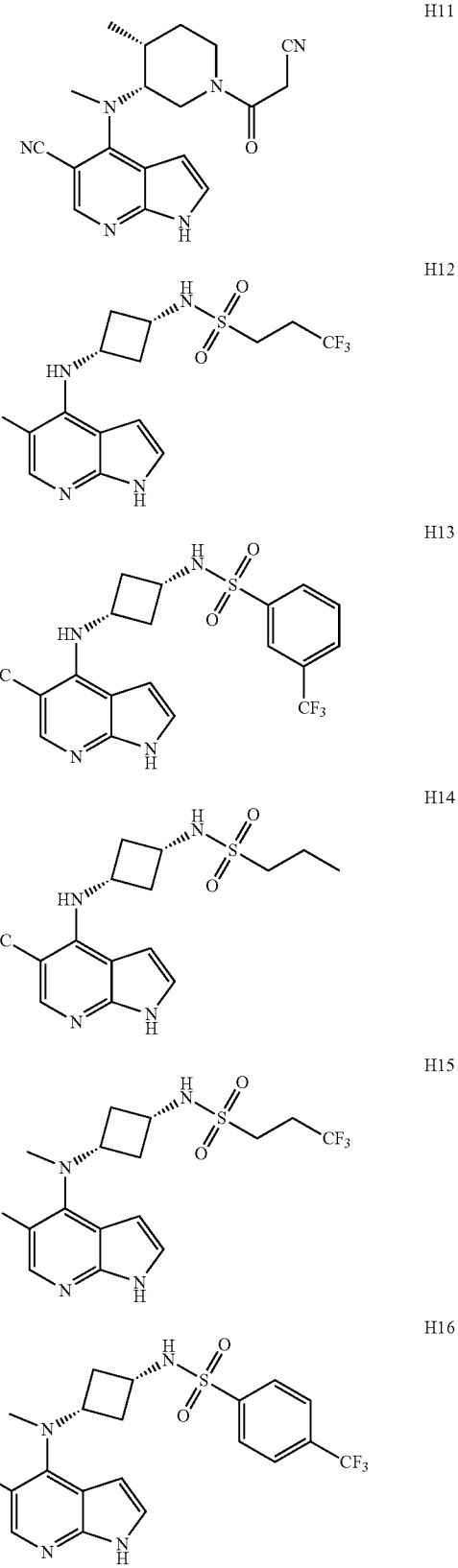

-continued
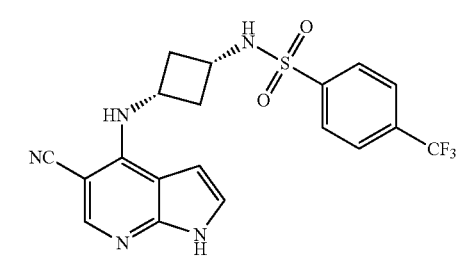 H17
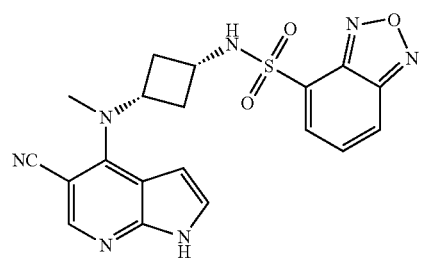 H18
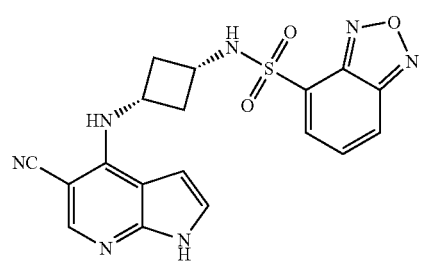 H19
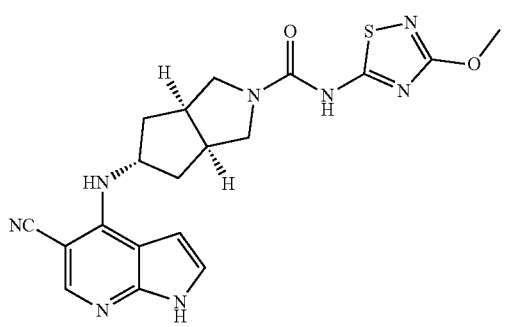 H20
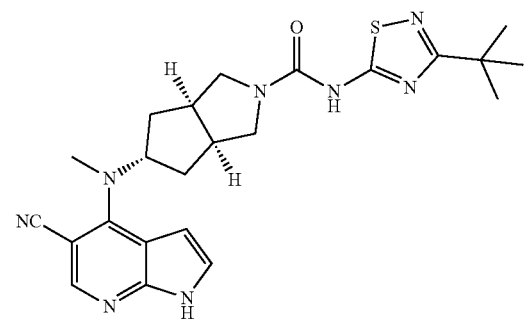 H21
-continued
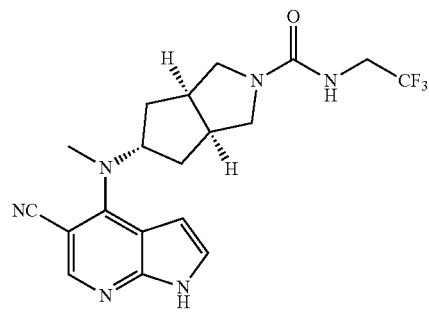 H22
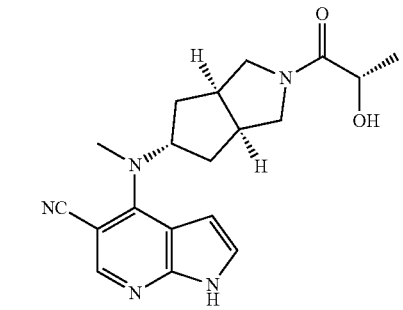 H23
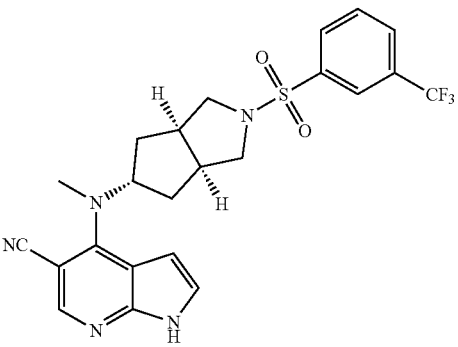 H24
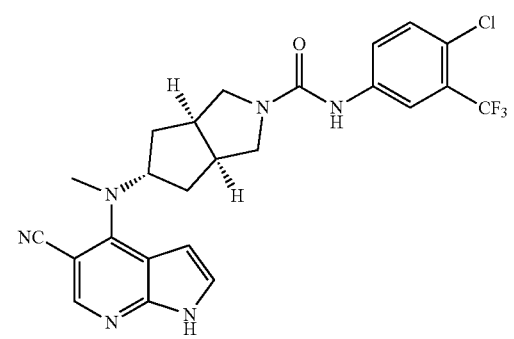 H25
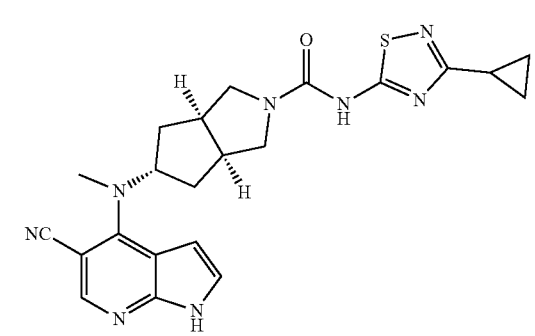 H26

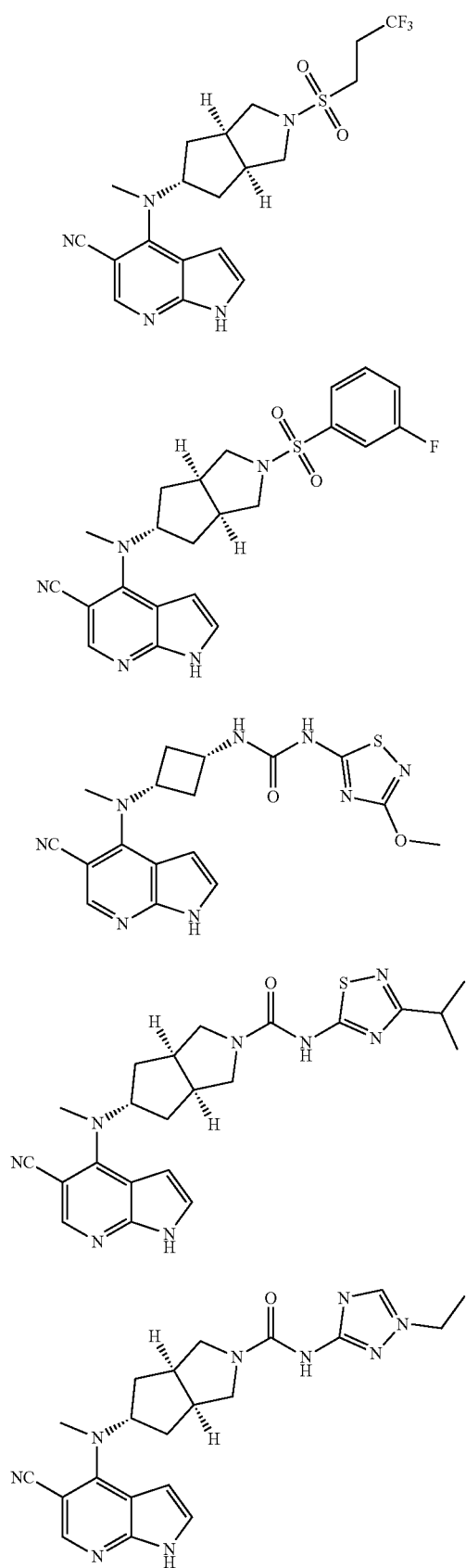
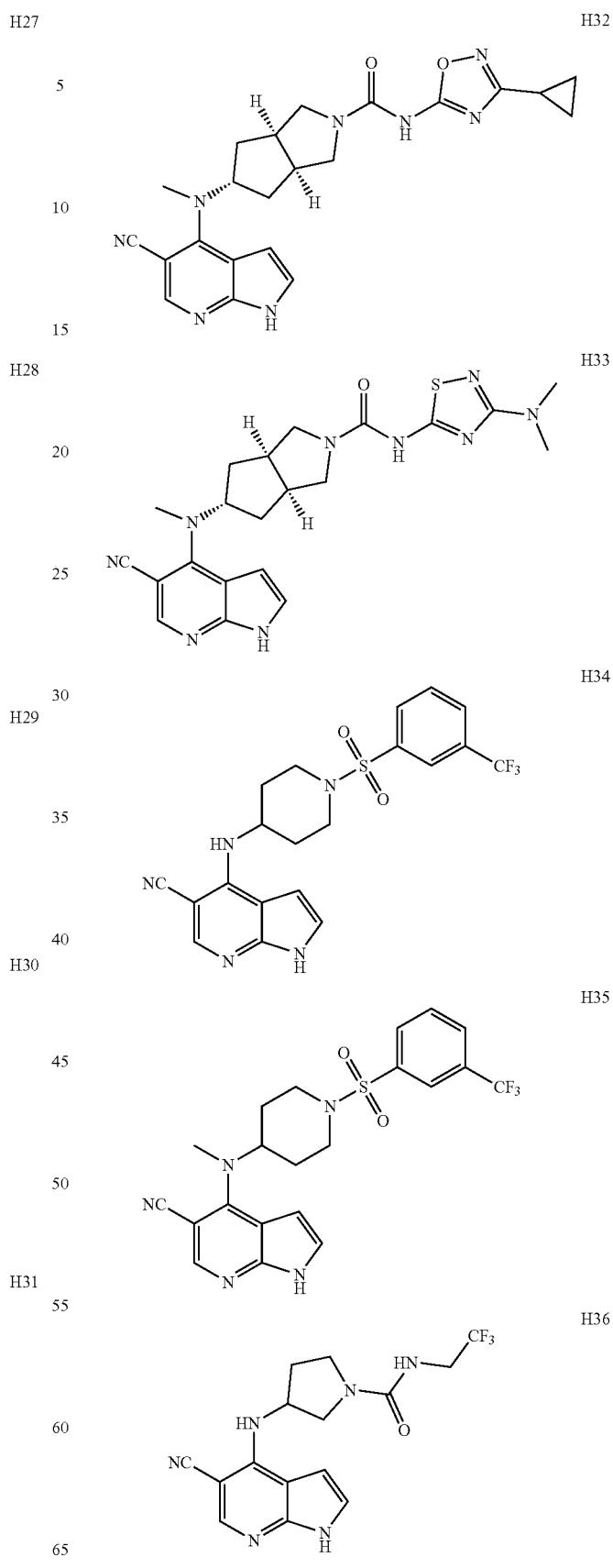

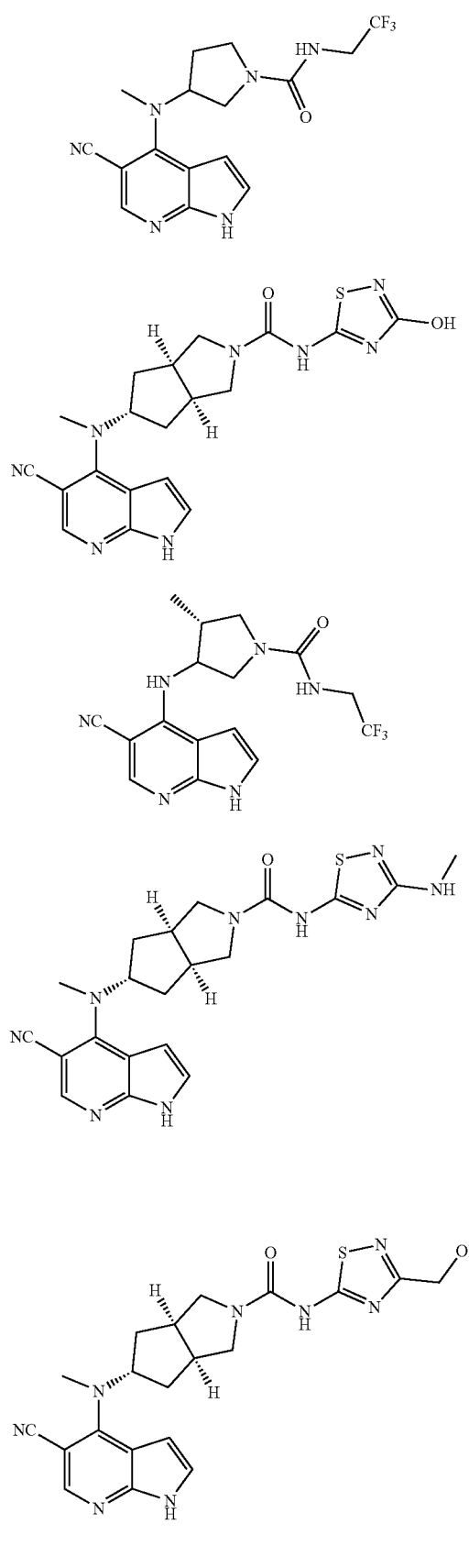
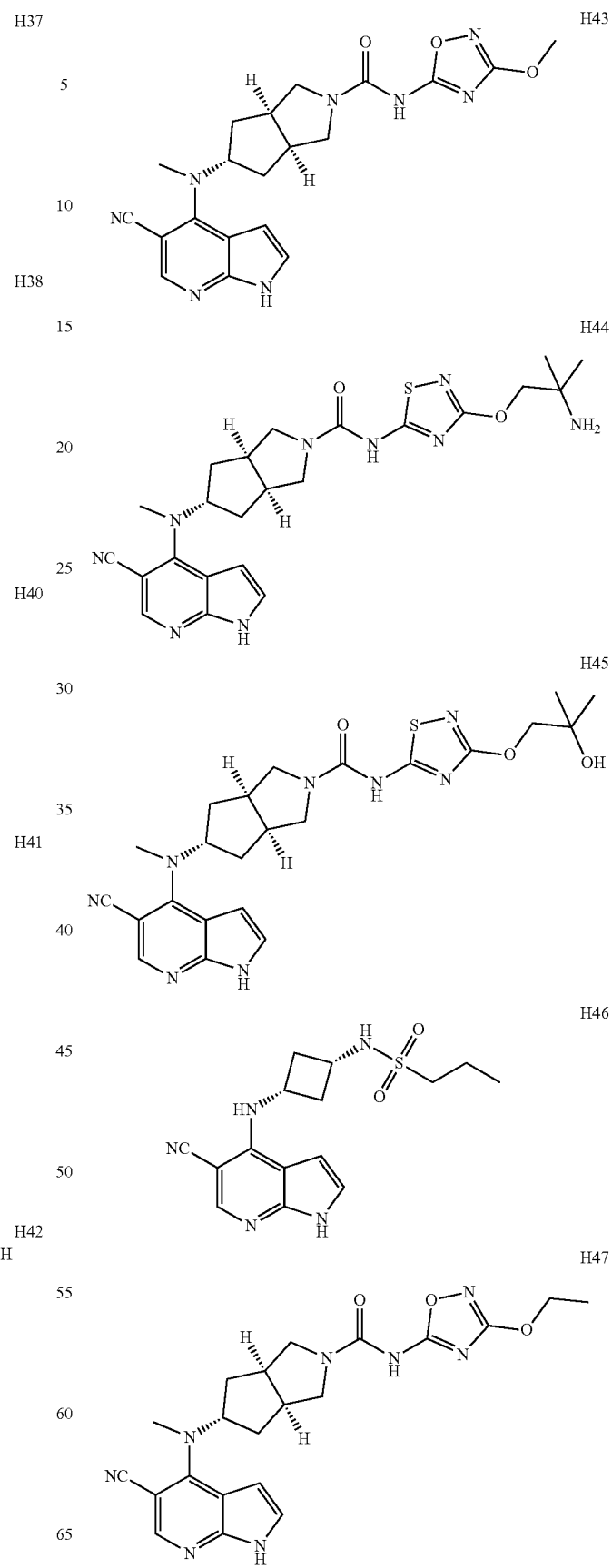

169
-continued
H48
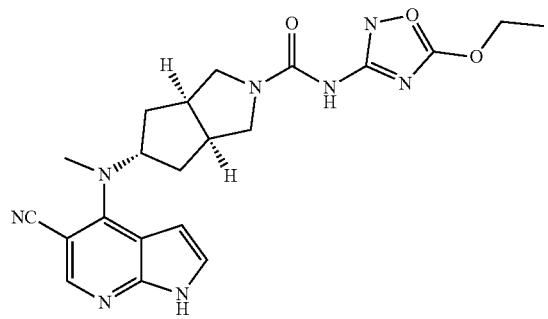
H49
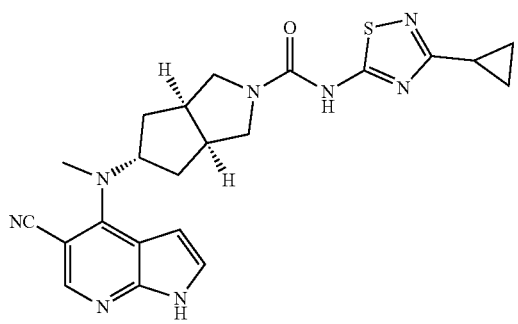
H51
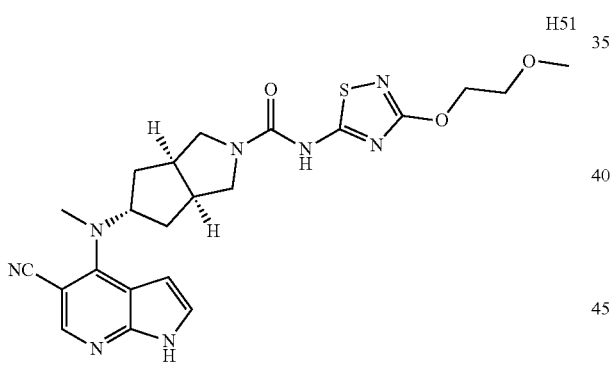
H52
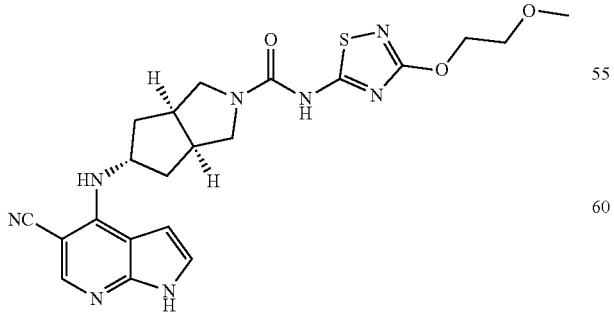
170
-continued
H56
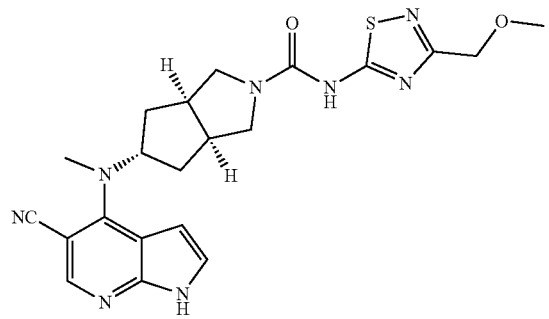
H57
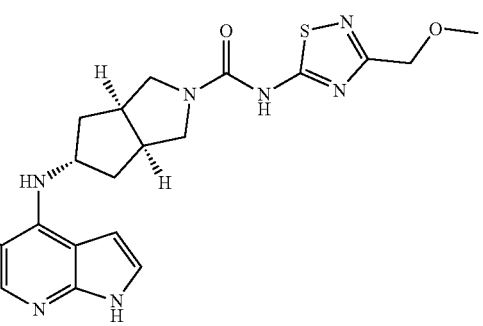
H73
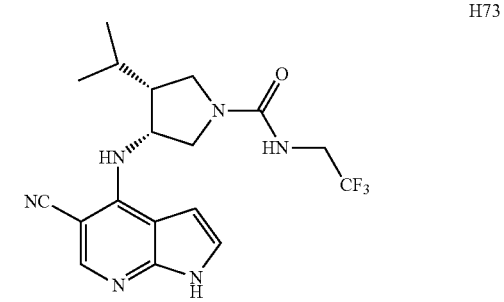
H75
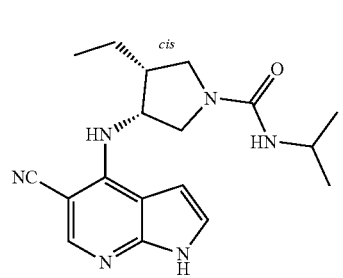
H76
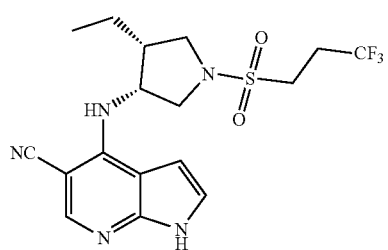

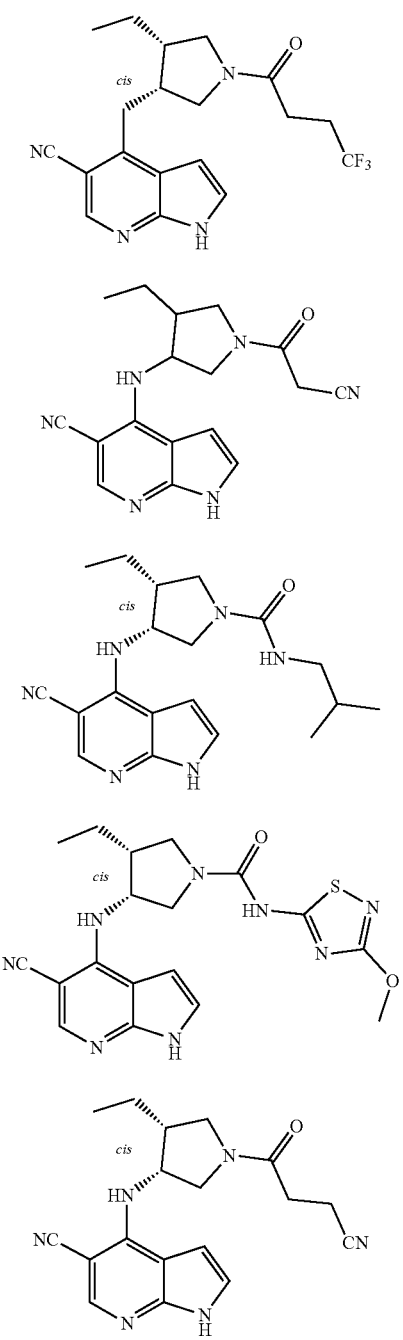

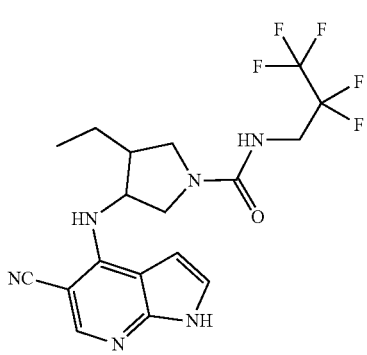

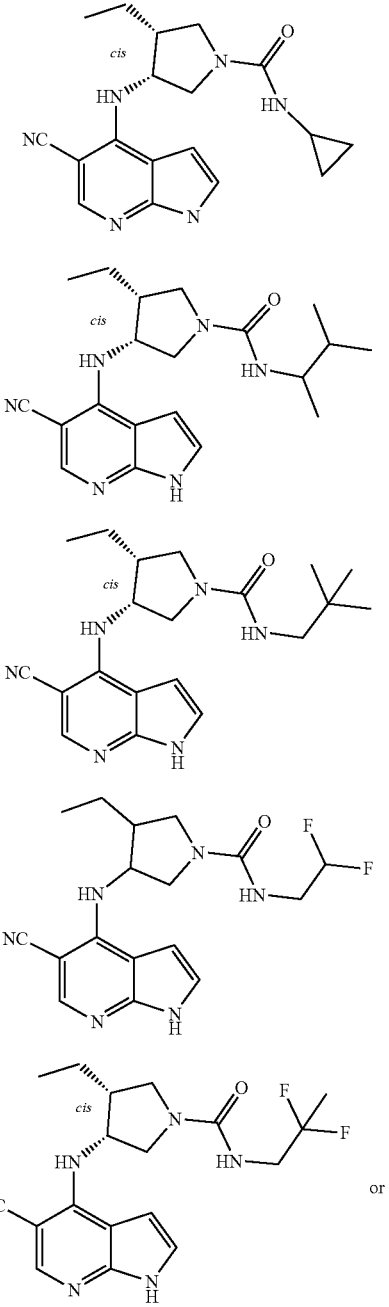

6. The compound or tautomers, mesomers, racemates, enantiomers, diastereoisomers, or mixtures thereof, pharmaceutically acceptable salts, polymorphs, solvates, or isotope derivatives thereof according to claim 1, wherein the pharmaceutically acceptable salts are acid addition salts, alkali addition salts, inner salts or betaines.

7. A pharmaceutical composition, comprising a therapeutically effective amount of the compound or tautomers, mesomers, racemates, enantiomers, diastereoisomers, or mixtures thereof, pharmaceutically acceptable salts, polymorphs, solvates, or isotope derivatives thereof according to claim 1, and optionally one or more pharmaceutically acceptable carriers and excipients, wherein the pharmaceutical composition also comprises additional one or more agents, anticarcinogens or anti-inflammatory agents that regulate immune systems of mammals.

8. A method for preparing the compound of formula (II) or tautomers, mesomers, racemates, enantiomers, diastereoisomers, or mixtures thereof, pharmaceutically acceptable salts, polymorphs, solvates, or isotope derivatives thereof according to claim 1, wherein the compound of formula (II) is prepared by:

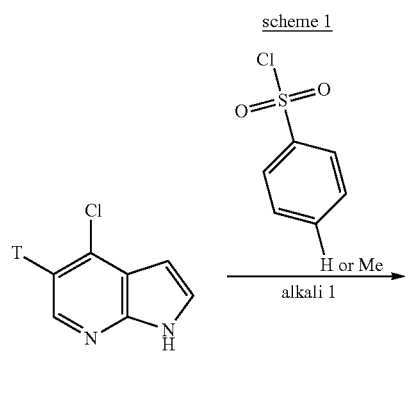

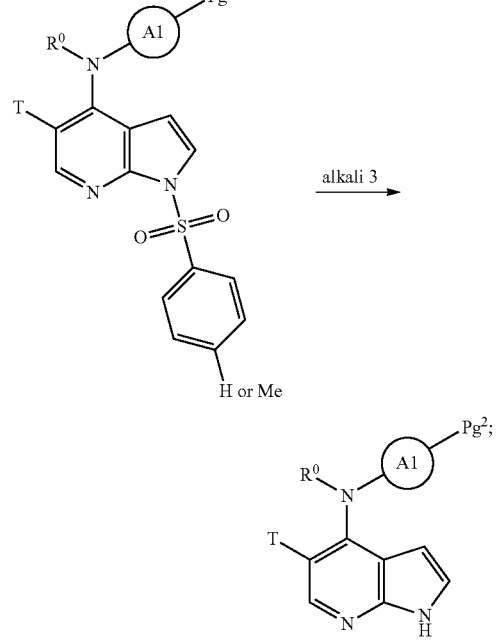

or

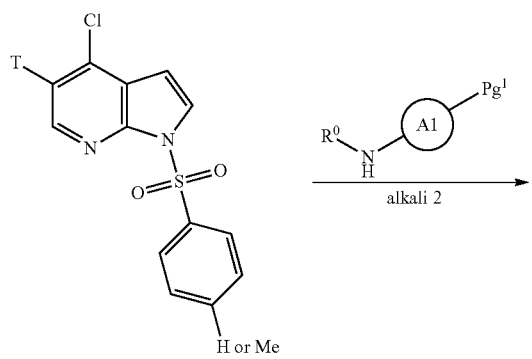

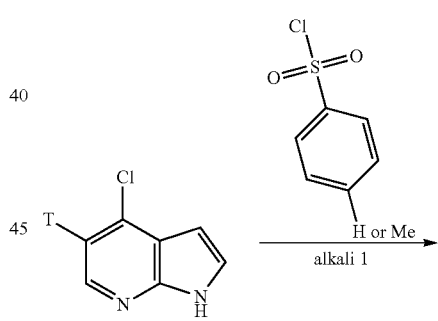

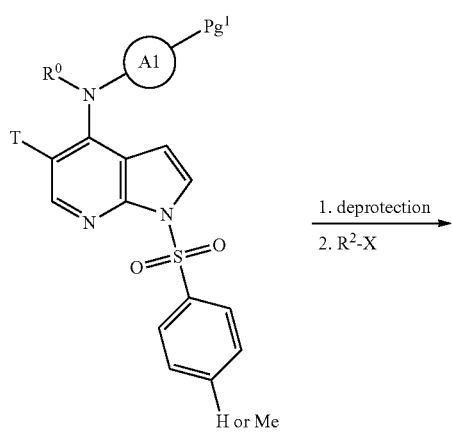

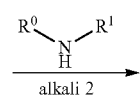

-continued

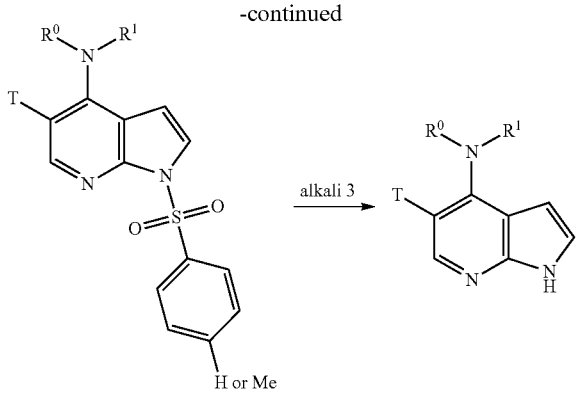

wherein, Pg¹ is an aliphatic amine protecting group, and A1 is

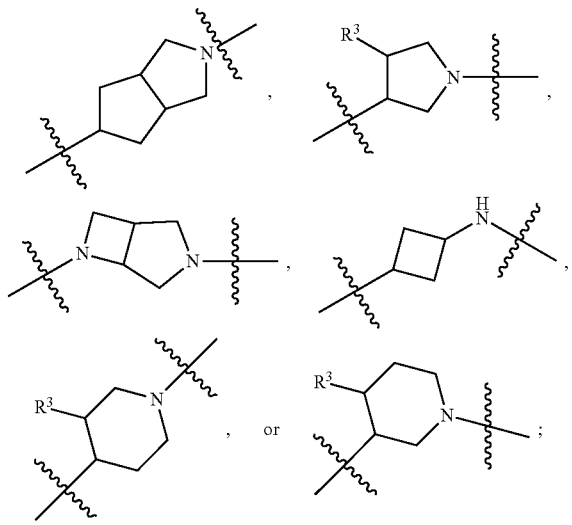

R²—X is an active form of R², and X is selected from the group consisting of bromine, chloride, phenoxyl and p-nitrophenoxy, or R²—X is isocyanate form of R²; alkali 1, alkali 2 and alkali 3 are each independently selected from the group consisting of triethylamine, diisopropyl ethylamine, potassium carbonate, cesium carbonate, sodium carbonate, sodium hydroxide and potassium hydroxide.

9. The method according to claim 8, wherein Pg¹ is tert-butoxycarbonyl or benzyloxycarbonyl.

10. A method for preventing and/or treating JAK-mediated diseases, comprising administering the compound or tautomers, mesomers, racemates, enantiomers, diastereoisomers, or mixtures thereof, pharmaceutically acceptable salts, polymorphs, solvates, or isotope derivatives thereof according to claim 1, optionally in combination with additional one or more agents, anticarcinogen or anti-inflammatory agents that regulate immune systems of mammals to a subject.

11. The method according to claim 10, wherein the JAK-mediated diseases is selected from immune system diseases; autoimmune diseases; dermatosis; allergic diseases; viral diseases; type 1 diabetes and diabetic complication; alzheimer disease; xerophthalmia; myelofibrosis; thrombocytosis; polycythemia or leukemia; cancers; inflammatory bowel disease; myelodysplastic syndrome; and myeloma.

12. The method according to claim 11, wherein the immune system disease is allograft rejection or graft-versus-host disease.

13. The method according to claim 11, wherein the autoimmune disease is lupus, multiple sclerosis, rheumatoid arthritis, juvenile arthritis, psoriasis, ulcerative colitis, Crohn's disease, or an autoimmune thyroid disease.

14. The method according to claim 11, wherein the dermatosis is psora, skin rash, or atopic dermatitis.

15. The method according to claim 11, wherein the allergic disease is allergies, asthma, or rhinitis.

16. The method according to claim 11, wherein the viral disease is hepatitis B, hepatitis C, or varicella-zoster virus.

17. The method according to claim 11, wherein the cancer is solid tumor, hematologic malignancy, or skin cancer.

18. The method according to claim 17, wherein the solid tumor is prostate cancer, renal carcinoma, liver cancer, pancreatic cancer, gastric cancer, breast cancer, lung cancer, head-neck carcinoma, thyroid cancer, glioblastoma, or melanoma.

19. The method according to claim 17, wherein the hematologic malignancy is lymphoma or leukemia.

20. The method according to claim 17, wherein the skin cancer is cutaneous T-cell lymphoma or cutaneous B-cell lymphoma.

* * * * *